(12) United States Patent
Kimbrel et al.

(10) Patent No.: US 8,961,956 B2
(45) Date of Patent: Feb. 24, 2015

(54) MESENCHYMAL STROMAL CELLS AND USES RELATED THERETO

(71) Applicant: Advanced Cell Technology, Inc., Marlborough, MA (US)

(72) Inventors: Erin Anne Kimbrel, Sudbury, MA (US); Robert Lanza, Clinton, MA (US); Jianlin Chu, Bedford, MA (US); Nicholas Arthur Kouris, Hudson, MA (US)

(73) Assignee: Ocata Therapeutics, Inc., Marlborough, MA (US)

( * ) Notice: Subject to any disclaimer, the term of this patent is extended or adjusted under 35 U.S.C. 154(b) by 0 days.

(21) Appl. No.: 13/905,526

(22) Filed: May 30, 2013

(65) Prior Publication Data

US 2014/0072537 A1 Mar. 13, 2014

Related U.S. Application Data

(63) Continuation-in-part of application No. 13/691,349, filed on Nov. 30, 2012.

(60) Provisional application No. 61/565,358, filed on Nov. 30, 2011.

(51) Int. Cl.
*A61K 35/12* (2006.01)
*A61K 35/28* (2006.01)
*A61K 48/00* (2006.01)
*C12N 5/0789* (2010.01)
*C12N 5/0775* (2010.01)

(52) U.S. Cl.
CPC ............ *A61K 35/28* (2013.01); *A61K 48/00* (2013.01); *C12N 5/0647* (2013.01); *C12N 5/0662* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/26* (2013.01); *C12N 2506/02* (2013.01); *C12N 2506/11* (2013.01); *C12N 2533/90* (2013.01)
USPC ...................................................... 424/93.7

(58) Field of Classification Search
None
See application file for complete search history.

(56) References Cited

U.S. PATENT DOCUMENTS

| | | | |
|---|---|---|---|
| 7,794,704 | B2 | 9/2010 | Klimanskaya et al. |
| 8,017,393 | B2 | 9/2011 | Lanza et al. |
| 8,198,085 | B2 | 6/2012 | Kanias et al. |
| 2002/0103542 | A1 | 8/2002 | Bilbo |
| 2007/0031386 | A1 | 2/2007 | Klimanskaya |
| 2009/0010896 | A1 | 1/2009 | Centeno et al. |
| 2009/0232777 | A1 | 9/2009 | Lundgren-Akerlund et al. |
| 2011/0123498 | A1 | 5/2011 | Westenfelder |
| 2011/0129918 | A1 | 6/2011 | Hung |
| 2011/0195054 | A1 | 8/2011 | Cohen et al. |
| 2011/0236971 | A2 | 9/2011 | Vodyanyk et al. |
| 2012/0077181 | A1 | 3/2012 | Schmidt et al. |
| 2012/0087933 | A1 | 4/2012 | Tom et al. |
| 2013/0183272 | A1 | 7/2013 | Kimbrel et al. |

FOREIGN PATENT DOCUMENTS

| | | |
|---|---|---|
| EP | 1 454 641 A2 | 9/2004 |
| KR | 2007-0114449 A | 12/2007 |
| WO | WO 2004/098285 A2 | 11/2004 |
| WO | WO 2009/051671 A1 | 4/2009 |
| WO | WO 2011/063005 A2 | 5/2011 |
| WO | WO 2011/097242 A2 | 8/2011 |

OTHER PUBLICATIONS

International Search Report and Written Opinion mailed Mar. 28, 2013 for Application No. PCT/US2012/067464.
International Preliminary Report on Patentability mailed Jun. 12, 2014 for Application No. PCT/US2012/067464.
Advanced Cell Technology, Inc. ACT secures first patent for generating hemangioblast cells to treat a broad spectrum of vascular and hematopoietic disorders. Sep. 19, 2011. http://www.advancedcell.com/news-and-media/press-releases/act-secures-first-patent-for-generating-hemangioblast-cells-to-treat-a-broad-spectrum-of-vascular-and-hematopoietic-disorders/ [Last accessed Aug. 18, 2014.].
Aggarwal et al., Human mesenchymal stem cells modulate allogeneic immune cell responses. Blood. Feb. 15, 2005;105(4):1815-22. Epub Oct. 19, 2004.
Auletta et al., The potential of mesenchymal stromal cells as a novel cellular therapy for multiple sclerosis. Immunotherapy. May 2012;4(5):529-47. doi: 10.2217/imt.12.41.
Bai et al., Human bone marrow-derived mesenchymal stem cells induce Th2-polarized immune response and promote endogenous repair in animal models of multiple sclerosis. Glia. Aug. 15, 2009;57(11):1192-203. doi: 10.1002/glia.20841.
Barberi et al,, Derivation of multipotent mesenchymal precursors from human embryonic stem cells. PLoS Med. Jun. 2005;2(6):e161. Epub Jun. 28, 2005.
Barlow et al., Comparison of human placenta- and bone marrow-derived multipotent mesenchymal stem cells. Stem Cells Dev. Dec. 2008;17(6):1095-107. doi: 10.1089/scd.2007.0154. Abstract Only.
Barry et al., The SH-3 and SH-4 antibodies recognize distinct epitopes on CD73 from human mesenchymal stem cells. Biochem Biophys Res Commun. Nov. 30, 2001;289(2):519-24. Abstract Only.
Bartholomaus et al., Effector T cell interactions with meningeal vascular structures in nascent autoimmune CNS lesions. Nature. Nov. 5, 2009;462(7269):94-8. doi: 10.1038/nature08478. Epub Oct. 14, 2009. Abstract Only.
Benito-Leon, Are the prevalence and incidence of multiple sclerosis changing? Neuroepidemiology. 2011;36(3):148-9. doi: 10.1159/000325368. Epub Apr. 20, 2011.

(Continued)

*Primary Examiner* — Allison Fox
(74) *Attorney, Agent, or Firm* — Wolf, Greenfield & Sacks, P.C.

(57) ABSTRACT

The present invention generally relates to novel preparations of mesenchymal stromal cells (MSCs) derived from hemangioblasts, methods for obtaining such MSCs, and methods of treating a pathology using such MSCs. The methods of the present invention produce substantial numbers of MSCs having a potency-retaining youthful phenotype, which are useful in the treatment of pathologies.

11 Claims, 38 Drawing Sheets

(56) References Cited

OTHER PUBLICATIONS

Bennett et al., Blood-brain barrier disruption and enhanced vascular permeability in the multiple sclerosis model EAE. J Neuroimmunol. Dec. 15, 2010;229(1-2):180-91. doi: 10.1016/j.jneuroim.2010.08.011. Epub Sep. 15, 2010. Abstract Only.
Bocelli-Tyndall et al., Bone marrow mesenchymal stromal cells (BM-MSCs) from healthy donors and auto-immune disease patients reduce the proliferation of autologous- and allogeneic-stimulated lymphocytes in vitro. Rheumatology (Oxford). Mar. 2007;46(3):403-8. Epub Aug. 18, 2006.
Bordoni et al., Hepatocyte-conditioned medium sustains endothelial differentiation of human hematopoietic-endothelial progenitors. Hepatology. May 2007;45(5):1218-28.
Brown et al., The derivation of mesenchymal stem cells from human embryonic stem cells. Cells Tissues Organs. 2009;189(1-4):256-60. doi: 10.1159/000151746. Epub Aug. 27, 2008.
Carrion et al., Opposing effect of mesenchymal stem cells on Th1 and Th17 cell polarization according to the state of CD4+ T cell activation. Immunol Lett. Mar. 30, 2011;135(1-2):10-6. doi: 10.1016/j.imlet.2010.09.006. Epub Oct. 1, 2010. Abstract Only.
Chamberlain et al., Mesenchymal stem cells exhibit firm adhesion, crawling, spreading and transmigration across aortic endothelial cells: effects of chemokines and shear. PLoS One. 2011;6(9):e25663. doi: 10.1371/journal.pone.0025663. Epub Sep. 28, 2011.
Chao et al., Mesenchymal stem cell transplantation attenuates blood brain barrier damage and neuroinflammation and protects dopaminergic neurons against MPTP toxicity in the substantia nigra in a model of Parkinson's disease. J Neuroimmunol. Nov. 30, 2009;216(1-2):39-50. doi: 10.1016/j.jneuroim.2009.09.003. Epub Oct. 9, 2009. Abstract Only.
Choi et al., A common precursor for hematopoietic and endothelial cells. Development. Feb. 1998;125(4):725-32.
Ciraci et al., Adult human circulating $CD34^-Lin^-CD45^-CD133^-$ cells can differentiate into hematopoietic and endothelial cells. Blood. Aug. 25, 2011;118(8):2105-15. doi: 10.1182/blood-2010-10-316596. Epub Jun. 29, 2011.
Connick et al., Autologous mesenchymal stem cells for the treatment of secondary progressive multiple sclerosis: an open-label phase 2a proof-of-concept study. Lancet Neurol. Feb. 2012;11(2):150-6. doi: 10.1016/S1474-4422(11)70305-2. Epub Jan. 10, 2012.
Copland et al., The clinical time-course of experimental autoimmune uveoretinitis using topical endoscopic fundal imaging with histologic and cellular infiltrate correlation. Invest Ophthalmol Vis Sci. Dec. 2008;49(12):5458-65. doi: 10.1167/iovs.08.-2348. Epub Aug. 29, 2008.
Costa et al., The hESC line Envy expresses high levels of GFP in all differentiated progeny. Nat Methods. Apr. 2005;2(4):259-60. Epub Mar. 23, 2005. Abstract Only.
Crocker et al., Cell and agonist-specific regulation of genes for matrix metalloproteinases and their tissue inhibitors by primary glial cells. J Neurochem. Aug. 2006;98(3):812-23.
Darlington et al., Reciprocal Th1 and Th17 regulation by mesenchymal stem cells: Implication for multiple sclerosis. Ann Neurol. Oct. 2010;68(4):540-5. doi: 10.1002/ana.22065. Abstract Only.
Dazzi et al., Mesenchymal stem cells and autoimmune diseases. Best Pract Res Clin Haematol. Mar. 2011;24(1):49-57. doi: 10.1016/j.beha.2011.01.002. Epub Feb. 23, 2011. Abstract Only.
De Becker et al., Migration of culture-expanded human mesenchymal stem cells through bone marrow endothelium is regulated by matrix metalloproteinase-2 and tissue inhibitor of metalloproteinase-3. Haematologica. Apr. 2007;92(4):440-9.
Djouad et al., Immunosuppressive effect of mesenchymal stem cells favors tumor growth in allogeneic animals. Blood. Nov. 15, 2003;102(10):3837-44. Epub Jul. 24, 2003.
Duijvestein et al., Pretreatment with interferon-γ enhances the therapeutic activity of mesenchymal stromal cells in animal models of colitis. Stem Cells. Oct. 2011;29(10):1549-58. doi: 10.1002/stem.698.
Giuliani et al., Long-lasting inhibitory effects of fetal liver mesenchymal stem cells on T-lymphocyte proliferation. PLoS One. 2011;6(5):e19988. doi: 10.1371/journal.pone.0019988. Epub May 19, 2011.
Gordon et al., Human mesenchymal stem cells abrogate experimental allergic encephalomyelitis after intraperitoneal injection, and with sparse CNS infiltration. Neurosci Lett. Dec. 19, 2008;448(1):71-3. doi: 10.1016/j.neulet.2008.10.040. Epub Oct. 17, 2008.
Gotherstrom et al., Difference in gene expression between human fetal liver and adult bone marrow mesenchymal stem cells. Haematologica. Aug. 2005;90(8):1017-26.
Gotherstrom et al., Immunologic properties of human fetal mesenchymal stem cells. Am J Obstet Gynecol. Jan. 2004;190(1):239-45. Abstract Only.
Gruenloh et al., Characterization and in vivo testing of mesenchymal stem cells derived from human embryonic stem cells. Tissue Eng Part A. Jun. 2011;17(11-12):1517-25. doi: 10.1089/ten.TEA.2010.0460. Epub Mar. 4, 2011.
Haruta et al., In vitro and in vivo characterization of pigment epithelial cells differentiated from primate embryonic stem cells. Invest Ophthalmol Vis Sci. Mar. 2004;45(3):1020-5.
Hofstetter et al., Marrow stromal cells form guiding strands in the injured spinal cord and promote recovery. Proc Natl Acad Sci U S A. Feb. 19, 2002;99(4):2199-204.
Huber et al., Haemangioblast commitment is initiated in the primitive streak of the mouse embryo. Nature. Dec. 2, 2004;432(7017):625-30. Abstract Only.
Hwang et al., In vivo commitment and functional tissue regeneration using human embryonic stem cell-derived mesenchymal cells. Proc Natl Acad Sci U S A. Dec. 30, 2008;105(52):20641-6. doi: 10.1073/pnas.0809680106. Epub Dec. 18, 2008.
Itskovitz-Eldor et al., Differentiation of human embryonic stem cells into embryoid bodies compromising the three embryonic germ layers. Mol Med. Feb. 2000;6(2):88-95.
Karlsson et al., Human embryonic stem cell-derived mesenchymal progenitors—potential in regenerative medicine. Stem Cell Res. Jul. 2009;3(1):39-50. doi: 10.1016/j.scr.2009.05.002. Epub May 19, 2009. Abstract Only.
Kennedy et al., A common precursor for primitive erythropoiesis and definitive haematopoiesis. Nature. Apr. 3, 1997;386(6624):488-93. Abstract Only.
Lazarevic et al., T-bet represses T(H)17 differentiation by preventing Runx1-mediated activation of the gene encoding RORγt. Nat Immunol. Jan. 2011;12(1):96-104. doi: 10.1038/ni.1969. Epub Dec. 12, 2010.
Le Blanc et al., HLA expression and immunologic properties of differentiated and undifferentiated mesenchymal stem cells. Exp Hematol. Oct. 2003;31(10):890-6. Abstract Only.
Lee et al., Human umbilical cord blood-derived mesenchymal stem cells improve neuropathology and cognitive impairment in an Alzheimer's disease model through modulation of neuroinflammation. Neurobiol Aging. Mar. 2012;33(3):588-602. doi: 10.1016/j.neurobiolaging.2010.03.024. Epub May 14, 2010. Abstract Only.
Lian et al., Derivation of clinically compliant MSCs from CD105+, CD24− differentiated human ESCs. Stem Cells. Feb. 2007;25(2):425-36. Epub Oct. 19, 2006.
Liang et al., Human umbilical cord mesenchymal stem cells ameliorate mice trinitrobenzene sulfonic acid (TNBS)-induced colitis. Cell Transplant. 2011;20(9):1395-408. doi: 10.3727/096368910X557245. Epub Mar. 9, 2011.
Lu et al., Generation of functional hemangioblasts from human embryonic stem cells. Nat Methods. Jun. 2007;4(6):501-9. Epub May 7, 2007.
Lu et al., Robust generation of hemangioblastic progenitors from human embryonic stem cells. Regen Med. Sep. 2008;3(5):693-704. doi: 10.2217/17460751.3.5.693.
McFarland et al., Multiple sclerosis: a complicated picture of autoimmunity. Nat Immunol. Sep. 2007;8(9):913-9. Abstract Only.
Meisel et al., Human bone marrow stromal cells inhibit allogeneic T-cell responses by indoleamine 2,3-dioxygenase-mediated tryptophan degradation. Blood. Jun. 15, 2004;103(12):4619-21. Epub Mar. 4, 2004.

(56) References Cited

OTHER PUBLICATIONS

Mohanty et al., A small molecule modulator of prion protein increases human mesenchymal stem cell lifespan, ex vivo expansion, and engraftment to bone marrow in NOD/SCID mice. Stem Cells. Jun. 2012;30(6):1134-43. doi: 10.1002/stem.1065.

Musina et al., Comparison of mesenchymal stem cells obtained from different human tissues. Bull Exp Biol Med. Apr. 2005;139(4):504-9. Abstract Only.

Newman et al., Treatment of inflammatory diseases with mesenchymal stem cells Inflamm Allergy Drug Targets. Jun. 2009;8(2):110-23.

Noth et al., Technology insight: adult mesenchymal stem cells for osteoarthritis therapy. Nat Clin Pract Rheumatol. Jul. 2008;4(7):371-80. doi: 10.1038/ncprheum0816. Epub May 13, 2008.

Olivier et al., Differentiation of human embryonic stem cells into bipotent mesenchymal stem cells. Stem Cells. Aug. 2006;24(8):1914-22. Epub Apr. 27, 2006.

Parekkadan et al., Aire controls mesenchymal stem cell-mediated suppression in chronic colitis. Mol Ther. Jan. 2012;20(1):178-86. doi: 10.1038/mt.2011.192. Epub Sep. 27, 2011.

Pati et al., Bone marrow derived mesenchymal stem cells inhibit inflammation and preserve vascular endothelial integrity in the lungs after hemorrhagic shock. PLoS One. 2011;6(9):e25171. doi: 10.1371/journal.pone.0025171. Epub Sep. 28, 2011.

Payne et al., Distinct immunomodulatory and migratory mechanisms underpin the therapeutic potential of human mesenchymal stem cells in autoimmune demyelination. Cell Transplant. 2013;22(8):1409-25. doi: 10.3727/096368912X657620. Epub Oct. 4, 2012.

Perlingeiro et al., A role for thrombopoietin in hemangioblast development. Stem Cells. 2003;21(3):272-80.

Pizarro et al., Mouse models for the study of Crohn's disease. Trends Mol Med. May 2003;9(5):218-22. Abstract Only.

Rasmusson et al., Immune modulation by mesenchymal stem cells. Exp Cell Res. Jul. 15, 2006;312(12):2169-79. Epub Apr. 24, 2006. Abstract Only.

Rombouts et al., Primary murine MSC show highly efficient homing to the bone marrow but lose homing ability following culture. Leukemia. Jan. 2003;17(1):160-70.

Salem et al., Mesenchymal stromal cells: current understanding and clinical status. Stem Cells. Mar. 31, 2010;28(3):585-96. doi: 10.1002/stem.269.

Sanchez et al., Enrichment of human ESC-derived multipotent mesenchymal stem cells with immunosuppressive and anti-inflammatory properties capable to protect against experimental inflammatory bowel disease. Stem Cells. Feb. 2011 ;29(2):251-62. doi: 10.1002/stem.569.

Selmani et al., Human leukocyte antigen-G5 secretion by human mesenchymal stem cells is required to suppress T lymphocyte and natural killer function and to induce CD4+CD25highFOXP3+ regulatory T cells. Stem Cells. Jan. 2008;26(1):212-22. Epub Oct. 11, 2007.

Sheikh et al., Mesenchymal stem cell transplantation modulates neuroinflammation in focal cerebral ischemia: contribution of fractalkine and IL-5. Neurobiol Dis. Mar. 2011;41(3):717-24. doi: 10.1016/j.nbd.2010.12.009. Epub Dec. 17, 2010. Abstract Only.

Singer et al., Mesenchymal stem cells: mechanisms of inflammation. Annu Rev Pathol. 2011;6:457-78. doi: 10.1146/annurev-pathol-011110-130230. Abstract Only.

Sun et al., An adult uterine hemangioblast: evidence for extramedullary self-renewal and clonal bilineage potential. Blood. Oct. 21, 2010;116(16):2932-41. doi: 10.1182/blood-2010-01-266882. Epub Jul. 6, 2010.

Teo et al., Mesenchymal stem cells transmigrate between and directly through tumor necrosis factor-α-activated endothelial cells via both leukocyte-like and novel mechanisms. Stem Cells. Nov. 2012;30(11):2472-86. doi: 10.1002/stem.1198.

Trivedi et al., Simultaneous generation of CD34+ primitive hematopoietic cells and CD73+ mesenchymal stem cells from human embryonic stem cells cocultured with murine OP9 stromal cells. Exp Hematol. Jan. 2007;35(1):146-54. Abstract Only.

Vodyanik et al., A mesoderm-derived precursor for mesenchymal stem and endothelial cells. Cell Stem Cell. Dec. 3, 2010;7(6):718-29. doi: 10.1016/j.stem.2010.11.011.

Wagner et al., Replicative senescence of mesenchymal stem cells: a continuous and organized process. PLoS One. May 21, 2008;3(5):e2213. doi: 10.1371/journal.pone.0002213.

Wakitani et al., Human autologous culture expanded bone marrow mesenchymal cell transplantation for repair of cartilage defects in osteoarthritic knees. Osteoarthritis Cartilage. Mar. 2002;10(3):199-206. Abstract Only.

Wong, Mesenchymal stem cells: angels or demons? J Biomed Biotechnol. 2011;2011:459510. doi: 10.1155/2011/459510. Epub Jul. 24, 2011.

Yamout et al., Bone marrow mesenchymal stem cell transplantation in patients with multiple sclerosis:a pilot study. J Neuroimmunol. Oct. 8, 2010;227(1-2):185-9. doi:10.1016/j.jneuroim.2010.07.013. Epub Aug. 21, 2010. Abstract Only.

Yu et al., Retinoic acid enhances the generation of hematopoietic progenitors from human embryonic stem cell-derived hemato-vascular precursors. Blood. Dec. 2, 2010;116(23):4786-94. doi: 10.1182/blood-2010-01-263335. Epub Apr. 28, 2010.

Zappia et al., Mesenchymal stem cells ameliorate experimental autoimmune encephalomyelitis inducing T-cell anergy. Blood. Sep. 1, 2005;106(5):1755-61. Epub May 19, 2005.

Zhang et al., Bone marrow stromal cells reduce axonal loss in experimental autoimmune encephalomyelitis mice. J Neurosci Res. Aug. 15, 2006;84(3):587-95. Abstract Only.

Zhang et al., Human bone marrow stromal cell treatment improves neurological functional recovery in EAE mice. Exp Neurol. Sep. 2005;195(1):16-26. Abstract Only.

FIG. 4

| | MSC derived from pluripotent cells plated on gelatin coated plastic | MSC derived from pluripotent cells plated on Matrigel coated plastic | MSC derived from hemangioblasts plated on Matrigel coated plastic |
|---|---|---|---|
| Number of starting pluripotent cells: | 300,000 | 350,000 | ~200,000 |
| Yield: | n/a | 4 million | 85 million |
| Yield collected at: | n/a | 48 days | 44 days |

Figure : Comparison of MSCs stimulated with 50ng/ml IFNγ for 3 days, with resulting kynurenine concentration. For each cell line, 1x10^6 cells were lysed and assayed for IDO expression.

BWF1 mice injected MSC at the 6 months age

Survival of Data 2:Survival proportions

Proteinuria after 7 weeks post treatment (mice were treated at 6 month of age)

MESENCHYMAL STROMAL CELLS AND USES RELATED THERETO

CROSS-REFERENCE TO RELATED APPLICATIONS

This application is a continuation-in-part of U.S. Ser. No. 13/691,349, filed Nov. 30, 2012, entitled "MESENCHYMAL STROMAL CELLS AND USES RELATED THERETO", now pending, which claims the benefit of priority to U.S. Provisional Application Ser. No. 61/565,358, filed Nov. 30, 2011, entitled "METHODS OF GENERATING MESENCHYMAL STROMAL CELLS USING HEMANGIOBLASTS" each of which is incorporated by reference in its entirety.

FIELD OF THE INVENTION

The present invention relates to the use of cell-based therapies to reduce the manifestations of a pathology such as that characterized by an inappropriate immune response in a subject, and also to affect the origin of a pathology such that the abnormality defining the pathology is returned to a normal posture. In particular, the present invention relates to mesenchymal stromal cells (MSCs) that retain a phenotype of "youthful" cells that imparts a high potency in the reduction of a manifestation of a pathology in a subject.

BACKGROUND OF THE INVENTION

Many pathologies manifest clinically through unwanted or excessive immune responses within a host, e.g., transplant rejection, inflammatory and autoimmune disorders. Immunosuppressive therapies have been developed to treat the symptoms, but not the underlying cause of pathologies characterized by excessive immune responses. These therapies are effective at down-modulating immune function and, as such, carry the potential for severe adverse events, including cancer and opportunistic infection, as well as side effects such as cataracts, hyperglycemia, bruising, and nephrotoxicity from agents such as prednisone, cyclosporine, and tacrolimus.

Although therapies that do not suppress the entire immune system have been developed, there are limitations associated with these regimens as well. These immunomodulatory treatments target a narrower point of intervention within the immune system and, as such, have different, sometimes less severe side effects. Examples of such immunomodulatory therapies include the use of antibodies, e.g., anti-CD3 or anti-IL2R. While successful at inducing a heightened state of non-responsiveness, the withdrawal of these immunomodulatory therapies results in a reversion to the unwanted pathology.

Mesenchymal stem cells (MSC or MSCs) are multipotent stem cells with self-renewal capacity and the ability to differentiate into osteoblasts, chondrocytes, and adipocytes, among other mesenchymal cell lineages. In recent years, the intense research on the multilineage differentiation potential and immunomodulatory properties of human MSC has indicated that these cells can be used to treat a range of clinical conditions, including immunological disorders as well as degenerative diseases. Consequently, the number of clinical studies with MSC has been steadily increasing for a wide variety of conditions: graft-versus-host disease (GVHD), myocardial infarction and inflammatory and autoimmune diseases and disorders, among others. Currently, clinical programs utilizing MSCs rely on isolation of these cells from adult sources and cord blood. The high cell doses required for MSC clinical applications (up to several million cells per kg of the patient) demands a reliable, reproducible and efficient expansion protocol, capable of generating a large number of cells from those isolated from the donor source.

To reach the clinically meaningful cell numbers for cellular therapy and tissue engineering applications, MSC ex-vivo expansion is mandatory. Sequential ex-vivo cell passaging of MSCs from cord blood, fetal and adult sources (such as bone marrow or adipose tissues) can cause replicative stress, chromosomal abnormalities, or other stochastic cellular defects, resulting in the progressive loss of the proliferative, clonogenic and differentiation potential of the expanded MSCs, which ultimately can jeopardize MSC clinical safety and efficacy. The issues with use of senescent MSCs in treatment should not be underestimated since cells lose part of their differentiation potential and their secretory profile is also altered. MSC senescence during culture was found to induce cell growth arrest, concurrently with telomere shortening. A continuous decrease in adipogenic differentiation potential was reported for bone marrow (BM) MSC along increasing passages, whereas the propensity for differentiation into the osteogenic lineage increased.

Accordingly, some essential problems remain to be solved before the clinical application of MSC. MSCs derived from ESCs can be generated in sufficient quantities and in a highly controllable manner, thus alleviating the problems with donor-dependent sources. Since long-term engraftment of MSCs is not required, there is basically no concern for mismatch of major histocompatibility (MHC) [7,8]. In the art, MSCs derived from ESCs have been obtained through various methods including co-culture with murine OP9 cells or handpicking procedures [9-13]. These methods, however, are tedious and generate MSCs with a low yield, varying quality and a lack of potency. Moreover, maximizing the potency of the injected cells is desirable, in terms of being able to provide a cellular product with a better therapeutic index, ability to be used at a reduce dosage (number of cells) relative to CB-derived, BM-derived or adipose-derived MSCs, and/or the ability for the MSCs to provide a tractable therapy for inflammatory and autoimmune diseases for which CB-derived, BM-derived or adipose-derived MSCs are not efficacious enough.

SUMMARY OF PREFERRED EMBODIMENTS

The present invention relates to mesenchymal stromal cells (MSCs) and methods for generating MSCs. The methods of the present invention produce substantial numbers of high quality mesenchymal stromal cells, characterized by the phenotype of youthful cells that imparts a high potency. In an embodiment of the invention, the MSCs are derived from hemangioblasts. Preparations of the subject MSCs are useful in the treatment of pathologies, including unwanted immune responses, e.g., autoimmune diseases and disorders, as well as inflammatory diseases and disorders.

In one aspect, the present invention comprises improved preparations of MSCs generated from hemangioblasts using improved methods for culturing the hemangioblasts. In exemplary embodiments, mesenchymal stromal cells of the present invention retain higher levels of potency and do not clump or clump substantially less than mesenchymal stromal cells derived directly from embryonic stems cells (ESCs). Mesenchymal stromal cells generated according to any one or more of the processes of the present invention may retain higher levels of potency, and may not clump or may clump substantially less than mesenchymal stromal cells derived directly from ESCs.

In one aspect, the invention provides pharmaceutical preparations comprising mesenchymal stromal cells, wherein said mesenchymal stromal cells are able to undergo at least 10 population doublings, e.g., at least 10 population doublings occur within about 22-27 days. In another aspect, the invention provides pharmaceutical preparations comprising mesenchymal stromal cells, wherein said mesenchymal stromal cells are able to undergo at least 15 population doublings, e.g., at least 15 population doublings occur within about 22-27 days. The pharmaceutical preparations may be produced by in vitro differentiation of hemangioblasts. The mesenchymal stromal cells may be primate cells, e.g., human cells. The mesenchymal stromal cells may be able to undergo at least 15 population doublings. For example, the mesenchymal stromal cells undergo at least 20, 25, 30, 35, 40, 45, 50 or more population doublings. The preparation may comprise less than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% pluripotent cells. Preferably, the preparation is devoid of pluripotent cells. The preparation may comprise at least 90%, 91%, 92%, 93%, 94%, 95%, 96%, 97%, 98%, 99%, or 100% mesenchymal stromal cells.

In one aspect, at least 50% of said mesenchymal stromal cells are positive for (i) at least one of CD10, CD24, IL-11, AIRE-1, ANG-1, CXCL1, CD105, CD73 and CD90; (ii) at least one of CD10, CD24, IL-11, AIRE-1, ANG-1, CXCL1, CD105, CD73, CD90, CD105, CD13, CD29, CD 44, CD166, CD274, and HLA-ABC; or (iii) any combination thereof. In another aspect, at least 50% of said mesenchymal stromal cells are positive for (i) at least two of CD10, CD24, IL-11, AIRE-1, ANG-1, CXCL1, CD105, CD73 and CD90; (ii) all of CD10, CD24, IL-11, AIRE-1, ANG-1, CXCL1, CD105, CD73, CD90, CD105, CD13, CD29, CD 44, CD166, CD274, and HLA-ABC. In yet another aspect, at least 50% of said mesenchymal stromal cells are (i) positive for all of CD10, CD24, IL-11, AIRE-1, ANG-1, CXCL1, CD105, CD73, CD90, CD105, CD13, CD29, CD 44, CD166, CD274, and HLA-ABC and (ii) do not express or express low levels of at least one of CD31, 34, 45, 133, FGFR2, CD271, Stro-1, CXCR4, TLR3. Additionally, at least 60%, 70%, 80% or 90% of such mesenchymal stromal cells may be positive for (i) one or more of CD10, CD24, IL-11, AIRE-1, ANG-1, CXCL1, CD105, CD73 and CD90; or (ii) one or more of CD10, CD24, IL-11, AIRE-1, ANG-1, CXCL1, CD105, CD73, CD90, CD105, CD13, CD29, CD44, CD166, CD274, and HLA-ABC.

In one aspect, the pharmaceutical preparation comprises an amount of mesenchymal stromal cells effective to treat or prevent an unwanted immune response in a subject in need thereof. The pharmaceutical preparation may further comprise other cells, tissues or organs for transplantation into a recipient in need thereof. Exemplary other cells or tissues include RPE cells, skin cells, corneal cells, pancreatic cells, liver cells, or cardiac cells or tissue containing any of said cells. In another aspect, the pharmaceutical preparation comprises an amount of mesenchymal stromal cells effective to treat or prevent pain, heat sensitivity, and/or cold sensitivity.

In another aspect, the mesenchymal stromal cells are not derived from bone marrow and the potency of the preparation in an immune regulatory assay is greater than the potency of a preparation of bone marrow derived mesenchymal stromal cells, e.g., at least 20%, 25%, 30%, 35%, 40%, 45%, 50% greater than the potency of a preparation of bone marrow derived mesenchymal stromal cells. Potency may be assayed by an immune regulatory assay that determines the EC50 dose.

In one aspect, the preparation comprising MSCs retains between about 50 and 100% of its proliferative capacity after ten population doublings.

In another aspect, the mesenchymal stromal cells of the pharmaceutical preparation are not derived directly from pluripotent cells and said mesenchymal stromal cells of the pharmaceutical preparation (a) do not clump or clump substantially less than mesenchymal stromal cells derived directly from ESCs; (b) more easily disperse when splitting compared to mesenchymal stromal cells derived directly from ESCs; (c) are greater in number than mesenchymal stromal cells derived directly from ESCs when starting with equivalent numbers of ESCs; and/or (d) acquire characteristic mesenchymal cell surface markers earlier than mesenchymal stromal cells derived directly from ESCs.

The present invention further encompasses methods for generating mesenchymal stromal cells comprising culturing hemangioblast cells under conditions that give rise to mesenchymal stem cells. The hemangioblasts may be cultured in feeder-free conditions. Additionally, hemangioblasts may be plated on a matrix, e.g., comprising transforming growth factor beta (TGF-beta), epidermal growth factor (EGF), insulin-like growth factor 1, bovine fibroblast growth factor (bFGF), and/or platelet-derived growth factor (PDGF). The matrix may be selected from the group consisting of: laminin, fibronectin, vitronectin, proteoglycan, entactin, collagen, collagen I, collagen IV, heparan sulfate, Matrigel (a soluble preparation from Engelbreth-Holm-Swarm (EHS) mouse sarcoma cells), a human basement membrane extract, and any combination thereof. The matrix may comprise a soluble preparation from Engelbreth-Holm-Swarm mouse sarcoma cells.

In one aspect, the mesenchymal stromal cells are mammalian. Preferably, the mesenchymal stromal cells are human, canine, or equine.

In one aspect, the hemangioblasts may be cultured in a medium comprising αMEM. In another aspect, the hemangioblasts may be cultured in a medium comprising serum or a serum replacement. For example, the hemangioblasts cells may be cultured in a medium comprising, αMEM supplemented with 0%, 1%, 2%, 3%, 4%, 5%, 6%, 7%, 8%, 9%, 10%, 11%, 12%, 13%, 14%, 15%, 16%, 17%, 18%, 19%, or 20% fetal calf serum. In additional exemplary embodiments the medium may comprise higher percentages of fetal calf serum, e.g., more than 20%, e.g., at least 25%, at least 30%, at least 35%, at least 40%, or even higher percentages of fetal calf serum. The hemangioblasts may be cultured on said matrix for at least about 14, 15, 16, 17, 18, 19, 20, 21, 22, 23, 24, 25, 26, 27, 28, 29, or 30 days.

In one aspect, the hemangioblasts are differentiated from pluripotent cells, e.g., iPS cells, or blastomeres. The pluripotent cells may be derived from one or more blastomeres without the destruction of a human embryo. Additionally, the hemangioblasts may be differentiated from pluripotent cells by a method comprising (a) culturing said pluripotent cells to form clusters of cells. In one aspect, the pluripotent cells are cultured in the presence of vascular endothelial growth factor (VEGF) and/or bone morphogenic protein 4 (BMP-4). VEGF and BMP-4 may be added to the pluripotent cell culture within 0-48 hours of initiation of said cell culture, and said VEGF is optionally added at a concentration of 20-100 nm/mL and said BMP-4 is optionally added at a concentration of 15-100 ng/mL.

In one aspect, the hemangioblasts are differentiated from pluripotent cells by a method further comprising: (b) culturing said single cells in the presence of at least one growth factor in an amount sufficient to induce the differentiation of said clusters of cells into hemangioblasts. The at least one growth factor added in step (b) may comprise one or more of basic fibroblast growth factor (bFGF), vascular endothelial growth factor (VEGF), bone morphogenic protein 4 (BMP-4), stem cell factor (SCF), Flt 3L (FL), thrombopoietin (TPO), EPO, and/or tPTD-HOXB4. The one or more of said at least one growth factor added in step (b) may be added to said culture within 36-60 hours from the start of step (a). Preferably, the one or more of said at least one growth factor added in step (b) is added to said culture within 40-48 hours from the start of step (a). The at least one factor added in step (b) may comprise one or more of bFGF, VEGF, BMP-4, SCF, FL and/or tPTD-HOXB4. The concentration of said growth factors if added in step (b) may range from about the following: bFGF is about 20-25 ng/ml, VEGF is about 20-100 ng/ml, BMP-4 is about 15-100 ng/ml, SCF is about 20-50 ng/ml, FL is about 10-50 ng/ml, TPO is about 20-50 ng/ml, and tPTD-HOXB4 is about 1.5-5 U/ml.

In another aspect, the method further comprises (c) dissociating said clusters of cells, optionally into single cells. In another aspect, the method further comprises (d) culturing said hemangioblasts in a medium comprising at least one additional growth factor, wherein said at least one additional growth factor is in an amount sufficient to expand the hemangioblasts. The at least one additional growth factor of (d) may comprise one or more of: insulin, transferrin, granulocyte macrophage colony-stimulating factor (GM-CSF), interleukin-3 (IL-3), interleukin-6 (IL-6), granulocyte colony-stimulating factor (G-CSF), erythropoietin (EPO), stem cell factor (SCF), vascular endothelial growth factor (VEGF), bone morphogenic protein 4 (BMP-4), and/or tPTD-HOXB4. Exemplary concentrations in step (d) include insulin about 10-100 µg/ml, transferrin about 200-2,000 µg/ml, GM-CSF about 10-50 ng/ml, IL-3 about 10-20 ng/ml, IL-6 about 10-1000 ng/ml, G-CSF about 10-50 ng/ml, EPO about 3-50 U/ml, SCF about 20-200 ng/ml, VEGF about 20-200 ng/ml, BMP-4 about 15-150 ng/ml, and/or tPTD-HOXB4 about 1.5-15 U/ml. The medium in step (a), (b), (c) and/or (d) may be a serum-free medium.

In one aspect, the method generates at least 80, 85, 90, 95, 100, 125, or 150 million mesenchymal stromal cells. The hemangioblasts may be harvested after at least 10, 11, 12, 13, 14, 15, 16, 17 or 18 days of starting to induce differentiation of said pluripotent cells. The mesenchymal stromal cells may be generated within at least 25, 26, 27, 28, 29, 30, 31, 32, 33, 34, 35, 36, 37, 38, 39, 40, 41, 42, 43, 44, 45, 46, 47, 48, 49, or 50 days of starting to induce differentiation of said pluripotent cells. In another aspect, the method results in at least 80, 85, 90, 95, 100, 125, or 150 million mesenchymal stromal cells being generated from about 200,000 hemangioblasts within about 15, 16, 17, 18, 19, 20, 21, 22, 23, 24, 25, 26, 27, 28, 29, 30, 31, 32, 33, 34, or 35 days of culture. The mesenchymal stromal cells may be generated from hemangioblasts in a ratio of hemangioblasts to mesenchymal stromal cells of at least 1:200, 1:250, 1:300, 1:350, 1:400, 1:415, 1:425, 1:440; 1:450, 1:365, 1:475, 1:490 and 1:500 within about 26, 27, 28, 29, 30, 31, 32, 33, 34 or 35 days of culture. The cells may be human.

The present invention also contemplates mesenchymal stromal cells derived from hemangioblasts obtained by the described methods. In one aspect, the invention includes mesenchymal stromal cells derived by in vitro differentiation of hemangioblasts. At least 50% of said mesenchymal stromal cells may (i) be positive for all of CD10, CD24, IL-11, AIRE-1, ANG-1, CXCL1, CD105, CD73, CD90, CD105, CD13, CD29, CD 44, CD166, CD274, and HLA-ABC and (ii) not express or express low levels of at least one of CD31, 34, 45, 133, FGFR2, CD271, Stro-1, CXCR4, TLR3. Alternatively, at least 50% of said mesenchymal stromal cells may be positive for (i) all of CD10, CD24, IL-11, AIRE-1, ANG-1, CXCL1, CD105, CD73 and CD90; or (ii) all of CD73, CD90, CD105, CD13, CD29, CD44, CD166, CD274, and HLA-ABC. At least 60%, 70%, 80% or 90% of these mesencyhmal stromal cells may be positive for (i) at least one of CD10, CD24, IL-11, AIRE-1, ANG-1, CXCL1, CD105, CD73 and CD90; or (ii) at least one of CD73, CD90, CD105, CD13, CD29, CD 44, CD166, CD274, and HLA-ABC. Preferably, the mesenchymal stromal cells do not express or express low levels of at least one of CD31, CD34, CD45, CD133, FGFR2, CD271, Stro-1, CXCR4, TLR3.

In another aspect, the invention encompasses a preparation of the mesenchymal stromal cells described herein. The preparation may comprise less than 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% pluripotent cells. Preferably, the preparation is devoid of pluripotent cells. The preparation may be substantially purified and optionally comprises at least 90%, 91%, 92%, 93%, 94%, 95%, 96%, 97%, 98%, 99%, or 100% human mesenchymal stromal cells. The preparation may comprise substantially similar levels of p53 and p21 protein or the levels of p53 protein as compared to p21 protein may be 1.5, 2, 3, 4, 5, 6, 7, 8, 9 or 10 times greater. The mesenchymal stromal cells may be capable of undergoing at least 5 population doublings in culture. Preferably, the mesenchymal stromal cells are capable of undergoing at least 10, 15, 20, 25, 30, 35, 40, 45, 50, 55, 60 or more population doublings in culture.

In one aspect, the mesenchymal stromal cells of the present invention (a) do not clump or clump substantially less than mesenchymal stromal cells derived directly from ESCs; (b) more easily disperse when splitting compared to mesenchymal stromal cells derived directly from ESCs; (c) are greater in number than mesenchymal stromal cells derived directly from ESCs when starting with equivalent numbers of ESCs; and/or (d) acquire characteristic mesenchymal cell surface markers earlier than mesenchymal stromal cells derived directly from ESCs. The invention contemplates a pharmaceutical preparation comprising such mesenchymal stromal cells, which comprises an amount of mesenchymal stromal cells effective to treat an unwanted immune response. The invention also contemplates a pharmaceutical preparation comprising such mesenchymal stromal cells, which comprises an amount of mesenchymal stromal cells effective to treat or prevent pain, heat sensitivity, and/or cold sensitivity. The preparation may comprise an amount of mesenchymal stromal cells effective to treat an unwanted immune response and may further comprise other cells or tissues for transplantation into a recipient in need thereof. Exemplary other cells include allogeneic or syngeneic pancreatic, neural, liver, RPE, or corneal cells or tissues containing any of the foregoing. The pharmaceutical preparation may be useful in treating an autoimmune disorder or an immune reaction against allogeneic cells including, but not limited to, multiple sclerosis, systemic sclerosis, hematological malignancies, myocardial infarction, organ transplantation rejection, chronic allograft nephropathy, cirrhosis, liver failure, heart failure, GvHD, tibial fracture, bone fractures, left ventricular dysfunction, leukemia, myelodysplastic syndrome, Crohn's disease, diabetes, obesity, metabolic diseases and disorders (such as lysosomal storage diseases including Tay-Sachs disease, Gaucher disease, Pompe disease, Hurler syndrome and metachromatic leukodystrophy), fatty liver disease, chronic obstructive pulmonary disease, osteogenesis imperfecta, homozygous familial hypocholesterolemia, hypocholesterolemia, treatment following meniscectomy, adult periodontitis, periodontitis, vasculogenesis in patients with severe myocardial ischemia, spinal cord injury, osteodysplasia, critical limb ischemia, diabetic foot disease, primary Sjogren's syndrome, osteoarthritis, cartilage defects, laminitis, multisystem atrophy, amyotropic lateral sclerosis, cardiac surgery, systemic lupus erythematosis, living kidney allografts, nonmalignant red blood cell disorders, thermal burn, radiation burn, Parkinson's disease, microfractures, epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, bone regeneration, uveitis or combinations thereof. The MSCs of the invention (including formulations or preparations thereof) may be used to treat respiratory conditions, particularly those including inflammatory components or acute injury, such as Adult Respiratory Distress Syndrome, post-traumatic Adult Respiratory Distress Syndrome, transplant lung disease, Chronic Obstructive Pulmonary Disease, emphysema, chronic obstructive bronchitis, bronchitis, an allergic reaction, damage due to bacterial or viral pneumonia, asthma, exposure to irritants, and tobacco use. Additionally, the MSCs of the invention (including formulations or preparations thereof) may be used to treat atopic dermatitis, allergic rhinitis, hearing loss (particularly autoimmune hearing loss or noise-induced hearing loss), psoriasis. Additionally, the subject MSC (including formulations or preparations thereof) may be useful to treat or prevent pain, heat sensitivity, and/or cold sensitivity.

The invention further encompasses kits comprising the mesenchymal stromal cells or preparation of mesenchymal stromal cells described herein. The kits may comprise mesenchymal stromal cells or preparations of mesenchymal stromal cells that are frozen or cryopreserved. The mesenchymal stromal cells or preparation of mesenchymal stromal cells comprised in the kit may be contained in a cell delivery vehicle.

Moreover, the invention contemplates methods for treating a disease or disorder, comprising administering an effective amount of mesenchymal stromal cells or a preparation of mesenchymal stromal cells described herein to a subject in need thereof. The method may further comprise the transplantation of other cells or tissues, e.g., retinal, RPE, corneal, neural, immune, bone marrow, liver or pancreatic cells. Exemplary diseases or disorders treated include, but are not limited to, multiple sclerosis, systemic sclerosis, hematological malignancies, myocardial infarction, organ transplantation rejection, chronic allograft nephropathy, cirrhosis, liver failure, heart failure, GvHD, tibial fracture, bone fractures, left ventricular dysfunction, leukemia, myelodysplastic syndrome, Crohn's disease, diabetes, obesity, metabolic diseases and disorders (such as lysosomal storage diseases including Tay-Sachs disease, Gaucher disease, Pompe disease, Hurler syndrome and metachromatic leukodystrophy), fatty liver disease, chronic obstructive pulmonary disease, osteogenesis imperfecta, homozygous familial hypocholesterolemia, hypocholesterolemia, treatment following meniscectomy, adult periodontitis, periodontitis, vasculogenesis in patients with severe myocardial ischemia, spinal cord injury, osteodysplasia, critical limb ischemia, diabetic foot disease, primary Sjogren's syndrome, osteoarthritis, cartilage defects, laminitis, multisystem atrophy, amyotropic lateral sclerosis, cardiac surgery, refractory systemic lupus erythematosis, living kidney allografts, nonmalignant red blood cell disorders, thermal burn, radiation burn, Parkinson's disease, microfractures, epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, bone regeneration, or combinations thereof. In one aspect, the disease or disorder is uveitis. In another aspect, the disease or disorder is an autoimmune disorder, e.g., multiple sclerosis, or an immune reaction against allogeneic cells. Additional exemplary diseases or disorders treated include, but are not limited to, pain, heat sensitivity, and/or cold sensitivity.

In another aspect the present disclosure provides a pharmaceutical preparation as described herein comprising an amount of mesenchymal stromal cells effective to treat pain, heat sensitivity, or cold sensitivity in a subject in need thereof.

In another aspect the present disclosure provides a method of treating a pain, heat sensitivity, or cold sensitivity, the method comprising administering mesenchymal stromal cells, such as mesenchymal stromal cells produced as described herein, to a subject in need thereof.

The invention further encompasses methods of treating bone loss or cartilage damage comprising administering an effective amount of mesenchymal stromal cells or preparation of mesenchymal stromal cells described herein to a subject in need thereof. The mesenchymal stromal cells may be administered in combination with an allogeneic or syngeneic transplanted cell or tissue, e.g., retinal pigment epithelium cell, retinal cell, corneal cell, or muscle cell.

The present invention comprises methods of culturing hemangioblasts that generate preparations MSCs, which retain potency, despite increasing numbers of population doublings. The pharmaceutical preparations of mesenchymal stromal cells of the present invention demonstrate improved therapeutic properties when administered to a mammalian host in need of such administration.

In certain embodiments, the MSC preparation is characterized by the MSCs expressing TNF-alpha receptor Type I in an amount of at least 13 pg/$10^6$ cells, and even more preferably at least 15 pg/$10^6$ cells, 18 pg/$10^6$ cells or even 20 pg/$10^6$ cells.

In certain embodiments, the MSCs of the present invention secrete IL6 protein at a lower level than the same number of BM-MSCs, both in naïve cultures and activated by PHA. For instance, the concentration of IL-6 protein in culture may be more than 10% less from the MSCs of the present invention when compared to the same number of BM-MSCs from young (20 to 30 years old) donors, and even more preferably more than 20%, 30%, 40% or even 50% less. IL-6 levels can be analyzed, for example, using readily available ELISA kits (such as available from Mabtech, Nacka Strand, Sweden) following the manufacturer's instructions. IL-6 can be assessed, to further illustrate, in the supernatants following 24 and 48 h of co-culture with PBMC.

BRIEF DESCRIPTION OF THE DRAWINGS

FIG. 4. Mesenchymal stromal cell yield from pluripotent cells. This figure shows the yields of cells positive for MSC surface markers obtained from culturing ESC on gelatin coated plates (first column—no yield), ESC on Matrigel coated plates (second column), and hemangioblasts on Matrigel coated plates (third column).

FIG. 11A shows that hemangioblast-derived mesenchymal stromal cells were able to increase the percentage of CD4/CD25 double positive Tregs that are induced in response to IL2 stimulus.

FIG. 11B shows that hemangioblast-derived mesenchymal stromal cells inhibit Th1 secretion of IFNγ.

DETAILED DESCRIPTION OF THE INVENTION

Figure 1:
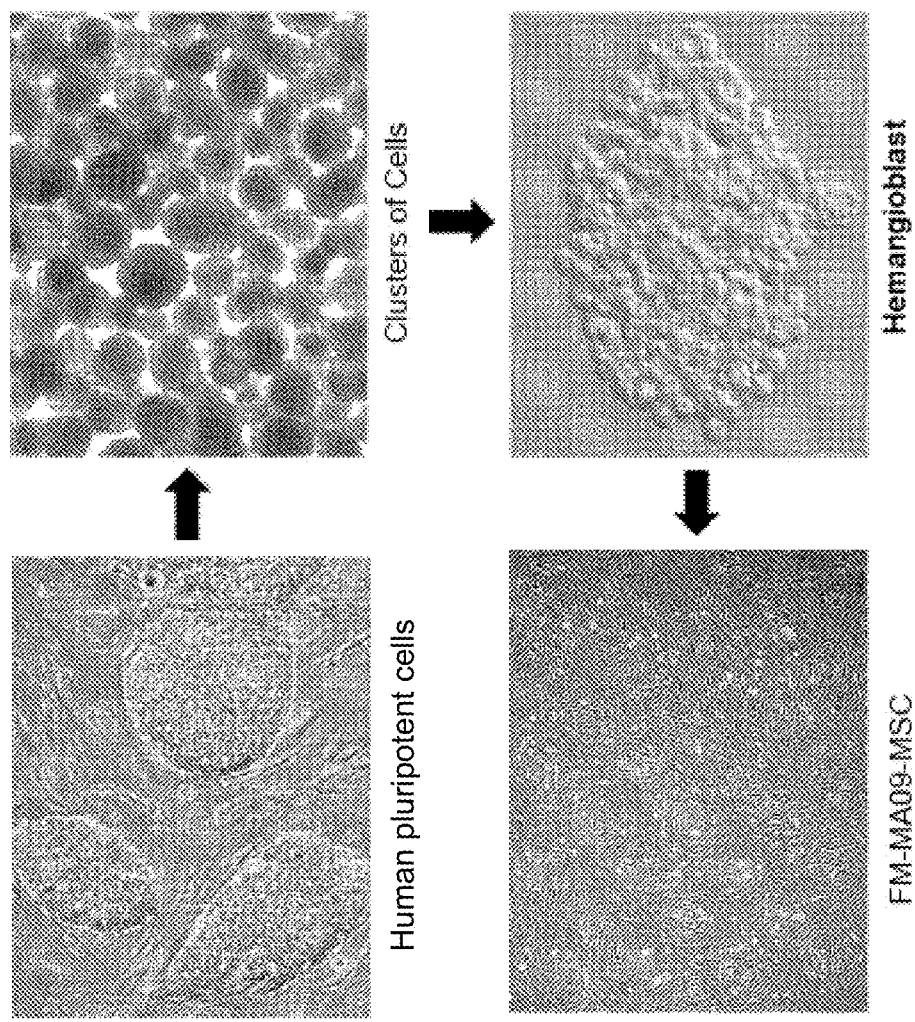
FIG. 1. Generation of the FM-MA09-MSC line from pluripotent cells. This figure shows a microscopic view of generating mesenchymal stromal cells from the MA09 ESC via hemangioblasts.

The instant invention relates to methods of generating mesenchymal stromal cells, preparations of mesenchymal stromal cells from culturing hemangioblasts, methods of culturing hemangioblasts, and methods of treating a pathology using mesenchymal stromal cells.

The methods of the instant invention, whereby hemangioblast cultures produce increased yields of mesenchymal stromal cells, compared to prior processes, are more efficient than previous processes at producing substantially ESC-free mesenchymal stromal cells. The hemangioblast-derived mesenchymal stromal cells of the instant invention retain a novel, youthful phenotype as defined by expression or lack thereof of specific markers.

In certain embodiments, the MSC preparation (such as cultures having at least $10^3$, $10^4$, $10^5$ or even $10^6$ MSCs) may have, as an average, telomere lengths that are at least 30 percent of the telomere length of an ESC and/or human iPS cell (or the average of a population of ESC and/or human iPS cells), and preferably at least 40, 50, 60, 70 80 or even 90 percent of the telomere length of an ESC and/or human iPS cell (or of the average of a population of ESC and/or human iPS cells). For example, said ESC and/or human iPS cell (or said population of ESC and/or human iPS cells) may be a cell or cell population from which said MSC cells were differentiated.

The MSC preparation may, as a population, have a mean terminal restriction fragment length (TRF) that is longer than 4 kb, and preferably longer than 5, 6, 7, 8, 9, 10, 11, 12 or even 13 kb. In an exemplary embodiment, the MSCs of the preparation may have an average TRF that is 10 kb or longer.

In certain embodiments, the MSC preparation (such as cultures having at least $10^3$, $10^4$, $10^5$, $10^6$, $10^7$ or even $10^8$ MSCs) has a replicative lifespan that is greater than the replicative lifespan of MSC preparations obtained from other sources (e.g., cultures derived from donated human tissue, such as fetal, infant, child, adolescent or adult tissue). Replicative lifespan may be assessed by determining the number of population doublings or passages in culture prior to replicative senescence, i.e., where more than 10, 20, 30, 40 or even 50 percent of the cells in culture senesce before the next doubling or passage. For example, the subject MSC preparations may have a replicative lifespan that is at least 10 doublings greater than that of an MSC preparation derived from donated human tissue (particularly derived from adult bone marrow or adult adipose tissue), and preferably at least 20, 30, 40, 50, 60, 70 80, 90 or even 100 population doublings. In certain embodiments, the MSC preparations may have a replicative lifespan that permits at least 8 passages before more than 50 percent of the cells senesce and/or differentiate into non-MSC cell types (such as fibroblasts), and more preferably at least 10, 12, 14, 16, 18 or even 20 passages before reaching that point. In certain embodiments, the MSC preparation may have a replicative lifespan that permits at least 2 times as many doublings or passages relative to adult bone marrow-derived MSC preparations and/or adipose-derived MSC preparations (e.g., equivalent starting number of cells) before more than 50 percent of the cells senesce and/or differentiate into non-MSC cell types (such as fibroblasts), and more preferably at least 4, 6, 8 or even 10 times as many doublings or passages.

In certain embodiments, the MSC preparation of the present invention (such as cultures having at least $10^3$, $10^4$, $10^5$, $10^6$, $10^7$ or even $10^8$ MSCs) have a statistically significant decreased content and/or enzymatic activity of proteins involved in cell cycle regulation and aging relative to passage 1 (P1), passage 2 (P2), passage 3 (P3), passage 4 (P4) and/or passage 5 (P5) MSC preparations derived from other sources (e.g., cultures derived from donated human tissue, such as fetal, infant, child, adolescent or adult tissue), and particularly bone marrow-derived MSCs and adipose-derived MSCs. For example, the subject MSC preparation has a proteasome 26S subunit, non-ATPase regulatory subunit 11 (PSMD11) protein content that is less than 75 percent of the content in MSCs from donated human tissue (particularly derived from adult bone marrow or adult adipose tissue), and even more preferably less than 60, 50, 40, 30, 20 or even 10 percent.

In certain embodiments, the MSC preparation of the present invention (such as cultures having at least $10^3$, $10^4$, $10^5$, $10^6$, $10^7$ or even $10^8$ MSCs) have a statistically significant decreased content and/or enzymatic activity of proteins involved in energy and/or lipid metabolism of the cell relative to passage 1 (P1), passage 2 (P2), passage 3 (P3), passage 4 (P4) and/or passage 5 (P5) MSC preparations derived from other sources (e.g., cultures derived from donated human tissue, such as fetal, infant, child, adolescent or adult tissue), and particularly bone marrow-derived MSCs and adipose-derived MSCs. To illustrate, the subject MSC preparation has a protein content that is less than 90 percent of the content in MSCs from donated human tissue (particularly derived from adult bone marrow or adult adipose tissue), and even more preferably less than 60, 50, 40, 30, 20 or even 10 percent, for one or more proteins involved in metabolic pathways for ATP or NADPH synthesis such as glycolysis (such as fructose-biphosphate aldolase A, ALDOA; aldo-keto reductase family 1, member A1, AKR1A1); glyceraldehyde-3-phosphate, GAPDH), the tricarboxylic acid cycle (TCA cycle) (such as isocitrate dehydrogenase 1, IDH1), the pentose phosphate pathway (such as glucose-6-phosphate dehydrogenase, G6PD) and the biosynthesis of UDP-glucose in the glucuronic acid biosynthetic pathway (such as UDP-glucose 6-dehydrogenase, UGDH). To further illustrate, the subject MSC preparation has a protein content that is less than 90 percent of the content in MSCs from donated human tissue (particularly derived from adult bone marrow or adult adipose tissue), and even more preferably less than 60, 50, 40, 30, 20 or even 10 percent, for one or more proteins involved in lipid metabolism, such as enoyl-CoA hydratase, short chain, 1 (ECHS1) and/or acetyl-CoA acetyltransferase (ACAT2).

In certain embodiments, the MSC preparation of the present invention (such as cultures having at least $10^3$, $10^4$, $10^5$, $10^6$, $10^7$ or even $10^8$ MSCs) have a statistically significant decreased content and/or enzymatic activity of proteins involved in apoptosis of the cell relative to passage 1 (P1), passage 2 (P2), passage 3 (P3), passage 4 (P4) and/or passage 5 (P5) MSC preparations derived from other sources (e.g., cultures derived from donated human tissue, such as fetal, infant, child, adolescent or adult tissue), and particularly bone marrow-derived MSCs and adipose-derived MSCs. To illustrate, the subject MSC preparation has a protein content that is less than 90 percent of the content in MSCs from donated human tissue (particularly derived from adult bone marrow or adult adipose tissue), and even more preferably less than 60, 50, 40, 30, 20 or even 10 percent, for one or more proteins annexin A1 (ANXA1), A2 (ANXA2), A5 (ANXA5), the voltage-dependent anion-selective channel protein 1 (VDAC1), and/or glyceraldehyde-3-phosphate dehydrogenase (GAPDH).

Without being bound by theory, it is believed that the statistically significant difference in content and/or enzymatic activity of proteins involved in energy and/or lipid metabolism and/or apotosis of the cell displayed by the hemangioblast-derived MSCs of the present invention is attributable, at least in part, to the homogeneous nature of the preparations. For example, hemangioblast-derived MSCs of the present invention have homogeneous MHC gene expression, i.e., completely MHC matched, unlike adult derived MSC banks, in which the cells are derived from multiple different donors, i.e., MHC mismatched. A therapeutic dose of MSCs is about 2-8 million cells/kg (or about 130-500 million cells per dose).

DEFINITIONS

"Pluripotent cells" and "pluripotent stem cells" as used herein, refers broadly to a cell capable of prolonged or virtually indefinite proliferation in vitro while retaining their undifferentiated state, exhibiting a stable (preferably normal) karyotype, and having the capacity to differentiate into all three germ layers (i.e., ectoderm, mesoderm and endoderm) under the appropriate conditions. Typically pluripotent cells (a) are capable of inducing teratomas when transplanted in immunodeficient (SCID) mice; (b) are capable of differentiating to cell types of all three germ layers (e.g., ectodermal, mesodermal, and endodermal cell types); and (c) express at least one hES cell marker (such as Oct-4, alkaline phosphatase, SSEA 3 surface antigen, SSEA 4 surface antigen, NANOG, TRA 1 60, TRA 1 81, SOX2, REX1). Exemplary pluripotent cells may express Oct-4, alkaline phosphatase, SSEA 3 surface antigen, SSEA 4 surface antigen, TRA 1 60, and/or TRA 1 81. Additional exemplary pluripotent cells include but are not limited to embryonic stem cells, induced pluripotent cells (iPS) cells, embryo-derived cells, pluripotent cells produced from embryonic germ (EG) cells (e.g., by culturing in the presence of FGF-2, LIF and SCF), parthenogenetic ES cells, ES cells produced from cultured inner cell mass cells (ICM), ES cells produced from a blastomere, and ES cells produced by nuclear transfer (e.g., a somatic cell nucleus transferred into a recipient oocyte). Exemplary pluripotent cells may be produced without destruction of an embryo. For example, induced pluripotent cells may be produced from cells obtained without embryo destruction. As a further example, pluripotent cells may be produced from a biopsied blastomere (which can be accomplished without harm to the remaining embryo); optionally, the remaining embryo may be cryopreserved, cultured, and/or implanted into a suitable host. Pluripotent cells (from whatever source) may be genetically modified or otherwise modified to increase longevity, potency, homing, or to deliver a desired factor in cells that are differentiated from such pluripotent cells (for example, MSCs, and hemangioblasts). As non-limiting examples thereof, the pluripotent cells may be genetically modified to express Sirt1 (thereby increasing longevity), express one or more telomerase subunit genes optionally under the control of an inducible or repressible promoter, incorporate a fluorescent label, incorporate iron oxide particles or other such reagent (which could be used for cell tracking via in vivo imaging, MRI, etc., see Thu et al., Nat Med. 2012 Feb. 26; 18(3):463-7), express bFGF which may improve longevity (see Go et al., J. Biochem. 142, 741-748 (2007)), express CXCR4 for homing (see Shi et al., Haematologica. 2007 July; 92(7):897-904), express recombinant TRAIL to induce caspase-mediated apoptosis in cancer cells like Gliomas (see Sasportas et al., Proc Natl Acad Sci USA. 2009 Mar. 24; 106(12):4822-7), etc.

"Embryo" or "embryonic," as used herein refers broadly to a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

"Embryonic stem cells" (ES cells or ESC) encompasses pluripotent cells produced from embryonic cells (such as from cultured inner cell mass cells or cultured blastomeres) as well as induced pluripotent cells (further described below). Frequently such cells are or have been serially passaged as cell lines. Embryonic stem cells may be used as a pluripotent stem cell in the processes of producing hemangioblasts as described herein. For example, ES cells may be produced by methods known in the art including derivation from an embryo produced by any method (including by sexual or asexual means) such as fertilization of an egg cell with sperm or sperm DNA, nuclear transfer (including somatic cell nuclear transfer), or parthenogenesis. As a further example, embryonic stem cells also include cells produced by somatic cell nuclear transfer, even when non-embryonic cells are used in the process. For example, ES cells may be derived from the ICM of blastocyst stage embryos, as well as embryonic stem cells derived from one or more blastomeres. Such embryonic stem cells can be generated from embryonic material produced by fertilization or by asexual means, including somatic cell nuclear transfer (SCNT), parthenogenesis, and androgenesis. As further discussed above (see "pluripotent cells), ES cells may be genetically modified or otherwise modified to increase longevity, potency, homing, or to deliver a desired factor in cells that are differentiated from such pluripotent cells (for example, MSCs, and hemangioblasts).

ES cells may be generated with homozygosity or hemizygosity in one or more HLA genes, e.g., through genetic manipulation, screening for spontaneous loss of heterozygosity, etc. ES cells may be genetically modified or otherwise modified to increase longevity, potency, homing, or to deliver a desired factor in cells that are differentiated from such pluripotent cells (for example, MSCs and hemangioblasts). Embryonic stem cells, regardless of their source or the particular method used to produce them, typically possess one or more of the following attributes: (i) the ability to differentiate into cells of all three germ layers, (ii) expression of at least Oct-4 and alkaline phosphatase, and (iii) the ability to produce teratomas when transplanted into immunocompromised animals. Embryonic stem cells that may be used in embodiments of the present invention include, but are not limited to, human ES cells ("hESC" or "hES cells") such as CT2, MA01, MA09, ACT-4, No. 3, H1, H7, H9, H14 and ACT30 embryonic stem cells. Additional exemplary cell lines include NED1, NED2, NED3, NED4, NED5, and NED7. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." Nature 444: 481-485. The human ES cells used in accordance with exemplary embodiments of the present invention may be derived and maintained in accordance with GMP standards.

Exemplary hES cell markers include but are not limited to: alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand). Additionally, embryonic stem cells may express Oct-4, alkaline phosphatase, SSEA 3 surface antigen, SSEA 4 surface antigen, TRA 1 60, and/or TRA 1 81.

The ESCs may be initially co-cultivated with murine embryonic feeder cells (MEF) cells. The MEF cells may be mitotically inactivated by exposure to mitomycin C prior to seeding ESCs in co culture, and thus the MEFs do not propagate in culture. Additionally, ESC cell cultures may be examined microscopically and colonies containing non ESC cell morphology may be picked and discarded, e.g., using a stem cell cutting tool, by laser ablation, or other means. Typically, after the point of harvest of the ESCs for seeding for embryoid body formation no additional MEF cells are used.

"Embryo-derived cells" (EDC), as used herein, refers broadly to pluripotent morula-derived cells, blastocyst-derived cells including those of the inner cell mass, embryonic shield, or epiblast, or other pluripotent stem cells of the early embryo, including primitive endoderm, ectoderm, and mesoderm and their derivatives. "EDC" also including blastomeres and cell masses from aggregated single blastomeres or embryos from varying stages of development, but excludes human embryonic stem cells that have been passaged as cell lines.

Exemplary ESC cell markers include but are not limited to: alkaline phosphatase, Oct-4, Nanog, Stage-specific embryonic antigen-3 (SSEA-3), Stage-specific embryonic antigen-4 (SSEA-4), TRA-1-60, TRA-1-81, TRA-2-49/6E, Sox2, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (hTERT), SALL4, E-CADHERIN, Cluster designation 30 (CD30), Cripto (TDGF-1), GCTM-2, Genesis, Germ cell nuclear factor, and Stem cell factor (SCF or c-Kit ligand).

"Potency", as used herein, refers broadly to the concentration, e.g., molar, of a reagent (such as hemangioblast-derived MSCs) that produces a defined effect. Potency may be defined in terms of effective concentration (EC50), which does not involve measurements of maximal effect but, instead, the effect at various locations along the concentration axis of dose response curves. Potency may also be determined from either graded (EC50) or quantal dose-response curves (ED50, TD50 and LD50); however, potency is preferably measured by EC50. The term "EC50" refers to the concentration of a drug, antibody or toxicant which induces a response halfway between the baseline and maximum effect after some specified exposure time. The EC50 of a graded dose response curve therefore represents the concentration of a compound where 50% of its maximal effect is observed. The EC50 of a quantal dose response curve represents the concentration of a compound where 50% of the population exhibit a response, after a specified exposure duration. The EC50 may be determined using animal studies in which a defined animal model demonstrates a measurable, physiological change in response to application of the drug; cell-based assays that use a specified cell system, which on addition of the drug, demonstrate a measureable biological response; and/or enzymatic reactions where the biological activity of the drug can be measured by the accumulation of product following the chemical reaction facilitated by the drug. Preferably, an immune regulatory assay is used to determine EC50. Non-limiting examples of such immune regulatory assays include intracellular cytokine, cytotoxicity, regulatory capacity, cell signaling capacity, proliferative capacity, apoptotic evaluations, and other assays.

"Mesenchymal stem cells" (MSC) as used herein refers to multipotent stem cells with self-renewal capacity and the ability to differentiate into osteoblasts, chondrocytes, and adipocytes, among other mesenchymal cell lineages. In addition to these characteristics, MSCs may be identified by the expression of one or more markers as further described herein. Such cells may be used to treat a range of clinical conditions, including immunological disorders as well as degenerative diseases such as graft-versus-host disease (GVHD), myocardial infarction and inflammatory and autoimmune diseases and disorders, among others. Except where the context indicates otherwise, MSCs may include cells from adult sources and cord blood. MSCs (or a cell from which they are generated, such as a pluripotent cell) may be genetically modified or otherwise modified to increase longevity, potency, homing, or to deliver a desired factor in the MSCs or cells that are differentiated from such MSCs. As non-limiting examples thereof, the MSCs cells may be genetically modified to express Sirt1 (thereby increasing longevity), express one or more telomerase subunit genes optionally under the control of an inducible or repressible promoter, incorporate a fluorescent label, incorporate iron oxide particles or other such reagent (which could be used for cell tracking via in vivo imaging, MRI, etc., see Thu et al., Nat Med. 2012 Feb. 26; 18(3):463-7), express bFGF which may improve longevity (see Go et al., J. Biochem. 142, 741-748 (2007)), express CXCR4 for homing (see Shi et al., Haematologica. 2007 July; 92(7):897-904), express recombinant TRAIL to induce caspase-mediatedx apoptosis in cancer cells like Gliomas (see Sasportas et al., Proc Natl Acad Sci USA. 2009 Mar. 24; 106(12):4822-7), etc.

"Therapy," "therapeutic," "treating," "treat" or "treatment", as used herein, refers broadly to treating a disease, arresting or reducing the development of the disease or its clinical symptoms, and/or relieving the disease, causing regression of the disease or its clinical symptoms. "Therapy", "therapeutic," "treating," "treat" or "treatment" encompasses prophylaxis, prevention, treatment, cure, remedy, reduction, alleviation, and/or providing relief from a disease, signs, and/or symptoms of a disease. "Therapy", "therapeutic," "treating," "treat" or "treatment" encompasses an alleviation of signs and/or symptoms in patients with ongoing disease signs and/or symptoms (e.g., muscle weakness, multiple sclerosis.) "Therapy", "therapeutic," "treating," "treat" or "treatment" also encompasses "prophylaxis" and "prevention". Prophylaxis includes preventing disease occurring subsequent to treatment of a disease in a patient or reducing the incidence or severity of the disease in a patient. The term "reduced", for purpose of therapy, "therapeutic," "treating," "treat" or "treatment" refers broadly to the clinical significant reduction in signs and/or symptoms. "Therapy", "therapeutic," "treating," "treat" or "treatment" includes treating relapses or recurrent signs and/or symptoms (e.g., retinal degeneration, loss of vision.) "Therapy", "therapeutic," "treating," "treat" or "treatment" encompasses but is not limited to precluding the appearance of signs and/or symptoms anytime as well as reducing existing signs and/or symptoms and eliminating existing signs and/or symptoms. "Therapy", "therapeutic," "treating," "treat" or "treatment" includes treating chronic disease ("maintenance") and acute disease. For example, treatment includes treating or preventing relapses or the recurrence of signs and/or symptoms (e.g., muscle weakness, multiple sclerosis).

"Normalizing a pathology", as used herein, refers to reverting the abnormal structure and/or function resulting from a disease to a more normal state. Normalization suggests that by correcting the abnormalities in structure and/or function of a tissue, organ, cell type, etc. resulting from a disease, the progression of the pathology can be controlled and improved. For example, following treatment with the ESC-MSCs of the present invention the abnormalities of the immune system as a result of autoimmune disorders, e.g., MS, may be improved, corrected, and/or reversed.

Induced Pluripotent Stem Cells

Further exemplary pluripotent stem cells include induced pluripotent stem cells (iPS cells) generated by reprogramming a somatic cell by expressing or inducing expression of a combination of factors ("reprogramming factors"). iPS cells may be generated using fetal, postnatal, newborn, juvenile, or adult somatic cells. iPS cells may be obtained from a cell bank. Alternatively, iPS cells may be newly generated (by processes known in the art) prior to commencing differentiation to RPE cells or another cell type. The making of iPS cells may be an initial step in the production of differentiated cells. iPS cells may be specifically generated using material from a particular patient or matched donor with the goal of generating tissue-matched RPE cells. iPS cells can be produced from cells that are not substantially immunogenic in an intended recipient, e.g., produced from autologous cells or from cells histocompatible to an intended recipient. As further discussed above (see "pluripotent cells"), pluripotent cells including iPS cells may be genetically modified or otherwise modified to increase longevity, potency, homing, or to deliver a desired factor in cells that are differentiated from such pluripotent cells (for example, MSCs and hemangioblasts).

As a further example, induced pluripotent stem cells may be generated by reprogramming a somatic or other cell by contacting the cell with one or more reprogramming factors. For example, the reprogramming factor(s) may be expressed by the cell, e.g., from an exogenous nucleic acid added to the cell, or from an endogenous gene in response to a factor such as a small molecule, microRNA, or the like that promotes or induces expression of that gene (see Suh and Blelloch, Development 138, 1653-1661 (2011); Miyoshi et al., Cell Stem Cell (2011), doi:10.1016/j.stem.2011.05.001; Sancho-Martinez et al., Journal of Molecular Cell Biology (2011) 1-3; Anokye-Danso et al., Cell Stem Cell 8, 376-388, Apr. 8, 2011; Orkin and Hochedlinger, Cell 145, 835-850, Jun. 10, 2011, each of which is incorporated by reference herein in its entirety). Reprogramming factors may be provided from an exogenous source, e.g., by being added to the culture media, and may be introduced into cells by methods known in the art such as through coupling to cell entry peptides, protein or nucleic acid transfection agents, lipofection, electroporation, biolistic particle delivery system (gene gun), microinjection, and the like. iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct-4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell. iPS cells typically can be identified by expression of the same markers as embryonic stem cells, though a particular iPS cell line may vary in its expression profile.

The induced pluripotent stem cell may be produced by expressing or inducing the expression of one or more reprogramming factors in a somatic cell. The somatic cell is a fibroblast, such as a dermal fibroblast, synovial fibroblast, or lung fibroblast, or a non-fibroblastic somatic cell. The somatic cell is reprogrammed by expressing at least 1, 2, 3, 4, 5 reprogramming factors. The reprogramming factors may be selected from Oct 3/4, Sox2, NANOG, Lin28, c Myc, and Klf4. Expression of the reprogramming factors may be induced by contacting the somatic cells with at least one agent, such as a small organic molecule agents, that induce expression of reprogramming factors.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. See, e.g., Yu et al., Science. 2009 May 8; 324 (5928):797-801, which is hereby incorporated by reference in its entirety. When reprogramming factors are expressed using non-integrative vectors, the factors may be expressed in the cells using electroporation, transfection, or transformation of the somatic cells with the vectors. For example, in mouse cells, expression of four factors (Oct3/4, Sox2, c myc, and Klf4) using integrative viral vectors can be used to reprogram a somatic cell. In human cells, expression of four factors (Oct3/4, Sox2, NANOG, and Lin28) using integrative viral vectors can be used to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells. iPS cells typically can be identified by expression of the same markers as other embryonic stem cells, though a particular iPS cell line may vary in its expression profile. Exemplary iPS cells may express Oct-4, alkaline phosphatase, SSEA 3 surface antigen, SSEA 4 surface antigen, TRA 1 60, and/or TRA 1 81.

To confirm the pluripotency of the iPS cells, the cells may be tested in one or more assays of pluripotency. For example, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPS cell is obtained it may be used to produce hemangioblast and MSC cells.

Hemangioblasts

Hemangioblasts are multipotent and serve as the common precursor to both hematopoietic and endothelial cell lineages. During embryonic development, they are believed to arise as a transitional cell type that emerges during early mesoderm development and colonizes primitive blood islands (Choi et al. Development 125 (4): 725-732 (1998). Once there, hemangioblasts are capable of giving rise to both primitive and definitive hematopoietic cells, HSCs, and endothelial cells (Mikkola et al, J. Hematother. Stem Cell Res 11(1): 9-17 (2002).

Hemangioblasts may be derived in vitro from both mouse ESCs (Kennedy et al, Nature (386): 488-493 (1997); Perlingeiro et al, Stem Cells (21): 272-280 (2003)) and human ESCs (ref. 14, 15, Yu et al., Blood 2010 116: 4786-4794). Other studies claim to have isolated hemangioblasts from umbilical cord blood (Bordoni et al, Hepatology 45 (5) 1218-1228), circulating CD34-lin-CD45-CD133-cells from peripheral blood (Ciraci et al, Blood 118: 2105-2115), and from mouse uterus (Sun et al, Blood 116 (16): 2932-2941 (2010)). Both mouse and human ESC-derived hemangioblasts have been obtained through the culture and differentiation of clusters of cells grown in liquid culture followed by growth of the cells in semi-solid medium containing various cytokines and growth factors (Kennedy, Perlingeiro, ref 14, 15); see also, U.S. Pat. No. 8,017,393, which is hereby incorporated by reference in its entirety. For the purposes of this application, the term hemangioblasts also includes the hemangio-colony forming cells described in U.S. Pat. No. 8,017,393, which in addition to being capable of differentiating into hematopoietic and endothelial cell lineages, are capable of becoming smooth muscle cells and which are not positive for CD34, CD31, KDR, and CD133. Hemangioblasts useful in the methods described herein may be derived or obtained from any of these known methods. For example, embryoid bodies may be formed by culturing pluripotent cells under non-attached conditions, e.g., on a low-adherent substrate or in a "hanging drop." In these cultures, ES cells can form clumps or clusters of cells denominated as embryoid bodies. See Itskovitz-Eldor et al., Mol Med. 2000 February; 6(2):88-95, which is hereby incorporated by reference in its entirety. Typically, embryoid bodies initially form as solid clumps or clusters of pluripotent cells, and over time some of the embryoid bodies come to include fluid filled cavities, the latter former being referred to in the literature as "simple" EBs and the latter as "cystic" embryoid bodies. Id. The cells in these EBs (both solid and cystic forms) can differentiate and over time produce increasing numbers of cells. Optionally EBs may then be cultured as adherent cultures and allowed to form outgrowths. Likewise, pluripotent cells that are allowed to overgrow and form a multilayer cell population can differentiate over time.

In one embodiment, hemangioblasts are generated by the steps comprising (a) culturing an ESC line for 2, 3, 4, 5, 6 or 7 days to form clusters of cells, and (b) inducing said clusters of cells to differentiate into hemangioblasts. In a further embodiment, the clusters of cells in step (b) of are cultured in a cytokine-rich serum-free methylcellulose based medium (14, 15).

In one embodiment, hemangioblasts are generated by the steps comprising (a) culturing an ESC line selected from the group consisting of CT2, MA09, H7, H9, MA01, HuES3, H1gfp, NED1, NED2, NED3, NED4, NED5, and NED7 for 2, 3, 4, 5, 6 or 7 days to form clusters of cells, and (b) inducing said clusters of cells to differentiate into hemangioblasts by culturing in a cytokine-rich, serum-free, methylcellulose based medium.

In another embodiment, hemangioblasts are generated by inducing any pluripotent cell as described herein. In a further embodiment, hemangioblasts are generated by inducing differentiation of a pluripotent cell selected from the group comprising blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means, and ESC derived through reprogramming (e.g., iPS cells). In a still further embodiment, hemangioblasts are generated from iPS cells, wherein the iPS cells are generated using exogenously added factors or other methods known in the art such as proteins or microRNA (see Zhou et al., Cell Stem Cell (4): 1-4, 2009; Miyoshi et al. Cell Stem Cell (8): 1-6, 2011; Danso et al., Cell Stem Cell (8): 376-388, 2011).

In another aspect, the disclosure provides preparations of mesenchymal stromal cells (MSCs) and methods of generating MSCs using hemangioblasts. The MSC may differ from pre-existing MSC in one or more aspects, as further described herein. In one embodiment, hemangioblasts are harvested after at least 6, 7, 8, 9, 10, 11, 12, 13, 14, 15, 16, 17, 18, 19, or 20 days in culture using a serum free methylcellulose medium plus one or more ingredients selected from the group comprising penicillin/streptomycin (pen/strp), EX-CYTE® growth supplement (a water-soluble concentrate comprising 9.0-11.0 g/L cholesterol and 13.0-18.0 g/L lipoproteins and fatty acids at pH 7-8.4), Flt3-ligand (FL), vascular endothelial growth factor (VEGF), thrombopoietin (TPO), basic fibroblast growth factor (bFGF), stem cell derived factor (SCF), granulocyte macrophage colony stimulating factor (GM-CSF), interleukin 3 (IL3), and interleukin 6 (IL6), by inducing a pluripotent cell selected from the group comprising blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means, and cells derived through reprogramming (iPS cells). In a preferred embodiment of the instant invention, hemangioblasts are harvested between 6-14 days, of being cultured in, for example, serum-free methylcellulose plus the ingredients of the previous embodiment. In a preferred embodiment, the ingredients are present in said medium at the following concentrations: Flt3-ligand (FL) at 50 ng/ml, vascular endothelial growth factor (VEGF) at 50 ng/ml, thrombopoietin (TPO) at 50 ng/ml, and basic fibroblast growth factor (bFGF) at 20 ng/ml, 50 ng/ml stem cell derived factor (SCF), 20 ng/ml granulocyte macrophage colony stimulating factor (GM-CSF), 20 ng/ml interleukin 3 (IL3), 20 ng/ml interleukin 6 (IL6), 50 ng/ml FL, 50 ng/ml VEGF, 50 ng/ml TPO, and 30 ng/ml bFGF.

In another embodiment, a cluster of cells comprised substantially of hemangioblasts are re-plated and cultured for at least 8, 9, 10, 11, 12, 13, 14, 15, 16, 17, 18, 19, 20, 21, 22, 23, 24, 25, 26, 27, 28, 29, 30, 31, 32, 33, 34, 35, or 36 days forming a preparation of mesenchymal stromal cells. In one embodiment, mesenchymal stromal cells are generated by the steps comprising (a) culturing ESCs for 8-12 days, (b) harvesting hemangioblasts that form clusters of cells, (c) re-plating the hemangioblasts of step (b), and (d) culturing the hemangioblasts of step (c) for between 14-30 days.

In one embodiment, the hemangioblasts are harvested, re-plated and cultured in liquid medium under feeder-free conditions wherein no feeder layer of cells such as mouse embryonic fibroblasts, OP9 cells, or other cell types known to one of ordinary skill in the art are contained in the culture. In a preferred embodiment, hemangioblasts are cultured on an extracellular matrix. In a further preferred embodiment, hemangioblasts are cultured on an extracellular matrix, wherein said matrix comprises a soluble preparation from Engelbreth-Holm-Swarm (EHS) mouse sarcoma cells that gels at room temperature to form a reconstituted basement membrane (Matrigel). In a still further preferred embodiment, hemangioblasts are generated according to the steps comprising (a) culturing said hemangioblasts on Matrigel for at least 7 days, (b) transferring the hemangioblasts of step (a) to non-coated tissue culture plate and further culturing said hemangioblasts of step (b) for between about 7 to 14 days). The hemangioblasts may be cultured on a substrate comprising one or more of the factors selected from the group consisting of: transforming growth factor beta (TGF-beta), epidermal growth factor (EGF), insulin-like growth factor 1, bovine fibroblast growth factor (bFGF), and/or platelet-derived growth factor (PDGF), Human Basement Membrane Extract (BME) (e.g., Cultrex BME, Trevigen) or an EHS matrix, laminin, fibronectin, vitronectin, proteoglycan, entactin, collagen (e.g., collagen I, collagen IV), and heparan sulfate. Said matrix or matrix components may be of mammalian, or more specifically human, origin. In one embodiment, hemangioblasts are cultured in a liquid medium comprising serum on a Matrigel-coated plate, wherein the culture medium may comprise ingredients selected from αMEM (Sigma-Aldrich) supplemented with 10-20% fetal calf serum (αMEM+20% FCS), αMEM supplemented with 10-20% heat-inactivated human AB serum, and IMDM supplemented with 10-20% heat inactivated AB human serum.

Mesenchymal Stromal Cells Generated by Culturing Hemangioblasts

An embodiment of the instant invention comprises improved mesenchymal stromal cells. The mesenchymal stromal cells of the instant invention may be generated from hemangioblasts using improved processes of culturing hemangioblasts.

Mesenchymal stromal cells of the instant invention may retain higher levels of potency and may not clump or may clump substantially less than mesenchymal stromal cells derived directly from ESCs. In an embodiment of the instant invention, a preparation of mesenchymal stromal cells generated according to any one or more of the processes of the instant invention retains higher levels of potency, and do not clump or clump substantially less than mesenchymal stromal cells derived directly from ESCs.

An embodiment of the instant invention provides a process of culturing hemangioblasts that generate preparations of mesenchymal stromal cells, wherein said mesenchymal stromal cells retain a youthful phenotype. The pharmaceutical preparations of mesenchymal stromal cells of the instant invention may demonstrate improved therapeutic properties when administered to a mammalian host in need of treatment.

An embodiment of the instant invention provides a preparation of mesenchymal stromal cells generated by culturing human hemangioblasts. A further embodiment of the instant invention provides a process for generating a preparation of mesenchymal stromal cells by culturing human hemangioblasts. In an embodiment of a process of the instant invention, said human hemangioblasts are cultured in feeder-free conditions then plated on a matrix. In a still further embodiment of the instant invention, said matrix is selected from the group comprising transforming growth factor beta (TGF-beta), epidermal growth factor (EGF), insulin-like growth factor 1, bovine fibroblast growth factor (bFGF), platelet-derived growth factor (PDGF), laminin, fibronectin, vitronectin, proteoglycan, entactin, collagen, collagen I, collagen IV, heparan sulfate, a soluble preparation from Engelbreth-Holm-Swarm (EHS) mouse sarcoma cells, Matrigel, and a human basement membrane extract. In a still further embodiment, said matrix may derive from mammalian or human origin.

In another embodiment, hemangioblasts are cultured in a medium comprising serum or a serum replacement, such as αMEM supplemented with 20% fetal calf serum. In a further embodiment, hemangioblasts are cultured on a matrix for about 9, 10, 11, 12, 13, 14, 15, 16, 17, 18, 19, 20, 21, 22, 23, 24, 25, 26, 27, 28, 29 or 30 days. In a still further embodiment of the instant invention, a preparation of mesenchymal stromal cells is generated by the steps comprising (a) culturing hemangioblasts on Matrigel for about 7 days, (b) transferring the hemangioblasts of step (a) off Matrigel and growing the hemangioblasts on an uncoated tissue culture dish for an additional 9-100 days, about 9, 10, 11, 12, 13, 14, 15, 16, 17, 18, 19, 20, 21, 22, 23, 24, 25, 30, 35, 40, 50, 60, 70, 80, 90 or 100 days.

In an embodiment of the instant invention, a preparation of mesenchymal stromal cells is generated by culturing hemangioblasts in a medium comprising serum or a serum replacement such as α-MEM supplemented with 20% fetal calf serum. In further embodiment of the instant invention, said hemangioblasts are cultured on a matrix for about 9, 10, 11, 12, 13, 14, 15, 16, 17, 18, 19, 20, 21, 22, 23, 24, 25, 26, 27, 28, 29, or 30 days.

In an embodiment of the instant invention hemangioblasts are differentiated from ESCs. In a further embodiment of the instant invention, the hemangioblasts of the previous embodiment are differentiated from ESCs wherein, said ESCs are selected from the group comprising iPS, MA09, H7, H9, MA01, HuES3, H1gfp, NED1, NED2, NED3, NED4, NED5, NED7, inner cell mass cells and blastomere-derived ESCs.

An embodiment of the instant invention comprises a preparation of mesenchymal stromal cells generated by a process wherein hemangioblasts are differentiated from ESCs. In a further embodiment of the instant invention, the hemangioblasts of the previous embodiment are differentiated from ESCs wherein, said ESCs are selected from the group comprising iPS, MA09, H7, H9, MA01, HuES3, H1gfp, inner cell mass cells and blastomere-derived ESCs.

In an embodiment of the instant invention, hemangioblasts are differentiated from ESCs by following the steps comprising: (a) culturing ESCs in the presence of vascular endothelial growth factor (VEGF) and/or bone morphogenic protein 4 (BMP-4) (by way of non-limiting examples) to form clusters of cells; (b) culturing said clusters of cells in the presence of at least one growth factor (e.g., basic fibroblast growth factor (bFGF), vascular endothelial growth factor (VEGF), bone morphogenic protein 4 (BMP-4), stem cell factor (SCF), Flt 3L (FL), thrombopoietin (TPO), and/or tPTD-HOXB4) in an amount sufficient to induce the differentiation of said clusters of cells into hemangioblasts; and (c) culturing said hemangioblasts in a medium comprising at least one additional growth factor (e.g., insulin, transferrin, granulocyte macrophage colony-stimulating factor (GM-CSF), interleukin-3 (IL-3), interleukin-6 (IL-6), granulocyte colony-stimulating factor (G-CSF), erythropoietin (EPO), stem cell factor (SCF), vascular endothelial growth factor (VEGF), bone morphogenic protein 4 (BMP-4), and/or tPTD-HOXB4), wherein said at least one additional growth factor is provided in an amount sufficient to expand said clusters of cells in said culture, and wherein copper is optionally added to any of the steps (a)-(c).

In an embodiment of the instant invention, a preparation of mesenchymal stromal cells is generated by culturing hemangioblasts, wherein said hemangioblasts are differentiated from ESCs by following the steps comprising: (a) culturing ESCs in the presence of vascular endothelial growth factor (VEGF) and bone morphogenic protein 4 (BMP-4) within 0-48 hours of initiation of said culture to form clusters of cells; (b) culturing said clusters of cells in the presence of at least one growth factor selected from the group comprising basic fibroblast growth factor (bFGF), vascular endothelial growth factor (VEGF), bone morphogenic protein 4 (BMP-4), stem cell factor (SCF), Flt 3L (FL), thrombopoietin (TPO), and tPTD-HOXB4 in an amount sufficient to induce the differentiation of said clusters of cells into hemangioblasts; and (c) culturing said hemangioblasts in a medium comprising at least one additional growth factor selected from the group comprising insulin, transferrin, granulocyte macrophage colony-stimulating factor (GM-CSF), interleukin-3 (IL-3), interleukin-6 (IL-6), granulocyte colony-stimulating factor (G-CSF), erythropoietin (EPO), stem cell factor (SCF), vascular endothelial growth factor (VEGF), bone morphogenic protein 4 (BMP-4), and tPTD-HOXB4, wherein said at least one additional growth factor is provided in an amount sufficient to expand human clusters of cells in said culture.

In another embodiment, a preparation of mesenchymal stem cells is generated by the steps comprising: (a) harvesting hemangioblasts after at least 6, 7, 8, 9, 10, 11, 12, 13, or 14 days of inducing ESCs to differentiate into said hemangioblasts, and (b) harvesting mesenchymal stromal cells that are generated within about 25, 26, 27, 28, 29, 30, 31, 32, 33, 34, 35, 36, 37, 38, 39, 40, 41, 42, 43, 44, 45, 46, 47, 48, 49 or 50 days of inducing said hemangioblasts from step (a) to differentiate into said mesenchymal cells.

In yet another embodiment, a preparation of at least 80, 85, 90, 95, 100, 125 or 125 million mesenchymal stromal cells are generated from about 200,000 hemangioblasts within about 26, 27, 28, 29, 30, 31, 32, 33, 34, or 35 days of culturing the hemangioblasts, wherein said preparation of mesenchymal stromal cells comprises less than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% human embryonic stem cells. In still another embodiment, at least 80, 85, 90, 100, 125 or 150 million mesenchymal stromal cells are generated from about 200,000 hemangioblasts within about 26, 27, 28, 29, 30, 31, 32, 33, 34, or days of culturing the hemangioblasts.

In an embodiment of a process of the instant invention, a preparation of mesenchymal stromal cells are substantially purified with respect to human embryonic stem cells. In a further embodiment of a process of the instant invention, a preparation of mesenchymal stromal cells are substantially purified with respect to human embryonic stem cells such that said preparation comprises at least about 90%, 91%, 92%, 93%, 94%, 95%, 96%, 97%, 98%, 99%, or 100% mesenchymal stromal cells.

In another embodiment of the instant invention, a preparation of mesenchymal stromal cells generated by any one or more of the processes of the instant invention does not form a teratoma when introduced into a host.

In another embodiment of the instant invention, at least 50% of a preparation of mesenchymal stromal cells are positive for CD105 or CD73 within about 7-20 (e.g., 15) days of culture. In a preferred embodiment of the instant invention, at least 50% of a preparation of mesenchymal stromal cells generated according to any one or more processes of the instant invention are positive for CD105 or CD73 after about 7-15 days of culture. In a further embodiment of the instant invention, at least 80% of a preparation of mesenchymal stromal cells are positive for CD105 and CD73 within about 20 days of culture. In still a further embodiment of the instant invention, at least 80% of a preparation of mesenchymal stromal cells generated according to any one or more of the processes of the instant invention are positive for CD105 and CD73 within about 20 days of culture.

In an exemplary aspect, the present disclosure provides a pharmaceutical preparation suitable for use in a mammalian patient, comprising at least $10^6$ mesenchymal stromal cells and a pharmaceutically acceptable carrier, wherein the mesenchymal stromal cells have replicative capacity to undergo at least 10 population doublings in cell culture with less than 25 percent of the cells undergoing cell death, senescing or differentiating into non-MSC cells by the tenth doubling.

In order maintain regulatory compliance, MSC banks must maintain a sufficient supply of cells, e.g., to provide a sufficient number of cells to treat at least a few hundred to 10,000 patients, MSC banks must have at least 50 billion MSCs. The present invention encompasses GMP-complaint and/or cryopreserved MSC banks. In one aspect, the MSC preparation of the present invention comprise at least $10^{10}$ MSCs such as hemangioblast-derived MSCs. In another aspect, the present invention provides a MSC preparation comprising at least $10^{11}$, $10^{12}$, $10^{13}$, or $10^{14}$ MSCs such as hemangioblast-derived MSCs.

MSC of the present disclosure, including disclosed compositions, methods, uses, etc., can be derived from a renewable stem source; can be derived from hemgioblast intermediates; and/or may have one or more characteristics of the MSC described herein, such as: have, as an average, telomere lengths that are at least 30 percent of the telomere length of an ESC and/or human iPS cell; preparation may, as a population, have a mean terminal restriction fragment length (TRF) that is longer than 4 kb; has a replicative lifespan that is greater than the replicative lifespan of MSC preparations obtained from other sources (e.g., cultures derived from donated human tissue, such as fetal, infant, child, adolescent or adult tissue); have a statistically significant decreased content and/or enzymatic activity of proteins involved in cell cycle regulation and aging relative to passage 1 (P1), passage 2 (P2), passage 3 (P3), passage 4 (P4) and/or passage 5 (P5) MSC preparations derived from other sources; have a statistically significant decreased content and/or enzymatic activity of proteins involved in energy and/or lipid metabolism of the cell relative to passage 1 (P1), passage 2 (P2), passage 3 (P3), passage 4 (P4) and/or passage 5 (P5) MSC preparations derived from other sources; have a statistically significant decreased content and/or enzymatic activity of proteins involved in apoptosis of the cell relative to passage 1 (P1), passage 2 (P2), passage 3 (P3), passage 4 (P4) and/or passage 5 (P5) MSC preparations derived from other sources; and the MSCs present in the therapeutic dose (and bank from which it is drawn) are a homogeneous population with respect to which MHC genes/alleles are expressed (i.e., are MHC matched within the dose of cells).

In an exemplary aspect, the present disclosure provides a pharmaceutical preparation suitable for use in a mammalian patient comprising at least $10^6$ mesenchymal stromal cells and a pharmaceutically acceptable carrier, wherein the mesenchymal stromal cells have replicative capacity to undergo at least 5 passages in cell culture with less than 25 percent of the cells undergoing cell death, senescing or differentiating into fibroblasts by the $5^{th}$ passage.

In an exemplary aspect, the present disclosure provides a pharmaceutical preparation comprising at least $10^6$ mesenchymal stromal cells and a pharmaceutically acceptable carrier, wherein the mesenchymal stromal cells are differentiated from hemangioblasts.

In an exemplary aspect, the present disclosure provides a cryogenic cell bank comprising at least $10^8$ mesenchymal stromal cells, wherein the mesenchymal stromal cells have replicative capacity to undergo at least 10 population doublings in cell culture with less than 25 percent of the cells undergoing cell death, senescing or differentiating into fibroblasts by the tenth population doubling.

In an exemplary aspect, the present disclosure provides a purified cellular preparation comprising at least $10^6$ mesenchymal stromal cells and less than one percent of any other cell type, wherein the mesenchymal stromal cells have replicative capacity to undergo at least 10 population doublings in cell culture with less than 25 percent of the cells undergoing cell death, senescing or differentiating into non-MSC cells by the tenth population doubling.

The mesenchymal stromal cells may be differentiated from a pluripotent stem cell source, such as an embryonic stem cell line or induced pluripotent stem cell line. For example, all of the mesenchymal stromal cells of the preparation or bank may be differentiated from a common pluripotent stem cell source. Additionally, the mesenchymal stromal cells may be differentiated from a pluripotent stem cell source, passaged in culture to expand the number of mesenchymal stromal cells, and isolated from culture after less than twenty population doublings.

The mesenchymal stromal cells may be HLA-genotypically identical. The mesenchymal stromal cells may be genomically identical.

At least 30% of the mesenchymal stromal cells may be positive for CD10. Additionally, at least 60% of the mesenchymal stromal cells may be positive for markers CD73, CD90, CD105, CD13, CD29, CD44, and CD166 and HLA-ABC. In an exemplary embodiment, less than 30% of the mesenchymal stromal cells may be positive for markers CD31, CD34, CD45, CD133, FGFR2, CD271, Stro-1, CXCR4 and TLR3.

The mesenchymal stromal cells may have replicative rates to undergo at least 10 population doublings in cell culture in less than 25 days. The mesenchymal stromal cells may have a mean terminal restriction fragment length (TRF) that may be longer than 8 kb. The mesenchymal stromal cells may have a statistically significant decreased content and/or enzymatic activity, relative to mesenchymal stromal cell preparations derived from bone marrow that have undergone five population doublings, of proteins involved in one or more of (i) cell cycle regulation and cellular aging, (ii) cellular energy and/or lipid metabolism, and (iii) apoptosis. The mesenchymal stromal cells may have a statistically significant increased content and/or enzymatic activity of proteins involved in cytoskeleton structure and cellular dynamics relating thereto, relative to mesenchymal stromal cell preparations derived from bone marrow. The mesenchymal stromal cells may not undergo more than a 75 percent increase in cells having a forward-scattered light value, measured by flow cytometry, greater than 5,000,000 over 10 population doublings in culture. The mesenchymal stromal cells may, in a resting state, express mRNA encoding Interleukin-6 at a level which may be less than ten percent of the IL-6 mRNA level expressed by mesenchymal stromal cells preparations, in a resting state, derived from bone marrow or adipose tissue.

The preparation may be suitable for administration to a human patient. The preparation may be suitable for administration to a non-human veterinarian mammal.

In an exemplary aspect, the disclosure provides a pharmaceutical preparation comprising mesenchymal stromal cells, wherein said mesenchymal stromal cells are able to undergo at least 10 population doublings and wherein the 10 population doublings occur within about 27 days, more preferably less than about 26 days, preferably less than 25 days, more preferably less than about 24 days, still more preferably less than about 23 days, still more preferably less than about 22 days, or lower.

In an exemplary aspect, the disclosure provides a pharmaceutical preparation comprising mesenchymal stromal cells, wherein said mesenchymal stromal cells are able to undergo at least 15 population doublings.

Said mesenchymal stromal cells may be able to undergo at least 20, 25, 30, 35, 40, 45, 50 or more population doublings.

In an exemplary aspect, the disclosure provides a pharmaceutical preparation comprising mesenchymal stromal cells, wherein said mesenchymal stromal cells are able to undergo at least 15 population doublings, at least 20 population doublings, or at least 25 population doublings in culture.

The mesenchymal stromal cells may be produced by in vitro differentiation of hemangioblasts. The mesenchymal stromal cells may be primate cells or other mammalian cells. The mesenchymal stromal cells may be human cells.

Said population doublings occur within about 35 days, more preferably within about 34 days, preferably within 33 days, more preferably within 32 days, still more preferably within 31 days, or still more preferably within about 30 days.

The preparation may comprise less than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% pluripotent cells.

The preparation may be devoid of pluripotent cells.

The preparation may comprise at least 90%, 91%, 92%, 93%, 94%, 95%, 96%, 97%, 98%, 99%, or 100% mesenchymal stromal cells.

At least 50% of said mesenchymal stromal cells may be positive for (i) at least one of CD10, CD24, IL-11, AIRE-1, ANG-1, CXCL1, CD105, CD73 and CD90; (ii) at least one of CD10, CD24, IL-11, AIRE-1, ANG-1, CXCL1, CD105, CD73, CD90, CD105, CD13, CD29, CD 44, CD166, CD274, and HLA-ABC; (iii) CD105, CD73 and/or CD90 or (iv) any combination thereof. At least 50% of said mesenchymal stromal cells may be positive for (i) at least two of CD105, CD73 and/or CD90 (ii) at least two of CD10, CD24, IL-11, AIRE-1, ANG-1, CXCL1, CD105, CD73 and CD90; or (iii) all of CD10, CD24, IL-11, AIRE-1, ANG-1, CXCL1, CD105, CD73, CD90, CD105, CD13, CD29, CD 44, CD166, CD274, and HLA-ABC. At least 50% of said mesenchymal stromal cells (i) may be positive for all of CD105, CD73 and CD90; (ii) positive for all of CD10, CD24, IL-11, AIRE-1, ANG-1, CXCL1, CD105, CD73, CD90, CD105, CD13, CD29, CD 44, CD166, CD274, and HLA-ABC and/or (ii) may be negative for or less than 5% or less than 10% of the cells express CD31, 34, 45, 133, FGFR2, CD271, Stro-1, CXCR4, and/or TLR3. At least 60%, 70%, 80% or 90% of said mesenchymal stromal cells may be positive for (i) one or more of CD105, CD73 and CD90 (ii) one or more of CD10, CD24, IL-11, AIRE-1, ANG-1, CXCL1, CD105, CD73 and CD90; or (iii) one or more of CD10, CD24, IL-11, AIRE-1, ANG-1, CXCL1, CD105, CD73, CD90, CD105, CD13, CD29, CD 44, CD166, CD274, and HLA-ABC.

The pharmaceutical preparation may comprise an amount of mesenchymal stromal cells effective to treat an unwanted immune response in a subject in need thereof.

The pharmaceutical preparation may comprise other cells, tissue or organ for transplantation into a recipient in need thereof. The other cells or tissue may be RPE cells, skin cells, corneal cells, pancreatic cells, liver cells, cardiac cells or tissue containing any of said cells. Said mesenchymal stromal cells may be not derived from bone marrow and the potency of the preparation in an immune regulatory assay may be greater than the potency of a preparation of bone marrow derived mesenchymal stromal cells. Potency may be assayed by an immune regulatory assay that determines the EC50 dose. The preparation may retain between about 50 and 100% of its proliferative capacity after ten population doublings.

Said mesenchymal stromal cells may be not derived directly from pluripotent cells and wherein said mesenchymal stromal cells (a) do not clump or clump substantially less than mesenchymal stromal cells derived directly from pluripotent cells; (b) more easily disperse when splitting compared to mesenchymal stromal cells derived directly from pluripotent cells; (c) may be greater in number than mesenchymal stromal cells derived directly from pluripotent cells when starting with equivalent numbers of pluripotent cells; and/or (d) acquire characteristic mesenchymal cell surface markers earlier than mesenchymal stromal cells derived directly from pluripotent cells.

Said mesenchymal stromal cells may be mammalian. Said mesenchymal stromal cells may be human, canine, bovine, non-human primate, murine, feline, or equine In an exemplary aspect, the present disclosure provides a method for generating mesenchymal stromal cells comprising culturing hemangioblasts under conditions that give rise to mesenchymal stem cells. Said hemangioblasts may be cultured in feeder-free conditions. Said hemangioblasts may be plated on a matrix. Said matrix may comprise one or more of: transforming growth factor beta (TGF-beta), epidermal growth factor (EGF), insulin-like growth factor 1, bovine fibroblast growth factor (bFGF), and/or platelet-derived growth factor (PDGF). Said matrix may be selected from the group consisting of: laminin, fibronectin, vitronectin, proteoglycan, entactin, collagen, collagen I, collagen IV, heparan sulfate, Matrigel (a soluble preparation from Engelbreth-Holm-Swarm (EHS) mouse sarcoma cells), a human basement membrane extract, and any combination thereof. Said matrix may comprise a soluble preparation from Engelbreth-Holm-Swarm mouse sarcoma cells.

Said mesenchymal stromal cells may be mammalian. Said mesenchymal stromal cells may be human, canine, bovine, non-human primate, murine, feline, or equine.

Said hemangioblasts may be cultured in a medium comprising αMEM. Said hemangioblasts may be cultured in a medium comprising serum or a serum replacement. Said hemangioblasts may be cultured in a medium comprising, αMEM supplemented with 0%, 0.1%-0.9%, 1%, 2%, 3%, 4%, 5%, 6%, 7%, 8%, 9%, 10%, 11%, 12%, 13%, 14%, 15%, 16%, 17%, 18%, 19%, or 20% fetal calf serum. Said hemangioblasts may be cultured on said matrix for at least about 14, 15, 16, 17, 18, 19, 20, 21, 22, 23, 24, 25, 26, 27, 28, 29, or 30 days.

Said hemangioblasts may be differentiated from pluripotent cells.

Said pluripotent cells may be iPS cells or pluripotent cells produced from blastomeres. Said pluripotent cells may be derived from one or more blastomeres without the destruction of a human embryo.

Said hemangioblasts may be differentiated from pluripotent cells by a method comprising (a) culturing said pluripotent cells to form clusters of cells. The pluripotent cells may be cultured in the presence of vascular endothelial growth factor (VEGF) and/or bone morphogenic protein 4 (BMP-4). In step (a), the pluripotent cells may be cultured in the presence of vascular endothelial growth factor (VEGF) and/or bone morphogenic protein 4 (BMP-4). Said VEGF and BMP-4 may be added to the pluripotent cell culture within 0-48 hours of initiation of said cell culture, and said VEGF may be optionally added at a concentration of 20-100 nm/mL and said BMP-4 may be optionally added at a concentration of 15-100 ng/mL. Said VEGF and BMP-4 may be added to the cell culture of step (a) within 0-48 hours of initiation of said cell culture, and said VEGF may be optionally added at a concentration of 20-100 nm/mL and said BMP-4 may be optionally added at a concentration of 15-100 ng/mL. Said hemangioblasts may be differentiated from pluripotent cells by a method which may further comprise: (b) culturing said clusters of cells in the presence of at least one growth factor in an amount sufficient to induce the differentiation of said clusters of cells into hemangioblasts. Said at least one growth factor added in step (b) may comprise one or more of basic fibroblast growth factor (bFGF), vascular endothelial growth factor (VEGF), bone morphogenic protein 4 (BMP-4), stem cell factor (SCF), Flt 3L (FL), thrombopoietin (TPO), EPO, and/or tPTD-HOXB4.

Said at least one growth factor added in step (b) may comprise one or more of: about 20-25 ng/ml basic fibroblast growth factor (bFGF), about 20-100 ng/ml vascular endothelial growth factor (VEGF), about 15-100 ng/ml bone morphogenic protein 4 (BMP-4), about 20-50 ng/ml stem cell factor (SCF), about 10-50 ng/ml Flt 3L (FL), about 20-50 ng/ml thrombopoietin (TPO), EPO, and/or 1.5-5 U/ml tPTD-HOXB4.

One or more of said at least one growth factor optionally added in step (b) may be added to said culture within 36-60 hours or 40-48 hours from the start of step (a).

One or more of said at least one growth factor added in step (b) may be added to said culture within 48-72 hours from the start of step (a).

Said at least one factor added in step (b) may comprise one or more of bFGF, VEGF, BMP-4, SCF and/or FL.

The method may further comprise (c) dissociating said clusters of cells, optionally into single cells.

The method may further comprise (d) culturing said hemangioblasts in a medium comprising at least one additional growth factor, wherein said at least one additional growth factor may be in an amount sufficient to expand the hemangioblasts.

In step (d), said at least one additional growth factor may comprise one or more of: insulin, transferrin, granulocyte macrophage colony-stimulating factor (GM-CSF), interleukin-3 (IL-3), interleukin-6 (IL-6), granulocyte colony-stimulating factor (G-CSF), erythropoietin (EPO), stem cell factor (SCF), vascular endothelial growth factor (VEGF), bone morphogenic protein 4 (BMP-4), and/or tPTD-HOXB4.

In step (d), said at least one additional growth factor may comprise one or more of: about 10-100 µg/ml insulin, about 200-2,000 µg/ml transferrin, about 10-50 ng/ml granulocyte macrophage colony-stimulating factor (GM-CSF), about 10-20 ng/ml interleukin-3 (IL-3), about 10-1000 ng/ml interleukin-6 (IL-6), about 10-50 ng/ml granulocyte colony-stimulating factor (G-CSF), about 3-50 U/ml erythropoietin (EPO), about 20-200 ng/ml stem cell factor (SCF), about 20-200 ng/ml vascular endothelial growth factor (VEGF), about 15-150 ng/ml bone morphogenic protein 4 (BMP-4), and/or about 1.5-15 U/ml tPTD-HOXB4.

Said medium in step (a), (b), (c) and/or (d) may be a serum-free medium.

The method as described above may further comprise (e) mitotically inactivating the mesenchymal stromal cells.

At least 80, 85, 90, 95, 100, 125, or 150 million mesenchymal stromal cells may be generated.

Said hemangioblasts may be harvested after at least 10, 11, 12, 13, 14, 15, 16, 17 or 18 days of starting to induce differentiation of said pluripotent cells.

Said mesenchymal stromal cells may be generated within at least 25, 26, 27, 28, 29, 30, 31, 32, 33, 34, 35, 36, 37, 38, 39, 40, 41, 42, 43, 44, 45, 46, 47, 48, 49, or 50 days of starting to induce differentiation of said pluripotent cells.

The method may result in at least 80, 85, 90, 95, 100, 125, or 150 million mesenchymal stromal cells being generated from about 200,000 hemangioblasts within about 15, 16, 17, 18, 19, 20, 21, 22, 23, 24, 25, 26, 27, 28, 29, 30, 31, 32, 33, 34, or 35 days of culture.

The mesenchymal stromal cells may be generated from hemangioblasts in a ratio of hemangioblasts to mesenchymal stromal cells of at least 1:200, 1:250, 1:300, 1:350, 1:400, 1:415, 1:425, 1:440; 1:450, 1:365, 1:475, 1:490 and 1:500 within about 26, 27, 28, 29, 30, 31, 32, 33, 34 or 35 days of culture as hemangioblasts.

Said cells may be human.

In another aspect, the present disclosure provides mesenchymal stromal cells derived from hemangioblasts obtained by any of the methods described above.

In another aspect, the present disclosure provides mesenchymal stromal cells derived by in vitro differentiation of hemangioblasts.

At least 50% of said mesenchymal stromal cells (i) may be positive for all of CD10, CD24, IL-11, AIRE-1, ANG-1, CXCL1, CD105, CD73, CD90, CD105, CD13, CD29, CD 44, CD166, CD274, and HLA-ABC and (ii) may be negative for or less than 5% or less than 10% of the cells express CD31, 34, 45, 133, FGFR2, CD271, Stro-1, CXCR4 and/or TLR3.

At least 50% of said mesenchymal stromal cells may be positive for (i) all of CD10, CD24, IL-11, AIRE-1, ANG-1, CXCL1, CD105, CD73 and CD90; or (ii) all of CD73, CD90, CD105, CD13, CD29, CD44, CD166, CD274, and HLA-ABC.

At least 60%, 70%, 80% or 90% of said mesencyhmal stromal cells may be positive for (i) at least one of CD10, CD24, IL-11, AIRE-1, ANG-1, CXCL1, CD105, CD73 and CD90; or (ii) at least one of CD73, CD90, CD105, CD13, CD29, CD 44, CD166, CD274, and HLA-ABC.

The mesenchymal stromal may not express or less than 5% or less than 10% of the cells may express at least one of CD31, 34, 45, 133, FGFR2, CD271, Stro-1, CXCR4, or TLR3.

In another aspect, the present disclosure provides a preparation of mesenchymal stromal cells as described above.

Said preparation may comprise less than 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% pluripotent cells.

The preparation may be devoid of pluripotent cells.

Said preparation may be substantially purified and optionally may comprise at least 90%, 91%, 92%, 93%, 94%, 95%, 96%, 97%, 98%, 99%, or 100% human mesenchymal stromal cells.

The preparation may comprise substantially similar levels of p53 and p21 protein or wherein the levels of p53 protein as compared to p21 protein may be 1.5, 2, 3, 4, 5, 6, 7, 8, 9 or 10 times greater.

The mesenchymal stromal cells or the MSC in the preparation may be capable of undergoing at least 5 population doublings in culture, or may be capable of undergoing at least 10, 15, 20, 25, 30, 35, 40, 45, 50, 55, 60 or more population doublings in culture.

Said mesenchymal stromal cells: (a) may not clump or clump substantially less than mesenchymal stromal cells derived directly from pluripotent cells; (b) may more easily disperse when splitting compared to mesenchymal stromal cells derived directly from pluripotent cells; (c) may be greater in number than mesenchymal stromal cells derived directly from pluripotent cells when starting with equivalent numbers of pluripotent cells; and/or (d) may acquire characteristic mesenchymal cell surface markers earlier than mesenchymal stromal cells derived directly from pluripotent cells.

In another aspect, the disclosure provides a pharmaceutical preparation comprising any mesenchymal stromal cells or preparation of mesenchymal stromal cells as described above.

The pharmaceutical preparation may comprise an amount of mesenchymal stromal cells effective to treat an unwanted immune response.

The pharmaceutical preparation may comprise an amount of mesenchymal stromal cells effective to treat an unwanted immune response and may further comprise other cells or tissues for transplantation into a recipient in need thereof.

Said other cells or tissues may be allogeneic or syngeneic pancreatic, neural, liver, RPE, corneal cells or tissues containing any of the foregoing cells.

The pharmaceutical preparation may be for use in treating an autoimmune disorder or an immune reaction against allogeneic cells, or for use in treating multiple sclerosis, systemic sclerosis, hematological malignancies, myocardial infarction, organ transplantation rejection, chronic allograft nephropathy, cirrhosis, liver failure, heart failure, GvHD, tibial fracture, bone fractures, left ventricular dysfunction, leukemia, myelodysplastic syndrome, Crohn's disease, diabetes, obesity, metabolic diseases and disorders (such as lysosomal storage diseases including Tay-Sachs disease, Gaucher disease, Pompe disease, Hurler syndrome and metachromatic leukodystrophy), fatty liver disease, chronic obstructive pulmonary disease, osteogenesis imperfecta, homozygous familial hypercholesterolemia, hypocholesterolemia, treatment following meniscectomy, adult periodontitis, periodontitis, vasculogenesis in patients with severe myocardial ischemia, spinal cord injury, osteodysplasia, critical limb ischemia, diabetic foot disease, primary Sjogren's syndrome, osteoarthritis, cartilage defects, laminitis, multisystem atrophy, amyotropic lateral sclerosis, cardiac surgery, systemic lupus erythematosis, living kidney allografts, nonmalignant red blood cell disorders, thermal burn, radiation burn, Parkinson's disease, microfractures, epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, bone regeneration, uveitis or combinations thereof.

In another aspect, the disclosure provides a kit comprising any of the mesenchymal stromal cells or any preparation of mesenchymal stromal cells as described above.

In another aspect, the disclosure provides a kit comprising the mesenchymal stromal cells or preparation of mesenchymal stromal cells as described above, wherein said cells or preparation of cells may be frozen or cryopreserved.

In another aspect, the disclosure provides a kit comprising the mesenchymal stromal cells or preparation of mesenchymal stromal cells as described above, wherein said cells or preparation of cells may be contained in a cell delivery vehicle.

In another aspect, the disclosure provides a method for treating a disease or disorder, comprising administering an effective amount of mesenchymal stromal cells or a preparation of mesenchymal stromal cells as described above to a subject in need thereof.

The method may further comprise the transplantation of other cells or tissues. The cells or tissues may comprise retinal, RPE, corneal, neural, immune, bone marrow, kidney, liver or pancreatic cells. The disease or disorder may be selected from multiple sclerosis, systemic sclerosis, hematological malignancies, myocardial infarction, organ transplantation rejection, chronic allograft nephropathy, cirrhosis, liver failure, heart failure, GvHD, tibial fracture, bone fractures, left ventricular dysfunction, leukemia, myelodysplastic syndrome, Crohn's disease, diabetes, obesity, metabolic diseases and disorders (such as lysosomal storage diseases including Tay-Sachs disease, Gaucher disease, Pompe disease, Hurler syndrome and metachromatic leukodystrophy), fatty liver disease, chronic obstructive pulmonary disease, osteogenesis imperfecta, homozygous familial hypocholesterolemia, hypocholesterolemia, treatment following meniscectomy, adult periodontitis, periodontitis, vasculogenesis in patients with severe myocardial ischemia, spinal cord injury, osteodysplasia, critical limb ischemia, diabetic foot disease, primary Sjogren's syndrome, osteoarthritis, cartilage defects, multisystem atrophy, amyotropic lateral sclerosis, cardiac surgery, refractory systemic lupus erythematosis, living kidney allografts, nonmalignant red blood cell disorders, thermal burn, Parkinson's disease, microfractures, epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, bone regeneration, or combinations thereof.

The disease or disorder may be uveitis. Said disease or disorder may be an autoimmune disorder or an immune reaction against allogeneic cells. The autoimmune disorder may be multiple sclerosis.

In another aspect, the disclosure provides a method of treating bone loss or cartilage damage comprising administering an effective amount of mesenchymal stromal cells or preparation of mesenchymal stromal cells to a subject in need thereof.

The mesenchymal stromal cells may be administered in combination with an allogeneic or syngeneic transplanted cell or tissue. The allogeneic transplanted cell may comprise a retinal pigment epithelium cell, retinal cell, corneal cell, or muscle cell.

In another aspect, the disclosure provides a pharmaceutical preparation comprising mitotically inactivated mesenchymal stromal cells. The mesenchymal stromal cells may be differentiated from a hemangioblast cell.

The pharmaceutical may comprise at least $10^6$ mesenchymal stromal cells and a pharmaceutically acceptable carrier.

In another aspect, the disclosure provides a pharmaceutical preparation comprising mitotically inactivated mesenchymal stromal cells produced by the method above.

The preparation may be suitable for administration to a human patient. The preparation may be suitable for administration to a non-human veterinarian mammal.

The pharmaceutical preparation may be devoid of pluripotent cells.

The pharmaceutical preparation may comprise an amount of mesenchymal stromal cells effective to treat an unwanted immune response in a subject in need thereof.

The pharmaceutical preparation may comprise an amount of mesenchymal stromal cells effective to treat a disease or condition selected from the group consisting of: inflammatory respiratory conditions, respiratory conditions due to an acute injury, Adult Respiratory Distress Syndrome, post-traumatic Adult Respiratory Distress Syndrome, transplant lung disease, Chronic Obstructive Pulmonary Disease, emphysema, chronic obstructive bronchitis, bronchitis, an allergic reaction, damage due to bacterial pneumonia, damage due to viral pneumonia, asthma, exposure to irritants, tobacco use, atopic dermatitis, allergic rhinitis, hearing loss, autoimmune hearing loss, noise-induced hearing loss, psoriasis and any combination thereof.

Preparation of Mesenchymal Stromal Cells

Figure 5:
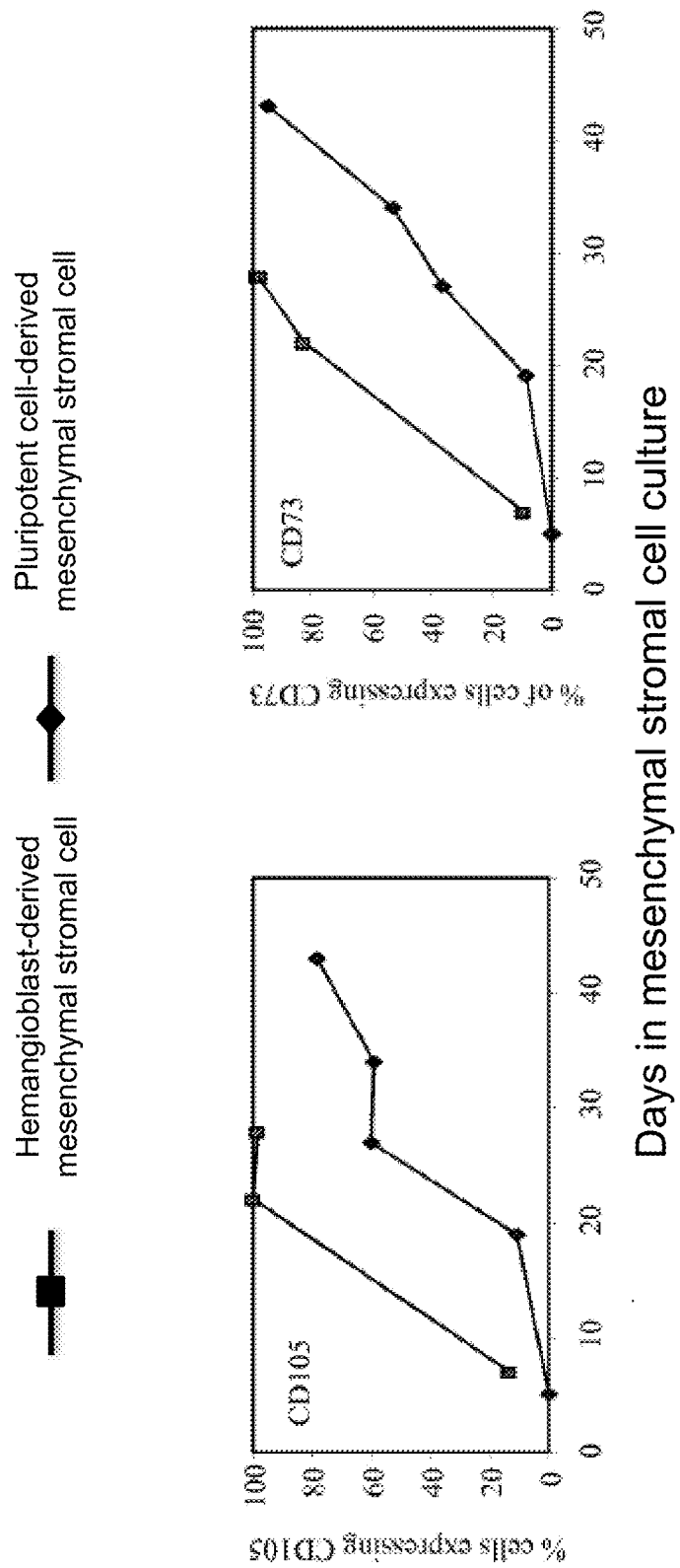
FIG. 5. Acquisition of mesenchymal stromal cell markers. This figure depicts the time for MSC surface markers to be acquired using hemangioblasts (top line) and ESC (lower line).

In an embodiment of the instant invention, a preparation of the subject mesenchymal stromal cells (e.g., generated by culturing hemangioblasts) is provided, wherein the desired phenotype of said mesenchymal stromal cells presents earlier as compared to mesenchymal stromal cells by ESC culture (See FIG. 5). In a further embodiment of the instant invention, a preparation of the subject mesenchymal stromal cells (e.g., generated by culturing hemangioblasts) is provided, wherein the desired phenotype of said mesenchymal stromal cells presents earlier as compared to mesenchymal stromal cells by ESC culture, and wherein said desired phenotype is defined by the expression of at least two markers selected from the group comprising CD9, CD13, CD29, CD44, CD73, CD90, CD105, CD166, and HLA-ABC.

A further embodiment of the instant invention comprises a preparation of mesenchymal stromal cells, wherein the phenotype of said mesenchymal stromal cells is defined by the expression of at least two markers selected from the group comprising CD9, CD13, CD29, CD44, CD73, CD90, CD105, CD166, and HLA-ABC. A still further embodiment of the instant invention comprises a preparation of mesenchymal stromal cells, wherein the phenotype of said mesenchymal stromal cells is defined by the expression of at least two markers selected from the group comprising CD9, CD13, CD29, CD44, CD73, CD90 and CD105, and wherein said mesenchymal stromal cells do not express CD2, CD3, CD4, CD5, CD7, CD8, CD14, CD15, CD16, CD19, CD20, CD22, CD33, CD36, CD38, CD61, CD62E and CD133.

In an embodiment of the instant invention about 50%, 55%, 60%, 65%, 70%, 75%, 80%, 85%, 90%, 95%, 98%, 99%, or 100% of the subject mesenchymal stromal cells (e.g., generated by culturing hemangioblasts) present a phenotype defined by the expression of the markers CD9, CD13, CD29, CD44, CD73, CD90, CD105, CD166, and HLA-abc after about 15, 16, 17, 18, 19, 20, 21, 22, 23, 24, 25, 26, 27, 28, 29, or 30 days in culture. In an embodiment of the instant invention at least 50%, 55%, 60%, 65%, 70%, 75%, 80%, 85%, 90%, 95%, 98%, 99%, or 100% of the subject mesenchymal stromal cells (e.g., generated by culturing hemangioblasts) present a phenotype defined by the expression of at least two markers selected from the group comprising CD9, CD13, CD29, CD44, CD73, CD90, CD105, CD166, and HLA-ABC and a lack of expression of CD2, CD3, CD4, CD5, CD7, CD8, CD14, CD15, CD16, CD19, CD20, CD22, CD33, CD36, CD38, CD61, CD62E, CD133 and Stro-1 after about 15, 16, 17, 18, 19, 20, 21, 22, 23, 24, 25, 26, 27, 28, 29, or 30 days in culture. The previous embodiment, wherein said phenotype is further defined by the markers selected from the group comprising AIRE-1, IL-11, CD10, CD24, ANG-1, and CXCL1.

A preferred process of the instant invention is provided, wherein the number of mesenchymal stromal cells derived from hemangioblasts is about $8\times10^7$, $8.5\times10^7$, $9\times10^7$, $9.5\times10^7$, $1\times10^8$, $1.25\times10^8$, or $1.5\times10^8$ mesenchymal stromal cells derived from about $2\times10^5$ hemangioblasts within about 30 days of culture of mesenchymal stromal cells. In an alternative embodiment of the instant invention, mesenchymal stromal cells may be generated from hemangioblasts in a ratio of hemangioblasts to mesenchymal stromal cells of about 1:200, 1:400, 1:415, 1:425, 1:440; 1:450, 1:465, 1:475, 1:490, and 1:500, within about 30 days of culture of mesenchymal stromal cells.

In a preferred embodiment of the instant invention, the number of mesenchymal stromal cells obtained by hemangioblast culture is higher than the number of mesenchymal stromal cells obtained directly from ESCs. In a further preferred embodiment of the instant invention, the number of mesenchymal stromal cells obtained by hemangioblast culture is at least 5 times, 10 times, 20 times, 22 times higher than the number of mesenchymal stromal cells obtained directly from ESCs than the number of mesenchymal stromal cells obtained directly from ESCs (See FIG. 4).

In another embodiment of the instant invention, a preparation of the subject mesenchymal stromal cells does not form teratomas when introduced into mammalian host.

An embodiment of the instant invention provides a preparation of mesenchymal stromal cells generated by culturing hemangioblasts using any of the process embodiments of the instant invention. An embodiment of the instant invention comprising a preparation of mesenchymal stromal cells is generated by culturing hemangioblasts using any of the process embodiments of the instant invention, wherein the phenotype of said preparation is defined by the presence of any or all of the markers selected from the group comprising AIRE-1, IL-11, CD10, CD24, ANG-1, and CXCL1. A further embodiment of the instant invention comprising a preparation of mesenchymal stromal cells is generated by culturing hemangioblasts using any of the process embodiments of the instant invention, wherein the phenotype of said preparation is defined by the presence of any or all of the markers selected from the group comprising AIRE-1, IL-11, CD10, CD24, ANG-1, and CXCL1, and wherein said preparation presents a reduced expression of IL-6, Stro-1 and VEGF.

In an embodiment of the instant invention, a preparation of the subject mesenchymal stromal cells (e.g., generated by culturing hemangioblasts) is provided, wherein said preparation comprises substantially similar levels of p53 and p21 protein, or wherein the levels of p53 as compared to p21 are 1.5, 2, 3, 4, 5, 6, 7, 8, 9, or 10 times greater. In an embodiment of the instant invention, a pharmaceutical preparation of the subject mesenchymal stromal cells (e.g., generated by culturing hemangioblasts) is provided, wherein said pharmaceutical preparation comprises substantially similar levels of p53 and p21 protein, or wherein the levels of p53 as compared to p21 are 1.5, 2, 3, 4, 5, 6, 7, 8, 9, or 10 times greater.

In an embodiment of the instant invention, a preparation of the subject mesenchymal stromal cells (e.g., generated by culturing hemangioblasts) is provided, wherein said preparation comprises a substantially similar percentage of cells positive for p53 and p21 protein, or wherein the percentage of cells positive for p53 as compared to p21 are 1.5, 2, 3, 4, 5, 6, 7, 8, 9, or 10 times greater. In an embodiment of the instant invention, a preparation of the subject mesenchymal stromal cells (e.g., generated by culturing hemangioblasts) is provided wherein said preparation comprises a substantially similar percentage of cells positive for p53 and p21 protein, or wherein the percentage of cells positive for p53 as compared to p21 are 1.5, 2, 3, 4, 5, 6, 7, 8, 9, or 10 times greater. In an embodiment of the instant invention, a pharmaceutical preparation of the subject mesenchymal stromal cells (e.g., generated by culturing hemangioblasts) is provided, wherein said pharmaceutical preparation comprises a substantially similar percentage of cells positive for p53 and p21 protein, or wherein the percentage of cells positive for p53 as compared to p21 are 1.5, 2, 3, 4, 5, 6, 7, 8, 9, or 10 times greater.

In an embodiment of the instant invention, a preparation of the subject mesenchymal stromal cells (e.g., generated by culturing hemangioblasts) is provided, wherein said preparation comprises a substantially similar percentage of cells having background levels of aging markers selected from the group comprising S100A1, VIM, MYADM, PIM1, ANXA2, RAMP, MEG3, IL13R2, S100A4, TREM1, DGKA, TPBG, MGLL, EML1, MYO1B, LASS6, ROBO1, DKFZP586H2123, LOC854342, DOK5, UBE2E2, USP53, VEPH1, SLC35E1, ANXA2, HLA-E, CD59, BHLHB2, UCHL1, SUSP3, CREDBL2, OCRL, OSGIN2, SLEC3B, IDS, TGFBR2, TSPAN6, TM4SF1, MAP4, CAST, LHFPL2, PLEKHM1, SAMD4A, VAMP1, ADD1, FAM129A, HPDC1, KLF11, DRAM, TREM140, BHLHB3, MGC17330, TBC1D2, KIAA1191, C5ORF32, C15ORF17, FAM791, CCDC104, PQLC3, EIF4E3, C7ORF41, DUSP18, SH3PX3, MYO5A, PRMT2, C8ORF61, SAMD9L, PGM2L1, HOM-TES-103, EPOR, and TMEM112 or from the group comprising S100A1, VIM, MYADM, PIM1, ANXA2, RAMP, MEG3, IL13R2, S100A4, TREM1, DGKA, TPBG, MGLL, EMLI, MYO1B, LASS6, ROBO1, DKFZP586H2123, LOC854342, DOK5, UBE2E2, USP53, VEPH1, and SLC35E1, or wherein the percentage of cells positive for aging markers selected from the group comprising S100A1, VIM, MYADM, PIM1, ANXA2, RAMP, MEG3, IL13R2, S100A4, TREM1, DGKA, TPBG, MGLL, EML1, MYO1B, LASS6, ROBO1, DKFZP586H2123, LOC854342, DOK5, UBE2E2, USP53, VEPH1, SLC35E1, ANXA2, HLA-E, CD59, BHLHB2, UCHL1, SUSP3, CREDBL2, OCRL, OSGIN2, SLEC3B, IDS, TGFBR2, TSPAN6, TM4SF1, MAP4, CAST, LHFPL2, PLEKHM1, SAMD4A, VAMP1 ADD1, FAM129A, HPDC1, KLF11, DRAM, TREM140, BHLHB3, MGC17330, TBC1D2, KIAA1191, C5ORF32, C15ORF17, FAM791, CCDC104, PQLC3, EIF4E3, C7ORF41, DUSP18, SH3PX3, MYO5A, PRMT2, C8ORF61, SAMD9L, PGM2L1, HOM-TES-103, EPOR, TMEM112 or from the group comprising S100A1, VIM, MYADM, PIM1, ANXA2, RAMP, MEG3, IL13R2, S100A4, TREM1, DGKA, TPBG, MGLL, EML1, MYO1B, LASS6, ROBO1, DKFZP586H2123, LOC854342, DOK5, UBE2E2, USP53, VEPH1, and SLC35E1, are 1.5, 2, 3, 4, 5, 6, 7, 8, 9, or 10 times greater than background. In an embodiment of the instant invention, a preparation of the subject mesenchymal stromal cells (e.g., generated by culturing hemangioblasts) is provided, wherein said preparation comprises a substantially similar percentage of cells having background levels of markers selected from the group comprising HoxB3, HoxB7, MID1, SNAPC5, PPARG, ANXA2, TIPIN, MYLIP, LAX1, EGR1CRIP1, SULT1A3, STMN1, CCT8, SFRS10, CBX3, CBX1, FLJ11021, DDX46, ACADM, KIAA0101, TYMS, BCAS2, CEP57, TDG, MAP2K6, CSRP2, GLMN, HMGN2, HNRPR, EIF3S1, PAPOLA, SFRS10, TCF3, H3F3A, LOC730740, LYPLA1, UBE3A, SUMO2, SHMT2, ACP1, FKBP3, ARL5A, GMNN, ENY2, FAM82B, RNF138, RPL26L1, CCDC59, PXMP2, POLR3B, TRMT5, ZNF639, MRPL47, GTPBP8, SUB1, SNHG1, ATPAF1, MRPS24, C16ORF63, FAM33A, EPSTL1, CTR9, GAS5, ZNF711, MTO1, and CDP2, or wherein the percentage of cells positive for markers selected from the group comprising HoxB3, HoxB7, MID1, SNAPC5, PPARG, ANXA2, TIPIN, MYLIP, LAX1, EGR1, CRIP1, SULT1A3, STMN1, CCT8, SFRS10, CBX3, CBX1, FLJ11021, DDX46, ACADM, KIAA0101, TYMS, BCAS2, CEP57, TDG, MAP2K6, CSRP2, GLMN, HMGN2, HNRPR, EIF3S1, PAPOLA, SFRS10, TCF3, H3F3A, LOC730740, LYPLA1, UBE3A, SUMO2, SHMT2, ACP1, FKBP3, ARL5A, GMNN, ENY2, FAM82B, RNF138, RPL26L1, CCDC59, PXMP2, POLR3B, TRMT5, ZNF639, MRPL47, GTPBP8, SUB1, SNHG1, ATPAF1, MRPS24, C16ORF63, FAM33A, EPSTL1, CTR9, GAS5, ZNF711, MTO1, and CDP2 are 1.5, 2, 3, 4, 5, 6, 7, 8, 9, or 10 times less than background.

In an embodiment of the instant invention, a preparation of the subject mesenchymal stromal cells (e.g., generated by culturing hemangioblasts) is provided wherein said preparation comprises a substantially similar percentage of cells having background levels of aging markers selected from the group comprising HoxB3, HoxB7, MID1, SNAPC5, PPARG, ANXA2, TIPIN, MYLIP, LAX1, EGR1, CRIP1, SULT1A3, STMN1, CCT8, SFRS10, CBX3, CBX1, FLJ11021, DDX46, ACADM, KIAA0101, TYMS, BCAS2, CEP57, TDG, MAP2K6, CSRP2, GLMN, HMGN2, HNRPR, EIF3S1, PAPOLA, SFRS10, TCF3, H3F3A, LOC730740, LYPLA1, UBE3A, SUMO2, SHMT2, ACP1, FKBP3, ARL5A, GMNN, ENY2, FAM82B, RNF138, RPL26L1, CCDC59, PXMP2, POLR3B, TRMT5, ZNF639, MRPL47, GTPBP8, SUB1, SNHG1, ATPAF1, MRPS24, C16ORF63, FAM33A, EPSTL1, CTR9, GAS5, ZNF711, MTO1, and CDP2, or from the group comprising HoxB3, HoxB7, MID1, SNAPC5, PPARG, ANXA2, TIPIN, MYLIP, LAX1, EGR1, CRIP1 and SULT1A3 or wherein the percentage of cells positive for aging markers selected from the group comprising HoxB3, HoxB7, MID1, SNAPC5, PPARG, ANXA2, TIPIN, MYLIP, LAX1, EGR1, CRIP1, SULT1A3, STMN1, CCT8, SFRS10, CBX3, CBX1, FLJ11021, DDX46, ACADM, KIAA0101, TYMS, BCAS2, CEP57, TDG, MAP2K6, CSRP2, GLMN, HMGN2, HNRPR, EIF3S1, PAPOLA, SFRS10, TCF3, H3F3A, LOC730740, LYPLA1, UBE3A, SUMO2, SHMT2, ACP1, FKBP3, ARL5A, GMNN, ENY2, FAM82B, RNF138, RPL26L1, CCDC59, PXMP2, POLR3B, TRMT5, ZNF639, MRPL47, GTPBP8, SUB1, SNHG1, ATPAF1, MRPS24, C16ORF63, FAM33A, EPSTL1, CTR9, GAS5, ZNF711, MTO1, and CDP2 or the group comprising HoxB3, HoxB7, MID1, SNAPC5, PPARG, ANXA2, TIPIN, MYLIP, LAX1, EGR1, CRIP1, SULT1A3 are 1.5, 2, 3, 4, 5, 6, 7, 8, 9, or 10 times less than background.

In another embodiment, the MSCs (such as hemangioblast-derived MSCs) possess phenotypes of younger cells as compared to adult-derived MSCs. In one embodiment, the subject MSCs are capable of undergoing at least or about 5, 10, 15, 20, 25, 30, 35, 40, 45, 50, 55, 60, or more population doublings in culture. In contrast, adult-derived mesenchymal stromal cells typically undergo 2-3 doublings in culture. In another embodiment, the MSCs (such as hemangioblast-derived MSCs) have longer telomere lengths, greater immunosuppressive effects, fewer vacuoles, divide faster, divide more readily in culture, higher CD90 expression, are less lineage committed, or combinations thereof, compared to adult-derived MSCs. In another embodiment, the hemangioblast-derived MSC have increased expression of transcripts promoting cell proliferation (i.e., have a higher proliferative capacity) and reduced expression of transcripts involved in terminal cell differentiation compared to adult-derived MSCs.

In an embodiment of the instant invention, a preparation of mesenchymal stromal cells is generated by any one or more of the processes of the instant invention, wherein said mesenchymal stromal cells are capable of undergoing at least or about 5, 10, 15, 20, 25, 30, 35, 40, 45, 50, 55, 60, or more population doublings in culture.

In another embodiment of the instant invention, a preparation of the subject mesenchymal stromal cells (e.g., generated by culturing hemangioblasts) are capable of undergoing at least or about 5, 10, 15, 20, 25, 30, 35, 40, 45, 50, 55, 60, or more population doublings in culture. In another embodiment of the instant invention, a preparation of the subject mesenchymal stromal cells are capable of undergoing at least or about 5, 10, 15, 20, 25, 30, 35, 40, 45, 50, 55, 60, or more population doublings in culture, wherein after said population doublings less than 50%, 40%, 30%, 20%, 15%, 10%, 5%, or 1% of mesenchymal stromal cells have undergone replicative senescence. In a further embodiment, said preparation is a pharmaceutical preparation.

In another embodiment of the instant invention, a preparation of mesenchymal stromal cells is provided, wherein said mesenchymal stromal cells have undergone at least or about 5, 10, 15, 20, 25, 30, 35, 40, 45, 50, 55, or 60 doublings in culture, In another embodiment of the instant invention, a preparation of mesenchymal stromal cells is provided, wherein said mesenchymal stromal cells have undergone at least or about 5, 10, 15, 20, 25, 30, 35, 40, 45, 50, 55, or 60 doublings in culture, wherein less than 50%, 40%, 30%, 20%, 15%, 10%, 5%, or 1% of said mesenchymal stromal cells have undergone replicative senescence, wherein said mesenchymal stromal cells retain a youthful phenotype and potency, and wherein said preparation is a pharmaceutical preparation. Said preparation may comprise an effective number of mesenchymal stromal cells for the treatment of disease, such as an immunological disorder, degenerative disease, or other disease amenable to treatment using MSCs.

In another embodiment of the instant invention, a preparation of the subject mesenchymal stromal cells (e.g., generated by culturing hemangioblasts) is provided, wherein said mesenchymal stromal cells have undergone at least or about 5, 10, 15, 20, 25, 30, 35, 40, 45, 50, 55, or 60 doublings in culture, wherein less than 50%, 40%, 30%, 20%, 15%, 10%, 5%, or 1% of said mesenchymal stromal cells have undergone replicative senescence after such doublings, wherein said mesenchymal stromal cells retain a youthful phenotype and potency, and wherein said preparation is a pharmaceutical preparation. Said preparation may comprise an effective number of mesenchymal stromal cells for the treatment of disease, such as an immunological disorder, degenerative disease, or other disease amenable to treatment using MSCs.

In another embodiment of the instant invention, a preparation of the subject mesenchymal stromal cells (e.g., generated by culturing hemangioblasts) is provided, wherein said mesenchymal stromal cells have undergone about 5, 10, 15, 20, 25, 30, 35, 40, 45, 50, 55, or 60 doublings in culture. The previous embodiment wherein less than 50%, 40%, 30%, 20%, 15%, 10%, 5% 1% of said mesenchymal stromal cells have undergone replicative senescence, wherein said mesenchymal stromal cells retain a youthful phenotype and potency, wherein said preparation is a pharmaceutical preparation, wherein said pharmaceutical preparation comprises an effective number of mesenchymal stromal cells, and wherein said pharmaceutical preparation is preserved.

In another embodiment, the instant invention provides a kit comprising a pharmaceutical preparation of mesenchymal stromal cells. In another embodiment, the instant invention provides a kit comprising a pharmaceutical preparation of mesenchymal stromal cells, wherein said preparation is preserved. In another embodiment, the instant invention provides a kit comprising a pharmaceutical preparation of the subject mesenchymal stromal cells (e.g., generated by culturing hemangioblasts). In another embodiment, the instant invention provides a kit comprising a pharmaceutical preparation of the subject mesenchymal stromal cells (e.g., generated by culturing hemangioblasts), wherein said preparation is preserved.

In another embodiment, the instant invention provides for a method of treating a pathology by administering an effective amount of mesenchymal stromal cells derived from hemangioblasts to a subject in need thereof. Said pathology may include, but is not limited to an autoimmune disorder, uveitis, bone loss or cartilage damage.

The mesenchymal stromal cells obtained by culturing hemangioblasts have improved characteristics as compared to MSCs derived directly from ESCs. For example, ESC-derived MSCs clump more, are more difficult to disperse when splitting, do not generate nearly as many MSCs when starting with equivalent numbers of ESCs, and take longer to acquire characteristics MSC cell surface markers compared to hemangioblast-derived MSCs. See Example 2 and FIGS. 3-6.

In one embodiment, the instant invention provides a preparation of the subject mesenchymal stromal cells (e.g., generated by culturing hemangioblasts), wherein said preparation is effective at normalizing a pathology. In a further embodiment of the instant invention a preparation of the subject mesenchymal stromal cells (e.g., generated by culturing hemangioblasts) is provided, wherein said preparation is effective at reducing excessive or unwanted immune responses. In a further embodiment of the instant invention, a preparation of the subject mesenchymal stromal cells (e.g., generated by culturing hemangioblasts) is provided, wherein said preparation is effective at ameliorating an autoimmune disorder. In a further embodiment of the instant invention, normalization of a pathology by administering to a host an effective amount of the subject mesenchymal stromal cells (e.g., generated by culturing hemangioblasts) is provided. A further embodiment of the instant invention provides for normalization of a pathology, wherein such normalization of a pathology is characterized by effects selected from the group comprising cytokine release by said MSCs, stimulating an increase in the number of regulatory T cells, inhibiting a certain amount of IFN gamma release from Th1 cells, and stimulating a certain amount of IL4 secretion from Th2 cells. In a further embodiment, administration of a preparation of the subject mesenchymal stromal cells (e.g., generated by culturing hemangioblasts) results in the release from said mesenchymal stromal cells of cytokines selected from the group comprising transforming growth factor beta, indoleamine 2, 3dioxygenase, prostaglandin E2, hepatocyte growth factor, nitric oxide, interleukin 10, interleukin 6, macrophage-colony stimulating factor, and soluble human leukocyte antigen (HLA) G5.

In a further embodiment of the instant invention, administration of a preparation of the subject mesenchymal stromal cells (e.g., generated by culturing hemangioblasts) results in the release from said mesenchymal stromal cells of cytokines selected from the group comprising transforming growth factor beta, indoleamine 2, 3dioxygenase, prostaglandin E2, hepatocyte growth factor, nitric oxide, interleukin 10, interleukin 6, macrophage-colony stimulating factor, soluble human leukocyte antigen (HLA) G5, interleukin 4, 8, 11, granulocyte macrophage colony stimulating factor, vascular endothelium growth factor, insulin-like growth factor 1, Phosphatidylinositol-glycan biosynthesis class F protein, monocyte chemoattractant protein 1, stromal derived factor 1, tumor necrosis factor 1, transforming growth factor beta, basic fibroblast growth factor, angiopoietin 1 and 2, monokine induced by interferon gamma, interferon inducible protein 10, brain derived neurotrophic factor, interleukin 1 receptor alpha, chemokine ligand 1 and 2.

Pharmaceutical Preparations of MSCs

MSCs of the instant invention may be formulated with a pharmaceutically acceptable carrier. For example, MSCs of the invention may be administered alone or as a component of a pharmaceutical formulation, wherein said MSCs may be formulated for administration in any convenient way for use in medicine. One embodiment provides a pharmaceutical preparation of mesenchymal stromal cells comprising said mesenchymal stromal cells in combination with one or more pharmaceutically acceptable sterile isotonic aqueous or non-aqueous solutions selected from the group consisting of: dispersions, suspensions, emulsions, sterile powders optionally reconstituted into sterile injectable solutions or dispersions just prior to use, antioxidants, buffers, bacteriostats, solutes or suspending and thickening agents.

In an embodiment of the instant invention, a pharmaceutical preparation of mesenchymal stromal cells is provided, wherein said mesenchymal stromal cells have undergone between about 5 and about 100 population doublings. In a further embodiment of the instant invention, a pharmaceutical preparation of mesenchymal stromal cells is provided, wherein said mesenchymal stromal cells have undergone between about 10 and about 80 population doublings. In a further embodiment of the instant invention, a pharmaceutical preparation of mesenchymal stromal cells is provided, wherein said mesenchymal stromal cells have undergone between about 25 and about 60 population doublings. In a further embodiment of the instant invention, a pharmaceutical preparation of mesenchymal stromal cells is provided, wherein said mesenchymal stromal cells have undergone less than about 10 population doublings. In a still further embodiment of the instant invention, a pharmaceutical preparation of mesenchymal stromal cells is provided, wherein said mesenchymal stromal cells have undergone less than about 20 population doublings. In a further embodiment of the instant invention, a pharmaceutical preparation of mesenchymal stromal cells is provided, wherein said mesenchymal stromal cells have undergone less than about 30 population doublings, wherein said mesenchymal stromal cells have not undergone replicative senescence. In a further embodiment of the instant invention, a pharmaceutical preparation of mesenchymal stromal cells is provided, wherein said mesenchymal stromal cells have undergone less than about 30 population doublings, wherein less than about 25% of said mesenchymal stromal cells have undergone replicative senescence. In a further embodiment of the instant invention, a pharmaceutical preparation of mesenchymal stromal cells is provided, wherein said mesenchymal stromal cells have undergone less than about 30 population doublings, wherein less than about 10% of said mesenchymal stromal cells have undergone replicative senescence. In a further embodiment of the instant invention, a pharmaceutical preparation of mesenchymal stromal cells is provided, wherein said mesenchymal stromal cells have undergone less than about 30 population doublings, wherein less than about 10% of said mesenchymal stromal cells have undergone replicative senescence, and wherein said mesenchymal stromal cells express the markers selected from the group comprising AIRE-1, IL-11, CD10, CD24, ANG-1, and CXCL1.

Concentrations for injections of pharmaceutical preparations of MSCs may be at any amount that is effective and, for example, substantially free of ESCs. For example, the pharmaceutical preparations may comprise the numbers and types of MSCs described herein. In a particular embodiment, the pharmaceutical preparations of MSCs comprise about $1 \times 10^6$ of the subject MSCs (e.g., generated by culturing hemangioblasts) for systemic administration to a host in need thereof or about $1 \times 10^4$ of said MSCs by culturing hemangioblasts for local administration to a host in need thereof.

Exemplary compositions of the present disclosure may be formulation suitable for use in treating a human patient, such as pyrogen-free or essentially pyrogen-free, and pathogen-free. When administered, the pharmaceutical preparations for use in this disclosure may be in a pyrogen-free, pathogen-free, physiologically acceptable form.

The preparation comprising MSCs used in the methods described herein may be transplanted in a suspension, gel, colloid, slurry, or mixture. Also, at the time of injection, cryopreserved MSCs may be resuspended with commercially available balanced salt solution to achieve the desired osmolality and concentration for administration by injection (i.e., bolus or intravenous).

One aspect of the invention relates to a pharmaceutical preparation suitable for use in a mammalian patient, comprising at least $10^6$, $10^7$, $10^8$ or even $10^9$ mesenchymal stromal cells and a pharmaceutically acceptable carrier. Another aspect of the invention relates to a pharmaceutical preparation comprising at least $10^6$, $10^7$, $10^8$ or even $10^9$ mesenchymal stromal cells and a pharmaceutically acceptable carrier, wherein the mesenchymal stromal cells are differentiated from a hemangioblast cell. Yet another aspect of the invention provides a cryogenic cell bank comprising at least $10^8$, $10^9$, $10^{10}$, $10^{11}$, $10^{12}$ or even $10^{13}$ mesenchymal stromal cells. Still another aspect of the invention provides a purified cellular preparation free of substantially free of non-human cells and/or non-human animal products, comprising at least $10^6$, $10^7$, $10^8$ or even $10^9$ mesenchymal stromal cells and less than 1% of any other cell type, more preferably less than 0.1%, 0.01% or even 0.001% of any other cell type. Certain preferred embodiments of the above preparations, compositions and bank include, but are not limited to those listed in the following paragraphs:

In certain embodiments, the mesenchymal stromal cells have replicative capacity to undergo at least 10 population doublings in cell culture with less than 25, 20, 15, 10 or even 5 percent of the cells undergoing cell death, senescing or differentiating into non-MSC cells (such as fibroblasts, adipocytes and/or osteocytes) by the $10^{th}$ doubling.

In certain embodiments, the mesenchymal stromal cells have replicative capacity to undergo at least 15 population doublings in cell culture with less than 25, 20, 15, 10 or even 5 percent of the cells undergoing cell death, senescing or differentiating into non-MSC cells (such as fibroblasts, adipocytes and/or osteocytes) by the $15^{th}$ doubling.

In certain embodiments, the mesenchymal stromal cells have replicative capacity to undergo at least 20 population doublings in cell culture with less than 25, 20, 15, 10 or even 5 percent of the cells undergoing cell death, senescing or differentiating into non-MSC cells (such as fibroblasts, adipocytes and/or osteocytes) by the $20^{th}$ doubling.

In certain embodiments, the mesenchymal stromal cells have replicative capacity to undergo at least 5 passages in cell culture with less than 25, 20, 15, 10 or even 5 percent of the cells undergoing cell death, senescing or differentiating into non-MSC cells (such as fibroblasts, adipocytes and/or osteocytes) by the $5^{th}$ passage.

In certain embodiments, the mesenchymal stromal cells have replicative capacity to undergo at least 10 passages in cell culture with less than 25, 20, 15, 10 or even 5 percent of the cells undergoing cell death, senescing or differentiating into non-MSC cells (such as fibroblasts, adipocytes and/or osteocytes) by the $10^{th}$ passage.

In certain embodiments, the mesenchymal stromal cells are differentiated from a pluripotent stem cell source, such as a pluripotent stem cell that expresses OCT-4, alkaline phosphatase, Sox2, SSEA-3, SSEA-4, TRA-1-60, and TRA-1-80 (such as, and embryonic stem cell line or induced pluripotency stem cell line), and even more preferably from a common pluripotent stem cell source.

In certain embodiments, the mesenchymal stromal cells are HLA-genotypically identical.

In certain embodiments, the mesenchymal stromal cells are genomically identical.

In certain embodiments, at least 30%, 35%, 40%, 45% or even 50% of the mesenchymal stromal cells are positive for CD10.

In certain embodiments, at least 60%, 65%, 70%, 75%, 80%, 85% or even 90% of the mesenchymal stromal cells are positive for markers CD73, CD90, CD105, CD13, CD29, CD44, CD166 and CD274 and HLA-ABC.

In certain embodiments, less than 30%, 25%, 20%, 15% or even 10% of the mesenchymal stromal cells are positive for markers CD31, CD34, CD45, CD133, FGFR2, CD271, Stro-1, CXCR4 and TLR3.

In certain embodiments, the mesenchymal stromal cells have replicative rates to undergo at least 10 population doublings in cell culture in less than 25, 24, 23, 22, 21 or even 20 days.

In certain embodiments, the mesenchymal stromal cells have a mean terminal restriction fragment length (TRF) that is longer than 7 kb, 7.5 kb, 8 kb, 8.5 kb, 9 kb, 9.5 kb, 10 kb, 10.5 kb, 11 kb, 11.5 kb or even 12 kb.

In certain embodiments, the mesenchymal stromal cells do not undergo more than a 75%, 70%, 65%, 60%, 55%, 50%, or even 45% percent increase in cells having a forward-scattered light value, measured by flow cytometry, greater than 5,000,000 over 10, 15 or even 20 population doublings in culture.

In certain embodiments, the mesenchymal stromal cells, in a resting state, express mRNA encoding Interleukin-6 at a level which is less than 10%, 8%, 6%, 4% or even 2% of the IL-6 mRNA level expressed by mesenchymal stromal cells preparations, in a resting state, derived from cord blood, bone marrow or adipose tissue.

In certain embodiments, the mesenchymal stromal cells are at least 2, 4, 6, 8, 10, 20, 50 or even 100 times more potent than MSCs derived from cord blood, bone marrow or adipose tissue.

In certain embodiments, one million of the mesenchymal stromal cells, when injected into an MOG35-55 EAE mouse model (such as C57BL/6 mice immunized with the MOG35-55 peptide) will, on average, reduce a clinical score of 3.5 to less than 2.5, and even more preferably will reduce the clinical score to less 2, 1.5 or even less than 1.

In certain embodiments, the preparation is suitable for administration to a human patient, and more preferably pyrogen free and/or free of non-human animal products.

In other embodiments, the preparation is suitable for administration to a non-human veterinarian mammal, such as a dog, cat or horse.

Diseases and Conditions Treatable Using MSCs Derived from Culturing Hemangioblasts MSCs have been shown to be therapeutic for a variety of diseases and conditions. In particular, MSCs migrate to injury sites, exert immunosuppressive effects, and facilitate repair of damaged tissues. An embodiment of the instant invention is provided, wherein a pharmaceutical preparation of mesenchymal stromal cells reduces the manifestations of a pathology. An embodiment of the instant invention is provided, wherein a pharmaceutical preparation of mesenchymal stromal cells are administered to a host suffering from a pathology. In a further embodiment of the instant invention, a pharmaceutical preparation of the subject MSCs (e.g., generated by culturing hemangioblasts) reduces the manifestations of a pathology selected from the group comprising wound healing, graft-versus-host disease (GvHD), disease, chronic eye disease, retinal degeneration, glaucoma, uveitis, acute myocardial infarction, chronic pain, hepatitis, and nephritis. In a further embodiment of the instant invention, a pharmaceutical preparation of mesenchymal stromal cells by culturing hemangioblasts reduces the manifestations of equine laminitis. As a further example, MSCs may be administered in combination with an allogeneic transplanted cell or tissue (e.g., a preparation comprising cells that have been differentiated from ES cells, such as retinal pigment epithelium (RPE) cells, oligodendrocyte precursors, retinal, corneal, muscle such as skeletal, smooth, or cardiac muscle or any combination thereof, or others) thereby decreasing the likelihood of an immune reaction against the transplanted cell or tissue and potentially avoiding the need for other immune suppression. The subject MSCs (e.g., generated by culturing hemangioblasts) described herein may be used in similar applications. An embodiment of a process of the instant invention, wherein the administration of a pharmaceutical preparation of the subject MSCs (e.g., generated by culturing hemangioblasts) to a host reduces the need for future therapy. An embodiment of a process of the instant invention is provided, wherein the administration of a pharmaceutical preparation of the subject MSCs (e.g., generated by culturing hemangioblasts) to a host reduces the need for future therapy, wherein said therapy suppresses immune function.

In an embodiment of the instant invention, a pharmaceutical preparation of the subject MSCs (e.g., generated by culturing hemangioblasts) is administered to a host for the treatment of a pathology. In an embodiment of the instant invention, a pharmaceutical preparation of the subject MSCs (e.g., generated by culturing hemangioblasts) is administered to a host for the treatment of pathologies selected from the list comprising wound healing, multiple sclerosis, systemic sclerosis, hematological malignancies, myocardial infarction, tissue and organ transplantation, tissue and organ rejection, chronic allograft nephropathy, cirrhosis, liver failure, heart failure, GvHD, tibial fracture, bone fractures, left ventricular dysfunction, leukemia, myelodysplastic syndrome, Crohn's disease, Type I or Type II diabetes, obesity, metabolic diseases and disorders (such as lysosomal storage diseases including Tay-Sachs disease, Gaucher disease, Pompe disease, Hurler syndrome and metachromatic leukodystrophy), fatty liver disease mellitus, chronic obstructive pulmonary disease, pulmonary hypertension, chronic pain, osteogenesis imperfecta, homozygous familial hypocholesterolemia, hypocholesterolemia, treatment following meniscectomy, adult periodontitis, periodontitis, vasculogenesis in patients with severe myocardial ischemia, spinal cord injury, osteodysplasia, critical limb ischemia associated with diabetes, obesity, metabolic diseases and disorders (such as lysosomal storage diseases including Tay-Sachs disease, Gaucher disease, Pompe disease, Hurler syndrome and metachromatic leukodystrophy), fatty liver disease mellitus, diabetic foot disease, primary Sjogren's syndrome, osteoarthritis, cartilage defects (e.g., articular cartilage defects), laminitis, multisystem atrophy, amyotropic lateral sclerosis, cardiac surgery, refractory systemic lupus erythematosis, living kidney allografts, nonmalignant red blood cell disorders, thermal burn, radiation burn, Parkinson's disease, microfractures (e.g., in patients with knee articular cartilage injury of defects), epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, and bone regeneration.

In a further embodiment of the instant invention, a pharmaceutical preparation of the subject MSCs (e.g., generated by culturing hemangioblasts) is administered to a host for the treatment of autoimmune pathologies selected from the list comprising Acute necrotizing hemorrhagic leukoencephalitis, Addison's disease, Agammaglobulinemia, Alopecia greata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticarial, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes, obesity, metabolic diseases and disorders (such as lysosomal storage diseases including Tay-Sachs disease, Gaucher disease, Pompe disease, Hurler syndrome and metachromatic leukodystrophy), fatty liver disease (type1), Interstitial cystitis, Juvenile arthritis, Juvenile diabetes, obesity, metabolic diseases and disorders (such as lysosomal storage diseases including Tay-Sachs disease, Gaucher disease, Pompe disease, Hurler syndrome and metachromatic leukodystrophy), fatty liver disease, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Neuritis (including optic neuritis), Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA).

Treatment Regimens Using MSCs Derived from Culturing Hemangioblasts

The MSCs and pharmaceutical preparations comprising MSCs described herein may be used for cell-based treatments. In particular, the instant invention provides methods for treating or preventing the diseases and conditions described herein comprising administering an effective amount of a pharmaceutical preparation comprising MSCs, wherein the MSCs are derived from culturing hemangioblasts.

The MSCs of the instant invention may be administered using modalities known in the art including, but not limited to, injection via intravenous, intramyocardial, transendocardial, intravitreal, or intramuscular routes or local implantation dependent on the particular pathology being treated.

The mesenchymal stromal cells of the instant invention may be administered via local implantation, wherein a delivery device is utilized. Delivery devices of the instant invention are biocompatible and biodegradable. A delivery device of the instant invention can be manufactured using materials selected from the group comprising biocompatible fibers, biocompatible yarns, biocompatible foams, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biopolymers; homopolymers and copolymers of lactide, glycolide, epsilon-caprolactone, para-dioxanone, trimethylene carbonate; homopolymers and copolymers of lactide, glycolide, epsilon-caprolactone, para-dioxanone, trimethylene carbonate, fibrillar collagen, non-fibrillar collagen, collagens not treated with pepsin, collagens combined with other polymers, growth factors, extracellular matrix proteins, biologically relevant peptide fragments, hepatocyte growth factor, platelet-derived growth factors, platelet rich plasma, insulin growth factor, growth differentiation factor, vascular endothelial cell-derived growth factor, nicotinamide, glucagon like peptides, tenascin-C, laminin, anti-rejection agents, analgesics, anti-oxidants, anti-apoptotic agents anti-inflammatory agents and cytostatic agents.

The particular treatment regimen, route of administration, and adjuvant therapy may be tailored based on the particular pathology, the severity of the pathology, and the patient's overall health. Administration of the pharmaceutical preparations comprising MSCs may be effective to reduce the severity of the manifestations of a pathology or and/or to prevent further degeneration of the manifestation of a pathology.

A treatment modality of the present invention may comprise the administration of a single dose of MSCs. Alternatively, treatment modalities described herein may comprise a course of therapy where MSCs are administered multiple times over some period of time. Exemplary courses of treatment may comprise weekly, biweekly, monthly, quarterly, biannually, or yearly treatments. Alternatively, treatment may proceed in phases whereby multiple doses are required initially (e.g., daily doses for the first week), and subsequently fewer and less frequent doses are needed.

In one embodiment, the pharmaceutical preparation of mesenchymal stromal cells obtained by culturing hemangioblasts is administered to a patient one or more times periodically throughout the life of a patient. In a further embodiment of the instant invention, a pharmaceutical preparation of the subject MSCs (e.g., generated by culturing hemangioblasts) is administered once per year, once every 6-12 months, once every 3-6 months, once every 1-3 months, or once every 1-4 weeks. Alternatively, more frequent administration may be desirable for certain conditions or disorders. In an embodiment of the instant invention, a pharmaceutical preparation of the subject MSCs (e.g., generated by culturing hemangioblasts) is administered via a device once, more than once, periodically throughout the lifetime of the patient, or as necessary for the particular patient and patient's pathology being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

In accordance with the present invention, the diseases or conditions can be treated or prevented by intravenous administration of the mesenchymal stem cells described herein. In some embodiments, about 20 million, about 40 million, about 60 million, about 80 million, about 100 million, about 120 million, about 140 million, about 160 million, about 180 million, about 200 million, about 220 million, about 240 million, about 260 million, about 280 million, about 300 million, about 320 million, about 340 million, about 360 million, about 380 million, about 400 million, about 420 million, about 440 million, about 460 million, about 480 million, about 500 million, about 520 million, about 540 million, about 560 million, about 580 million, about 600 million, about 620 million, about 640 million, about 660 million, about 680 million, about 700 million, about 720 million, about 740 million, about 760 million, about 780 million, about 800 million, about 820 million, about 840 million, about 860 million, about 880 million, about 900 million, about 920 million, about 940 million, about 960 million, or about 980 million cells are injected intravenously. In some embodiments, about 1 billion, about 2 billion, about 3 billion, about 4 billion or about 5 billion cells or more are injected intravenously. In some embodiments, the number of cells ranges from between about 20 million to about 4 billion cells, between about 40 million to about 1 billion cells, between about 60 million to about 750 million cells, between about 80 million to about 400 million cells, between about 100 million to about 350 million cells, and between about 175 million to about 250 million cells.

The methods described herein may further comprise the step of monitoring the efficacy of treatment or prevention using methods known in the art.

Kits

The present invention provides for kits comprising any of the compositions described herein. A preparation of mesenchymal stromal cells may be contained in a delivery device manufactured according to methods known by one of ordinary skill in the art, and include methods in US Patent Application Publication 2002/0103542, European Patent Application EP 1 454 641, or preserved according to methods known by one of ordinary skill in the art, and include methods in U.S. Pat. No. 8,198,085, PCT Application WO2004/098285, and US Patent Application Publication 2012/0077181. In an embodiment of the instant invention, a kit comprising a preparation of about at least $8 \times 10^7$, $8.5 \times 10^7$, $9 \times 10^7$, $9.5 \times 10^7$, $1 \times 10^8$, $1.25 \times 10^8$, or $1.25 \times 10^8$ MSCs derived from culturing hemangioblasts. In another embodiment, a kit comprising a preparation of about $8 \times 10^7$, $8.5 \times 10^7$, $9 \times 10^7$, $9.5 \times 10^7$, $1 \times 10^8$, $1.25 \times 10^8$, or $1.25 \times 10^8$ the subject MSCs (e.g., generated by culturing hemangioblasts) is provided, wherein said preparation is pharmaceutical preparation. In a still further embodiment of the instant invention, a kit comprising a pharmaceutical preparation of about $8 \times 10^7$, $8.5 \times 10^7$, $9 \times 10^7$, $9.5 \times 10^7$, $1 \times 10^8$, $1.25 \times 10^8$, or $1.25 \times 10^8$ the subject MSCs (e.g., generated by culturing hemangioblasts) is provided, wherein said pharmaceutical preparation is preserved. In a still further embodiment of the instant invention, a kit comprising a pharmaceutical preparation of about $8 \times 10^7$, $8.5 \times 10^7$, $9 \times 10^7$, $9.5 \times 10^7$, $1 \times 10^8$, $1.25 \times 10^8$, or $1.25 \times 10^8$ the subject MSCs (e.g., generated by culturing hemangioblasts) is provided, wherein said pharmaceutical preparation is contained in a cell delivery vehicle.

Additionally, the kits may comprise cryopreserved MSCs or preparations of cryopreserved MSCs, frozen MSCs or preparations of frozen MSCs, thawed frozen MSCs or preparations of thawed frozen MSCs.

Combinations of Various Embodiments and Concepts

It will be understood that the embodiments and concepts described herein may be used in combination. For example, the instant invention provides for a method of generating MSCs comprising generating hemangioblasts from ESCs, culturing the hemangioblasts for at least four days, harvesting the hemangioblasts, re-plating the hemangioblasts on a Matrigel-coated plate, and culturing the hemangioblasts as described herein for at least fourteen days, wherein the method generates at least 85 million MSCs that are substantially free of ESCs.

EXAMPLES

The following examples are not intended to limit the invention in any way.

Example 1

Generating MSCs from Hemangioblasts

Hemangioblasts were generated from the clinical grade, single-blastomere derived ESC line, MA09 [16], as follows:

First, early-stage clusters of cells were generated from MA09 ESC cultured in serum-free medium supplemented with a combination of morphogens and early hematopoietic cytokines, specifically bone morphogenetic protein-4 (BMP-4), vascular endothelial growth factor (VEGF), basic fibroblast growth factor (bFGF), stem cell factor (SCF), thrombopoietin (Tpo) and fms-related tyrosine kinase 3 ligand (FL). More specifically, ESCs from one well of a 6-well tissue-culture treated plate were plated in one well of a six well ultra low adherence place (Corning) in 3 ml Stemline II medium (Sigma) supplemented with 50 ng/ml of VEGF and 50 ng/ml of BMP-4 (R & D) and incubated at 37° C. with 5% $CO_2$. Clusters of cells were formed within the first 24 hr. After 40-48 hours, half of the medium (1.5 ml) was replaced with fresh Stemline II medium supplemented with 50 ng/ml of VEGF, 50 ng/ml of BMP-4, and 20-22.5 ng/ml bFGF, and incubation continued for an additional 40-48 hours (i.e., 3.5-4 days total).

Clusters of cells were dissociated and plated as single cells in serum-free semisolid blast-colony growth medium (BGM). Specifically, clusters of cells were dissociated by 0.05% trypsin-0.53 mM EDTA (Invitrogen) for 2-5 min. The cell suspension was pipetted up and down and then DMEM+ 10% FCS was added to inactivate the trypsin. Cells were then passed through a 40 µm strainer to obtain a single cell suspension. Cells were then counted and resuspended in Stemline II medium at $1-1.5 \times 10^6$ cells/ml.

The single cell suspension (0.3 ml, 3 to $4.5 \times 10^5$ cells) was mixed with 2.7 ml of hemangioblast (HB) Growth Medium (H4536 based medium recipe: base medium methycellulose product H4536 (StemCell Technologies) plus penicillin/ streptomycin (pen/strp), Excyte growth supplement (Millipore), and the cytokines, Flt3-ligand (FL) at 50 ng/ml, vascular endothelial growth factor (VEGF) at 50 ng/ml, thrombopoietin (TPO) at 50 ng/ml, and basic fibroblast growth factor (bFGF) at 20 ng/ml) with a brief vortex, and let stand for 5 min. The cell mixture was then transferred to one well of a six-well ultra low adherence plate by using a syringe (3 ml) attached with an 18G needle, and incubated at 37° C. with 5% $CO_2$.

Some of the cells developed into grape-like blast colonies (BCs). Specifically, BCs were visible at 3 days (typically contained less than 10 cells at the beginning of day 3), and after 4-6 days, grape-like hES-BCs were easily identified under microscopy (containing greater than 100 cells per BC). The number of BCs present in the culture gradually increased over the course of several days. After 6-7 days, BCs could be picked up using a mouth-glass capillary.

Figure 2:
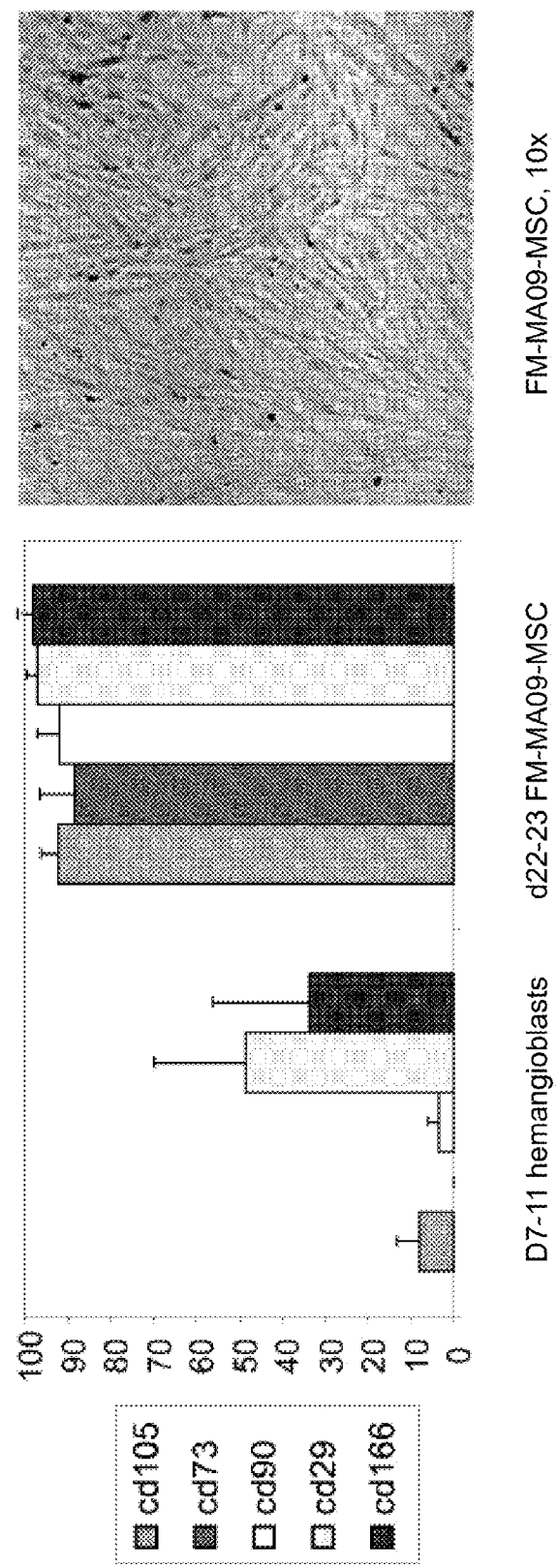
FIG. 2. A phenotype of FM-MA09-MSC obtained from pluripotent cell-derived hemangioblasts. This figure shows the percentage of cells positive for MSC surface markers in the initial hemangioblast population (left side of graph, day 7-11 hemangioblast) and after culturing hemangioblasts on Matrigel coated plates (right side of graph) and a microscopic view of the mesenchymal stromal cells derived from the hemangioblasts (right panel photograph).

Hemangioblasts can be harvested between days 7-12 of culture and replated onto Matrigel-coated tissue culture plates in α MEM+20% FCS. Flow cytometry analysis shows that expression levels of 5 cell surface markers typically found on MSCs are relatively low in the starting hemangioblast population. (FIG. 2, left panel, average of 4 experiments+/−standard deviation). However, after three weeks of culture in MSC growth conditions, a homogenous adherent cell population arises that stains>90% positive for these 5 characteristic MSC markers (FIG. 2, right panel—22-23 days, average of 4 experiments+/−standard deviation). Upon MSC culture conditions, the amount of time it takes for differentiating cells to acquire MSC surface markers may vary depending on the specific ESC line used, the day of hemangioblast harvest, and the number of hemangioblasts plated onto Matrigel. In some experiments, markers arise in 90% of the cells by 7-14 days, whereas in other experiments, it may take 22-24 days for this many cells to acquire these MSC markers.

Figure 17:
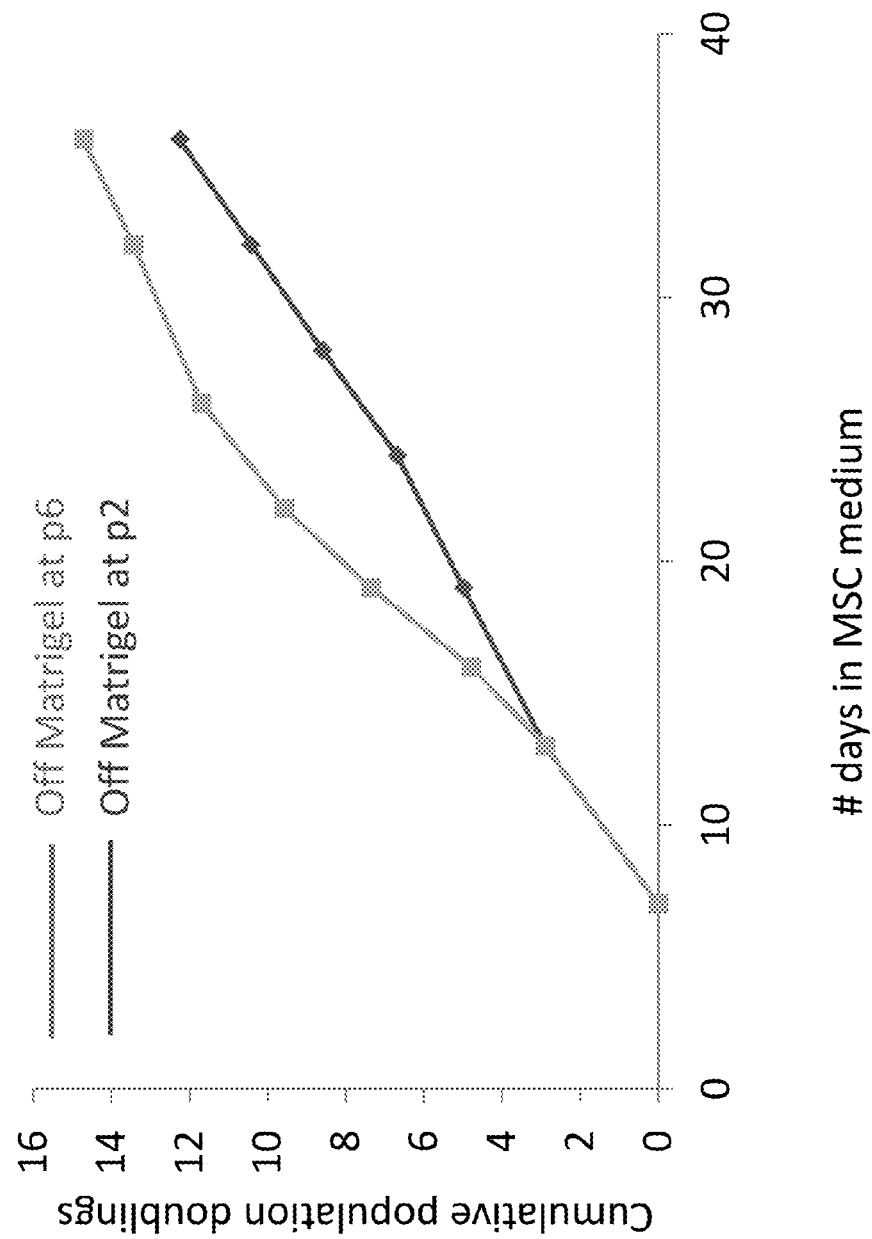
FIG. 17. Process of FM-MA09-MSC generation; Matrigel effect. Removing cells from Matrigel at an early passage (i.e., p2) may temporarily slow MSC growth as compared to those maintained on Matrigel until p6.

Relating to the above experiments, FIG. 1 shows the generation of FM-MA09-MSC from pluripotent cells, and a microscopic view of generating mesenchymal stromal cells from ESCs via hemangioblasts. In addition, FIG. 2 contains a phenotype of FM-MA09-MSC obtained from pluripotent cell-derived hemangioblasts produced as above-described. This figure shows the percentage of cells positive for MSC surface markers in the initial hemangioblast population (left side of graph, day 7-11 hemangioblast) and after culturing hemangioblasts on Matrigel coated plates (right side of graph) and a microscopic view of the mesenchymal stromal cells derived from the hemangioblasts (right panel photograph). Also, relating to the above experiments FIG. 17 depicts the process of FM-MA09-MSC generation; and the effects of Matrigel, i.e., that removing cells from Matrigel at an early passage (ie, p2) may temporarily slow MSC growth as compared to those maintained on Matrigel until p6.

Figure 18:
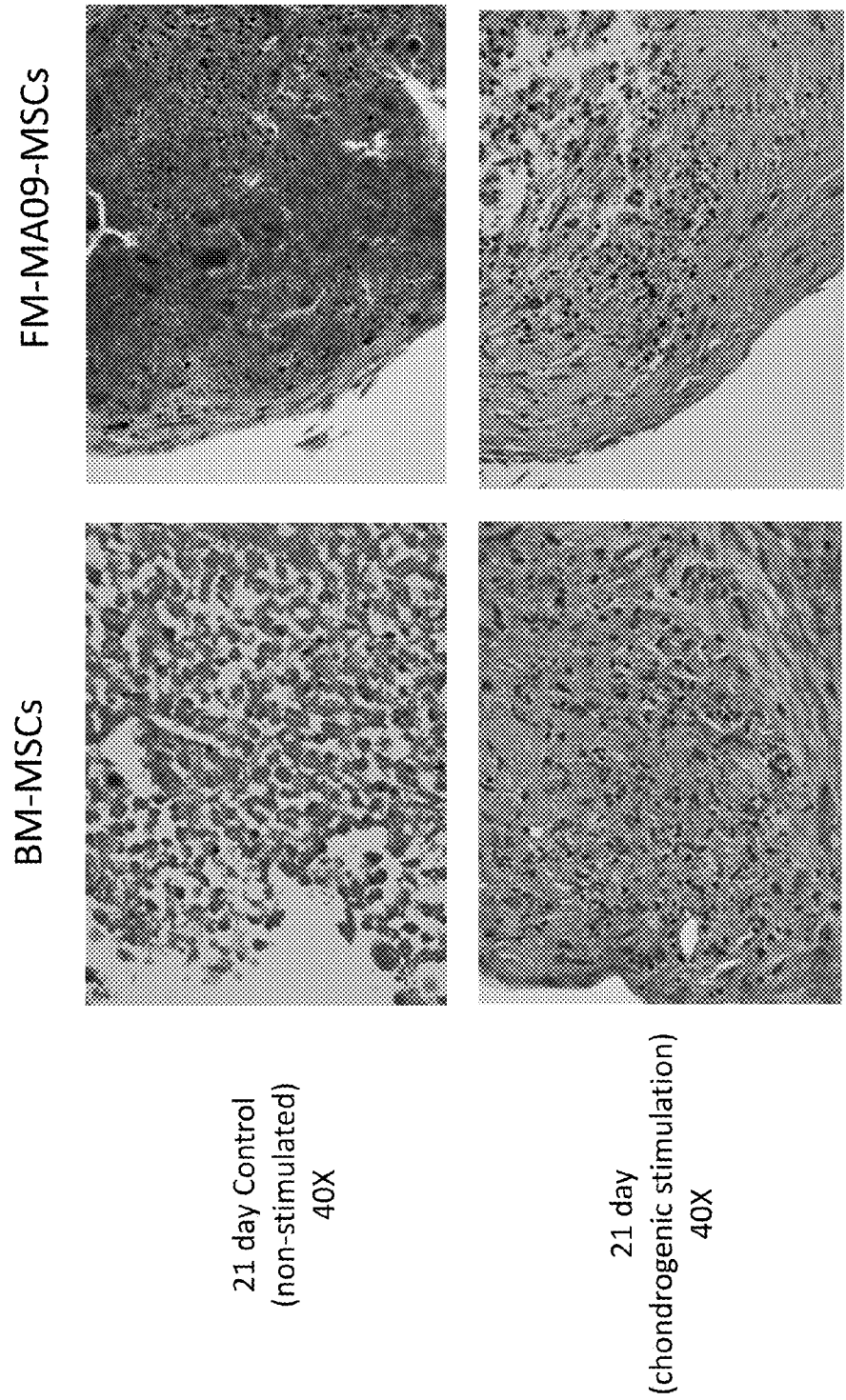
FIG. 18. BM-MSCs and FM-MA09-MSCs undergo chondrogenesis. Safranin O staining (indicative of cartilaginous matrix deposition) was performed on paraffin-embedded pellet mass cultures after 21 days. Images are 40× magnification.

FIG. 18 further shows that the obtained BM-MSCs and FM-MA09-MSCs undergo chondrogenesis.

Example 2

Comparison of Differentiation of ESCs and MSC-Derived Hemangioblasts

Figure 3:
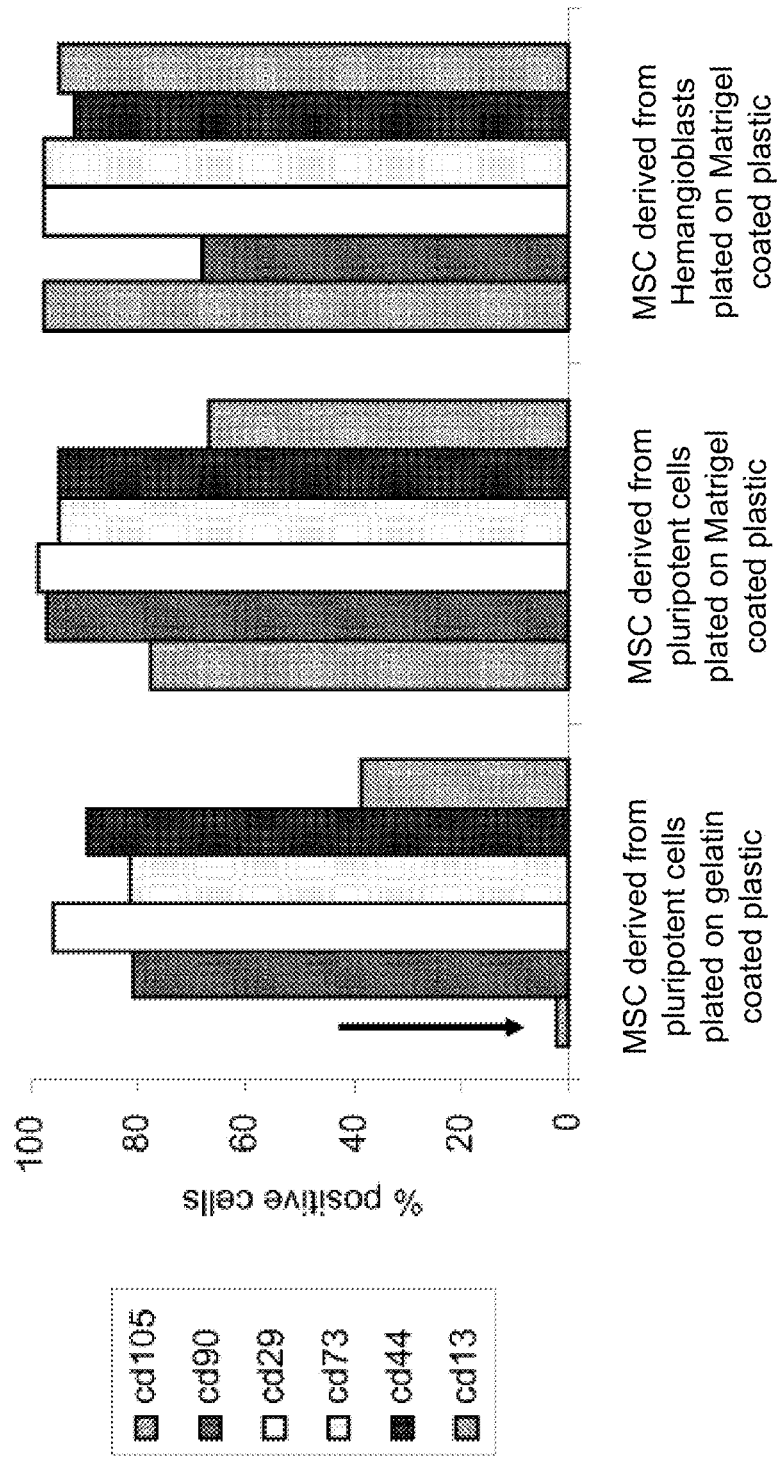
FIG. 3. Phenotypes of mesenchymal stromal cells derived from different culture methods. This figure shows the percentage of cells positive for MSC surface markers after culturing human embryonic stem cells (ESC) on gelatin coated plates (left panel), ESC on Matrigel coated plates (middle panel), and hemangioblasts on Matrigel coated plates (right panel).

This example describes comparison of the differentiation of ESCs into MSCs by two methods: either direct differentiation (in which ESCs were directly plated on gelatin or Matrigel) or the hemangioblast method (in which ESCs were first differentiated into hemangioblasts and then plated on Matrigel, as described in Example 1). Direct differentiation on gelatin gave rise to MSC-like cells, but the cells lacked CD105 expression, suggesting incomplete adoption of MSC fate (FIG. 3, left panel). When ESCs were plated directly on Matrigel, the resulting cells did express CD105 as expected for MSCs (FIG. 3, middle panel). However, compared to MSCs produced by the hemangioblast method, the directly differentiated MSCs cells grew in clumps, were more difficult to disperse when splitting, and did not generate nearly as many MSCs when starting from equivalent numbers of ESCs (FIG. 4).

Figure 6:
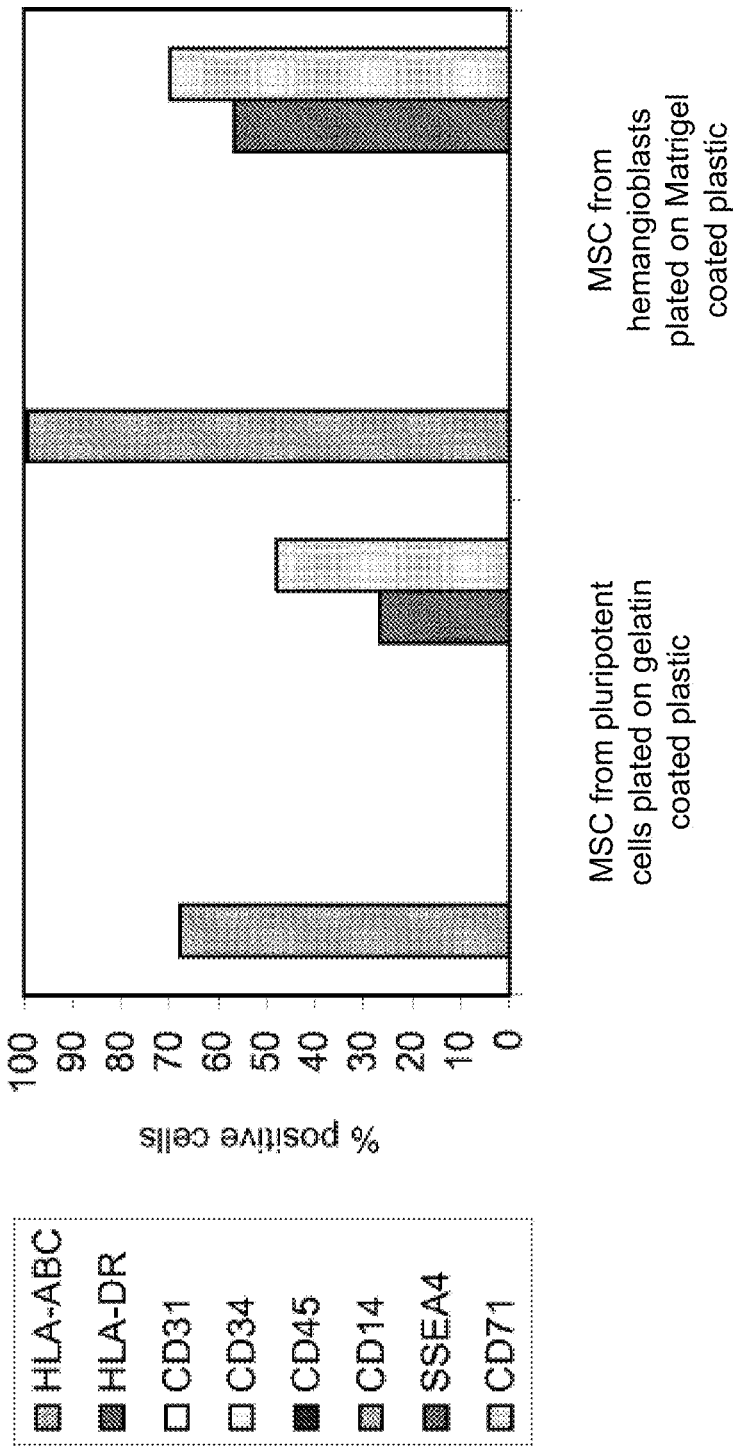
FIG. 6. Phenotypes of mesenchymal stromal cells derived from different culture methods. This figure shows the percentage of cells positive for MSC markers and negative for hematopoiesis and endothelial markers after culturing ESC on Matrigel coated plates (left panel) and hemangioblasts on Matrigel coated plates (right panel).

MSCs differentiated directly from ESCs also took longer to acquire characteristic MSC cell surface markers (FIG. 5). Once MSCs were obtained, extended immunophenotyping shows that MSCs from both methods are positive for other markers typically found on MSCs, such as HLA-ABC, while negative for hematopoiesis-associated markers such as CD34 and CD45 (FIG. 6). These results suggest that use of a hemangioblast-intermediate stage permits robust production of homogeneous MSCs from ESCs. Given these findings, additional studies on MSCs will be conducted with hemangioblast-derived MSCs.

Figure 13:
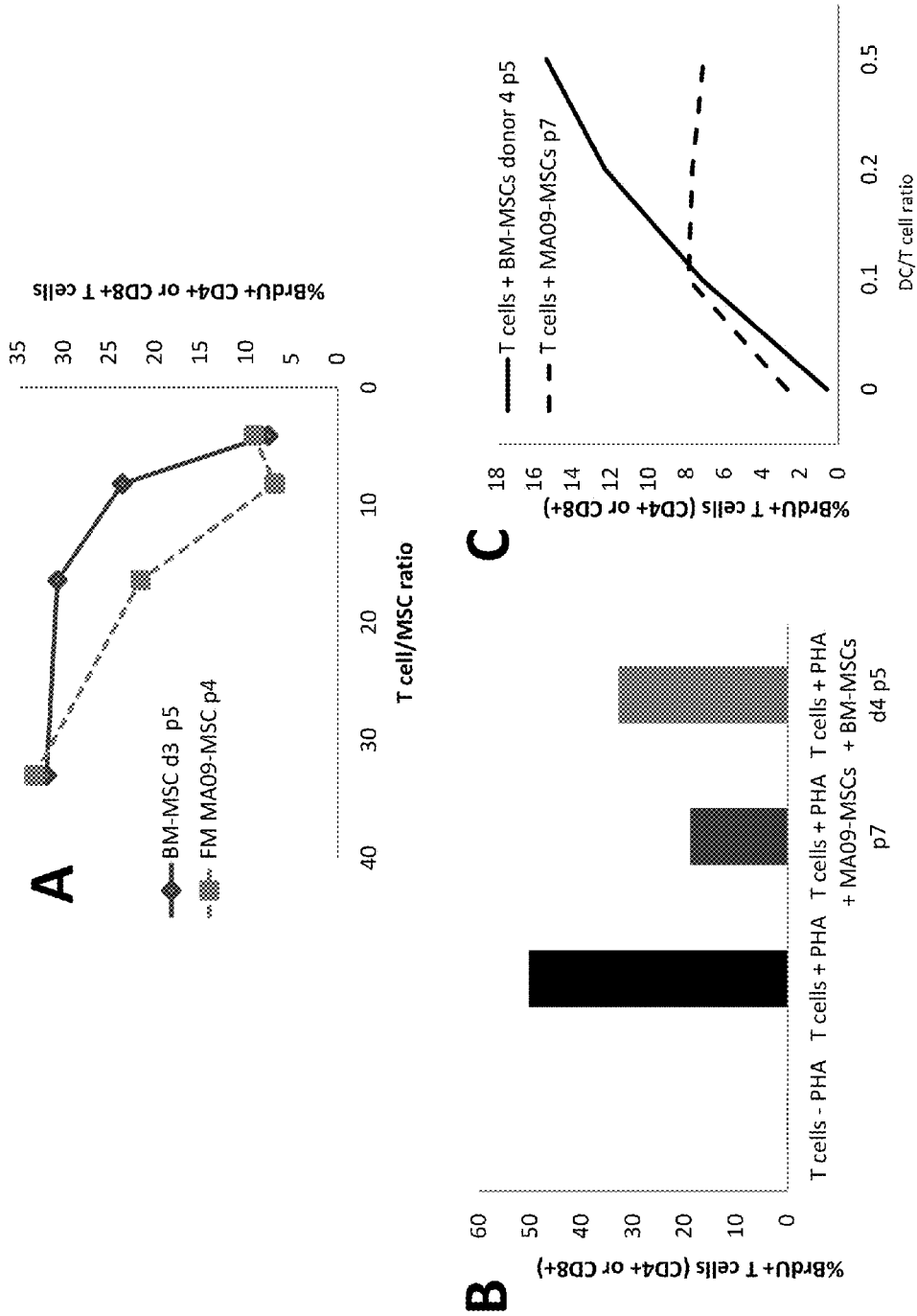
FIG. 13. Increased potency, greater inhibitory effects of FM-MA09-MSCs as compared to BM-MSCs. FM-MA09-MSCs exert greater inhibitory effects on T cell proliferation than do BM-MSCs. (A.) Increasing the amount of MSCs in co-culture with PBMCs causes a dose-dependent reduction in T cell proliferation in response to PMA and ionomycin. Young (p4) FM-MA09-MSCs are the most potent of all cell types tested. (B.) FM-MA09-MSCs inhibit T cell proliferation to a greater degree than do BM-MSCs in response to PHA. A 5:1 ratio of PBMCs:MSCs were co-cultured for 6 days. (C.) FM-MA09-MSCs inhibit T cell proliferation in response to increasing amounts of dendritic cells better than do BM-MSCs. In (A-C), percent T cell proliferation was assessed by BrdU incorporation in the CD4+ and/or CD8+ cell population.
Figure 15:
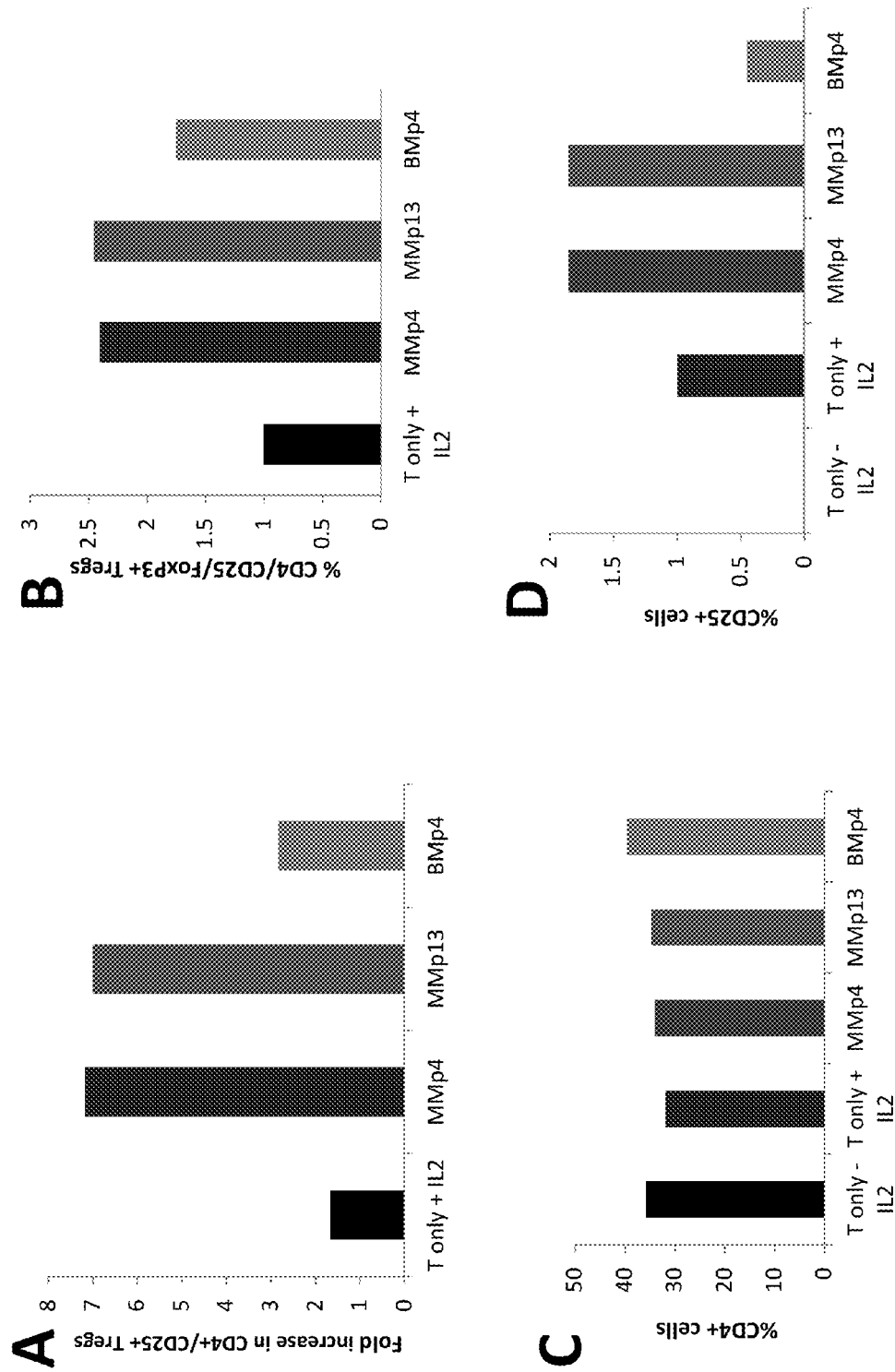
FIG. 15. Enhanced Treg expansion by FM-MA09-MSCs as compared to BM-MSCs. FM-MA09-MSCs induce Treg expansion better than do BM-MSCs. (A.) Fold increase in CD4/CD25 double positive Tregs. The minus IL2 condition was set to 1 and other groups are expressed as fold induction over this level. MM=MA09-MSCs, BM=bone marrow MSCs. "p"=passage number. (B.) FM MA09-MSCs (MM) induce CD4/CD25/FoxP3 triple positive Tregs better than do BM-MSCs. (C.) Percent of responding PBMCs that are CD4+ are consistent among the different treatment groups. (D.) Percent of responding PBMCs that are CD25+ vary among the different treatment groups. FM-MA09-MSCs induce greater expression of CD25 than do BM-MSCs. This difference may explain the difference in induction of Tregs.
Figure 16:
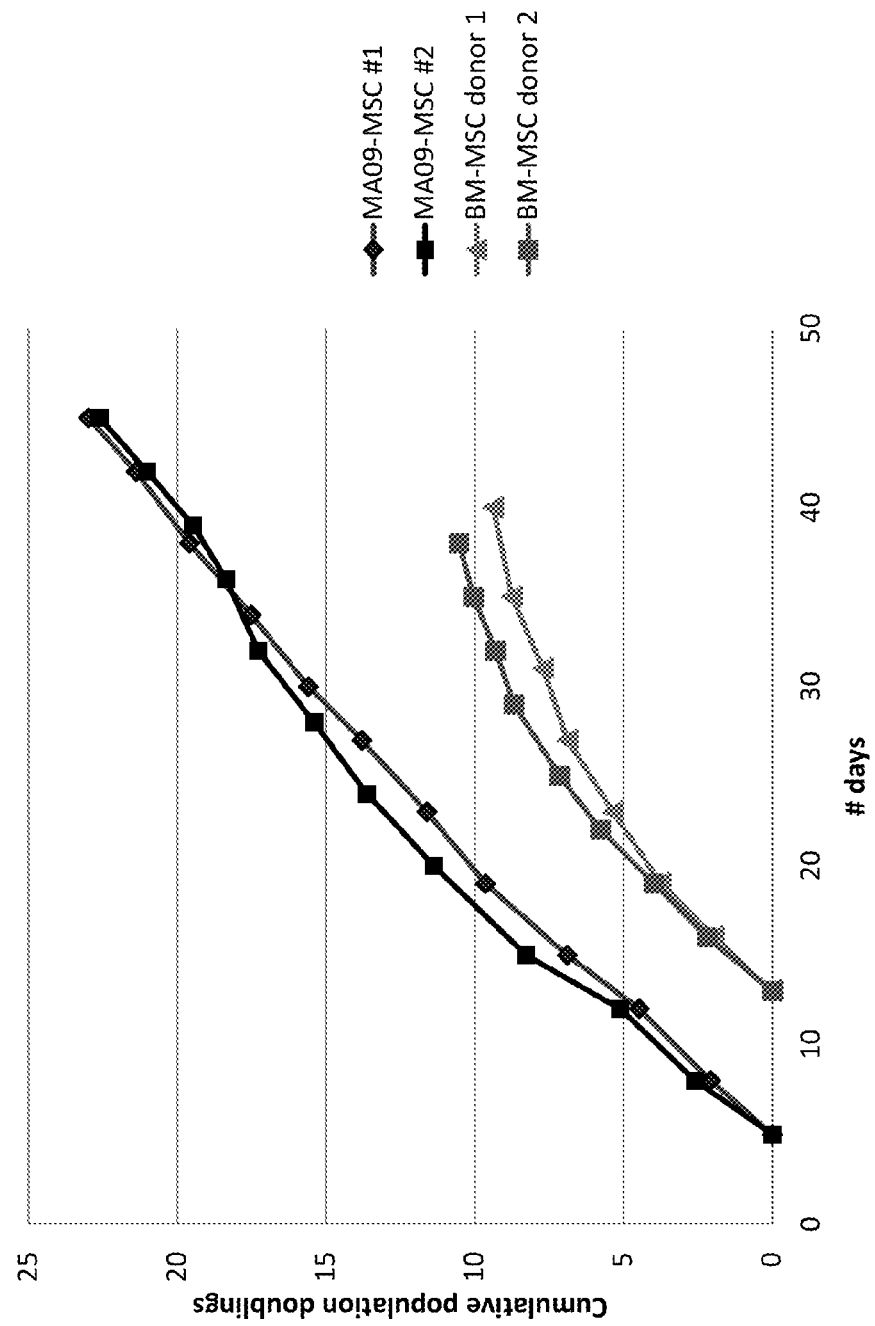
FIG. 16. FM-MA09-MSCs have greater proliferative capacity than BM-MSCs. FM-MA09-MSCs have a greater proliferative capacity than do BM-MSCs. Cumulative population doublings are plotted against the number of days in culture. After initial plating of ESC-derived hemangioblasts or bone marrow-derived mononuclear cells, adherent cells were considered p0 MSCs. Successive MSC passages were replated at a density of 7000 cells/sq cm and harvested when the cultures were approximately 70% confluent (every 3-5 days).
Figure 19:
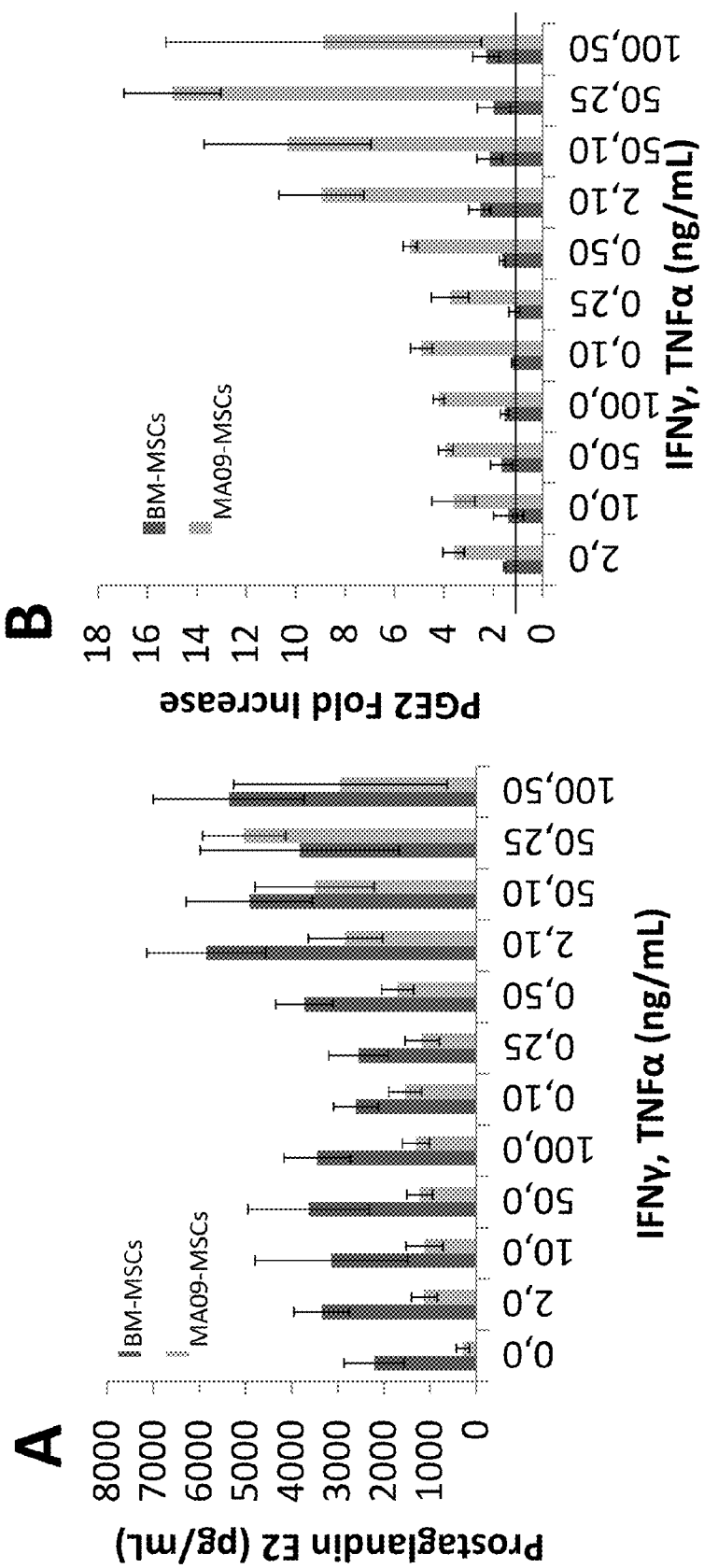
FIG. 19. In the basal state, FM-MA09-MSCs secrete less PGE2 than do BM-MSCs yet the fold increase upon IFNγ or TNFα stimulation is greater. (A.) The amount of prostaglandin E2 secretion (pg/ml) is shown for BM-MSCs versus FM-MA09-MSCs under basal or various stimulation conditions. PGE2 amounts are normalized to cell number. (B.) Basal PGE2 values are set to 1 (black line) and PGE2 secretion under various stimuli are expressed as fold increase over basal level.
Figure 22:
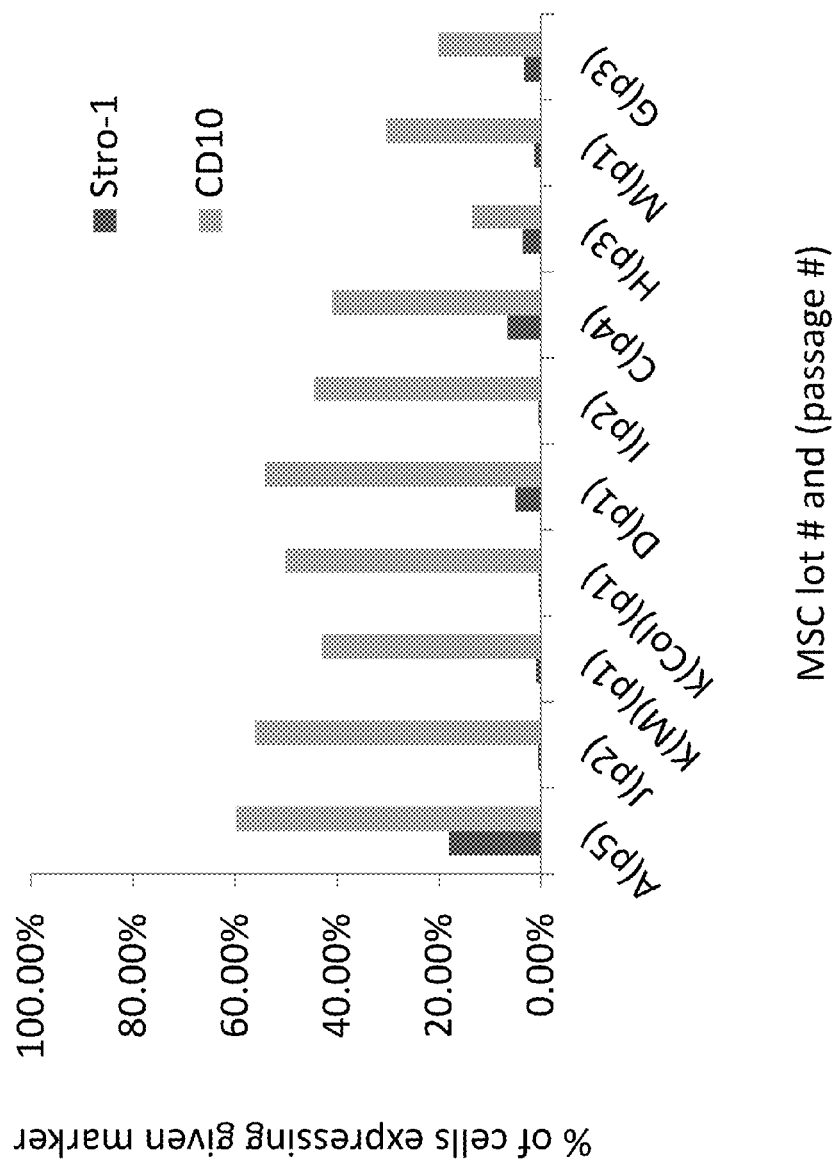
FIG. 22. Stro-1 and CD10 expression in 10 different lots of early passage FM-MA09-MSCs consistently show low Stro-1 and mid-range CD10 expression. Flow cytometry analysis of different MSC populations. Ten different lots of FM-MA09-MSCs were evaluated at the indicated passage number for expression of Stro-1 and CD10. Stro-1 expression is consistently low in the different lots of FM-MA09-MSCs (average of 5-10%). CD10 expression is consistently at amid-range level in the different lots of FM-MA09-MSCs (average of approximately 40%).
Figure 23:
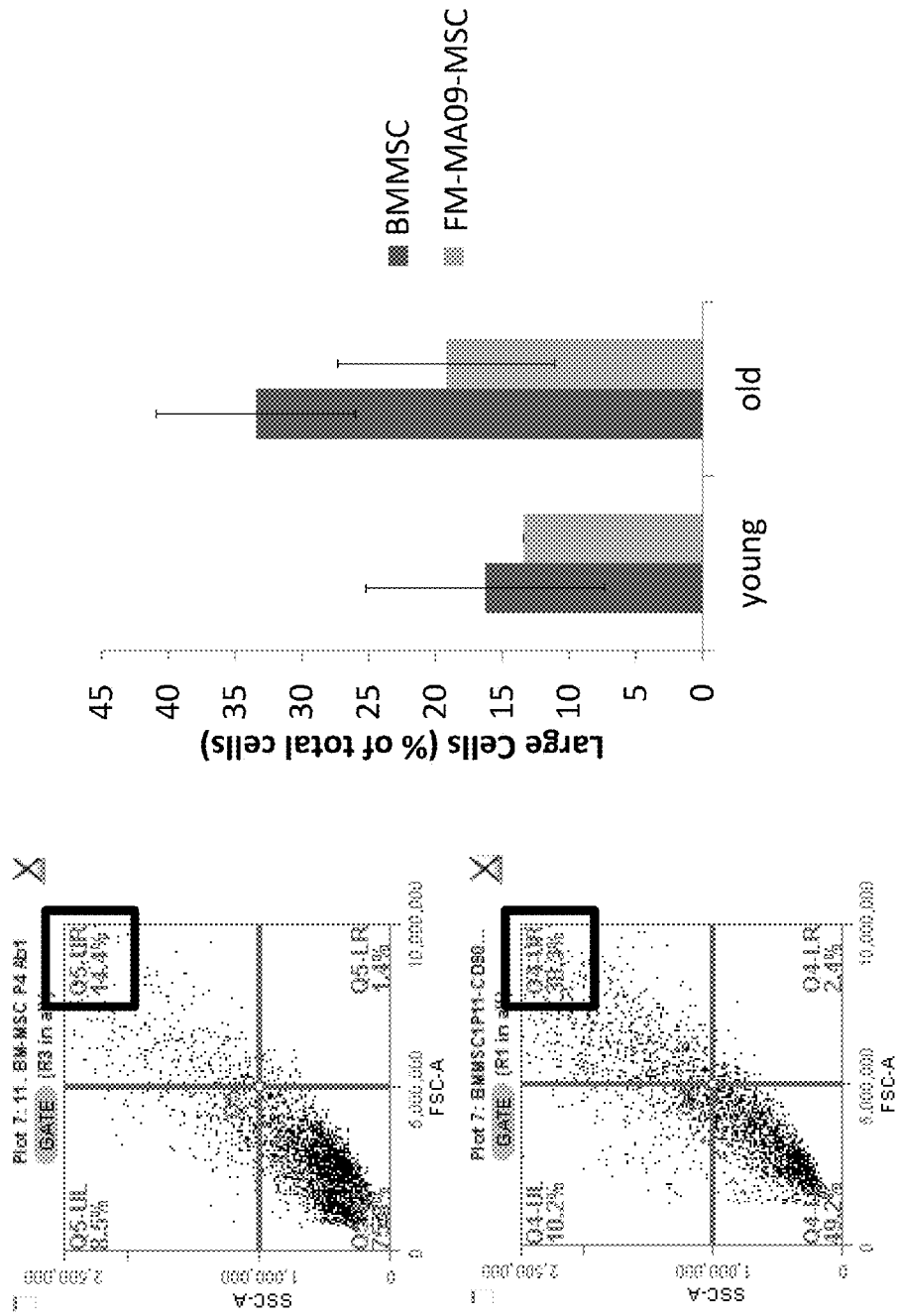
FIG. 23. FM-MA09-MSCs maintain their size as they age in culture while BM-MSC cell size increases with age. Forward scatter/side scatter dot plots on flow cytometry (shown on the left) were used to capture the size of MSCs. The percentage of cells in the upper right quadrant "large" cells were monitored and are displayed in the bar graph.
Figure 24:
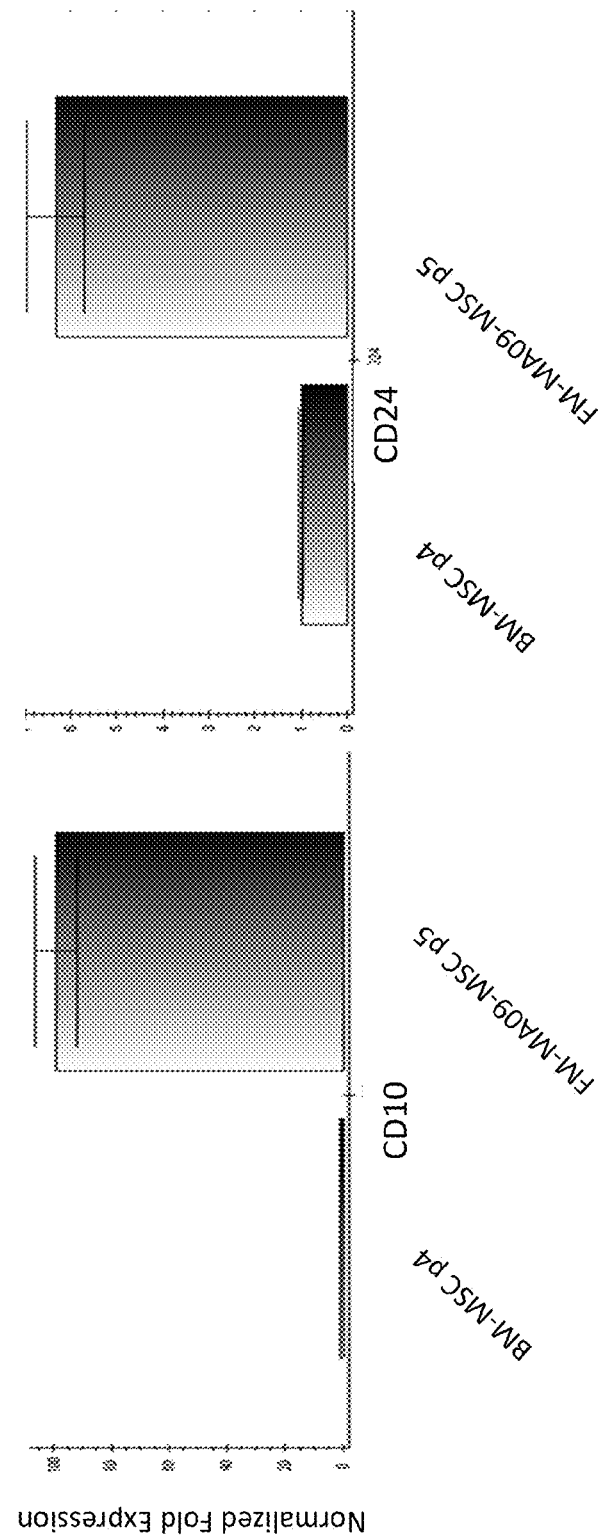
FIG. 24. CD10 and CD24 are upregulated in FM-MA09-MSCs as compared to BM-MSCs. Gene expression analysis is shown for BM-MSCs and FM-MA09-MSCs in the basal state. Quantitative RT-PCR with Taqman probes was used to assess the expression of the indicated genes and normalized to two housekeeping genes. The average of quadruplicate readings is shown +/−standard deviation.
Figure 25:
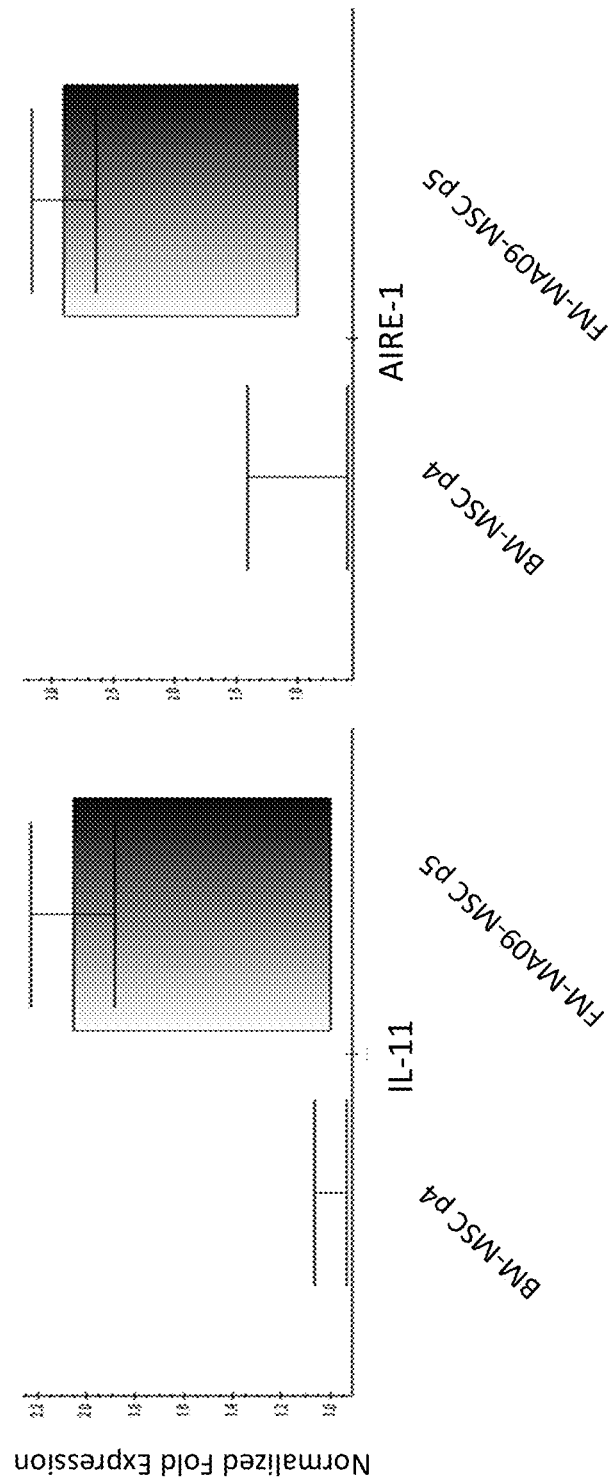
FIG. 25. Aire-1 and IL-11 are upregulated in FM-MA09-MSCs as compared to BM-MSCs. Gene expression analysis is shown for BM-MSCs and FM-MA09-MSCs in the basal state. Quantitative RT-PCR with Taqman probes was used to assess the expression of the indicated genes and normalized to two housekeeping genes. The average of quadruplicate readings is shown +/−standard deviation.
Figure 26:
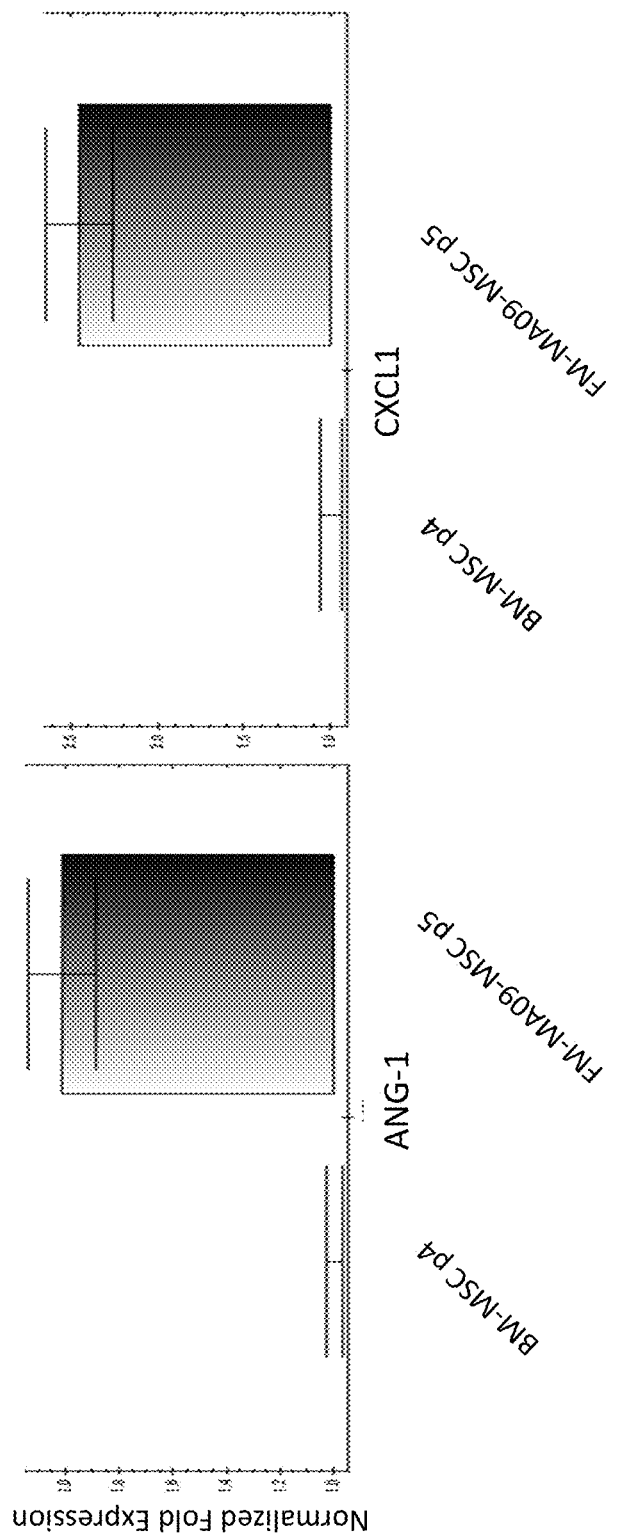
FIG. 26. Ang-1 and CXCL1 are upregulated in FM-MA09-MSCs as compared to BM-MSCs. Gene expression analysis is shown for BM-MSCs and FM-MA09-MSCs in the basal state. Quantitative RT-PCR with Taqman probes was used to assess the expression of the indicated genes and normalized to two housekeeping genes. The average of quadruplicate readings is shown +/−standard deviation.
Figure 27:
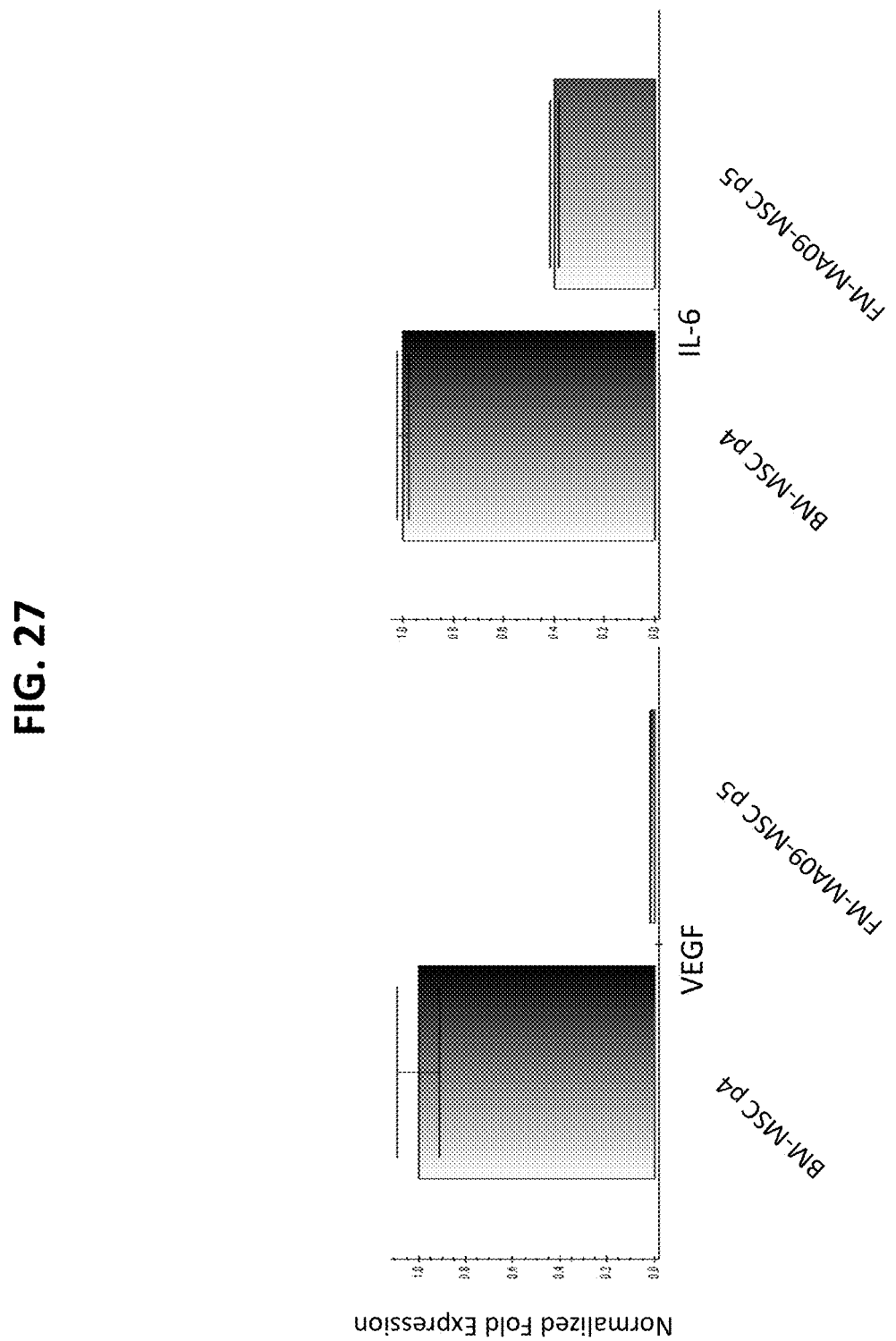
FIG. 27. IL6 and VEGF are downregulated in FM-MA09-MSCs as compared to BM-MSCs. Gene expression analysis is shown for BM-MSCs and FM-MA09-MSCs in the basal state. Quantitative RT-PCR with Taqman probes was used to assess the expression of the indicated genes and normalized to two housekeeping genes. The average of quadruplicate readings is shown +/−standard deviation.

In addition, experiments the results of which are contained in FIGS. 3-6, 13, 15, 16, 19, and 21-27 (described supra) compare different properties of ESC-MSCs or BM-MSCs versus hemangioblast-derived MSC's and reveal that these cells exhibit significant differences which may impact therapeutic efficacy of these cells and compositions derived therefrom. Particularly, FIG. 3 shows the percentage of cells positive for MSC surface markers after culturing human embryonic stem cells (ESC) on gelatin coated plates (left panel), ESC on Matrigel coated plates (middle panel), and hemangioblasts on Matrigel coated plates (right panel). Additionally, FIG. 4 shows the MSC yield from pluripotent cells, FIG. 5 illustrates the acquisition of mesenchymal stromal cell markers, and FIG. 6 shows phenotypes of mesenchymal stromal cells derived from different culture methods, including expression of MSC markers and lack of expression of hematopoiesis and endothelial markers. Further, FM-MA09-MSCs were assayed to detect notable differences (relative to BM-MSCs) in potency and inhibitory effects (FIG. 13), stimulation of Treg expansion (FIG. 15), proliferative capacity (FIG. 16), PGE2 secretion (FIG. 19), Stro-1 and CD10 expression (FIGS. 21-22), maintenance of size during passaging (FIG. 23), CD10 and CD24 expression (FIG. 24), Aire-1 and IL-11 expression (FIG. 25), Ang-1 and CXCL1 expression (FIG. 26), and IL6 and VEGF expression (FIG. 27).

Example 3

MSCs Derived from Hemangioblasts Differentiate into Other Cell Types

Figure 7:
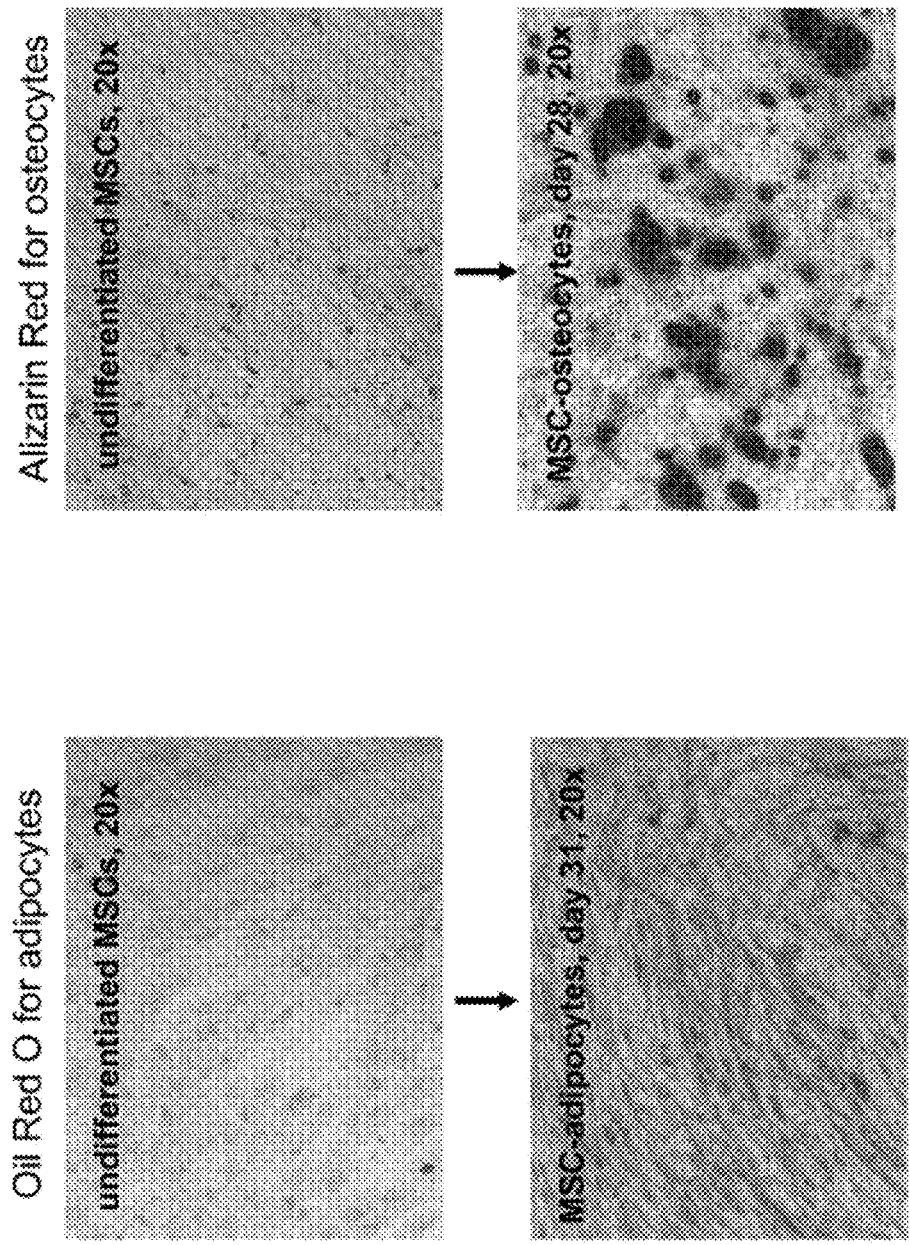
FIG. 7. FM-MA09-MSC display differentiation capabilities. This figure depicts the differentiation capabilities of mesenchymal stromal cells derived from hemangioblasts differentiated from MA09 ESC to form adipocytes and osteocytes.
Figure 8:
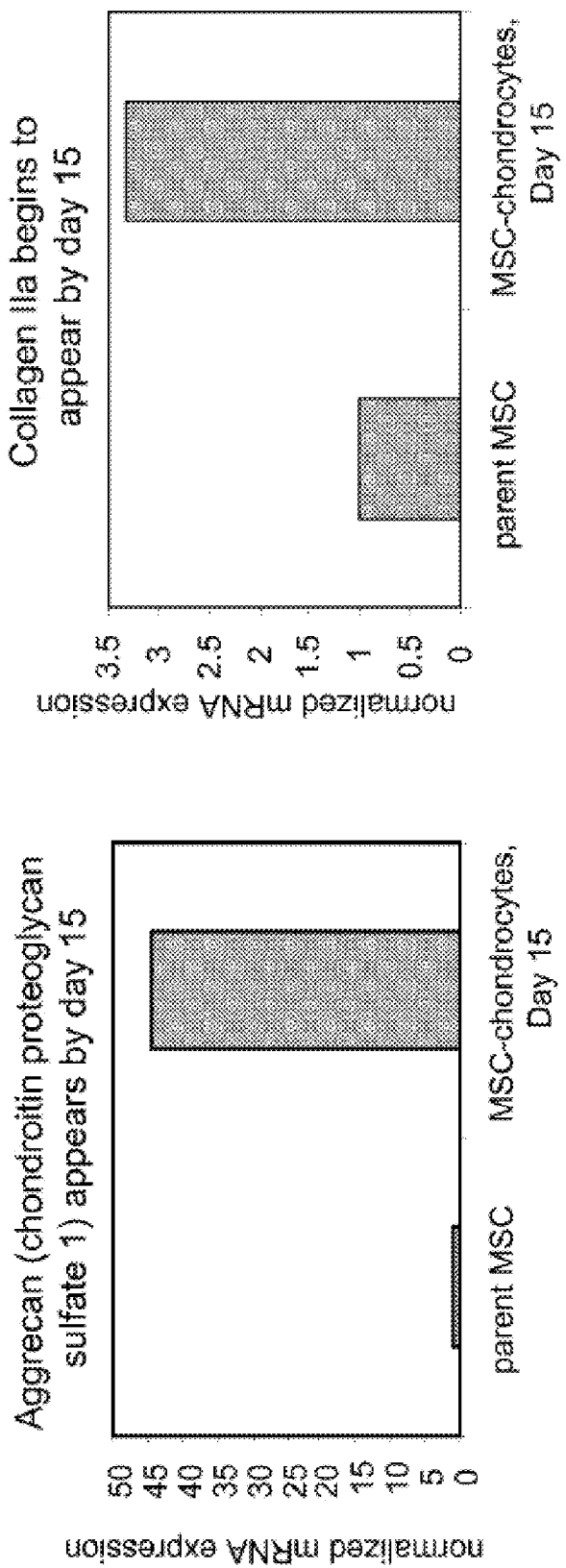
FIG. 8. MSC chondrogenic differentiation. This figure depicts chondrogenic differentiation of MA09 ESC hemangioblast-derived mesenchymal stromal cells by mRNA expression of Aggrecan (chondroitin proteoglycan sulfate 1) and Collagen IIa.

MSCs, by definition, should be able to give rise to adipocytes, osteocytes, and chondrocytes. Using standard methods, FIG. 7 shows the ability of hemangioblast-derived MSCs to differentiate into adipocytes and osteocytes, while FIG. 8 shows their potential to differentiate towards chondrocytes via the expression of chondrocyte-specific genes and FIG. 18 shows their potential to differentiate towards chondrocytes via safranin O staining of pellet mass cultures.

MSCs derived from hemangioblasts are expected to differentiate into adipocytes, osteocytes, and chondrocytes. These differentiation pathways may be examined using methods previously reported in the art. See Karlsson et al, Stem Cell Research 3: 39-50 (2009) (for differentiation of the hemangioblast-derived and direct ESC-derived MSCs into adipocytes and osteocytes). Particularly, FM-MA09-MSC display differentiation capabilities including the ability to differentiate into adipocytes and osteocytes (FIG. 7). For chondrocyte differentiation, methods have been adapted from Gong et al, J. Cell. Physiol. 224: 664-671 (2010) to study this process and continue to examine the acquisition of chondrocyte specific genes, (e.g., Aggrecan and Collagen IIa) as well as glycosaminoglycan deposition through safranin O, alcian blue, and/or toluene blue staining Particularly, chondrogenic differentiation of MA09 ESC hemangioblast-derived mesenchymal stromal cells (FM-MA09-MSC) was detected by mRNA expression of Aggrecan (chondroitin proteoglycan sulfate 1) and Collagen IIa (FIG. 8). It has been reported in the literature that none of these three cell types, adipocytes, osteocytes, or chondrocytes derived from MSCs will express the immunostimulatory HLA DR molecule (Le Blanc 2003, Gotherstrom 2004, Liu 2006). Immunostaining and/or flow cytometry will be performed on these fully differentiated MSC cell types to confirm these reported observations. This is important to confirm so that differentiation of MSCs in an in vivo environment will not induce an immune response from the host recipient. Of these three cell types, chondrogenic differentiation may be of particular interest due to its potential to be used in cartilage replacement therapies for sports injuries, aging joint pain, osteoarthritis, etc. For such therapies, MSCs may not need to be fully differentiated into chondrocytes in order to be used therapeutically.

Example 4

Confirmation that MSCs Derived from Hemangioblasts are Substantially Free of ESCs MSCs should also be devoid of the ESC propensity to form teratomas. MSCs were confirmed to contain normal karyotypes (data not shown) by passage 12 (~50 days in culture). To confirm that the blast-derived MSCs do not contain trace amounts of ESCs, teratoma formation assays were performed in NOD/SCID mice. $5 \times 10^6$ MSCs are injected subcutaneously into the left thigh muscle of 3 mice. CT2 ECs were used as positive controls and the mice will be monitored over the course of 6 weeks to compare teratoma formation in MSC versus ESCC-injected mice. No teratomas formed in the mice injected with MSCs.

Example 5

Reduction of EAE Scores by MSCs Derived from Hemangioblasts

A pilot study to treat experimental autoimmune encephalomyelitis (EAE) on 6-8 weeks old C57BL/6 mice with the hemangioblast-derived ESC-MSCs was conducted. EAE was induced by s.c. injection into the flanks of the mice on day 0 with 100 pL of an emulsion of 50 pg of myelin oligodentricyte glycoprotein MOG (35-55) peptide and 250 pg of *M. tuberculosis* in adjuvant oil (complete Freund's adjuvant, CFA), the mice were also i.p. injected with 500 ng of pertussis toxin. Six days later the mice were i.p. injected with either one million ESC-MSCs in PBS (n=3) or the vehicle as a control (n=4). The clinical scores of the animals were recorded for 29 days post the immunization. A remarkable reduction of the disease scores was observed (data not shown).

Example 6

Confirmation of the Efficacy of Hemangioblast-Derived ESC-MSCs in EAE Treatment and Use of Additional Animal Models of Disease A. Test ESC-MSCs on EAE Models in Mice to Confirm their Anti-EAE Effect.

To confirm the results obtained in Example 5, additional tests are conducted with increased animal numbers, varying cell doses, different administration protocols, and more controls. Clinical score and mortality rate are recorded. The degree of lymphocyte infiltration in the brain and spinal cord of mice will also be assessed. MSC anti-EAE effects are generally thought to involve immunosuppressive activities such as the suppression of Th17 cells and would be expected to reduce the degree of lymphocyte infiltration in the CNS.

B. Compare ESC-MSCs with Mouse Bone Marrow (BM)-MSCs, Human BM-MSCs and Human Umbilical Cord Derived (UCB)-MSCs.

Mouse BM-MSCs were the first to be used for EAE treatment and have been thoroughly studied [1]. ESC-MSCs (given their xenogenic nature) may be directly compared with murine BM-MSCs for anti-EAE efficacy. Human UCB-MSCs have been shown to also possess immunosuppressive activity [19]. The anti-EAE activity of human UCB-MSCs and human BM-MSCs may also be compared with that of ESC-MSCs in the EAE mouse models. The age or passage number of these various cell types may influence their anti-EAE behavior, thus we will also evaluate the consequences of age on the efficacy of MSCs in the EAE mouse model system.

C. Optimize the Administration Dose, Route, and Timing of ESC-MSCs.

Injection of the ESC-MSCs can reduce the scores of EAE as recorded within 29 days after immunization. To study long-term prevention and cure of disease, ESC-MSCs may be administered at various doses, routes, and times.

MSCs have been generated from H1gfp ESCs and confirmed that they still express GFP in the MSC state. EAE mice can be injected with these GFP+ ESC-MSCs and their distribution can be tracked in vivo by using a Xenogen In Vivo Imaging System. Through these approaches, various administration doses, routes, and timing of ESC-MSCs will be analyzed and provide information as to the mechanism of action for MSCs anti-EAE activity (ie, paracrine or endocrine effects), longevity of the MSCs within the mice and MSC biodistribution and routes of elimination/clearance.

Anti-EAE effects may be reflected by one or more of reduced clinical scores, increased survival, and/or attenuated lymphocyte infiltration and demyelination of the CNS. Different ESC lines may have different intrinsic abilities to generate MSCs. Therefore, multiple ESC lines may be used in this study and acquisition of MSC markers can be monitored over time and compared for each ESC line. To further reduce variations between experiments with ESC-MSCs, large stocks of frozen ESC-MSCs can be made in aliquots and each stock of aliquots can be used in multiple experiments.

D. Confirm Efficacy of Hemangioblast-Derived MSCs in Other Disease Models.

As mentioned above, MSCs may also have therapeutic activity against other types of autoimmune disorders such as Crohn's disease, ulcerative colitis, and the eye-disorder, uveitis. Animal models for these diseases exist and are well known in the art (see, e.g., Pizarro et al 2003, Duijvestein et al 2011, Liang et al 2011, Copland. et al 2008). In vivo studies may be expanded to include an assessment of MSC therapeutic utility in one or more of these animal model systems. Such models may allow us to examine the cytokine secretion profile of human MSCs by isolating and screening the serum of injected animals for human cytokines Particularly, the uveitis model may be useful as a local intravitreal injection may allow us to study the effects of MSCs in a non-systemic environment.

MSCs may also have great therapeutic utility in treating osteoarthritis conditions, including those that involve loss of articular cartilage and inflammation of the affected joints (Noth et al, 2008). Models for examining osteoarthritis, cartilage loss and joint inflammation are well known in the art (see, e.g., Mobasheri et al 2009). In some of these studies, human BM-MSCs are encapsulated in semi-solid scaffolds or microspheres and transplanted into an affected joint in human subjects to determine if the MSCs have a local, non-systemic therapeutic effect in terms of reduced inflammation and/or restoration of cartilage (Wakitani et al 2002). Such methods will assist in determining the therapeutic utility of our ESC hemangioblast-derived MSCs for treating degenerative joint conditions.

The life span of injected MSCs is very short [8], which indicates that long-term survival of the transplanted cells is not required. Thus, mitotically-inactivated ESC-MSCs (e.g., irradiated or treated with mitomycin C) may also be tested for an anti-EAE effect or other anti-disease effect in the animal models mentioned above. If so, live ESC-MSCs may not be needed, thus further decreasing the biosafety concern from potential residual ESC contamination in the transplanted ESC-MSCs.

E. Results

MSCs from different donor derive sources (mouse BM-MSCs, human BM-MSCs and human UCB-MSCs) are expected to harbor anti-EAE effects. However, their effects may vary between experiments as the MSCs are from donor-limited sources. In contrast, the ESC-MSCs of the present disclosure may have more consistent effects. Because many cell surface markers are used to characterize MSCs and not every MSC expresses all the markers, a subset of markers, e.g., CD73+ and CD45− may be used in order to compare efficacy of MSCs from different sources.

ESC-MSCs are expected to have therapeutic utility in animal models of Crohn's Disease, ulcerative colitis, and uveitis as these contain autoimmune components and inflammatory reactions.

Mitotically inactivated MSCs (e.g. irradiated or mitomycin C inactivated MSCs and/or ESC-MSCs) may retain, at least partially, the immunosuppressive function since they still secret cytokines and express cell surface markers that are related to the function [29]. Their effect may, however, be decreased due to their shortened life span in vivo. If so, the dose of irradiated or other mitotically inactivated cells and administration frequency may be increased to enhance the immunosuppressive function.

A second pilot study to treat EAE was conducted. Eight to ten week old C57BL/6 mice were immunized with the MOG35-55 peptide in complete Freund's adjuvant via subQ injection. Thus was done in conjunction with Intraperitoneal injection of pertussis toxin. Six days later, 1 million live (or 2 million irradiated) hemangioblast-derived pluripotent cell-mesenchymal stromal cells were injected intraperitoneally per mouse. Disease severity was scored on a scale of 0-5 by monitoring mouse limb/body motion, as previously published. Results demonstrated a significant reduction in clinical score as compared to vehicle control with hemangioblast-derived pluripotent cell-mesenchymal stromal cells at passage 4 and irradiated hemangioblast-derived pluripotent cell-mesenchymal stromal cells (data not shown). Scoring for both pilot studies was performed according to the following protocol: a score of 1 indicates limp tail, 2 indicates partial hind leg paralysis, 3 is complete hind leg paralysis, 4 is complete hind and partial front leg paralysis, 5 is moribund.

In addition, the efficacy of MSC's according to the invention and products derivable therefrom for use in different therapies may be confirmed in other animal models, e.g., other transplantation or autoimmune models depending on the contemplated therapeutic indication.

Example 7

Investigation of Functional Components of ESC-MSCs

MSCs may be defined as plastic adherent cells that express the following cell surface markers: CD105, CD73, CD29, CD90, CD166, CD44, CD13, and HLA-class I (ABC) while at the same time being negative for CD34, CD45, CD14, CD19, CD11b, CD79a and CD31 when cultured in an uninduced state (e.g., culture in regular αMEM+20% FCS with no cytokines). Under these conditions, they must express intracellular HLA-G and be negative for CD40 and HLA class II (DR). Functionally, such cells must also be able to differentiate into adipocytes, osteocytes, and chondrocytes as assessed by standard in vitro culture assays. After 7 days stimulation with interferon gamma (IFNγ), MSCs should express HLA-G on their cell surface as well as CD40 and HLA-class II (DR) on their cell surface. Despite these requirements, MSCs derived from any source may contain some heterogeneity, and due to the pluripotency of ESCs, it is possible that MSC cultures derived from ESCs may contain cells of any lineage from the three germ layers. While the culture system described herein indicated that >90% of cells routinely display the above mentioned immunophenotype and functional characteristics, small subpopulation(s) of cells within the MSC culture may exist that lack expression of one or more of the MSC cell surface markers or express one or more of the markers that should be absent. The extent of such subpopulations within our MSC cultures will be determined by examining the degree of contaminating heterogeneity. Multicolor flow cytometry (8+ colors simultaneously) can be performed on a BD LSR II flow cytometer in order to determine the overlap between the above mentioned markers. This may also help pinpoint the exact cell surface marker profile that is required for the greatest immunosuppressive activity.

A. Characterize the Differentiation Stage, Subpopulations, and Activation Status of ESC-MSCs in Relevance to their Immunosuppressive Effects.

Figure 9:
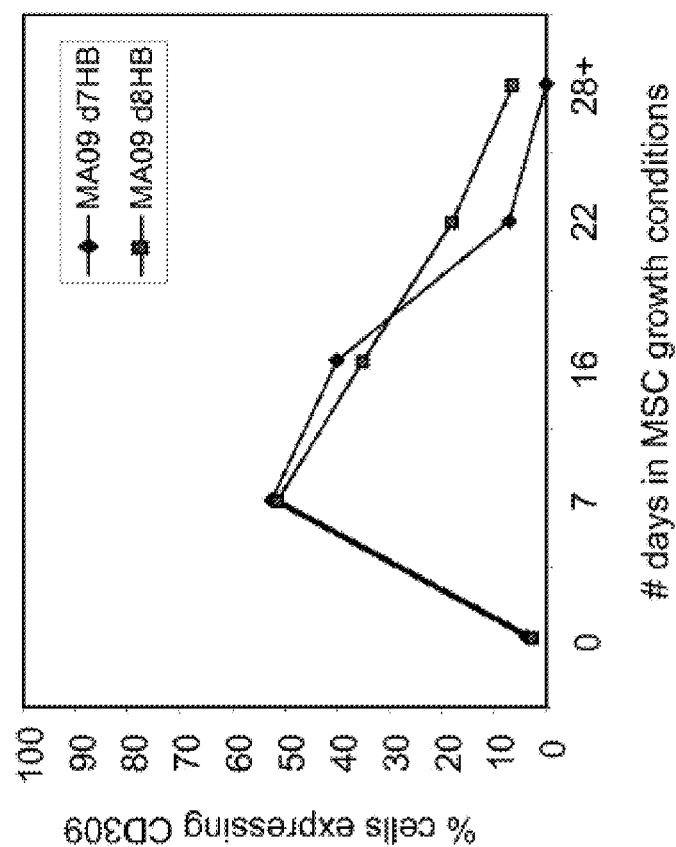
FIG. 9. Transient expression of CD309 by FM-MA09-MSC. This figure shows the transient expression of the cell surface marker CD309.

There is a large time window (e.g., at least from day 14 to 28 in the MSC differentiation medium) to harvest ESC-MSCs (see, e.g., FIG. 1). Several studies have indicated that MSCs tend to lose their immunosuppressive functions and may senesce as they are continually passaged and age during long culture periods. As such, the cells may be harvested at different time points in order to determine if a specific number of days in MSC Medium affords greater immunosuppressive activity. Indeed, MSCs collected at an early time point (e.g., 14 days in MSC culture conditions) may contain precursor cells that have not yet fully acquired all of the characteristic MSC cell surface markers, but that harbor highly potent immunosuppressive effects. To define potentially useful MSC precursor populations, the expression of a wide range of cell surface markers are being tracked throughout the MSC differentiation process, from day 7 through day 28. It has been observed that at least 50% of the culture will acquire the cell surface marker CD309 (other names include VEGFR2, KDR) within 14 days of MSC culture conditions. CD309 is largely absent from the starting hemangioblast population (FIG. 9, first time point, MA09 hemangioblasts harvested at day 7 and day 8), but rises within the first two weeks of MSC culture conditions and then declines again back to less than 5% of the cells by day 28 (FIG. 9, second, third, and fourth time points). This pattern has been found to occur not only with MA09 hemangioblast-derived MSCs but also with those from MA01, H1gfp, and H7 ESCs. In these experiments, hemangioblasts are routinely negative (less than 5% of cells stain positive) for CD309 regardless of their harvest date (day 6-14). However, the percentage of developing MSCs that acquire CD309 expression may be reduced when developing from older hemangioblasts (e.g., d10 or d12 blasts). In a similar fashion, it has been observed that the expansion properties of hemangioblast-derived MSCs may differ depending on the harvest date of hemangioblasts. MSCs developing from younger hemangioblasts (day 6 or 7) do not continue to expand as robustly as MSCs developing from older (day 8-12) hemangioblasts. The optimal date of hemangioblast harvest may be an intermediate one (day 8-10) as they may allow adequate acquisition of CD309 as a surrogate marker of MSC development while still maintaining a robust ability to expand through day 28 and beyond.

Except CD105, CD90 and CD73 that have proved the most typical markers for MSCs (as noted by the International Society for Cellular Therapy as the minimum classification of MSCs (Dominici et al., Cytotherapy 8 (4): 315-317 (2006)), many other cell surface molecules not mentioned above such as CD49a, CD54, CD80, CD86, CD271, VCAM, and ICAM have also been proposed or used as MSC markers [22]. It is therefore possible that ESC-MSCs may contain subpopulations that express various combinations of other markers during the differentiation from hemangioblasts, which may possess varying immunosuppressive activities. Subpopulations may be sorted (e.g., using FACS) based one or more markers (individually or in combination) for analysis to compare their immunosuppressive activity using in vitro or in vivo methods.

B. Optimize Differentiation and Expansion Conditions to Obtain Large Quantities of Functional ESC-MSCs.

Preliminary experiments have indicated that MSCs may be maintained in IMDM+10% heat-inactivated human serum. Different culture conditions are tested to determine whether substituting culture components (eg, base medium, serum source, serum replacement products, human serum platelet lysate) may enrich the effective subpopulations described herein. Different basal medium including animal-free and a defined culture (without FBS) system to culture ESCs and prepare MSCs are evaluated. Specifically, StemPro® MSC SFM from Invitrogen and the MSCM bullet kit from Lonza are examined to see if a serum-free defined culture system would generate ESC-MSCs with desired quality and quantity. Also, various growth factors such as FGFs, PDGF, and TGFI3, as well as small chemicals that regulate signaling pathways or cell structures, are used to enhance the quality and quantity of ESC-MSCs.

C. Results

Figure 20:
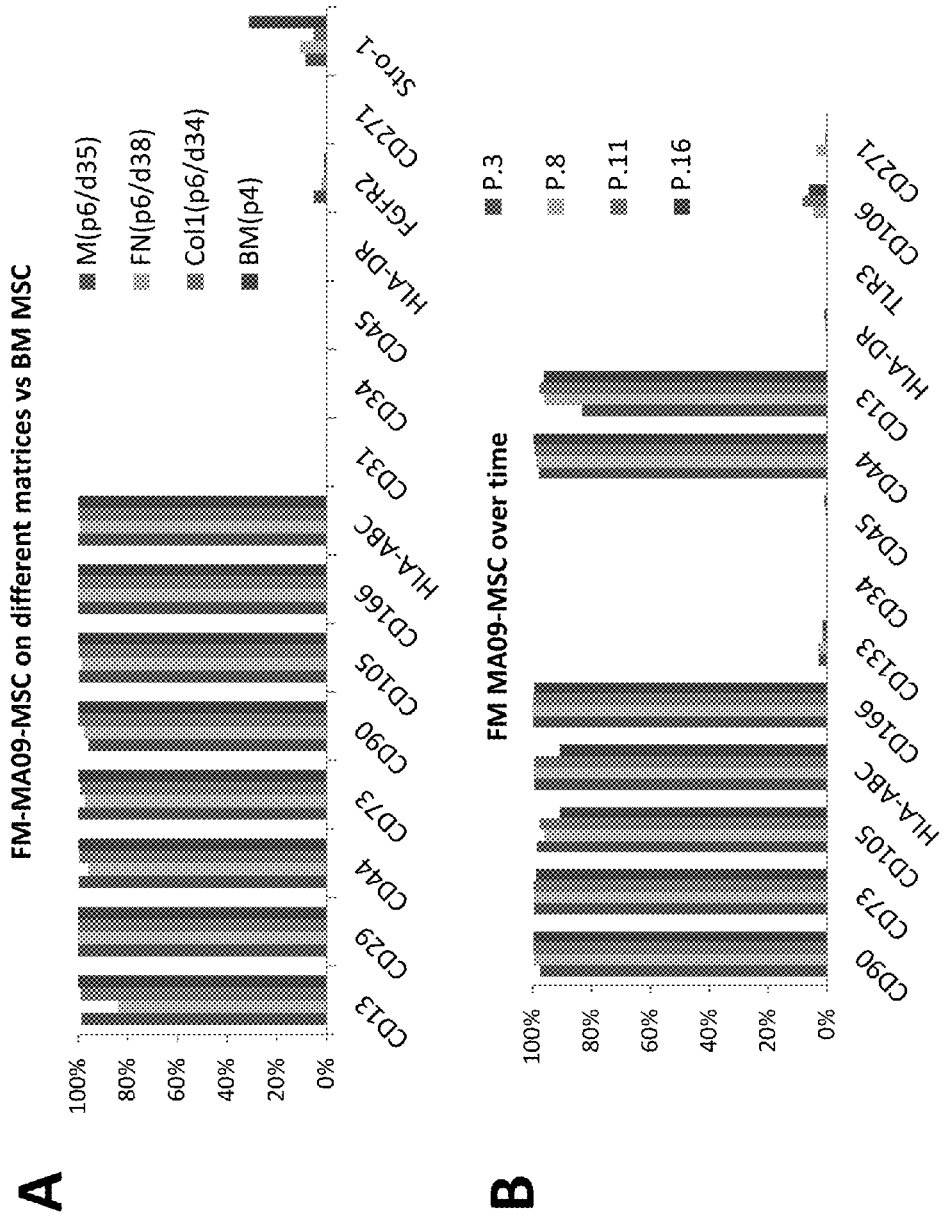
FIG. 20. FM-MA09-MSCs maintain phenotype over time. Flow cytometry analysis of different MSC populations. (A.) Cell surface marker expression of FM-MA09-MSCs is maintained on three different substrates and compared to BM- MSCs. (B.) Cell surface marker expression of FM-MA09-MSCs is evaluated over time (with successive passages, as indicated).

The ESC-MSCs express the typical markers CD73 (ecto-5'-nucleotidase [26]), CD90 and CD105. Also, FIG. 20 shows that FM-MA09-MSCs produced according to the invention maintain their phenotype over time (based on marker expression detected during flow cytometry analysis of different MSC populations over time and successive passaging).

Example 8

Mechanism of Immunosuppression by ESC-MSCs

A. Study how ESC-MSCs May Suppress Adaptive Immune Responses Mediated by T Cells.

A general response of T cells within PBMC is to proliferate when they are induced with mitotic stimulators such as phytohemaglutinin (PHA) or phorbol myristate acetate (PMA)/ionomycin or when they encounter antigen presenting cells (APCs) such as dendritic cells. This is best exemplified by the general proliferation of CD4+ and CD8+ T cells in a mixed leukocyte reaction (MLR) assay. Prior studies indicate that MSCs can suppress T cell proliferation in an MLR assay.

Figure 10A:
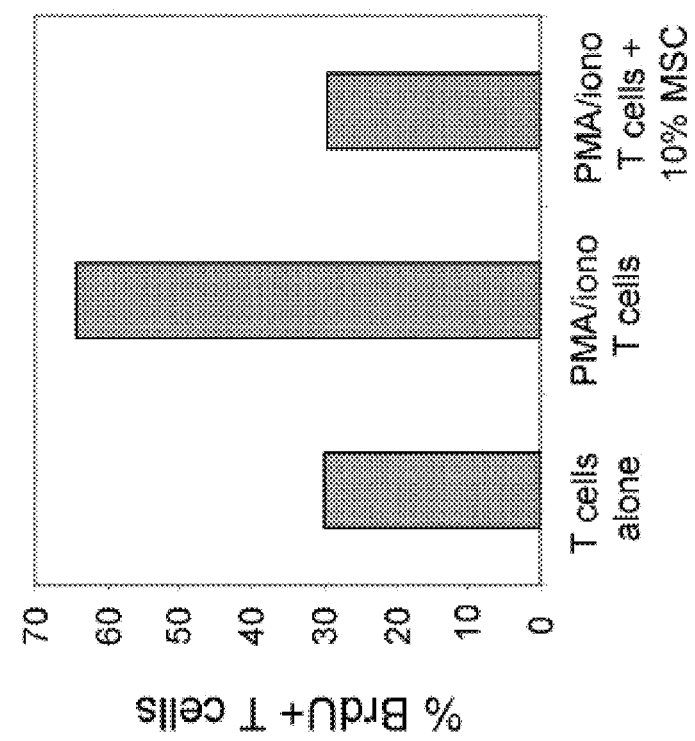
FIG. 10A. T cell proliferation in response to mitogen is suppressed by FM-MA09-MSC. This figure shows hemangioblast-derived mesenchymal stromal cells suppression of T cell proliferation caused by chemical stimulation (PMA/ionomycin).
Figure 10B:
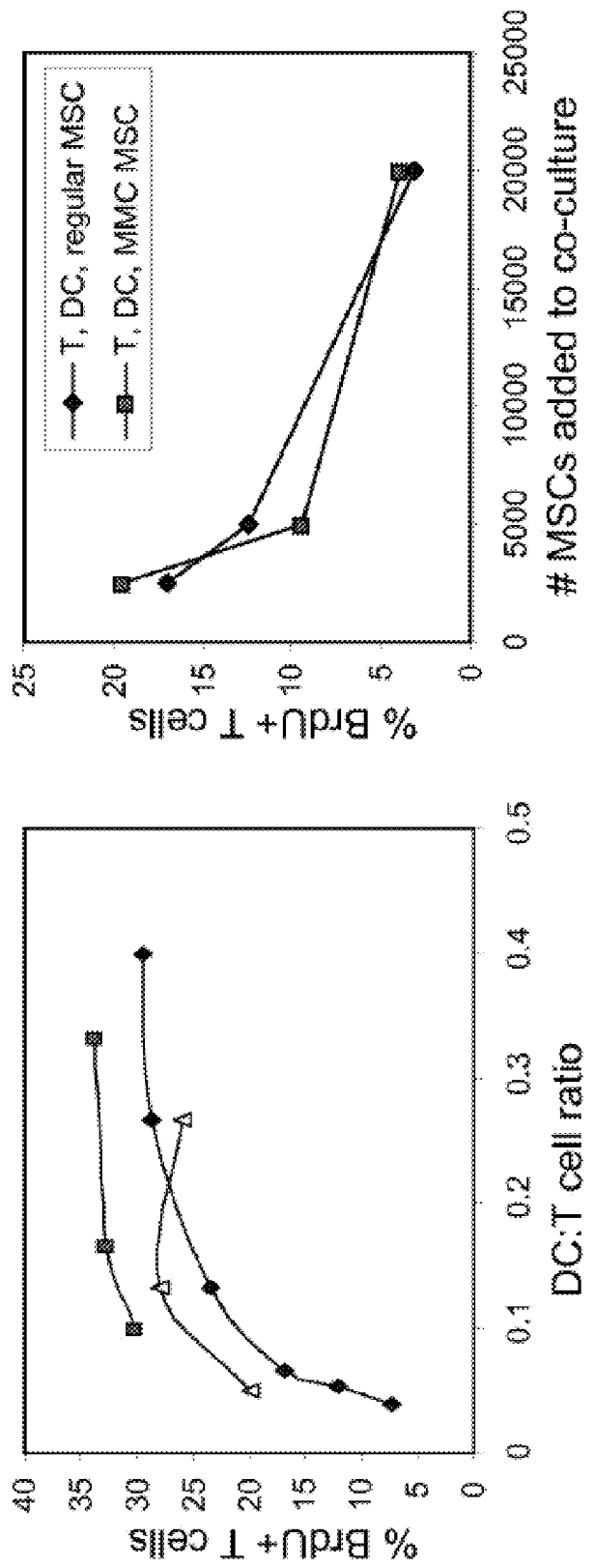
FIG. 10B. T cell proliferation in response to antigen presenting cells is suppressed by FM-MA09-MSC. This figure shows hemangioblast-derived mesenchymal stromal cells suppression of T cell proliferation caused by exposure to dendritic cells.

The ability of our ESC-hemangioblast derived MSCs to inhibit T cell proliferation caused by either chemical stimulation (PMA/ionomycin, FIGS. 10*a* and 13*a*) (PHA, FIG. 13*b*) or exposure to APCs (dendritic cells, FIGS. 10*b* and 13*c*) was examined. It was observed that MSCs dampened the proliferative response of T cells due to either chemical stimulation or co-culture with APCs and that this suppression occurred in a dose dependent manner (FIG. 10*b*, graph on right) Moreover, it was found that mitotically inactivated MSCs (FIG. 10*b*) were able to suppress T cell proliferation to an equivalent degree as live MSCs, suggesting that mitotically inactivated MSCs may indeed be useful in vivo for immunosuppression.

Various functional subsets of T cells exist and they carry out specific roles involved in proinflammatory responses, anti-inflammatory responses, or induction of T cell anergy. Regulatory T cells (Tregs) can be thought of as naturally occurring immunosuppressive T cells and in a normal setting, are responsible for dampening hypersensitive auto-reactive T cell responses. They usually represent only a small proportion of the body's T cells but their prevalence can be influenced by various environmental factors. MSCs have been shown to induce peripheral tolerance through the induction of Treg cells [33-35].

Figure 11:
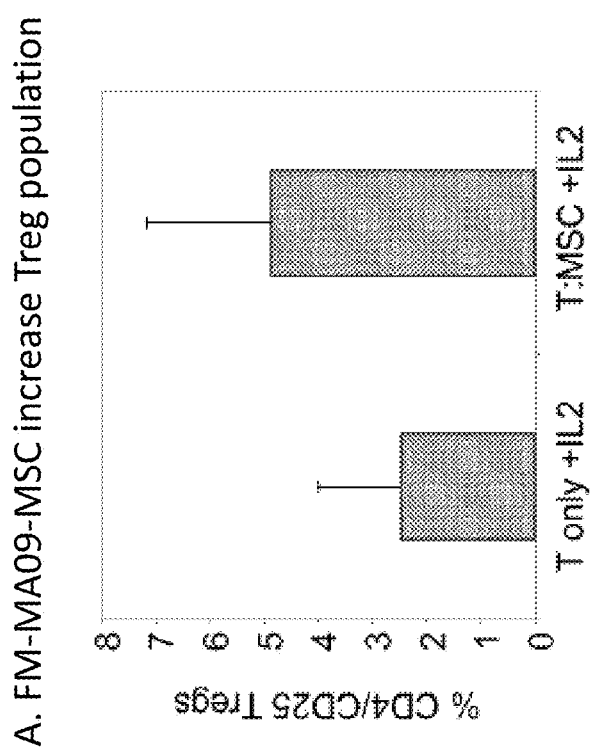
FIG. 11. T cell proliferation in response to antigen presenting cells is suppressed by FM-MA09-MSC.
Figure 14:
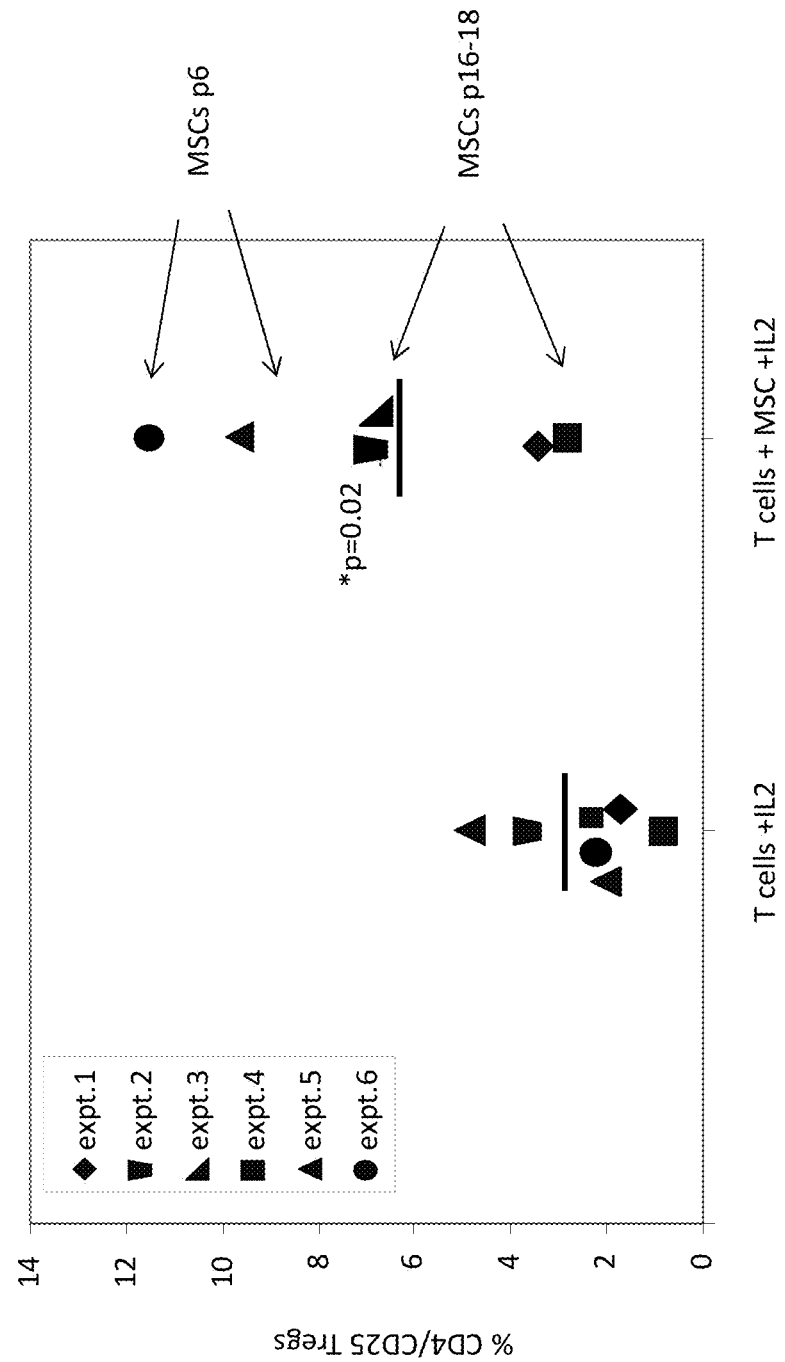
FIG. 14. FM-MA09-MSCs enhance Treg induction: early passage MSCs have greater effects than do late passage MSCs. Non-adherent PBMCs (different donors) were cultured+/−IL2 for 4 days in the absence or presence of FM-MA09-MSCs. The percentage of CD4/CD25 double positive Tregs was assessed by flow cytometry. Young (p6) or old (p16-18) FM-MA09-MSCs were used. The black bars indicate the average of 6 experiments. MSCs as a whole had a statistically significant effect on induction of Tregs. (p=0.02).

In a short, 5 day co-culture assay, it was found that, similar to prior studies, the hemangioblast-derived MSCs were able to increase the percentage of CD4/CD25 double positive Tregs that are induced in response to IL2 stimulus (FIG. 11*a*, 14, 15*a*). Co-culture of a mixed T cell population from non-adherent peripheral blood mononuclear cells (PBMCs) with MSCs (at a ratio of 10 PBMCs:1 MSC) shows that Treg induction nearly doubled when MSCs were included in the IL2 induced culture. This degree of Treg induction is similar to that observed in the highly cited Aggarwal et al study published in Blood, 2005. The amount of FoxP3 induced within the CD4/CD25 double positive population was examined to confirm that these are indeed true Tregs (FIG. 15*b*). Intracellular flow cytometry, was used to study FoxP3 induction in the absence and presence of MSCs in the IL2-induced T cell cultures. Both non-adherent PBMCs and purified CD4+ T cell populations may be used to study Treg induction in these assays. Without intent to be limited by theory, it is believed that ES-MSC are more effective at inducing Tregs because they increase expression of CD25 more effectively than BM—MSCs (FIG. 15*b*)

Th1 and Th17 cells are thought to play important roles in MS and in other autoimmune diseases. The differentiation and function of Th1 and Th17 CD4+ T cells will be analyzed first and foremost using in vitro assays; they may also be examined in the EAE model or in other animal models we may employ. The effects of MSCs on Th1 induction in vitro have begun to be examined. Culture conditions that promote Th1 specification from naïve CD4+ T cells are known in the field (Aggarwal et al). These culture conditions (which include anti-CD3, anti-CD28, and anti-CD4 antibodies together with human IL3 and IL12) have been employed to induce Th1 cells from naïve, non-adherent PBMCs in the absence or presence of MSCs (10 PBMCs:1 MSC). After 48 hours of co-culture, non-adherent cells were isolated, rinsed, and stimulated with PMA/ionomycin for 16 hours in a new well. After the 16 hour induction, supernatants were collected and analyzed for secretion of the Th1 cytokine, IFNγ. As anticipated, it was found that the PBMCs cultured with MSCs in the 48 hr Th1 inducing conditions did not produce as much IFNγ as those cultured without MSCs. This indicates that MSCs can suppress a major Th1 cell function, i.e., IFNγ secretion. (FIG. 11*b*) Similar studies will be performed by differentiating Th17 cells in vitro and determining the effects of MSCs on pro-inflammatory IL17 secretion using an ELISA assay on culture supernatants.

Th2 cells are known to secrete cytokines that have anti-inflammatory effects, such as IL4. MSCs may be able to enhance Th2 differentiation and secretion of IL4. Similar to the experiment described above for Th1 cells, Th2 inducing conditions will be used in a 48 hour culture system to stimulate Th2 differentiation from naïve PBMC containing T cells. The effects of MSC co-culture on IL4 secretion will be examined using an ELISA assay.

Recently, studies have suggested that CD8 T cells also play a pivotal role in EAE models and the underlying mechanism of MS [30]. The inventor will examine if co-culture with ESC-MSCs in vitro may affect the function of CD8 T cells. To do this, non-adherent PBMCs or purified CD8+ T cells will be exposed to EAE-associated MBP110-118 peptide through the use of APCs. This will cause an antigen-specific CD8+ T cell population to emerge and such a population can be expanded using CD3/CD28 expander beads (Invitrogen). Existence of the antigen-specific CD8+ T cells can be verified using a pentamer reagent specific for the MBP-peptide (Proimmune) in flow cytometry. Re-stimulation with MBP110-118-loaded APCs will be performed in order to induce an antigen specific immune response, which includes both expansion of the antigen-specific CD8+ T cells and secretion of IFNγ. The response from T cells cultured in the absence or presence of MSCs will be compared to determine if the MSCs can suppress the induction of these cytotoxic EAE-associated antigen specific T cells. Pentamer specific flow cytometry, BrdU incorporation, and ELISA assays will be employed for this purpose.

B. Determine if Inflammatory Factors and Inter-Cellular Adhesion Molecules (ICAMs) Contribute to the Immunosuppresive Effect of ESC-MSCs.

It has been shown that TGFbeta, PGE2, IDO, nitric oxide (NO), and ICAMs are important for the immunosuppressive function of MSCs [7]. The secretion of these molecules and expression of ICAMs by ESC-MSCs will be examined using ELISA assays and flow cytometry.

Figure 12:
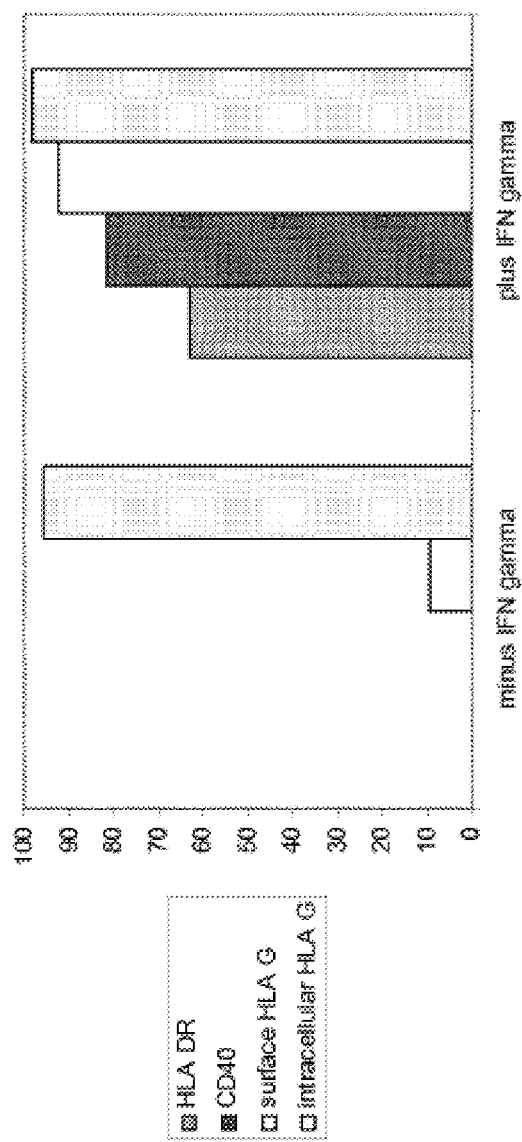
FIG. 12. Proinflammatory cytokine IFNg stimulates changes in FM-MA09-MSC surface marker expression. This figure shows that interferon gamma stimulates changes in MSC surface marker expression and may enhance MSC immunosuppressive effects.

It has been shown that the pro-inflammatory cytokine, IFNγ is required for the activation of MSCs [23], and various agonists for Toll-like receptors (TLRs) such as LPS and poly (I:C) can induce different subsets of MSCs [24]. For example, it has recently been shown that IFNγ-activated MSCs have greater therapeutic efficacy in a mouse model of colitis than do untreated MSCs (Duijvestein et al 2011). The effects of IFNγ on MSC properties have begun to be examined. FM-MA09-MSCs were treated in vitro with IFNγ for up to seven days and striking changes in cell surface marker expression resulted. These findings are consistent with observations made in previous studies (Gotherstrom et al 2004, Rasmusson et al 2006, Newman et al 2009) and confirm that the hemangioblast derived ESC-MSCs function similarly to MSCs isolated from the body. For example, in a resting state, MSCs typically do not express much (<10%) HLA G on their cell surface while they do harbor intracellular stores of this special class of immunotolerant HLA marker. Upon 7 days IFNγ treatment, HLA G can be readily detected at the cell surface of FM-MA09-MSCs (FIG. 12) and the cells may also be induced to be secreted (not yet tested). Additionally, IFNγ treatment causes an upregulation of CD40 expression and HLA DR expression at the cell surface (FIG. 12). These changes are proposed to enhance their immunosuppressive effects. For example, pretreatment of MSCs with IFNγ may enhance their ability to induce Treg populations, to suppress Th1 secretion of IFNγ, or to enhance IL4 secretion from Th2 cells by using in vitro co-culture assays described above. IFNγ may also influence the ability of MSCs to inhibit general T cell proliferation in MLR assays. The effects of TNFα, LPS, and/or poly I:C on these types of MSC immunosuppressive properties may also be tested.

C. Results

It was shown that the CD4/CD25 double positive population of Tregs induced by MSCs also express the transcription factor, FoxP3 as it has been reported that functional Tregs upregulate its expression in response to inducing stimuli (FIG. 15b).

It is expected that MSCs will inhibit, to some degree the pro-inflammatory secretion of IL17 by Th17 cells and that MSCs can also significantly enhance IL4 secretion by anti-inflammatory Th2 cells. Such observations have been made in previous studies and will assist in confirming the true functionality of the hemangioblast-derived MSCs.

The ESC-MSCs should inhibit at least partially the antigen-induced activation of CD8+ T cells. The function of NK cells, macrophages, and dendritic cells after ESC-MSC co-culture may also be examined. The effects of ESC-MSCs on maturation, cytotoxicity, and/or specific cytokine production by these other types of immune cells will be examined.

For example, the experiments in FIG. 11A show that FM-MA09-MSCs increase the percentage of CD4/CD25 double positive Tregs that are induced in response to IL2 stimulus. Also, the experiments in FIG. 12 show that the proinflammatory cytokine IFNg stimulates changes in FM-MA09-MSC surface marker expression and that interferon gamma stimulates changes in MSC surface marker expression and may enhance MSC immunosuppressive effects.

Moreover, the experiments in FIG. 14 show that FM-MA09-MSCs enhance Treg induction, and particularly that early passage MSCs had greater effects than late passage MSCs. Non-adherent PBMCs (different donors) were cultured with or without IL2 for 4 days in the absence or presence of FM-MA09-MSCs. The percentage of CD4/CD25 double positive Tregs was assessed by flow cytometry. Young (p6) or old (p16-18) FM-MA09-MSCs were used. The black bars indicate the average of 6 experiments. MSCs as a whole had a statistically significant effect on induction of Tregs. (p=0.02).

Example 9

Hemangioblast Derived ESC-MSCs have Increased Potency and Greater Inhibitory Effects than BM-MSCs A mixed lymphocyte reaction (MLR) assay was performed to determine if different MSC populations have different abilities to inhibit T cell proliferation. Results suggest that FM-MA09-MSCs are more potent than BM-MSCs in their ability to inhibit T cell proliferation in response to either mitogenic stimulus ("one-way MLR") (see FIGS. 13a and 13b) or to antigen-presenting cells (dendritic cells, DCs; "two-way" MLR) (see FIG. 13c).

The "one-way" MLR assay was performed as follows: Human PBMCs were purchased from AllCells. Upon thawing a frozen vial, PBMCs were plated for at least 1 hour or overnight in IMDM+10% heat-inactivated human serum to selectively adhere monocytes. The non-adherent cells (containing T cells) were used as a crude source of T cell responders. FM-MA09-MSCs or BM-derived MSCs were used as inhibitors. These MSCs were either live or mitotically-arrested with mitomycin C. Non-adherent PBMCs and MSCs were mixed together at varying ratios and allowed to co-culture for 5 days. On day 3, the mitogens, phorbol-12-myristate 13-acetate (PMA) and ionomycin or phytohemagglutinin (PHA) were added to the cultures to induce T cell proliferation. On day 4, bromodeoxyuridine (BrdU) was added. On day 5, T cell proliferation was assessed through flow cytometric staining with antibodies directed against CD4, CD8, and BrdU using the BrdU incorporation kit (B&D Biosystems). T cell proliferation was assessed as the % of CD4+ and/or CD8+ cells that had incorporated BrdU into their DNA (ie, BrdU+) (shown in FIGS. 13a and 13b). In FIG. 13b, MA09-MSCs p7 show an approximately 40% decrease in T-cell activation compared to BM-MSCs.

In the "two-way" MLR, FM-MA09-MSCs or BM-derived MSCs were used as inhibitors, non-adherent peripheral blood mononuclear cells (PBMCs) were used as a crude source of T cell responders, and monocyte-derived dendritic cells (DCs) were used as stimulators. To derive DCs, plastic-adherent monocytes were isolated from PBMCs PBMCs were plated for at least 1 hour or overnight in IMDM+10% heat-inactivated human serum (10% HuSer) to selectively adhere monocytes. Non-adherent cells were removed and the adherent cells were cultured in IMDM+10% HuSer for 4 days with SCF, FL, GM-CSF, IL3, and IL4. In this variation of the assay, no mitogen is added on day 3. BrdU is simply added 16-24 hours before harvesting the cells for flow cytometry as above. Both MSCs and DCs were mitotically-inactivated with Mitomycin C in this assay (shown in FIG. 13c). In FIG. 13c, the percent BRDU incorporation of the T cells does not substantially increase, preferably remains the same, more preferably decreases the DC/T cell ratio in the presence of the MA09-MSCs as compared to the BM-MSCs.

Example 10

Improved Induction of Treg Expansion by Young FM-MA09-MSCs Compared to BM-MSCs and Old FM-MA09-MSCs Co-culture experiments were performed with PBMCs and FM-MA09-MSCs to determine if the presence of these MSCs can induce regulatory T cell (Treg) expansion within the PBMC population. Results suggest that young FM-MA09-MSCs induced Treg expansion better than both BM-MSCs and old FM-MA09-MSCs (see FIG. 14 and FIG. 15).

Co-cultures were established with non-adherent PBMCs and different types of FM-MA09-MSCs ("young" ESC-derived (~p5-6), "old" ESC-derived (~p12 or higher), BM-derived) at a 10:1 ratio (PBMC:MSC). Co-cultures were incubated in IMDM+10% heat inactivated Human Serum+300 units/ml recombinant human IL2 for 4 days. The presence of Tregs was determined by the percentage of PBMCs that stained positive for CD4, CD25, and FoxP3 using a FoxP3 intracellular flow cytometry staining kit (Biolegend).

Example 11

ESC-MSC Derived Via Hemangioblasts have Greater Proliferative Capacity

The growth rates of different MSC populations were monitored over time to determine if the source of MSCs affects their proliferative capacity. Results show that FM-MA09-MSCs have greater proliferative capacity than BM-derived MSCs. Results also suggest that culturing FM-MA09-MSCs on a substrate (such as Matrigel) for a longer period of time (up to 6 passages) may help maintain a higher growth rate than if the cells are moved off of the substrate at an earlier passage, such as p2 (see FIG. 16 and FIG. 17).

ESC-derived hemangioblasts were seeded onto Matrigel-coated tissue-culture plastic at 50,000 cells/cm$^2$ in αMEM+20% Hyclone FBS+l-glutamine+non-essential amino acids (MSC growth medium) at p0. Bone-marrow mononuclear cells were seeded onto regular tissue culture plastic at 50,000 cells/cm$^2$ in MSC medium at p0. Cells were harvested with 0.05% trypsin-edta (Gibco) when they reached ~50-60% confluence at p0 or at 70-80% confluence from p1 onwards (usually every 3-5 days). Upon harvest, cells were spun down, counted, and replated at 7000 cells/cm$^2$. ESC-MSCs were removed from Matrigel and subsequently grown on regular tissue culture plastic starting at p3, unless otherwise indicated. Cumulative population doublings over time are plotted to show the rate of cell growth as the MSCs are maintained in culture.

Example 12

FM-MA09-MSCs Undergo Chondrogenic Differentiation

To determine the chondrogenic potential of different MSC populations, FM-MA09-MSCs or BM-MSCs were seeded as pellet mass cultures and induced to differentiate into chondrocytes with differentiation medium (or kept in regular MSC growth media as negative controls). Results suggest that FM-MA09-MSCs undergo chondrogenesis in a manner similar to that of BM-MSCs. Both ESC-MSC and BM-MSC pellets reveal extensive cartilaginous matrix (proteoglycan) deposition via Safranin O staining (see FIG. 18).

To form chondrogenic pellet culture, 2.5×10$^5$ cells FM-MA09-MSCs were centrifuged at 500×g for 5 min in a 15 mL conical tube. Culture medium was aspirated and 0.5 mL of chondrogenic culture medium, consisting of DMEM-HG (Life Technologies, Gaithersburg, Md.) supplemented with 1 mM Sodium Pyruvate (Life Technologies), 0.1 mM ascorbic acid 2-phosphate (Sigma-Aldrich, St. Louis, Mo.), 0.1 µM dexamethasone (Sigma-Aldrich), 1% ITS (Collaborative Biomedical Products, Bedford, Mass.), 10 ng/mL TGF-β3 (Peprotech, Rocky Hill, N.J.), or culture medium (control) was added to the pellet. Pellet cultures were maintained for 21 days with medium changes every 2-3 days. At the end of the 21 days, pellets were fixed with 4% paraformaldehyde and sent to MassHistology (Worcester, Mass.) for paraffin-embedding, sectioning, and Safranin O staining using standard procedures.

Example 13

Enhanced Secretion of Prostaglandin E2 (PGE2) Under IFN-γ or TNF-α Stimulation

ESC-MSCs exert immunomodulatory effects in part through the secretion of PGE2. Conditioned medium collected from FM-MA09-MSCs and BM-MSCs show that BM-MSCs secrete higher levels of PGE2 in the basal state than FM-MA09-MSCs. Experiments to determine PGE2 secretion under stimulated conditions (various concentrations of IFN-γ and/or TNF-α) show that FM-MA09-MSCs greatly increase their secretion of PGE2 in response to stimulation (see FIG. 19). In fact, the fold induction for PGE2 secretion from a basal to stimulated state is much greater for FM-MA09-MSCs than for BM-MSCs. However, the actual raw amounts of PGE2 secretion (in pg/ml) under stimulated conditions is similar for FM-MA09-MSCs and BM-MSCs.

FM-MA09-MSCs were plated at 7.5×10$^6$ cells/cm$_2$ in 6 well plates (BD Falcon, Franklin Lakes, N.J.). Cultures were maintained in culture medium for 24 hrs, followed by stimulation with 10, 50, 100, or 200 ng/ml IFN-γ and/or 10, 25, 50 ng/mL TNF-α (Peprotech). Supernatant was collected after 3 days of induction and stored at −20° C. FM-MA09-MSCs were harvested and counted to normalize PGE2 levels to cell number. $PGE_2$ concentration was measured with ELISA kits (R&D PGE2 Parameter or Prostaglandin E2 Express EIA kit, Cayman Chemicals) and used according to manufacturer's protocol.

Example 14

FM-MA09-MSCs Phenotypic Evaluation

The expression of various cell surface markers was assessed on different MSC populations to determine their individual immunophenotypes. FM-MA09-MSCs can be differentiated on various substrates. A panel of cell surface markers were examined to determine their expression profile on MSCs that had been derived on three different matrices (Matrigel, fibronectin, or collagen I) versus their expression on BM-MSCs. Results show similar patterns of expression for these markers regardless of the substrate used for their initial differentiation. They were over 95% positive for CD13, 29, 44, 73, 90, 105, 166, and HLA-ABC while negative for CD31, 34, 45, HLA-DR, FGFR2, CD271 (see FIG. 20A). Stro-1 expression varied, between approximately 5% for FM-MA09-MSCs to approximately 30% for BM-MSCs.

MSCs slow in growth and population doubling with increasing passage number. The aim of this experiment was to look at surface marker expression for a number of different MSC markers from passage 3 to 17 in FM-MA09-MSCs. Cells in all passages of FM-MA09-MSCs stained positive for CD90, CD73, CD105, HLA-ABC, CD166, CD13, and CD44. Cells were negative for CD34, CD45, TLR3, HLA-DR, CD106, CD133, and CD271 (see FIG. 20B).

For each line/passage number, the same protocol was followed. Cells were grown in T75 or T175 flasks, in MSC media. Cells were passaged every 3-4 days. Passaging cells consisted of washing flasks with PBS, collecting cells using cell dissociation media TryPLE Express, and washing with MSC media. Cells were counted for viability with trypan blue and aliquoted at 50-100,000 viable cells per condition. The following antibodies were used: CD34-Fitc, CD34-PE, CD44-Fitc, CD73-PE, CD106-PE, CD45-APC (BD); HLA-DR-APC, CD90-Fitc, HLA-ABC-Fitc, CD133-APC, CD29 (ebioscience); CD166-PE, CD105-APC, CD13-PE, CD13-APC, CD271-Fitc, CD10-Fitc, Stro-1-AF647, CD10 (Biolegend); TLR3-Fitc (Santa Cruz Biotech). Propidium Iodide was also added as a viability marker. Cells were incubated at room temperature for 30 minutes, spun down, passed through a 40 μm cell strainer, and analyzed with na Accuri C6 Flow Cytometer. For each cell type, cells were gated on the MSC population (FSC vs. SSC), PI negative. Percent positive was determined by gating histogram plots and using the unstained cell population as a negative control. See, Wagner W, et al. Replicative Senescence of Mesenchymal Stem Cells: A Continuous and Organized Process. *PLoS ONE* (2008). 3(5): e2213. doi:10.1371/journal.pone.0002213; and Musina, R, et al. Comparison of Mesenchymal Stem Cells Obtained from Different Human Tissues. Cell Technologies in Biology and Medicine (2005) April. 1(2), 504-509.

Figure 21:
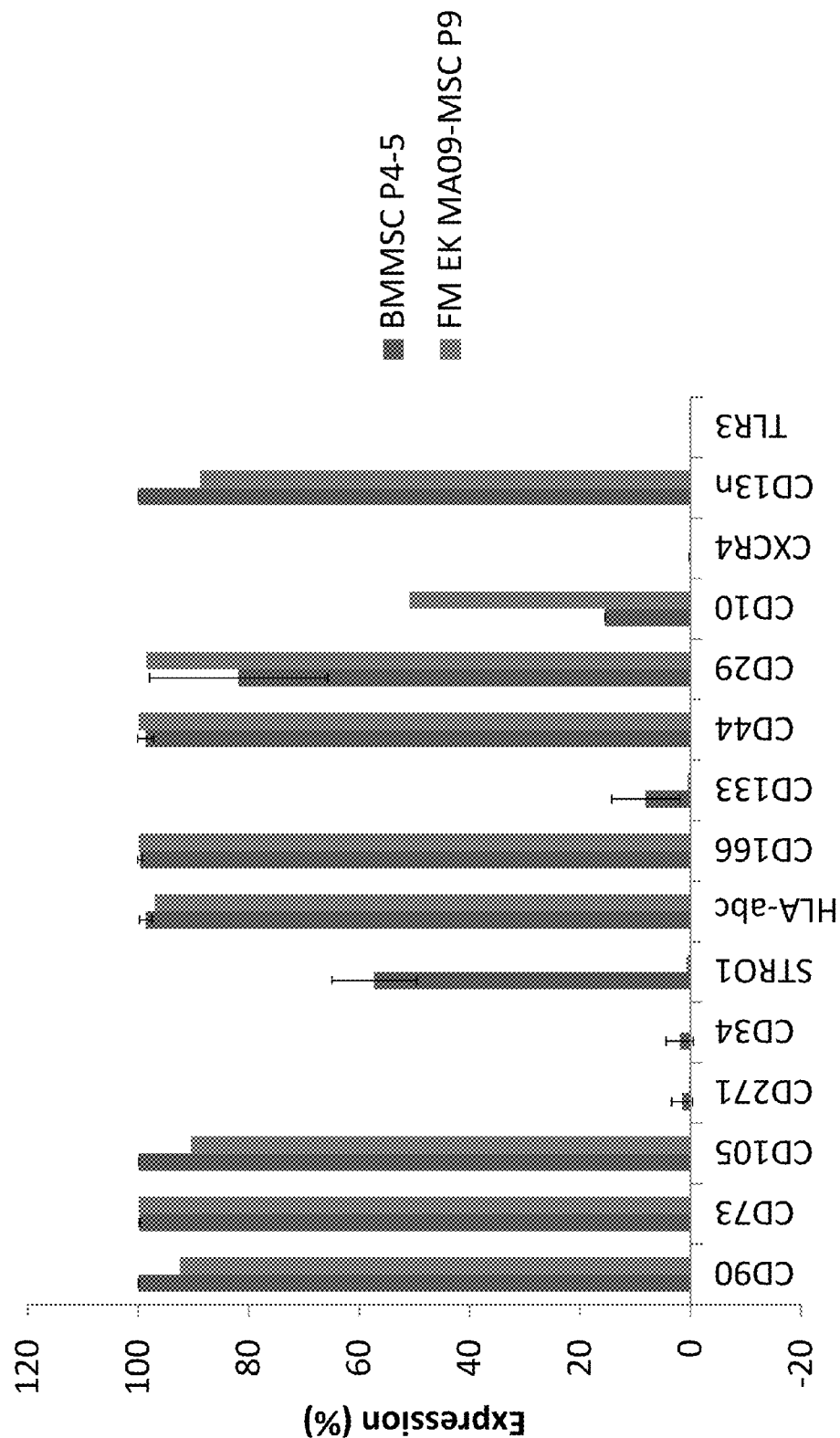
FIG. 21. FM-MA09-MSCs express less Stro-1 and more CD10 as compared to BM-MSCs. Flow cytometry analysis of different MSC populations. Stro-1 expression is lower in FM-MA09-MSCs than in BM-MSCs at the indicated passage number. CD10 expression is higher in FM-MA09-MSCs than in BM-MSCs. Other markers are the same for both MSC populations.

Additionally, FM-MA09-MSCs have a greater level of CD10 expression and less Stro-1 expression than BM-MSCs (see FIG. 21). This expression pattern of low Stro-1 (5-10% of cells) and mid-level CD 10 (~40% of cells) was confirmed in 10 different lots of FM-MA09-MSCs (see FIG. 22). Flow cytometry was also used on different populations to evaluate cell size (see FIG. 23). Results show that as the cells are maintained in culture for longer periods of time, the cell size of BM-MSCs increases while FM-MA09-MSCs maintain cell size. Cell size was determined by forward vs. side scatter on flow cytometry dot plots. A quadrant gate was used to divide the plot into 4 regions. The upper right quadrant contains the large cells, i.e., cells in that area have large forward scatter (cell volume) and also high side scatter (granularity).

FM-MA09-MSCs were harvested, as previously mentioned, and washed in 1×DPBS (Life Technologies). 75-100× $10^5$ cells were washed with flow buffer (3% FBS; Atlas Biologicals, Fort Collins, Colo.), followed by incubation with 100 μL of flow buffer containing either primary antibody or isotype control antibody for 45 min on ice. Cells were washed with 2 mL flow buffer and incubated in 100 μL flow buffer containing secondary antibody for 45 min on ice. Cells were washed a final time and resuspended in flow buffer containing propidium iodide and analyzed on an Accuri C6 flow cytometer (Accuri Cytometers Inc., Ann Arbor, Mich.).

Example 15

Gene Expression Analysis in FM-MA09-MSCs

The purpose of these studies was to determine the similarities and differences of mRNA expression between FM-MA09-MSCs and BM-MSC. In the first set of experiments (basal experiments), relative differences of mRNA expression of cells from FM-MA09-MSCs and BM-MSC were compared by Quantitative Polymerase Chain Reaction (QPCR). Taqman probes (Life Technologies) to the various genes were used to determine relative expression to the endogenous control, GAPDH, using the ΔΔCt method. From a list of 28 genes, the following genes were upregulated in the basal experiments in FM-MA09-MSCs vs BM-MSC: AIRE, ANGPT1 (ANG-1), CXCL1, CD10, CD24, and IL11 (see FIGS. 24-26). IL6 and VEGF were downregulated in FM-MA09-MSCs vs BM-MSC (see FIG. 27). There was no significant difference for the following genes between the sources of MSC: ALCAM, FGF7, HGF, LGALS1, NT5E, and TNFSF1B (data not shown). The following genes were not detected in any of the MSC sources: ANGPT2, CD31, CD34, CD45, HLA-G, IL2RA, IL3, IL12B (data not shown). As a negative control, all MSCs were tested for expression of the hematopoietic progenitor markers, CD34, CD41, and CD45. From these experiments, we have determined that FM-MA09-MSCs do express some genes at higher or lower levels than the equivalent BM-MSCs.

We also challenged the MSCs to an environment that mimics an immune response by treating the MSC with T cells and then adding the stimulant, Phytohemagglutinin (PHA FM-MA09-MSCs were grown in the presence of T cells (unstimulated) or T cells plus PHA (stimulated) for two days before adding 2.5 μg/ml PHA for an additional 2 days prior to RNA collection. The gene expression of ESC-MSC unstimulated and stimulated are currently being compared to unstimulated and stimulated BM-MSC mRNA levels.

For basal experiments: FM-MA09-MSCs and BM-MSC were cultured for 4 days at a starting density of approximately 500,000 cells in a 10 cm dish under previously described conditions. Additionally, a negative control for basal experiments was MA09 ESC derived hematopoetic progenitors.

For stimulation experiments: FM-MA09-MSCs and BM-MSC were cultured for 3-4 days at a starting density of approximately 500,000 cells in a 10 cm dish under previously described conditions. MSCs were then exposed to T cells for 2 days and then +/−exposure to 2.5 μg/ml PHA. As a control, MSCs were grown in the presence of T cells without PHA, and separately, T cells plus PHA (no MSCs) were also grown.

Media was aspirated, rinsed 2 times in PBS, and aspirated dry. RNA was isolated using the RNAeasy kit (Qiagen) as per manufacturer's directions. The concentration and purity of RNA was analyzed by using the Nanodrop 2000 (Thermo Scientific). cDNA synthesis was performed using the SuperScript® III First-Strand Synthesis SuperMix for qRT-PCR (Life Technologies) using 1 microgram RNA as the starting material. cDNA was diluted approximately 30 fold for 5 microliters/well. Diluted cDNA, 1 microliter of QPCR Taqman probe (Life Technologies), and 15 microliters of SSO Fast Mastermix (Biorad) were mixed per well. QPCR was performed on the Biorad CFX 96. Data was analyzed using CFX manager 2.1 (Biorad). Relative quantities of mRNA expression were determined using the endogenous control, GAPDH, and the ΔΔCt method.

Example 16

Indoleamine 2,3-Dioxygenase (IDO) Enzyme Activity in FM-MA09-MSCs

Figure 28:
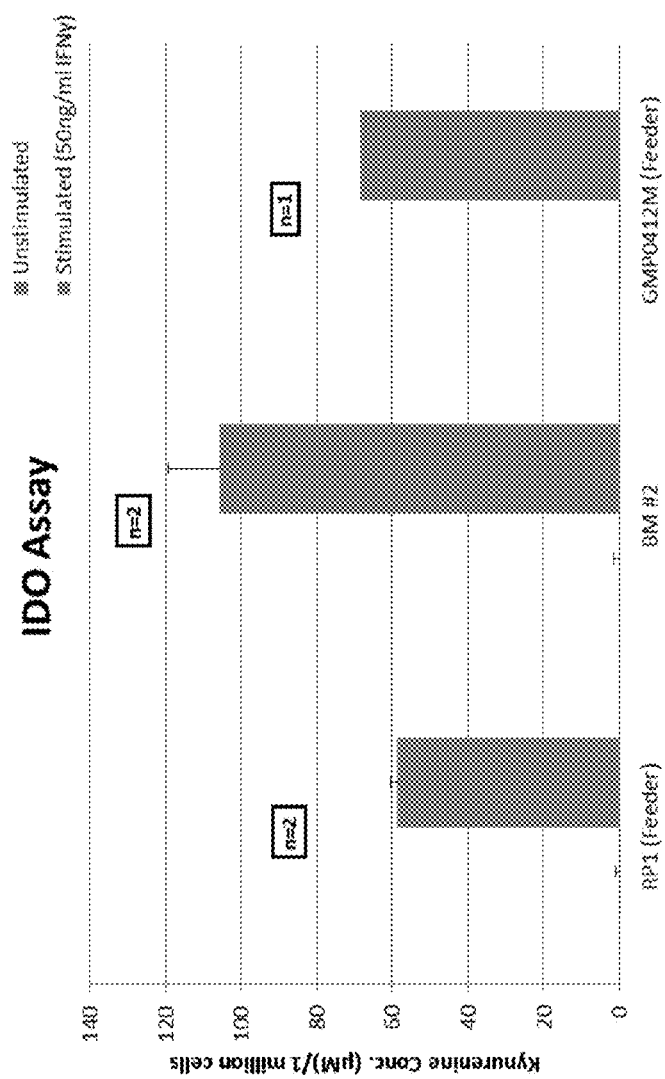
FIG. 28. FM-MA09-MSCs and BM-MSCs show increased indoleamine 2,3 deoxygenase (IDO) activity in response to 3 days of IFNγ stimulation. Comparison of MSCs stimulated with 50 ng/ml IFNg for 3 days, for their ability to convert tryptophan into kynurenine (indicative of IDO activity). For each MSC population, 1 million cells were lysed and used in the assay.

Indoleamine 2,3-dioxygenase (IDO) is an enzyme involved in the conversion of tryptophan to kynurenine. IFNγ-activated MSCs produce IDO and this may be partly responsible for their ability to suppress T cell proliferation as IDO interferes with T cell metabolism. In this study, we are testing the IDO activity of BM-MSCs compared with FM-MA09-MSCs. IDO expression is being measured before and after stimulation of cells with either IFNγ or by co-culturing with T cells. Experiments show all MSC populations greatly increase IDO activity upon stimulation with IFNgamma (see FIG. 28).

Cells were stimulated by the addition of either IFNγ (50 ng/ml) to media, or by co-culture with T cells for 3 days; measurement of IDO expression is performed using a spectrophotometric assay. After stimulation, cells were collected, and 1-2×10$^6$ cells are lysed. Lysates are collected, and mixed 1:1 with 2×IDO buffer (PBS with 40 mM ascorbate, 20 μM methylene blue, 200 μg/ml catalase, and 800 μM L-tryptophan) and incubated for 30 minutes at 37° C. The reaction was stopped by addition of 30% trichloroacetic acid, and incubated for 30 minutes at 52° C. Lysates were spun down, and supernatants are mixed 1:1 with Ehrlich's reagent (0.8% p-dimethylaminobenzaldehyde in acetic acid, freshly prepared). After color development, absorbance was read on a spectrophotometer at 492 nm. OD values were compared with a standard of kynurenine from 0-1000 μM for assessing the conversion of tryptophan to kynurenine.

See, Meisel R et. al. Human bone marrow stromal cells inhibit allogeneic T-cell responses by indoleamine 2,3-dioxygenase-mediated tryptophan degradation. *Blood*. (2004) June 15; 103 (12): 4619-21.

See, Braun, D et. al. A two-step induction of indoleamine 2,3 dioxygenase (IDO) activity during dendritic-cell maturation. *Blood*. (2005) October 1; 106 (7): 2375-81.

Example 17

Expression Levels of Aire-1 and Prion-Protein in FM-MA09-MSCs

Figure 29:
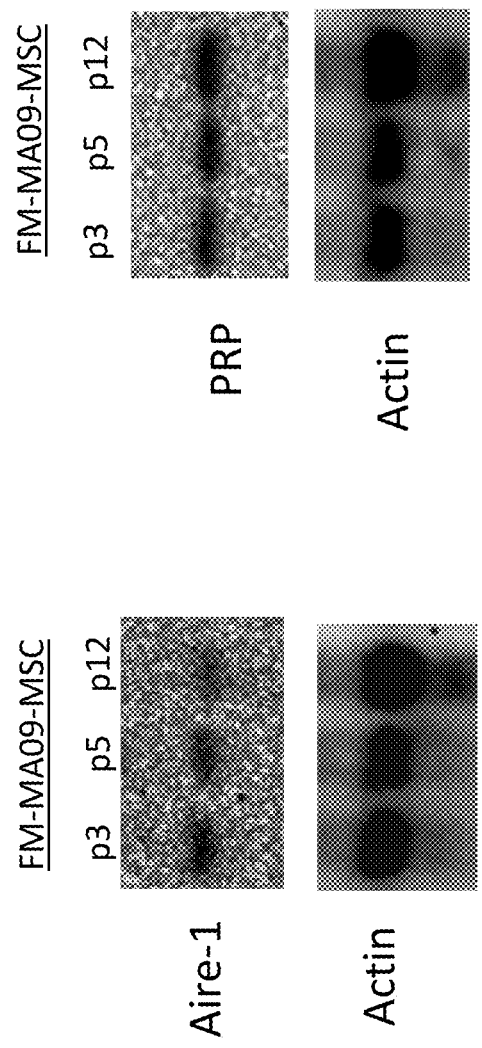
FIG. 29. Age-related changes in FM-MA09-MSC expression of Aire-1 and Prion Protein (PrP): two proteins involved in immune suppression and proliferation, respectively. Western blot analysis of Aire-1 and PrP expression in FM-MA09-MSCs whole cell lysates at different passage numbers (p). Actin expression is shown as loading control. Differences in Aire-1 and PrP expression are noted by referencing the actin loading controls.

The expression levels of Aire-1 and Prion-Protein (Prp) were monitored using western blot analysis to determine if there are differences among different MSC populations (based on cell source, derivation method, or passage number of the MSCs). Aire-1 helps induce transcription of rare peripheral tissue-restricted antigens (PTA) that are subsequently presented on MHC and quell the response of neighboring T cells. Aire-1 may also suppress expression of early T cell activation factor-1 (ETA-1) to inhibit T cell inflammatory response. Prion protein (PrP) has been shown to enhance the proliferation and self-renewal of various stem cell populations (hematopoietic, neural, etc) and its expression may correlate with the growth characteristics of different MSC populations in culture. Results show age-related decline in both proteins (after consideration of loading control, actin for each sample). FM MA09-MSCs appear to maintain expression of both Aire-1 and PrP over time (see FIG. 29).

MSCs whole cell lysates were run on 12% acrylamide SDS-PAGE gels according to standard protocols. Proteins were transferred to nitrocellulose membrane and blocked with 5% milk in PBS+0.05% tween 20. Membranes were probed with antibodies directed against Aire-1 (Santa Cruz Biotechnology) or Prion Protein (Abcam), followed by HRP-conjugated secondary antibodies. Enhanced chemiluminescent reagent was used to develop the signal prior to analysis on a Biorad GelDoc Imaging System.

See, Parekkadan et al. Molecular Therapy 20 (1): 178-186 (2011).

See, Mohanty et al. Stem Cells 30: 1134-1143 (2012).

Example 18

FM-MA09-MSCs Secretion of Cytokines

Figure 30:
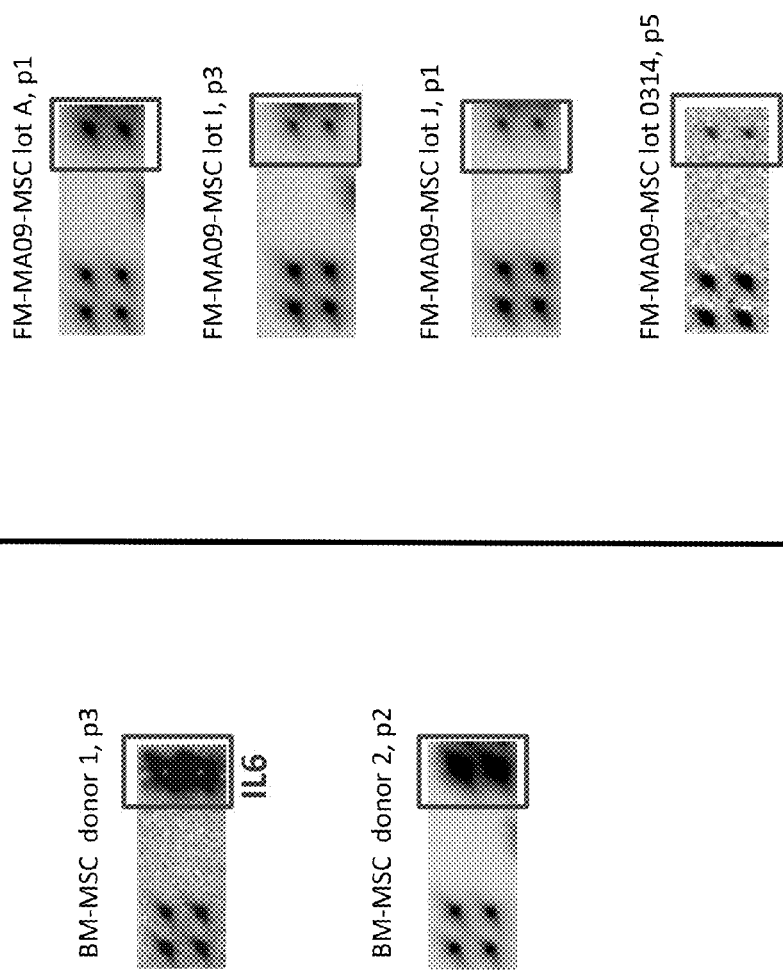
FIG. 30. FM-MA09-MSCs secrete less IL6 than BM-MSCs do in the basal state. Cytokine arrays showing positive controls for normalization (4 dots on left) and IL6 (boxed) in MSC conditioned medium. BM-MSCs from two different donors are compared to 4 different lots of FM-MA09-MSCs.
Figure 31:
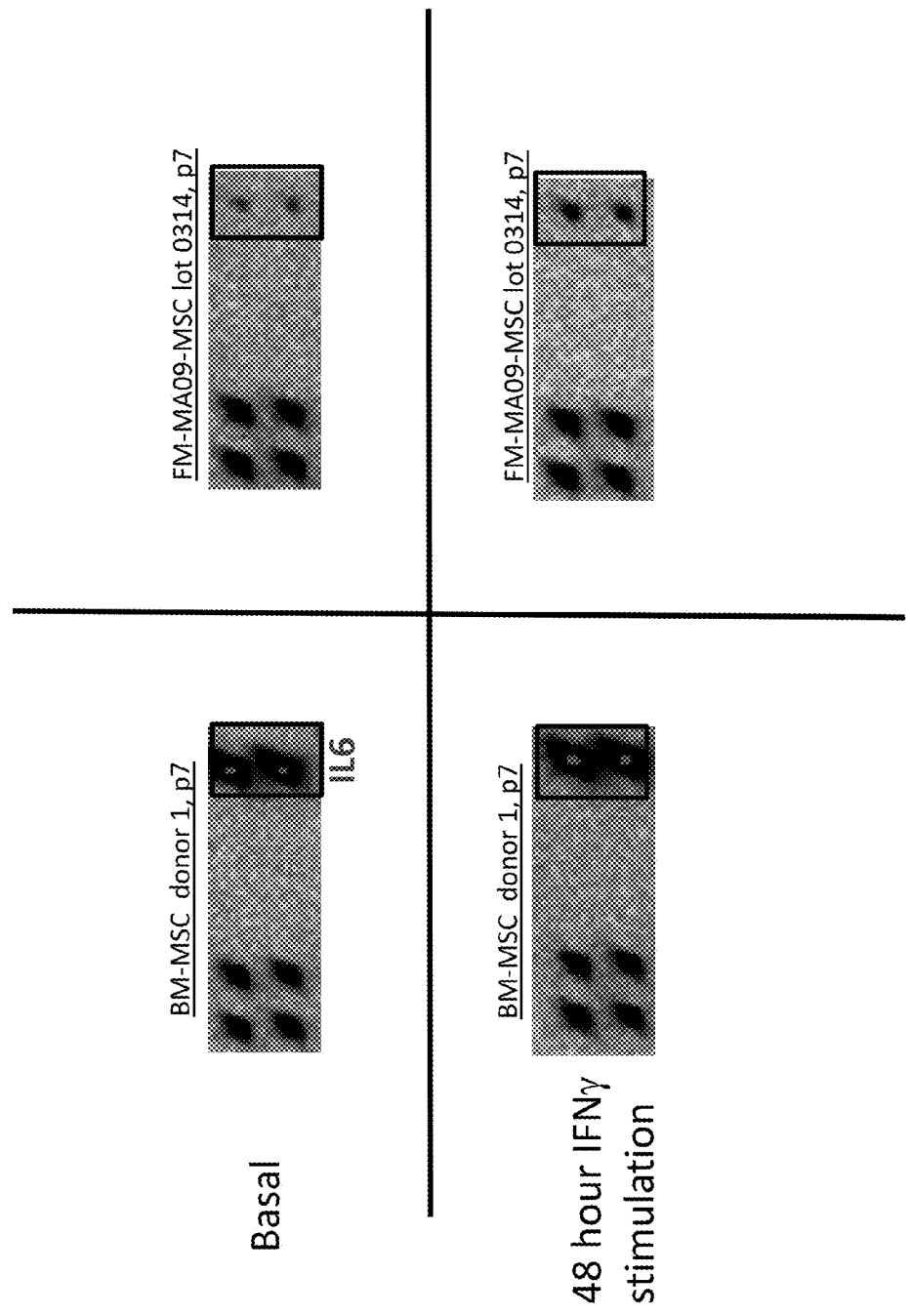
FIG. 31. FM-MA09-MSCs secrete less IL6 than BM-MSCs in the basal and IFNγ-stimulated state. Cytokine arrays showing positive controls for normalization (4 dots on left) and IL6 (boxed) in MSC conditioned medium. Passage 7 BM-MSCs are compared to p7 FM-MA09-MSCs after 48 hours+/−IFNγ treatment.
Figure 32:
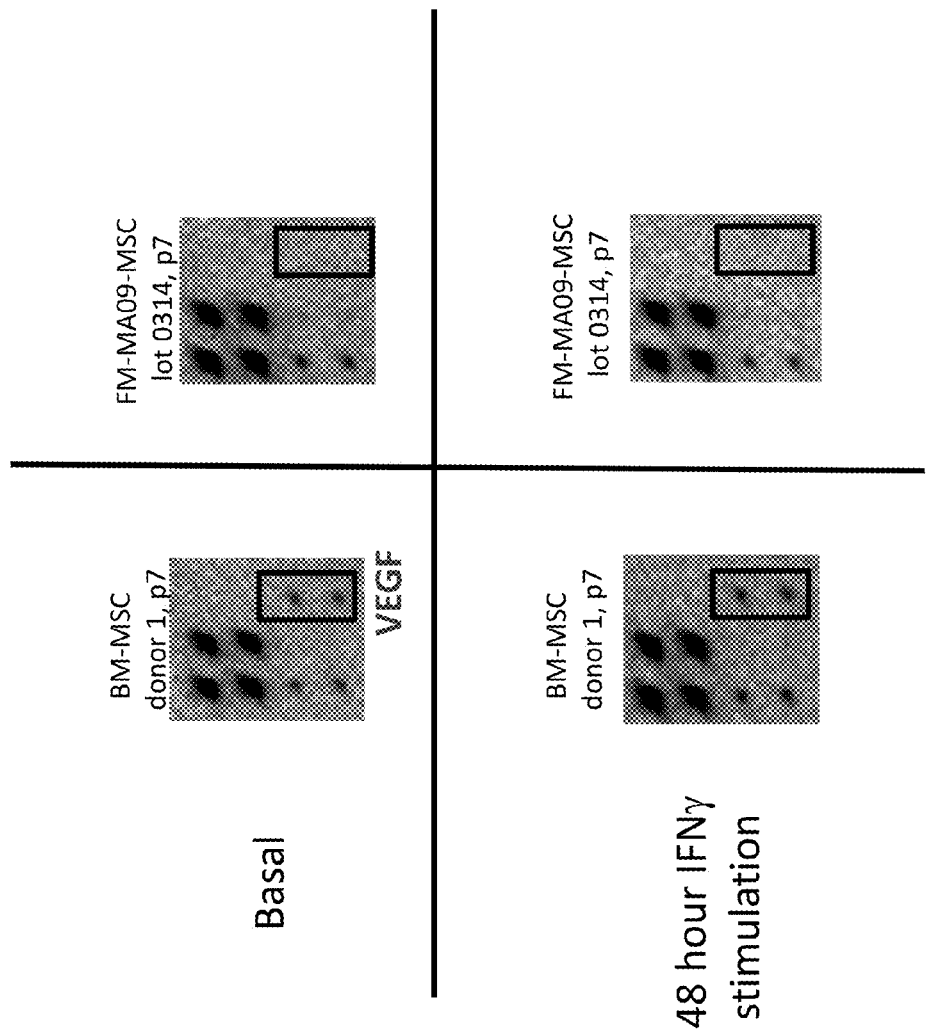
FIG. 32. FM-MA09-MSCs secrete less VEGF than BM-MSCs in the basal and IFNγ-stimulated state. Cytokine arrays showing positive controls for normalization (4 dots on left) and VEGF (boxed) in MSC conditioned medium. Passage 7 BM-MSCs are compared to p7 FM-MA09-MSCs after 48 hours+/−IFNγ treatment.

MSCs are known to secrete a variety of cytokines and growth factors in both the basal state and in response to various stimuli. More than 20 different secreted factors were analysed using cytokine arrays. Results show that there are a few key differences between FM-MA09-MSCs and BM-MSCs with respect to secreted factors in both the basal and stimulated states. BM-MSCs express higher levels of VEGF and IL6 than do FM-MA09-MSCs in both the basal and IFNγ-stimulated state (see FIGS. 30-32).

Equivalent numbers of MSCs were initially plated and conditioned medium from MSCs were collected 3-4 days after plating. CM was spun down briefly to remove cellular debris and then frozen at −20 C. CM was thawed for analysis on RayBiotech (Norcross, Ga.) custom membrane arrays or on various R&D Systems (Minneapolis, Minn.) ready-made cytokine arrays according to manufacturer's protocols.

Example 19

Human ES Cell Culture for the Differentiation of MSCs

The purpose of this experiment was to evaluate different growth media used for hESC culture prior to differentiation into MSCs.

Human ES cells were generally cultured on irradiated or mitomycin-C treated mouse embryonic fibroblasts (MEF) feeder cells in Human ES Cell Growth Medium (knockout DMEM or DMEM/F12 (1:1) base medium, 20% serum replacement, 1-glutamine, non-essential amino acids, and 10 ng/ml bFGF). Passaging is performed using 0.05% trypsin/EDTA. Alternatively, hESCs were cultured on MEF feeders in Primate Medium and passaged using Dissociation solution (both are purchased from ReproCELL). Results showed that Primate Medium consistently gave "better" looking hESC colonies (rounder, tighter colonies, less spontaneous differentiation) compared to cells grown on the Human ES Cell Growth Medium containing knockout DMEM.

Example 20

Pain Study

The effects of MSC produced from hES cells (MA09-MSCs) on orofacial pain sensitivity were tested in the mouse. The mouse system used operant conditioning to study orofacial pain sensitivity to extreme temperatures (both hot and cold) as described in Nolan et al., Behav Brain Res. 2011 Mar. 1; 217(2): 477-480, which is hereby incorporated by reference in its entirety. Sensitivity was further augmented by treatment with the chemotherapeutic agent, taxol, and the effect of MSC on hot and cold sensitivity was determined.

Methods:

MSCs were derived from hESC line MA09 generally as described in example 1 above. In brief and starting with MA09 hESCs grown on mouse embryonic fibroblasts (MEFs), we use a 3-step approach to generate MSCs. hESCs were first differentiated into embryoid bodies (EB) for 4 days and then into hemangioblasts for 9 days. The hemangioblasts were then transferred into an MSC derivation medium. Within about 14 days, the attached cells fully differentiated into MSCs cells with cell surface markers similar to those of BM-MSCs. hESC-MSC cultures were passaged every 3-4 days and replated at 5000 cells/sq cm. At the third passage (p3), cells were frozen down and then subsequently thawed and grown for 4 days as fourth passage (p4) MSCs prior to use in the model. Cells in culture were freshly harvested with 0.05% trypsin on the day of injection into SKH1 hairless mice for the pain study. Orofacial pain testing was performed using the Stoelting Orofacial Pain Assessment Device (OPAD) (www.stoeltingco.com/stoelting/3438/1465/1480/Physio/OroFacial-Pain-Assessment-Device-OPAD-NEW) as previously described (Rossi et al., Molecular Pain 2006, 2:37, which is hereby incorporated by reference in its entirety). In brief, mice undergo a two week training period whereby, after fasting, they are placed into a chamber containing a milk reward bottle located behind 2 temperature-controlled thermode elements. Mice are conditioned to push through the thermodes with their face in order to gain access to the milk reward. Milk licks per facial contact with the thermodes is measured in an automated fashion. After conditioning, baseline measurements (thermodes at 37 degrees) were taken in 2 independent sessions prior to any treatment and the licks per facial contact ratio was averaged for each group of mice, n=10 per group. Animals were then i.p. injected with 1×10E6 MA09 hESC-derived MSCs in 250 ul PBS or 250 ul PBS alone. 1 week later, mice were injected with 2 mg/kg of the chemotherapeutic agent, taxol. Heat or cold sensitivity was measured for each group of mice by changing the temperature in the thermode elements to either 42° C. or 18° C., respectively and recording their lick/facial contact ratio at these temperatures weekly for 4 weeks.

Results:

Results were computed as percentage of baseline licks/facial contact ratio over time. Pain sensitivity resulted in a decrease of the licks/facial contact ratio as compared to baseline, which is set as 100%. Thus, the mice avoided pushing through the electrodes due to the sensation of pain when they came in contact with heat or cold.

hMSCs blocked induction of chemotherapy induced heat hyperalgesia. Animals were pretreated with hMSCs (1×10E6 cells, 250 µl, i.p.) 1 week prior to injection of taxol (2 mg/kg). MSCs blocked the development of heat sensitivity when tested at 42° C. Animals treated with vehicle (PBS, 250 µl, i.p.) developed heat hyperalgesia over the 3-week period post-taxol injection. There was a significant between-subjects effect when comparing treatment (hMSC vs Veh; RM ANOVA, $F(1,15)=4.95$, $p=0.042$). Baseline values were not significantly different between the hMSC and Veh groups ($P=0.946$). Thus, a statistically significant block in taxol-induced sensitivity to heat for MSC-injected animals vs controls was observed. Taxol caused mice to feel more pain at 42° C. than they did before taxol treatment, with the percentage of baseline being decreased at weeks 1, 2, and 3. In animals administered MSCs, the taxol-induced sensitivity to heat was prevented. By week 4, the effects of the taxol in the vehicle control group had subsided and they returned to the same degree of heat sensitivity as they had before they were given the taxol (week 0 levels).

hMSCs also blocked induction of cold sensitivity. Animals were pretreated with hMSCs (1×10E6 cells, 250 µl, i.p.) 1 week prior to injection of taxol (2 mg/kg). This treatment blocked cold sensitivity when tested at 18° C. as compared to animals treated with vehicle (PBS, 250 µl, i.p.). There was a significant between-subjects effect when comparing treatment (hMSC vs Veh; RM ANOVA, $F(1,15)=16.71$, $p=0.01$). Thus, a statistically significant block in cold sensitivity was observed for MSC-injected animals vs controls. At weeks 1, 2, and 3, no drop in the percentage of baseline due to taxol was observed. Nonetheless, general sensitivity to cold was blocked by MSCs, as indicated by the fact that the percentage of baseline in the MSC-injected mice was significantly higher than in the control group in all 3 weeks tested. Thus, taxol treatment was not observed to cause an appreciable development of cold sensitivity in this experiment, but nonetheless there was a difference in overall cold sensitivity between the MSC-treated and control groups, with administration of MSC resulting in decreased cold sensitivity.

Example 21

Uveitis Study

Uveitis is an inflammatory eye disorder that affects the uvea of the eye (uvea is the middle layer of the eye and is comprised of the ciliary body, iris, and choroid). Causes include autoimmune-related mechanisms (i.e., inflammation is due to autoimmune attack on some component within the uvea, sometimes observed in lupus) and infectious mechanisms (i.e., inflammation is due to the immune system fighting an infection in the eye). In this example the effects of MSCs derived from hESC (MA09-MSCs) are evaluated using an established mouse model of uveitis (Tasso et al., Invest Ophthalmol V is Sci. 2012; 53:786-793, which is hereby incorporated by reference).

Methods:

FM-MA09-MSCs were generated as described in the preceding example. An experimental autoimmune uveitis (EAU) model of uveitis in C57BL/6 mice was established generally as previously described (Tasso et al., Invest Ophthalmol Vis Sci. 2012; 53:786-793). In brief, male mice aged 7-9 weeks were immunized with 500 ug of a peptide (aa1-20) derived from interphotoreceptor retinoid-binding protein 3 (IRBP) along with 1.5 ug pertussin toxin (PTX). As indicated, mice were also i.p. injected with a single bolus of $5\times10^6$ MA09 hESC-MSCs on the same day as the immunization (day 0). On day 21, mice were subjected to funduscope imaging and clinical evaluation and then sacrificed to collect eyes for histological evaluation as well as spleens and serum for tissue banking and follow-up (e.g., Treg evaluation). Three groups of mice were used in the experiment as follows: Group A contained 6 mice induced with EAU but NOT injected with MSCs (to evaluate the degree of disease induction without any treatment, i.e., a disease-specific positive control). Group B contained 8 mice that were not induced with EAU but did receive MSCs (negative control for non-specific effects of MSCs in wt mice) and Group C contained 7 mice that were induced with EAU and given MSCs, i.e. the experimental group).

Results

Histological analysis was performed for the 3 groups of mice. Uveitis induced in this model was rather mild, as noted by the histology images of the eye. There was an infiltration of polymorphonuclear leukocytes (PMN) and lymphocytes in the vitreous space for the IRBP+PTX treated mice (positive control for disease, no MSC) but no accompanying disorganization of retinal architecture, eg, retinal folds, nor damage to the photoreceptor layer (as comparing IRBP+PTX treated mice to MSC only treated mice, with the latter showing no uveitis disease, no infiltrated immune cells). IRBP+PTX+MSC-treated mice showed a striking reduction in the number of PMN and lymphocytes in the vitreous space (0 or 1 cells) as compared to IRBP+PTX only mice (typically more than 40 infiltrated immune cells in the vitreous space with additional cells in the retinal architecture).

To further quantify the effect of MSC treatment, histological samples and fundus examinations were independently scored in a blinded fashion by two investigators; the fundus and histological samples were performed in separate evaluations. The more severe the inflammation, inflammatory cell infiltration, and tissue damage, the higher the histology score. For funduscope examinations, higher scores represent more severe disease features. Additional disease features that do not readily appear in histology, such as mild vasculitis and optic nerve head erythema can be captured in funduscope imaging. Both eyes were scored separately for each mouse. Raw scoring numbers per eye per mouse showed general consistency between histology and funduscope scores for each eye/mouse. The results further confirmed that administration of MSC decreased the severity of uveitis in this model. Among the group A animals (in which EAU was induced without MSC administration), histology scores were "0" in 5 eyes and "0.5" in 7 eyes, and funduscope scores were "0" in 1 eye, "0.5" in 4 eyes, "1" in 1 eye, "1.5" in 2 eyes, and "2" in 4 eyes. Among the group B animals (in which MSC were administered without EAU induction), histology scores were "0" in all 16 eyes and funduscope scores were "0" in 11 eyes, "0.5" in 4 eyes, and "1" in 1 eye. Among the group C animals (in which EAU was induced and the MSC were administered), histology scores were "0" in 11 eyes, "0.25" in 2 eyes, and "0.5" in 1 eye; funduscope scores were "0" in 6 eyes, "0.5" in 3 eyes, "1" in 3 eyes, and "1.5" in 2 eyes.

Example 22

This example describes performance of human ES cell-derived MSCs (hES-MSC) in an EAE model of multiple sclerosis. Particularly, it is demonstrated in this example that hES-MSC outperform bone marrow MSC (BM-MSC) in this model. Additionally, the hES-MSC exhibited lower IL-6 expression compared to BM-MSC, which may contribute to better immunosuppression. Additionally, hES-MSC exhibited superior extravasation/migratory properties into injured CNS compared to BM-MSC.

Methods

Culture of hESCs and Generation of hES-MSCs hESC lines were cultured either on Matrigel in TeSR1 medium or on MEFs in DMEM:F12+20% KOSR+10 ng/ml bFGF. To generate hES-MSCs, hESCs were first differentiated into EBs for 4 days and then hemangioblasts (HBs) for an additional 6-12 days as previously described (Lu et al., 2008). HB-containing cell clusters were then transferred to αMEM with 20% FBS and cultured on Matrigel (BD Bioscience)-coated plates at a density of 5,000 cells/cm². The medium was refreshed every 3-4 days and after 7-14 days, the adherent cells gradually differentiated into spindle-shaped cells.

Culture of BM-MSCs

BM-MSCs #1, 2, 3 were derived from BM mononuclear cells (BMMNCs) obtained from AllCells, Inc (Alameda); #4 was derived from Lonza (Basel, Switzerland) BMMNCs, while #5 (GFP-labeled) and #6 were obtained as BM-MSCs from Dr. Darwin Prockop at Texas A&M. For derivation of #1-4, BMMNCs were thawed and plated onto tissue culture plastic dishes in αMEM+20% FBS. Adherent cells began to appear within the first 4-5 days and fed every 3 days until day ~10-12, when cells were harvested and replated at 3,000-5,000 cells/cm².

Analysis of Th1 and Th17 Cells in the CNS

EAE mice were perfused with cold PBS through the left ventricle. Brain and spinal cord were harvested, ground and digested with collagenase and Dispase (1 mg/ml each) at 37° C. for 20 minutes. Single cells passed through 40 µm cell strainer were washed and re-suspended in 4 ml of 40% Percoll, overlaid onto 5 ml of 70% Percoll and centrifuged at 2,000 rpm for 20 minutes. Inter layer cells were collected and stimulated with 12-O-tetradecanoylphorbol-13-acetate (TPA) at 50 ng/ml (Sigma) and ionomycin at 500 ng/ml (Sigma) in the presence of GolgiStop (BD Bioscience) for 6 h. Cells were then immunostained with anti-CD4-FITC and anti-CD8-Pacific Blue (BD Bioscience). Flow cytometry for IFNγ and IL-17 was performed using an intracellular staining kit (BD Bioscience) according to manufacturer's instructions.

Pathology of the Spinal Cord

Paraffin-embedded spinal cord cross sections were immunostained for CD3 (Biocare Medical) or Iba1 (Waco) and counterstained with anti-MBP (Millipore) or fluoromyelin as previously described (Crocker et al., 2006; Moore et al., 2011). Quantification of anti-MBP staining intensity was performed on the lateral columns of sections from the thoracic and lumbar levels of spinal cord samples using ImageJ (NIH) (Crocker et al., 2006). At least three regions of interest were analyzed for each subject in each treatment group.

In Vitro Assays of Th0, Th1, and Th17 Cells from Mouse Spleen

Naive CD4+ T cells were purified from mouse spleens with the Naive CD4 T Cell Enrichment kit (Stem Cell Technologies) and activated with anti-CD3 (1 µg/ml) and anti-CD28 (1 µg/ml). Cytokines and antibodies were added as follow: Th0 condition, anti-mIFNγ (5 µg/ml) and anti-mIL-4 (5 µg/ml) (eBioscience); Th1 condition, rmIL-12 (10 ng/ml) (Pepro-Tech), anti-mIL4 (5 ug/ml); Th17 condition, anti-mIL-4 (5 µg/ml), anti-mIFNγ (5 µg/ml), rmIL-6 (20 ng/ml) (Peprotech), rhTGF-β1 (1 ng/ml) (Peprotech). For some groups, anti-hIL-6 (10 µg/ml) (eBioscience) was added. hES- or BM-MSCs that had been mitotically-arrested through irradiation at 80 Gy, were added 1 hour later.

Cytokine Antibody Array 180,000 MSCs were plated per well of a 6-well plate and conditioned medium (CM) was collected 3 days after plating. CM was spun down briefly to remove cellular debris and then frozen at −20° C. CM was thawed for analysis on RayBiotech (Norcross) custom membrane arrays according to manufacturer's protocols.

Tracking of GFP+ MSCs in Perivascular Regions in the CNS

Spinal cord tissue was prepared as reported previously by Paul et al. (2013). In brief, after perfusion/fixation, spinal cords were harvested by laminectomy, and cryosectioned for immunostaining Anti-GFP-Alexa® 488, anti-CD31 (BD Bioscience), Alexa® 555 secondary antibody (Life Technologies) were used to detect GFP+ and endothelial cells, DRAQ5 (Biostatus Ltd.) were used to visualize the nuclei. Following staining, sections were mounted in Mowiol® and confocal z-stacks were acquired at 1 μm increments between z-slices, following a multitrack scan, using a Zeiss LSM 510 Meta confocal microscope. Images were analyzed with Imaris® suite version 7.1 software (Bitplane Inc.). The GFP channel was isosurface rendered to provide a better spatial perspective for visualizing GFP+ cells.

Statistical Analysis of In Vivo Data:

Clinical disease scores for each treatment group are expressed as mean±SE. The difference in 30 day clinical scores between groups was analyzed by two-way ANOVA and by t-test for the one-day scores in comparing the ability of GFP+ hES-MSCs and GFP+ BM-MSCs to extravasate from inflamed CNS venules and migrate into CNS parenchyma of EAE mice. Percentage data for CNS infiltrated T cells were arcsine-transformed prior to analysis. SPSS 15 software was used for statistical analysis. A probability of $P<0.05$ was considered to be significant, and $P<0.01$ to be highly significant.

Characterization of hES-MSCs

Flow cytometry staining was performed using standard methods. Antibodies include anti-CD31, CD34, CD29, CD73, CD90, CD105, CD44, CD45, CD166, HLA-ABC, HLA-DR, HLA-G (BD Bioscience, Biolegend, or eBioscience). Data were collected on FACS LSR II Flow Cytometer or Accuri C3 flow cytometer. Data analysis was performed with FlowJo (Treestar) or Accuri C6 software.

Immunofluorescence

Cells were fixed with 4% paraformaldehyde, permeabilized with PBS+0.2% Triton X-100 and stained with primary antibody in 5% goat serum overnight at 4° C. Cells were then washed 3× with PBS, stained with fluorochrome-conjugated secondary antibodies, washed 3× with PBS, and mounted under cover slips prior to phase and fluorescence microscopy.

Multi-Lineage Differentiation of hES-MSCs

Chemicals for all 3 differentiation conditions were purchased from Sigma-Aldrich unless otherwise indicated. Undifferentiated MSCs were stained as controls. Osteogenic differentiation was performed as previously described (Karlsson et al., 2009), In brief, MSCs were grown in low glucose DMEM plus 10% FCS, 80 μM ascorbic acid 2-phosphate, 1 μM dexamethasone, and 20 mM beta-glycerophosphate, fed every 3-4 days for 28 days, and stained with Alizarin Red. Adipogenic differentiation was performed as previously described (Karlsson et al., 2009). In brief, MSCs were grown in low glucose DMEM plus 20% FCS, 5 μg/ml insulin, 2 μM dexamethasone, 0.5 mM isobutylmethylxanthine, and 60 μM indomethacin, fed every 3-4 days for 30-32 days total, and stained with Oil Red O. Chondrogenic differentiation was performed as previously described (Barry et al., 2001). In brief, $2.5\times10^5$ cells MSCs were pelleted in 15 ml conical tubes and grown in high glucose DMEM, 1 mM Sodium Pyruvate, 0.1 mM ascorbic acid 2-phosphate, 0.1 μM dexamethasone, 1% ITS (Collaborative Biomedical Products), and 10 ng/mL TGF-β3 (Peprotech). Pellet cultures were fed every 2-3 days for 21-28 days total, fixed with 4% paraformaldehyde, and sent to MassHistology (Worcester, Mass.) for paraffin embedding and sectioning prior to Alcian Blue and Nuclear Fast Red staining Animal Model of Multiple Sclerosis The mouse EAE model was induced as previously described (Stromnes and Goverman, 2006). In brief, C57BL/6 mice were subcutaneously injected with a mixture of $MOG^{35-55}$, Freund's adjuvant, and pertussis toxin contained in the EAE Induction kit from Hooke Laboratories, Inc, MA (Cat. # EK-0114) following the manufacturer's protocol. BM- or hES-MSCs at $1\times10^6$ cells/mouse or PBS (a vehicle control) were i.p. injected on day 6 (for pre-onset) or 18 (for post-onset) after the immunization. Disease score was monitored every day for up to 31 days as follows: 0, no sign of disease; 1, loss of tone in the tail; 2, partial hind limb paralysis; 3, complete hind limb paralysis; 4, front limb paralysis; and 5, moribund (Stromnes and Goverman, 2006). For some experiments, cumulative and maximal disease scores were also calculated (e.g., in evaluating the ability of hES-MSCs to attenuate cumulative and maximal disease scores in EAE mice).

In Vitro Assay of T Cell Proliferation

Lymphocytes isolated from mouse peripheral lymph nodes were labeled with 5 μM of CFSE for 10 min. at 37° C. 1,000 hES- or BM-MSCs were mixed with 10,000 lymphocytes per well in a 96-well plate, and the cells were stimulated for proliferation with plate-bound anti-CD3 and soluble anti-CD28 antibodies (eBioscience, CA). The cells were collected 3 days after the stimulation, followed by flow cytometry staining with anti-CD4 and anti-CD8 antibodies (BD Bioscience, CA). CFSE dilution was gated on CD4 and CD8 T cells, respectively.

Quantitative RT-PCR

MSC RNA was isolated using the RNAeasy kit (Qiagen) per manufacturer's instructions. cDNA synthesis was performed using the SuperScript III First-Strand Synthesis SuperMix for qRT-PCR (Life Technologies). Quantitative RT-PCR (qRT-PCR) was performed using Taqman probes (Life Technologies) and SSO Fast Mastermix (Biorad) on a Biorad CFX 96 qRT-PCR machine. Data was analyzed using CFX Manager 2.1 software (Biorad) and the ΔΔCt method following normalization with GAPDH. For IL-6 RNA expression in the stimulation experiments, MSCs were co-cultured with non-adherent human PBMCs (containing T cells) for 4 days total. 2.5 ng/ml PHA was added for the final 2 days. Non-adherent PBMCs were then aspirated away and adherent cells were rinsed 3× with PBS prior to RNA processing.

Karyotyping:

The G-banded karyotyping of hES-MSCs was conducted by CellLine Genetics (Madison, Wis.).

Human T cell proliferation assayed via mixed leukocyte reaction to PHA stimulation Non-adherent human PBMC from 2 different donors were used as a source of T cell responders, hES-MSCs from 5 different lots and BM-MSCs from 3 different donors were used as inhibitors among 4 independent experiments. MSCs were mitotically-arrested with 5-10 μg/ml mitomycin C (Sigma-Aldrich) for 2.5-3 h, rinsed 2× with PBS and responder cells were added to the MSC culture at a 1:6 ratio in IMDM+10% heat-inactivated human serum. On day 3, 2.5 ng/ml PHA (Sigma) was added to induce T cell proliferation. On day 4, 10 μM BrdU (BD Bioscience) was added and on day 5, T cell proliferation was assessed through flow cytometric staining using anti-CD4-FITC, CD8-APC, and BrdU-PE antibodies with the BrdU Incorporation kit (BD Bioscience) according to manufacturer's protocol.

Human T$_{reg}$ Cell Stimulation

Human PBMCs (AllCells) were co-cultured for 4 days in suspension with adherent hES-MSCs or BM-MSCs that had been previously mitotically inactivated with mitomycin C (Sigma-Aldrich). Media was IMDM (Gibco)+10% heat-inactivated human serum (Mediatech), and 30 IU/ml rhIL-2 (Peprotech). T$_{reg}$ cells were determined by triple positivity for CD4, CD25, and FoxP3 by staining with anti-CD4-FITC, CD25-APC, and FoxP3-PE antibodies using the FoxP3 Intracellular Flow Staining kit (Biolegend) according to manufacturer's protocol.

Results

MSCs are efficiently derived from hESCs using our HB-enriching method

Figure 33:
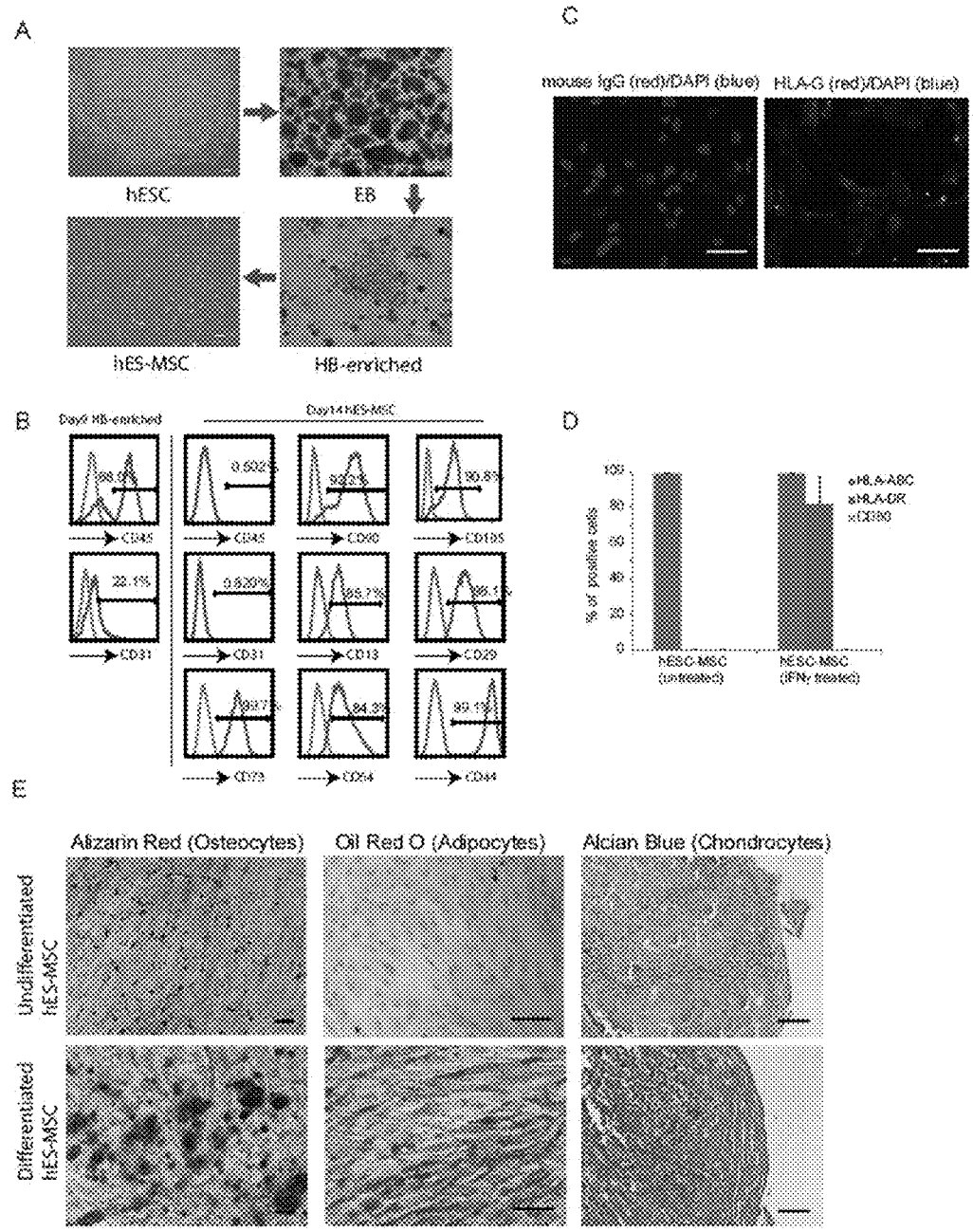
FIG. 33A-E. MSCs are efficiently derived from hESCs. (A) Phase contrast images for hESC (CT2) differentiation into MSCs through multiple stages. hESCs cultured on Matrigel in TeSR1 medium were used to form EBs for 4 days. The EB cells were then dissociated and cultured in hemangioblast (HB) Growth Medium for 6-12 days. HB-enriched cells were then harvested, rinsed, and cultured in MSC Medium for 7-14 days to form hES-MSCs. (B) Flow cytometric analyses of cell surface markers on day-9 HB-enriched cells and day-14 hES-MSCs (CT2). (C) Immunofluorescence for HLA-G (red) and DAPI (blue) of hES-MSCs (MA09). (D) hES-MSCs (MA09) were treated +/−IFNγ at 50 ng/ml for 7 days, and stained for HLA-ABC, HLA-DR and CD80. Bars indicate the mean of 4 independent experiments+/−SD. (E) In vitro multi-lineage differentiation of hES-MSCs (MA09) (bottom panel) with undifferentiated hES-MSCs as controls (top panel). Phase contrast images of Alizarin Red staining for osteogenic differentiation (left), Oil Red O staining for adipogenic differentiation (middle), and histological sections of chondrogenic pellets stained with Alcian Blue (right). Scale bars=50 μm.

Starting from either feeder-free hESCs or hESCs grown on mouse embryonic fibroblasts (MEFs), we obtained MSCs by using a 3-step approach that goes through both embryoid body (EB) and HB intermediate stages (FIG. 33A). The HB intermediate contains a heterogeneous population of cells including ~68% CD45+ cells (hematopoietic progenitors) and ~22% CD31+ cells (endothelial progenitors) (FIG. 33B). Replating these cells on Matrigel in an αMEM-based MSC medium allowed the emergence of MSC-like cells; 24 h after plating, 5-10% of the cells attached to the plate and 7-14 days thereafter, the attached cells fully differentiated into MSC-like cells with cell surface markers similar to those of BM-MSCs. They expressed high levels of CD73 (>99%), CD90 (>90%), CD105 (>90%), CD13 (>85%), CD29 (>90%), CD54 (>80%), CD44 (>99%), and CD166 (>90%), but did not express non-MSC markers such as CD31, CD34 and CD45 (FIG. 33B). Demonstrating the capability and reproducibility of this method, we found that cells harvested anytime between HB-d7 and HB-d12 could similarly give rise to hES-MSCs. Specifically, flow cytometric analysis of cell surface markers on hESC-derived HB-enriched cells and hES-MSCs was performed and expression levels were determined from the mean of four independent experiments. hESC (MA09) derived-HB-enriched cells were harvested after culture in methylcellulose-containing medium for 7-12 days, and hES-MSCs were harvested after culture in the MSC Medium for 14-21 days. In hES-MSC, over about 90-95% of cells were positive for CD105, CD90, CD29, CD73, CD166, CD44, and HLA-ABC, while less than 5% of cells were positive for CD34, CD45, or CD31. In contrast, in hESC-HB-enriched cells, less than about 10% of cells were positive for CD105, CD90, CD73, CD34, and CD31; about 45% of cells were positive for CD29; about 30% of cells were positive for CD166, about 90% of cells were positive for CD44; about 50% of cells were positive for HLA-ABC; and about 80% of cells were positive for CD45. Moreover, we have used this method to generate MSCs from 4 different hESC lines: H9 (Thomson et al., 1998), CT2 (derived at UConn) (Wang et al., 2009), MA09 (a FDA-approved, clinical-grade line derived at Advanced Cell Technology) (Klimanskaya et al., 2006), and ES03-Envy (Envy, a GFP-labeled line derived at ES International) (Costa et al., 2005).

Like BM-MSCs (Le Blanc et al., 2003; Selmani et al., 2008), our hES-MSCs express high levels of immunosuppressive non-classical MHC antigen HLA-G (FIG. 33C) and MHC class I antigen HLA-ABC (determined by flow cytometry as discussed above) but not MHC class II antigen HLA-DR and co-stimulatory molecule CD80; IFNγ treatment induces up-regulation of HLA-DR but not CD80 (FIG. 33D). Functionally, the hES-MSCs are multipotent as they can differentiate into osteocytes, adipocytes, and chondrocytes, a defining criterion for MSCs (FIG. 33E). The hES-MSCs can be cultured in vitro for at least 12 passages and were determined to have a normal karyotype at this time point; the cells also sustained their immunophenotype and differentiation capabilities (data not shown).

hES-MSCs Attenuate the Disease Score of EAE Mice in Both Prophylactic and Therapeutic Modes We employed a standard EAE model of MS in C57BL/6 mice to test the therapeutic utility of our hES-MSCs. EAE was induced as previously described (Stromnes and Goverman, 2006). Six days after immunization, mice were injected with $1\times10^6$ hES-MSCs or PBS intraperitoneally (i.p.). hES-MSCs derived from three hESC lines CT2, MA09, and H9 all significantly attenuated the daily disease scores (FIG. 34A) as well as cumulative and maximal disease scores. However, mice injected with parental CT2 hESCs manifested high disease scores similar to those of PBS controls (FIG. 34A). To confirm the clinical score data, we also histologically analyzed microglial inflammatory activity within the spinal cord. Immunostaining for ionized calcium-binding adapter molecule 1 (IBA1) revealed reduced microgliosis in EAE mice treated with hES-MSCs compared to those treated with PBS (FIG. 34B). Infiltration of total T cells (stained as CD3 cells) into the spinal cord was also decreased by hES-MSC-treatment (FIG. 34B). Strong immunostaining for myelin-binding protein (MBP) indicates that demyelination was prevented in mice treated with hES-MSCs compared to those treated with PBS (FIGS. 34B and 34C).

Figure 34:
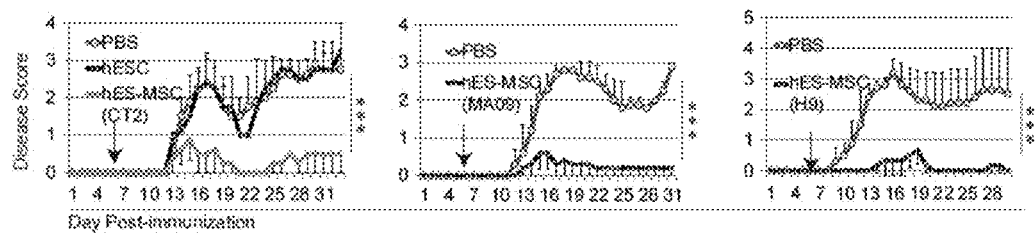
FIG. 34A-D. hES-MSCs attenuate the disease score of EAE mice and analyses of the CNS. (A) Disease scores of EAE mice treated with three different hES-MSC lines (CT2, MA09, and H9) pre-onset. $10^6$ hES-MSCs or undifferentiated hESCs as a control were i.p injected 6 days post-immunization. N=5, *P<0.001. (B) Analysis of demyelination and microglial responses in the CNS of EAE mice treated with hES-MSCs or PBS as a control. Immunohistochemical detection of MBP (red), CD3 for T cells (green) and IBA1 for microglia (green) on lumbar spinal cord cross sections from EAE mice treated with either hES-MSCs (a and c) or PBS (b and d). (C) Quantitative analysis of myelin in the spinal cord was performed using relative fluorescent intensity (RFI) measurement of MBP expression in digitally captured spinal cord hemi-sections. N=4-6, P<0.02. (D) Disease scores of EAE mice treated with hES-MSCs post-onset. $10^6$ hES-MSCs were i.p injected 18 days post-immunization. n=6, ***P<0.001.
Figure 34:
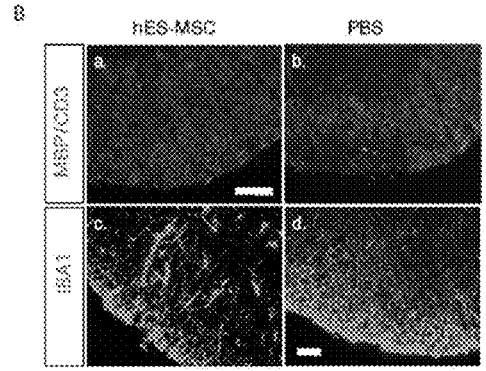
Figure 34:
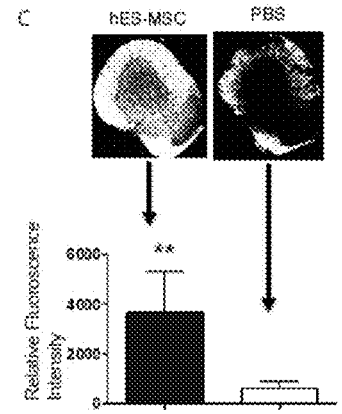
Figure 34:
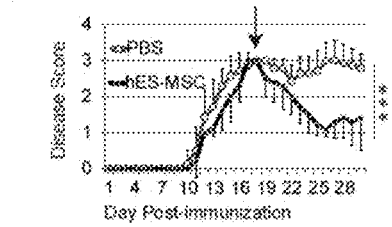

In addition to the prophylactic effects shown above, we also tested the effect of hES-MSCs treatment on mice that had already developed EAE (post-disease onset). When hES-MSCs were injected on day 18 post-immunization, we observed a gradual decline in disease scores from ~3.0 down to an average score of 1.67 by day 30 in hES-MSCs-treated mice, whereas the PBS-treated EAE mice showed an average score of 2.8 by day 30 (FIG. 34D). Collectively, data presented in FIG. 34 show that hES-MSCs can reproducibly decrease disease severity both prophylactically and therapeutically in the EAE model.

Figure 35:
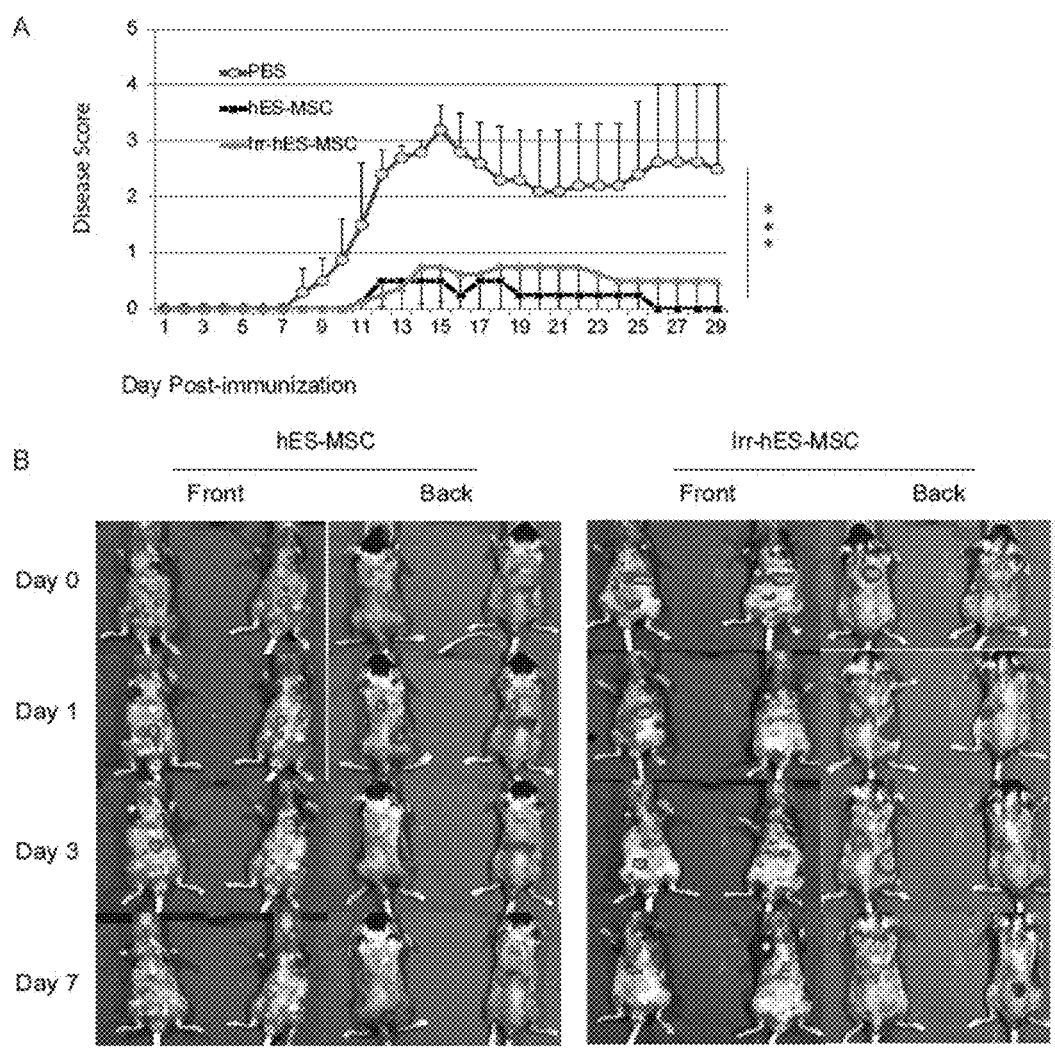
FIG. 35A-B. Irradiated hES-MSCs retain anti-EAE effect. (A) Irradiated hES-MSCs (Irr-hES-MSCs), derived from MA09 hESCs, reduced disease score in EAE mice. PBS, $1×10^6$ hES-MSCs or $2×10^6$ Irr-hES-MSCs were i.p. injected into EAE mice 6 days post-immunization followed by disease scoring. N=5, ***P<0.001. (B) Non-irradiated (left) and irradiated (right) luciferase-expressing hES-MSCs (CT2) were tracked in EAE mice. Luciferase signals were monitored at various days post-cell injection by injecting the mice with D-Luciferin. Images were taken using the Xenogen IVIS 100 system.

Additionally, control experiments demonstrated that hES-MSCs, but not parental hESCs, attenuated cumulative and maximal disease scores in EAE mice. Cumulative and maximal disease scores during the course of 28-32 days were compared for mice administered hES cells (CT2), hES-MSC (CT2), hES-MSC (H9), and hES-MSC (MA09), as well as negative controls (administered PBS only). N=5. Cumulative and maximal disease scores were similar for hES (CT2) administered mice and negative controls. Cumulative and maximal disease scores were significantly lower for each group of mice that were administered hES-MSC compared to negative controls (P<0.01).

hES-MSCs Maintain Anti-EAE Properties and In Vivo Lifespan Following Irradiation Some reports suggest that MSCs transplanted into animals may undergo malignant transformation or support tumor growth formed by host cells (Djouad et al., 2003; Wong, 2011). Yet, since short-term cytokine secretion and cell-cell contact may be sufficient to exert MSC functions (Uccelli and Prockop, 2010), we hypothesized that irradiated MSCs may still provide an anti-EAE effect. To test this hypothesis, we irradiated hES-MSCs at 80 Gy immediately before injecting cells into EAE mice at day 6 post-immunization. We observed comparable anti-EAE effects to the non-irradiated hES-MSC groups when we used $2\times10^6$ cells/mouse of irradiated cells (FIG. 35A). To test the actual lifespan of injected cells, we transduced CT2 hESCs with the lentiviral luciferase-expressing vector (Pomper et al., 2009), and generated a stable luciferase-positive hESC-MSC line. Stable luciferase expression was confirmed by immunostaining (not shown). We found that both the irradiated and non-irradiated hES-MSCs had roughly the same lifespan of ~7-10 days in the mice (FIG. 35B).

Teratogenicity is an additional concern for any therapeutic cell type differentiated from pluripotent cells. To assess this risk, we injected hES-MSCs into immunodeficient SCID-beige mice at $1 \times 10^6$ cells/mouse, and found no tumor formation at the injection sites within 2 months, whereas teratomas formed in mice injected with the same dose of parental hESCs (data not shown).

hES-MSCs have Stronger Anti-EAE Effects In Vivo than BM-MSCs

Figure 36:
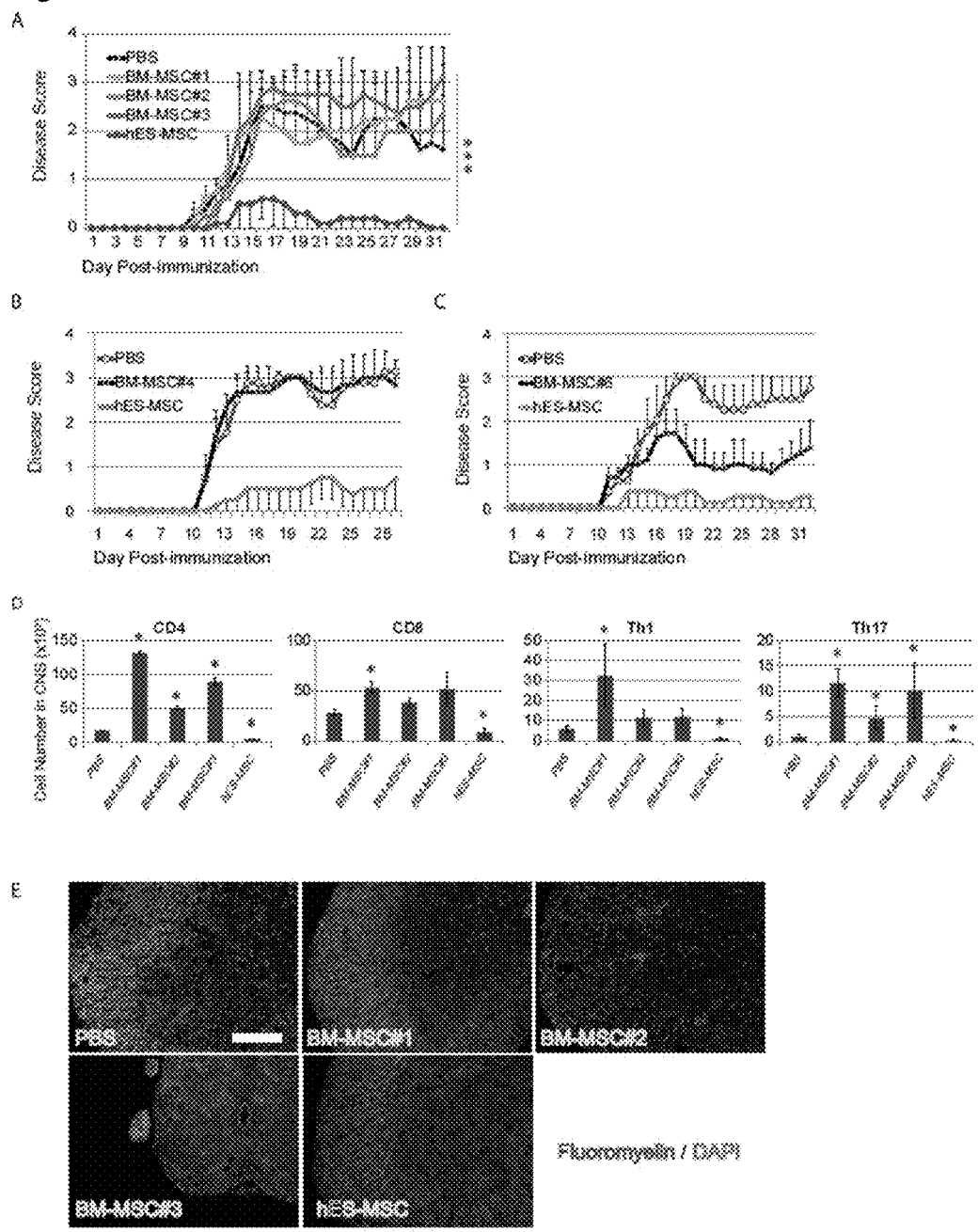
FIG. 36A-E. hES-MSCs have stronger anti-EAE effect in vivo than BM-MSCs. (A-C) Disease scores of EAE mice treated with PBS, BM-MSCs or hES-MSCs (MA09) pre-onset. $1\times10^6$ hES-MSCs or BM-MSCs (each BM-MSC # represents a different donor) were i.p injected 6 days post-immunization. N=5 per group, ***P<0.001 between hES-MSCs and any of the three BM-MSCs treated groups. (D) Total numbers of $CD4^+$, $CD8^+$, Th1, and Th17 cells in the CNS of EAE mice treated with PBS, hES-MSCs, or BM-MSCs on day 32 post-immunization. Lymphocytes purified from the CNS were analyzed for numbers of $CD4^+$ and $CD8^+$ cells using flow cytometry or stimulated with TPA and ionomycin followed by intracellular staining for numbers of $IL-17^+$ and $IFN\gamma^+$ cells (right panels). N=4, *P<0.05, **P<0.01. (E) Qualitative analysis of myelin content in spinal cord cross-sections of EAE mice treated with PBS, BM-MSCs, or hES-MSCs using Fluoromyelin stain (green) and counterstained with DAPI (blue) to indicate infiltration of nucleated cells.

Given the reported variability in in vivo efficacy of BM-MSCs, we decided to compare hES-MSCs and human BM-MSCs in the prophylactic EAE model. We obtained MSCs from 6 different BM donors and found 5 out of the 6 failed to significantly attenuate the disease score of EAE mice (FIGS. 36A, 36B, and GFP-expressing BM-MSCs) while one BM-MSC line (BM-MSC #6) showed a moderate effect (FIG. 36C). This is in marked contrast to the four different hES-MSC lines that all showed a strong anti-EAE effect (FIG. 34A, and GFP-expressing hES-MSCs).

EAE/MS is accompanied by infiltration of reactive T cells into the CNS (McFarland and Martin, 2007). Therefore, we purified all T cells that had penetrated into the CNS and found that hES-MSC-injected mice had significantly fewer CD4+ and CD8+ (FIG. 36D) T cell infiltrates than PBS control EAE mice, coinciding with their reduction of disease severity. In contrast, BM-MSC-treated mice had the opposite effect and actually displayed significantly more CD4+ and slightly more CD8+ T cell infiltrates (FIG. 36D) than PBS control EAE mice. The percentage of total numbers of CD4+ and CD8+ cells in the CNS of EAE mice treated with PBS, hESC or hES-MSCs was determined on day 15 post-immunization. Lymphocytes purified from the CNS were analyzed for numbers of CD4+ and CD8+ cells by flow cytometry (N=4). The number of Th17-expressing cells was significantly reduced ($P<0.05$) and the number of CD4, CD8, and Th1-expressing cells was highly significantly reduced ($P<0.01$) in the CNS of hES-MSC treated animals compared to PBS-treated controls. Parental hESC line CT2-injected mice had similar levels of CD4 and CD8 cell infiltrates as PBS controls. We also found that hES-MSC-treated EAE mice had significantly fewer proinflammatory Th1 and Th17 cells than PBS- or CT2 hESC-injected controls (FIG. 36D). Th1 (IFN$\gamma^+$) and Th17 (IL-17$^+$) cells in the CNS of EAE mice treated with PBS, hES-MSCs (CT2) on day 15 post-immunization were also quantified by intracellular flow cytometry dot plots; in PBS-treated mice 11.49% of cells were IL-17$^+$ only, 15.16% of cells were IFN$\gamma^+$ only, and 9.27% of cells were positive for both IL-17 and IFN$\gamma$. In contrast, from hES-MSC treated mice 4.37% of cells were IL-17$^+$ only, 2.52% of the cells were IFN$\gamma^+$ only, and 1.38% of cvells were positive for both IL-17 and IFN$\gamma$. BM-MSC-treated mice, on the other hand, had similar or greater Th1 numbers and consistently greater Th17 numbers as compared to controls (FIG. 36D). Reduced fluoromyelin staining of MBP in the spinal cord confirms severe damage in both PBS-treated and BM-MSC-treated mice while MBP levels were preserved in hES-MSC-treated mice (FIG. 36E). The damaged regions in BM-MSC-treated mice also show a high number of DAPI positive cells, suggesting more inflammatory cells infiltration.

Considering the important role of regulatory T cells ($T_{reg}$ cells detected as CD4+, Foxp3$^+$, and CD25$^+$) in suppressing inflammation, we examined the ratio of $T_{reg}$ cells among infiltrated CD4 T cells in the CNS and found no difference in hES-MSC-treated vs control EAE mice. Influence of hES-MSCs or BM-MSCs on regulatory T cell populations in vivo and in vitro was examined by flow cytometry, and percentage of Foxp3$^+$/CD25$^+$ cells among infiltrated CD4$^+$ T cells in the CNS of EAE mice treated with hES-MSCs (CT2) or PBS was determined. In PBS treated animals, 5.17% of cells were Foxp3$^+$ only, 11.5% of cells were CD25$^+$ only, and 21.7% of cells were both Foxp3$^+$ and CD25$^+$. In hES-MSC treated animals, 1.52% of cells were Foxp3$^+$ only, 13.1% of cells were CD25$^+$ only, and 17.2% of cells were both Foxp3$^+$ and CD25$^+$. This is similar to a previous report on murine BM-MSCs in EAE (Zappia et al., 2005). In vitro, both hES- and BM-MSCs increased $T_{reg}$ cell proliferation, but there was no remarkable difference between the two groups. Human PBMC were co-cultured with mitotically inactivated hES-MSCs (MA09) (n=6) or BM-MSCs (n=5) at a ratio of 1:10 and IL-2 at 30 IU/ml for 4 days. Percentages of $T_{reg}$ cells were determined via flow cytometry staining for CD4$^+$/CD25$^+$/Foxp3$^+$ cells and were less than 0.5% for T cells without IL-2, about 1.5% for T cells cultured with IL-2, about 5% for T cells cultured with hES-MSC and IL-2 ($p<0.01$ compared to T cells alone with IL-2), and about 4% for T cells cultured with BM-MSC and IL-2 ($p<0.05$ compared to T cells alone with IL-2). This suggests that enhanced $T_{reg}$ cell proliferation is a common response to both hES- and BM-MSCs, but not necessarily a contributor to the anti-EAE effect in vivo.

hES-MSCs have Stronger Inhibition of T Cell Functions In Vitro than BM-MSCs

We next compared hES-MSCs and BM-MSCs for their ability to inhibit T cell proliferation in vitro. We stimulated carboxyfluorescein succinimidyl ester (CFSE)-labeled mouse naïve T cells with increasing amounts of anti-CD3 antibody and found that hES-MSCs inhibited the proliferation of mouse CD4$^+$ and CD8$^+$ T cells when stimulated with anti-CD3 antibody at 0.2 and 0.6 µg/ml, or 0.1 and 0.3 µg/ml, whereas BM-MSCs only did so at low doses, i.e., 0.2 or 0.1 µg/ml of anti-CD3 antibody. hES-MSCs were observed to have stronger suppression of T cell functions in vitro than BM-MSCs. hES (MA09)- or BM-MSCs were incubated with CFSE-labeled mouse lymphocytes at a ratio of 1:10 and stimulated by various concentrations of anti-CD3 antibody. The ratios of proliferating CD4+ and CD8+ T cell were analyzed by flow cytometry (N=3). Flow cytometry histogram plots were carried out to show the percentage of divided CD4+ or CD8+ T cells with diluted CFSE signal.

Similarly, hES-MSCs showed stronger inhibition than BM-MSCs on proliferation of human T cells among phytohaemagglutinin (PHA)-stimulated human peripheral blood mononucleocytes (PBMCs). Mitotically inactivated hES (MA09)- or BM-MSCs were incubated with PHA-stimulated human PBMCs at a ratio of 1:6. The percentage of proliferating CD4+ or CD8+ cells was measured with BrdU incorporation and the mean of 4 independent experiments was determined. The percentage of BrdU+ human T cells was approximately 0% for T cells only, 30% for T cells only plus PHA, about 15% for T cells plus hES-MSC plus PHA, and about 25% for T cells plus BM-MSC plus PHA. The difference in percentage of BrdU positive T cells was statistically significant between T cells incubated with hES-MSC or BM-MSC (*$P<0.05$). Together, these data suggest that hES-MSCs are more potent inhibitors of mouse and human T cell proliferation than BM-MSCs.

Since EAE mice treated with BM-MSCs had more Th1 and Th17 cell infiltration in the CNS than mice treated with hES-MSCs (FIG. 36D), we examined these T cell subtypes in vitro in the presence or absence of hES- and BM-MSCs. Under the Th1 condition, differentiation of naïve CD4+ T cells into Th1 (CD4$^+$/IFN$\gamma^+$) cells was reduced by hES-MSCs, but was unaffected or even enhanced by different BM-MSC lines. In these experiments, hES (MA09)- or BM-MSCs were incubated with mouse naïve CD4+ T cells at a ratio of 1:10, followed by Th1 or Th17 differentiation for 5 days. IFNγ+ and IL-17+ CD4 T cells were detected via intracellular flow cytometry staining after TPA/ionomycin stimulation and results were obtained from four independent experiments. Under Th1 condition, the fraction of CD4/IFNγ double positive cells was 29.7% in controls, 18.0% for hES-MSC, 26.9% for BM-MSC#2, 43.6% for BM-MSC#3, and 33.6% for BM-MSC#6. Of note, even the BM-MSC line that gave a modest therapeutic response in the EAE model (BM-MSC #6, FIG. 36C) could not effectively reduce Th1 differentiation in this in vitro assay. Under the Th17 differentiation condition, both hES- and BM-MSCs reduced the differentiation of Th17 (CD4+/IL17+) cells; the fraction of IFNγ−/IL17+ cells was 21.4%, 5.15%, 1.13%, 2.73%, and 2.20% for control, hES-MSC, BM-MSC#2, BM-MSC#3, and BM-MSC#6, respectively. However, under the same Th17-inducing conditions, BM-MSCs but not hES-MSCs significantly increased the percentage of IFNγ+/IL17− (i.e., Th1) cells; the fraction of IFNγ+/IL17− cells was 0.190%, 0.611%, 17.7%, 12.1%, and 14.2% for control, hES-MSC, BM-MSC#2, BM-MSC#3, and BM-MSC#6, respectively. Collectively, these results show that hES-MSCs effectively dampen both Th1 and Th17 differentiation cascades in vitro while BM-MSCs can surprisingly promote Th1 differentiation under a Th17-inducing environment.

BM-MSCs Express Higher IL-6 than hES-MSCs, and IL-6 Blockage Enhances the Immunosuppressive Effect of BM-MSCs A large number of soluble or matrix factors have been reported to mediate the immunomodulatory and/or neuroprotective effects of MSCs (Uccelli and Prockop, 2010). Therefore, we conducted microarray analysis to identify differences in the expression of these factors between BM-MSCs and hES-MSCs. The overall expressional profiles of hES- and BM-MSCs samples were quite similar (data not shown), yet a small set of genes was expressed differentially. Among these, IL6 appeared to be much more highly expressed in BM-MSCs than in hES-MSCs. Multiple methods including qRT-PCR, intracellular flow cytometry, and cytokine antibody arrays confirmed this finding. By qRT-PCR, the average of three independent experiments demonstrated that the relative normalized expression of IL-6 was about 0.05 for hES-MSC and about 1.0 for BM-MSC ($p<0.05$). Intracellular flow cytometry staining was conducted for IL-6 in BM-MSCs from 3 different donors and 3 hES-MSCs from three hESC lines. The percentages of IL-6−/IL10−, IL-6+/IL10−, IL-6−/IL10+, and IL-6+/IL10+ cells respectively were 0.12, 0.00, 50.3, and 49.5 for BM-MSC#1; 0.05, 0.00, 65.7, and 34.2 for BM-MSC#2, 0.074, 0.00, 60.5, and 39.4 for BM-MSC#6, 0.25, 0.00, 96.7, and 3.05 for hES-MSC#1, 2.07, 0.00, 96.9, and 1.07 for hES-MSC#2, and 0.00, 0.00, 97.2, and 2.81 for hES-MSC#3. Cytokine antibody arrays were also conducted to show the level of IL6 and IL8 proteins in conditioned medium from hES-MSCs or BM-MSCs. Cytokine antibodies were present on the membrane in duplicate, and array controls were also included. In representative mages of at least 5 independent experiments it was observed that the detected level IL-6 was substantially lower in the hES-MSC compared to BM-MSC.

Upon IFNγ stimulation, the percentage of IL-6 expressing hES-MSCs did not change, however the percentage of IL6-expressing cells BM-MSCs nearly doubled, as determined by intracellular flow cytometry which showed the percentage of IL6-expressing cells+/−IFNγ (10 ng/ml for 12 h). We also tested MSC production of IL6 following co-culture with stimulated PBMCs/T cells as the latter produces high levels of IFNγ and TNFα upon stimulation. After removing the PBMCs in suspension, much higher IL-6 expression was detected, via qRT-PCR in the adherent BM-MSCs than in the adherent hES-MSCs. Specifically, the IL-6 level in BM-MSCs, but not hES-MSCs (MA09), was dramatically enhanced following co-culture with non-adherent human PBMCs for 4 days. In these experiments, 2.5 ng/ml PHA was added for the final 2 days. PBMCs were washed away, and qRT-PCR was used to determine IL-6 expression normalized to GAPDH. Relative normalized IL-6 gene expression for hES-MSC with PHA-stimulated T cells was about 3, but was about 25 for BM-MSC treated in the same manner. When incubated with unstimulated T cells, relative normalized IL-6 gene expression was about 1 for hES-MSC and about 2 for BM-MSC.

Since IL-6 has been found to enhance T cell survival and differentiation (Dienz and Rincon, 2009), we sought to determine the effects of MSC-secreted human IL6 on mouse T cell differentiation. Under Th0 conditions (i.e., without mouse cytokines plus anti-mouse IFNγ and anti-mouse IL4), co-culture with three different BM-MSC samples, including BM-MSC #6, was found to enhance the percentage of IFNγ-secreting CD4+ T cells (Th1 cells) while hES-MSCs had no effect; for Th0 condition plus IgGkappa, the percentage of CD4+/IFN was 3.22, 3.57, 39.4, 41.6, and 36.8 in controls, hES-MSC, BM-MSC#2, BM-MSC#3, and BM-MSC#6 treated cells, respectively. An anti-human-IL-6 neutralizing antibody reduced this BM-MSC effect by ~23%-50% (FIG. 6E). Specifically, for TH0 condition plus anti-IL-6, the percentage of CD4+/IFN was 2.89, 0.672, 26.7, 21.4, and 28.2 in controls, hES-MSC, BM-MSC#2, BM-MSC#3, and BM-MSC#6 treated cells, respectively. Thus, elevated IL-6 production may be at least partially responsible for the compromised anti-EAE effects of BM-MSCs by promoting proinflammatory differentiation of T cells.

Both hES-MSCs and BM-MSCs Home to Spinal Cord but Only hES-MSCs Successfully Extravasate into the Inflamed Tissue To determine if hES- and BM-MSCs home to the injured CNS and extravasate through the damaged BBB and/or BSCB, we tracked the migration of MSCs differentiated from the constitutively GFP-expressing hESC line "Envy" (Costa et al., 2005), and GFP-labeled human BM-MSCs (Hofstetter et al., 2002) in EAE mice. Cells were injected on day 6 after immunization, and spinal cords were analyzed 8 days later, a time point when clinical scores for GFP+ BM-MSCs-injected mice and PBS controls were ~1.5-2.0 and scores for GFP+ hES-MSCs were effectively 0 when comparing average clinical scores on day of spinal cord harvest (day 14 post immunization, N=3 mice per group). As indicated by 3D reconstruction of confocal z-stacks from fluorescently-stained spinal cord cryosections, while both BM- and hES-MSCs homed to the injured EAE spinal cord, the vascular associations of the two type MSC lines were vastly different. Both parenchymal and meningeal venules were analyzed, as leukocytes are thought to first exit from the latter vascular bed during neuroinflammation (Bartholomaus et al., 2009; Kivisakk et al., 2003). The GFP+ hES-MSCs were clearly observed to migrate out from both vessel populations into the perivascular space. With regard to parenchymal vessels, hES-MSCs also extended well beyond the perivascular space—migrating deeper into the parenchymal tissue. hES-MSCs also conclusively extravasated across meningeal venules into the subarachnoid space surrounding the spinal parenchyma. In marked contrast, GFP+ BM-MSCs appeared to remain closely associated with parenchymal vessels, as if trapped inside or not capable of effectively exiting from vessels and migrating into the parenchyma. BM-MSCs also failed to show as extensive extravasation from meningeal vessels compared to hES-MSC. These observations pinpoint a key difference between hES- and BM-MSCs in vivo functionality in the EAE model. For the 3D reconstructions, 3D confocal datasets from spinal cord cryosections (60 µm) of MSC-injected EAE mice were used. Sections were stained with anti-GFP to track MSC, anti-CD31 to identify endothelial cells, and DRAQ5 to label nuclei. Clusters of GFP+ MSCs were observed in the parenchymal and meningeal venules. GFP/DRAQ5 and isolated GFP channels were observed. Isosurface rendered GFP+ cells, highlighted within the selected region of interest (ROI) were detectable. DISCUSSION In this study, we describe a novel, reproducible, and highly efficient method for generating hES-MSCs and show that hES-MSCs derived from multiple hESC lines all significantly attenuate disease scores in a mouse EAE model of MS. In stark contrast, human BM-MSCs displayed little to no therapeutic activity in the EAE model and limited immunosuppressive effects in vitro as compared to hES-MSCs. Mechanistically, the superior anti-EAE effects of hES-MSCs may, in part, be related to their lower expression of IL6 and greater ability to extravasate the BBB/BSCB and migrate into inflamed CNS tissue than their BM-MSCs counterparts.

In examining the anti-EAE effects of hES-MSCs, we observed that prophylactic treatment of EAE mice was more effective in attenuating disease scores than therapeutic treatment. This is not surprising since prophylactic treatment may only require MSC immunosuppressive activity while therapeutic intervention may additionally require extensive neural repair and regeneration. hES-MSCs may also contribute to neuroregeneration (perhaps through recruitment of endogenous progenitors). More effective therapeutic intervention may be possible with larger doses and/or repeated injections of cells. Of note, irradiated hES-MSCs were also effective in reducing EAE disease score and had the same lifespan in vivo as their non-irradiated counterparts. Mitotic inactivation (through irradiation or mitomycin C treatment) is routinely used in mixed leukocyte reaction (MLR) assays and does not appear to greatly affect MSC cytokine secretion or immunomodulatory activities in these assays (Bocelli-Tyndall et al., 2007). Thus, irradiation of cells may have important clinical value since being able to reduce the concern for tumorigenic potential may outweigh a slight reduction in potency.

The muted in vivo efficacy of BM-MSCs that we observed is consistent with previous reports that showed only mild (Gordon et al., 2008; Zhang et al., 2005) or negligible (Payne et al., 2012) effects of human BM-MSCs on EAE mice. Interestingly, BM-MSC #6, the one BM-MSC line in our studies that caused a modest reduction in EAE clinical scores was injected at passage 2 while the other BM-MSCs, which showed no effect, were used at passage 3 or 4. Despite being injected at later passages (p4-6), all hES-MSC lines offered large reductions in the clinical score of EAE mice. This suggests that the therapeutic potency of BM-MSCs is more sensitive to in vitro culture and expansion (a requirement for clinical scale use) than that of hES-MSCs. Indeed, other studies have shown that BM-MSCs have lower proliferative capacity than do hES-MSCs (Sanchez et al., 2011) and may readily senesce with even limited culturing (Wagner et al., 2008). While we did not observe massive senescence or changes in immunophenotype in BM-MSC cultures by passage 4 (data not shown), identifying biomarkers that accurately predict the in vivo functionality of MSCs is an ongoing area of investigation in our lab and others.

In our search for molecular differences between hES- and BM-MSCs, we found that IL-6 was expressed much higher in BM-MSCs than in hES-MSCs in both the basal and IFNγ-stimulated state. Elevated IL-6 levels have been found in blood and brain tissue from MS patients (Patanella et al., 2010) while site-specific production of IL-6 in the CNS can re-target and enhance inflammation in EAE (Quintana et al., 2009). Interestingly, mice lacking IL-6 receptor α at the time of T cell priming are resistant to EAE (Leech et al., 2012) and an IL-6-neutralizing antibody can reduce symptoms in EAE mice (Gijbels et al., 1995). As discussed further below, high levels of IL-6 may contribute to functional differences between BM-MSCs and hES-MSCs in terms of how they influence immune effector cells and how potent they are in a therapeutic setting. Indeed, it would be interesting to determine if combined treatment of BM-MSCs with an IL-6-neutralizing antibody or use of BM-MSCs with IL-6 knockdown enhances the anti-EAE effect.

Many studies have reported that MSCs can inhibit the differentiation of both Th1 and Th17 cells yet recent reports have noted that they can actually promote differentiation of pro-inflammatory T cells under certain permissive environments (Carrion et al., 2011; Darlington et al., 2010). In vivo and in comparison to PBS controls, we observed reduced CNS infiltration of Th1 and Th17 cells with hES-MSC treatment but increased CNS infiltration of Th1 and Th17 cells with BM-MSC treatment. In vitro and unlike hES-MSCs, we found that BM-MSCs skewed T cell differentiation to a Th1 phenotype under both Th0 (non-polarizing) and Th17 conditions. It is possible that certain factors produced highly by human BM-MSCs, but not hES-MSC, can trigger Th1 differentiation, thus overriding Th17 differentiation under these artificial in vitro conditions (Lazarevic et al., 2011). An anti-human IL-6 antibody was able to partially reverse the effect under Th0 conditions but not Th17 conditions (data not shown), presumably because the presence of exogenous mouse IL-6, which is added for Th17-induction, cannot be neutralized by the anti-human IL-6 antibody. Together these suggest that high IL6 secretion by BM-MSCs may impact the local cytokine milieu and augment the overall inflammatory response resulting into a striking difference in Th1/Th17 CNS infiltration between hES- and BM-MSC-treated mice. Lastly, as the BBB and BSCB show evidence of structural damage and functional impairment in EAE (Bennett et al., 2010), it is possible that MSCs at least partially execute their therapeutic effects in this disease by repairing these barriers (Pati et al., 2011). Since both GFP-labeled hES- and BM-MSC homed to the CNS, while only hES-MSC showed high therapeutic potential with capacity to effectively extravasate and migrate into the parenchyma, we hypothesize therapeutic efficacy and extravasation may be mechanistically linked. That MSCs might need to extravasate during EAE therapy is consistent with evidence these cells can downregulate pro-inflammatory effector functions of parenchymal microglia (FIG. 34B) (Lee et al., 2012; Sheikh et al., 2011). It is significant that in vitro culture and expansion of MSCs have both been implicated as factors that impair homing and transendothelial migration (De Becker et al., 2007; Rombouts and Ploemacher, 2003). A priori, it may be that BM-MSCs are more sensitive to these factors than hES-MSCs, and this is a determinant of the differences in therapeutic efficacy observed between the two MSC types. A variety of adhesion molecules and chemokine receptors, including α4β1, α4β7 integrins and several CXCRs and CCRs that are involved in leukocyte transmigration may also participate in MSC transmigration (Chamberlain et al., 2011). However, MSC extravasation may involve additional or unique mechanisms (Teo et al., 2012)—especially in the context of breaching the BBB and BSCB. Determining the dynamic changes and differences in expression of these molecules between hES- and BM-MSCs in situ will be critical in delineating the molecular requirements for MSC extravasation. In situ gene profiling of both MSC types is currently in play, and should further shed light on the mechanism(s) responsible for the unique therapeutic efficacy of hES-MSCs.

REFERENCES

Auletta, J. J., Bartholomew, A. M., Maziarz, R. T., Deans, R. J., Miller, R. H., Lazarus, H. M., and Cohen, J. A. (2012). The potential of mesenchymal stromal cells as a novel cellular therapy for multiple sclerosis. Immunotherapy 4, 529-547.

Bai, L., Lennon, D. P., Eaton, V., Maier, K., Caplan, A. I., Miller, S. D., and Miller, R. H. (2009). Human bone marrow-derived mesenchymal stem cells induce Th2-polarized immune response and promote endogenous repair in animal models of multiple sclerosis. Glia 57, 1192-1203.

Barberi, T., Willis, L. M., Socci, N. D., and Studer, L. (2005). Derivation of multipotent mesenchymal precursors from human embryonic stem cells. PLoS Med 2, e161.

Barlow, S., Brooke, G., Chatterjee, K., Price, G., Pelekanos, R., Rossetti, T., Doody, M., Venter, D., Pain, S., Gilshenan, K., et al. (2008). Comparison of human placenta- and bone marrow-derived multipotent mesenchymal stem cells. Stem cells and development 17, 1095-1107. Bartholomaus, I., Kawakami, N., Odoardi, F., Schlager, C., Miljkovic, D., Ellwart, J. W., Klinkert, W. E., Flugel-Koch, C., Issekutz, T. B., Wekerle, H., et al. (2009). Effector T cell interactions with meningeal vascular structures in nascent autoimmune CNS lesions. Nature 462, 94-98. Benito-Leon, J. (2011). Are the prevalence and incidence of multiple sclerosis changing? Neuroepidemiology 36, 148-149.

Bennett, J., Basivireddy, J., Kollar, A., Biron, K. E., Reickmann, P., Jefferies, W. A., and McQuaid, S. (2010). Blood-brain barrier disruption and enhanced vascular permeability in the multiple sclerosis model EAE. Journal of neuroimmunology 229, 180-191.

Bocelli-Tyndall, C., Bracci, L., Spagnoli, G., Braccini, A., Bouchenaki, M., Ceredig, R., Pistoia, V., Martin, I., and Tyndall, A. (2007). Bone marrow mesenchymal stromal cells (BM-MSCs) from healthy donors and auto-immune disease patients reduce the proliferation of autologous- and allogeneic-stimulated lymphocytes in vitro. Rheumatology (Oxford) 46, 403-408.

Brown, S. E., Tong, W., and Krebsbach, P. H. (2009). The derivation of mesenchymal stem cells from human embryonic stem cells. Cells Tissues Organs 189, 256-260.

Carrion, F., Nova, E., Luz, P., Apablaza, F., and Figueroa, F. (2011). Opposing effect of mesenchymal stem cells on Th1 and Th17 cell polarization according to the state of CD4+ T cell activation. Immunology letters 135, 10-16.

Chamberlain, G., Smith, H., Rainger, G. E., and Middleton, J. (2011). Mesenchymal stem cells exhibit firm adhesion, crawling, spreading and transmigration across aortic endothelial cells: effects of chemokines and shear. PLoS One 6, e25663.

Chao, Y. X., He, B. P., and Tay, S. S. (2009). Mesenchymal stem cell transplantation attenuates blood brain barrier damage and neuroinflammation and protects dopaminergic neurons against MPTP toxicity in the substantia nigra in a model of Parkinson's disease. Journal of neuroimmunology 216, 39-50.

Connick, P., Kolappan, M., Crawley, C., Webber, D. J., Patani, R., Michell, A. W., Du, M. Q., Luan, S. L., Altmann, D. R., Thompson, A. J., et al. (2012). Autologous mesenchymal stem cells for the treatment of secondary progressive multiple sclerosis: an open-label phase 2a proof-of-concept study. Lancet neurology 11, 150-156.

Costa, M., Dottori, M., Ng, E., Hawes, S. M., Sourris, K., Jamshidi, P., Pera, M. F., Elefanty, A. G., and Stanley, E. G. (2005). The hESC line Envy expresses high levels of GFP in all differentiated progeny. Nat Methods 2, 259-260.

Crocker, S. J., Milner, R., Pham-Mitchell, N., and Campbell, I. L. (2006). Cell and agonist-specific regulation of genes for matrix metalloproteinases and their tissue inhibitors by primary glial cells. Journal of neurochemistry 98, 812-823.

Darlington, P. J., Boivin, M. N., Renoux, C., Francois, M., Galipeau, J., Freedman, M. S., Atkins, H. L., Cohen, J. A., Solchaga, L., and Bar-Or, A. (2010). Reciprocal Th1 and Th17 regulation by mesenchymal stem cells: Implication for multiple sclerosis. Annals of neurology 68, 540-545.

De Becker, A., Van Hummelen, P., Bakkus, M., Vande Broek, I., De Wever, J., De Waele, M., and Van Riet, I. (2007). Migration of culture-expanded human mesenchymal stem cells through bone marrow endothelium is regulated by matrix metalloproteinase-2 and tissue inhibitor of metalloproteinase-3. Haematologica 92, 440-449.

Dienz, O., and Rincon, M. (2009). The effects of IL-6 on CD4 T cell responses. Clinical immunology 130, 27-33.

Djouad, F., Plence, P., Bony, C., Tropel, P., Apparailly, F., Sany, J., Noel, D., and Jorgensen, C. (2003). Immunosuppressive effect of mesenchymal stem cells favors tumor growth in allogeneic animals. Blood 102, 3837-3844.

Gijbels, K., Brocke, S., Abrams, J. S., and Steinman, L. (1995). Administration of neutralizing antibodies to interleukin-6 (IL-6) reduces experimental autoimmune encephalomyelitis and is associated with elevated levels of IL-6 bioactivity in central nervous system and circulation. Mol Med 1, 795-805.

Giuliani, M., Fleury, M., Vernochet, A., Ketroussi, F., Clay, D., Azzarone, B., Lataillade, J. J., and Durrbach, A. (2011). Long-lasting inhibitory effects of fetal liver mesenchymal stem cells on T-lymphocyte proliferation. PLoS One 6, e19988.

Gordon, D., Pavlovska, G., Glover, C. P., Uney, J. B., Wraith, D., and Scolding, N. J. (2008). Human mesenchymal stem cells abrogate experimental allergic encephalomyelitis after intraperitoneal injection, and with sparse CNS infiltration. Neurosci Lett 448, 71-73.

Gordon, D., Pavlovska, G., Uney, J. B., Wraith, D. C., and Scolding, N. J. (2010). Human mesenchymal stem cells infiltrate the spinal cord, reduce demyelination, and localize to white matter lesions in experimental autoimmune encephalomyelitis. J Neuropathol Exp Neurol 69, 1087-1095.

Gruenloh, W., Kambal, A., Sondergaard, C., McGee, J., Nacey, C., Kalomoiris, S., Pepper, K., Olson, S., Fierro, F., and Nolta, J. A. (2011). Characterization and in vivo testing of mesenchymal stem cells derived from human embryonic stem cells. Tissue Eng Part A 17, 1517-1525.

Hofstetter, C. P., Schwarz, E. J., Hess, D., Widenfalk, J., El Manira, A., Prockop, D. J., and Olson, L. (2002). Marrow stromal cells form guiding strands in the injured spinal cord and promote recovery. Proceedings of the National Academy of Sciences of the United States of America 99, 2199-2204.

Huber, T. L., Kouskoff, V., Fehling, H. J., Palis, J., and Keller, G. (2004). Haemangioblast commitment is initiated in the primitive streak of the mouse embryo. Nature 432, 625-

630. Hwang, N. S., Varghese, S., Lee, H. J., Zhang, Z., Ye, Z., Bae, J., Cheng, L., and Elisseeff, J. (2008). In vivo commitment and functional tissue regeneration using human embryonic stem cell-derived mesenchymal cells. Proc Natl Acad Sci USA 105, 20641-20646.

Karussis, D., Karageorgiou, C., Vaknin-Dembinsky, A., Gowda-Kurkalli, B., Gomori, J. M., Kassis, I., Bulte, J. W., Petrou, P., Ben-Hur, T., Abramsky, O., et al. (2010). Safety and immunological effects of mesenchymal stem cell transplantation in patients with multiple sclerosis and amyotrophic lateral sclerosis. Arch Neurol 67, 1187-1194.

Kivisakk, P., Mahad, D. J., Callahan, M. K., Trebst, C., Tucky, B., Wei, T., Wu, L., Baekkevold, E. S., Lassmann, H., Staugaitis, S. M., et al. (2003). Human cerebrospinal fluid central memory CD4+ T cells: evidence for trafficking through choroid plexus and meninges via P-selectin. Proceedings of the National Academy of Sciences of the United States of America 100, 8389-8394.

Klimanskaya, I., Chung, Y., Becker, S., Lu, S. J., and Lanza, R. (2006). Human embryonic stem cell lines derived from single blastomeres. Nature 444, 481-485.

Kyriakou, C., Rabin, N., Pizzey, A., Nathwani, A., and Yong, K. (2008). Factors that influence short-term homing of human bone marrow-derived mesenchymal stem cells in a xenogeneic animal model. Haematologica 93, 1457-1465.

Lalu, M. M., McIntyre, L., Pugliese, C., Fergusson, D., Winston, B. W., Marshall, J. C., Granton, J., and Stewart, D. J. (2012). Safety of cell therapy with mesenchymal stromal cells (SafeCell): a systematic review and meta-analysis of clinical trials. PLoS One 7, e47559.

Lazarevic, V., Chen, X., Shim, J. H., Hwang, E. S., Jang, E., Bolm, A. N., Oukka, M., Kuchroo, V. K., and Glimcher, L. H. (2011). T-bet represses T(H)17 differentiation by preventing Runx1-mediated activation of the gene encoding RORgammat. Nature immunology 12, 96-104.

Le Blanc, K., Tammik, C., Rosendahl, K., Zetterberg, E., and Ringden, O. (2003). HLA expression and immunologic properties of differentiated and undifferentiated mesenchymal stem cells. Exp Hematol 31, 890-896.

Lee, H. J., Lee, J. K., Lee, H., Carter, J. E., Chang, J. W., Oh, W., Yang, Y. S., Suh, J. G., Lee, B. H., Jin, H. K., et al. (2012). Human umbilical cord blood-derived mesenchymal stem cells improve neuropathology and cognitive impairment in an Alzheimer's disease mouse model through modulation of neuroinflammation. Neurobiology of aging 33, 588-602.

Leech, M. D., Barr, T. A., Turner, D. G., Brown, S., O'Connor, R. A., Gray, D., Mellanby, R. J., and Anderton, S. M. (2012). Cutting Edge: IL-6-Dependent Autoimmune Disease: Dendritic Cells as a Sufficient, but Transient, Source. J. Immunol.

Lu, S. J., Luo, C., Holton, K., Feng, Q., Ivanova, Y., and Lanza, R. (2008). Robust generation of hemangioblastic progenitors from human embryonic stem cells. Regen Med 3, 693-704. McFarland, H. F., and Martin, R. (2007). Multiple sclerosis: a complicated picture of autoimmunity. Nat Immunol 8, 913-919.

Mohyeddin Bonab, M., Yazdanbakhsh, S., Lotfi, J., Alimoghaddom, K., Talebian, F., Hooshmand, F., Ghavamzadeh, A., and Nikbin, B. (2007). Does mesenchymal stem cell therapy help multiple sclerosis patients? Report of a pilot study. Iranian journal of immunology: IJI 4, 50-57.

Moore, C. S., Milner, R., Nishiyama, A., Frausto, R. F., Serwanski, D. R., Pagarigan, R. R., Whitton, J. L., Miller, R. H., and Crocker, S. J. (2011). Astrocytic tissue inhibitor of metalloproteinase-1 (TIMP-1) promotes oligodendrocyte differentiation and enhances CNS myelination. The Journal of neuroscience: the official journal of the Society for Neuroscience 31, 6247-6254.

Olivier, E. N., Rybicki, A. C., and Bouhassira, E. E. (2006). Differentiation of human embryonic stem cells into bipotent mesenchymal stem cells. Stem Cells 24, 1914-1922.

Patanella, A. K., Zinno, M., Quaranta, D., Nociti, V., Frisullo, G., Gainotti, G., Tonali, P. A., Batocchi, A. P., and Marra, C. (2010). Correlations between peripheral blood mononuclear cell production of BDNF, TNF-alpha, IL-6, IL-10 and cognitive performances in multiple sclerosis patients. J Neurosci Res 88, 1106-1112.

Pati, S., Gerber, M. H., Menge, T. D., Wataha, K. A., Zhao, Y., Baumgartner, J. A., Zhao, J., Letourneau, P. A., Huby, M. P., Baer, L. A., et al. (2011). Bone marrow derived mesenchymal stem cells inhibit inflammation and preserve vascular endothelial integrity in the lungs after hemorrhagic shock. PLoS One 6, e25171.

Payne, N. L., Sun, G., McDonald, C., Layton, D., Moussa, L., Emerson-Webber, A., Veron, N., Siatskas, C., Herszfeld, D., Price, J., et al. (2012). Distinct immunomodulatory and migratory mechanisms underpin the therapeutic potential of human mesenchymal stem cells in autoimmune demyelination. Cell Transplant.

Peron, J. P., Jazedje, T., Brandao, W. N., Perin, P. M., Maluf, M., Evangelista, L. P., Halpern, S., Nisenbaum, M. G., Czeresnia, C. E., Zatz, M., et al. (2012). Human endometrial-derived mesenchymal stem cells suppress inflammation in the central nervous system of EAE mice. Stem Cell Rev 8, 940-952.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Pomper, M. G., Hammond, H., Yu, X., Ye, Z., Foss, C. A., Lin, D. D., Fox, J. J., and Cheng, L. (2009). Serial imaging of human embryonic stem-cell engraftment and teratoma formation in live mouse models. Cell Res 19, 370-379.

Quintana, A., Muller, M., Frausto, R. F., Ramos, R., Getts, D. R., Sanz, E., Hofer, M. J., Krauthausen, M., King, N. J., Hidalgo, J., et al. (2009). Site-specific production of IL-6 in the central nervous system retargets and enhances the inflammatory response in experimental autoimmune encephalomyelitis. Journal of immunology 183, 2079-2088.

Rombouts, W. J., and Ploemacher, R. E. (2003). Primary murine MSC show highly efficient homing to the bone marrow but lose homing ability following culture. Leukemia 17, 160-170.

Sanchez, L., Gutierrez-Aranda, I., Ligero, G., Rubio, R., Munoz-Lopez, M., Garcia-Perez, J. L., Ramos, V., Real, P. J., Bueno, C., Rodriguez, R., et al. (2011). Enrichment of human ESC-derived multipotent mesenchymal stem cells with immunosuppressive and anti-inflammatory properties capable to protect against experimental inflammatory bowel disease. Stem cells 29, 251-262.

Selmani, Z., Naji, A., Zidi, I., Favier, B., Gaiffe, E., Obert, L., Borg, C., Saas, P., Tiberghien, P., Rouas-Freiss, N., et al. (2008). Human leukocyte antigen-G5 secretion by human mesenchymal stem cells is required to suppress T lymphocyte and natural killer function and to induce CD4+CD25highFOXP3+ regulatory T cells. Stem cells 26, 212-222.

Sheikh, A. M., Nagai, A., Wakabayashi, K., Narantuya, D., Kobayashi, S., Yamaguchi, S., and Kim, S. U. (2011). Mesenchymal stem cell transplantation modulates neuroinflammation in focal cerebral ischemia: contribution of fractalkine and IL-5. Neurobiology of disease 41, 717-724.

Stromnes, I. M., and Goverman, J. M. (2006). Active induction of experimental allergic encephalomyelitis. Nat Protoc 1, 1810-1819.

Teo, G. S., Ankrum, J. A., Martinelli, R., Boetto, S. E., Simms, K., Sciuto, T. E., Dvorak, A. M., Karp, J. M., and Carman, C. V. (2012). Mesenchymal stem cells transmigrate between and directly through tumor necrosis factor-alpha-activated endothelial cells via both leukocyte-like and novel mechanisms. Stem Cells 30, 2472-2486.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Uccelli, A., and Prockop, D. J. (2010). Why should mesenchymal stem cells (MSCs) cure autoimmune diseases? Curr Opin Immunol 22, 768-774.

Wagner, W., Horn, P., Castoldi, M., Diehlmann, A., Bork, S., Saffrich, R., Benes, V., Blake, J., Pfister, S., Eckstein, V., et al. (2008). Replicative senescence of mesenchymal stem cells: a continuous and organized process. PLoS One 3, e2213.

Wang, X., Lin, G., Martins-Taylor, K., Zeng, H., and Xu, R. H. (2009). Inhibition of caspase-mediated anoikis is critical for bFGF-sustained culture of human pluripotent stem cells. J Biol Chem.

Weber, M. S., Menge, T., Lehmann-Horn, K., Kronsbein, H. C., Zettl, U., Sellner, J., Hemmer, B., and Stuve, O. (2012). Current treatment strategies for multiple sclerosis—efficacy versus neurological adverse effects. Current pharmaceutical design 18, 209-219.

Wong, R. S. (2011). Mesenchymal stem cells: angels or demons? J Biomed Biotechnol 2011, 459510.

Yamout, B., Hourani, R., Salti, H., Barada, W., El-Hajj, T., Al-Kutoubi, A., Herlopian, A., Baz, E. K., Mahfouz, R., Khalil-Hamdan, R., et al. (2010). Bone marrow mesenchymal stem cell transplantation in patients with multiple sclerosis: a pilot study. J Neuroimmunol 227, 185-189.

Zappia, E., Casazza, S., Pedemonte, E., Benvenuto, F., Bonanni, I, Gerdoni, E., Giunti, D., Ceravolo, A., Cazzanti, F., Frassoni, F., et al. (2005). Mesenchymal stem cells ameliorate experimental autoimmune encephalomyelitis inducing T-cell anergy. Blood 106, 1755-1761.

Zhang, J., Li, Y., Chen, J., Cui, Y., Lu, M., Elias, S. B., Mitchell, J. B., Hammill, L., Vanguri, P., and Chopp, M. (2005). Human bone marrow stromal cell treatment improves neurological functional recovery in EAE mice. Exp Neurol 195, 16-26.

Example 23

Lupus Model

Figure 37A:
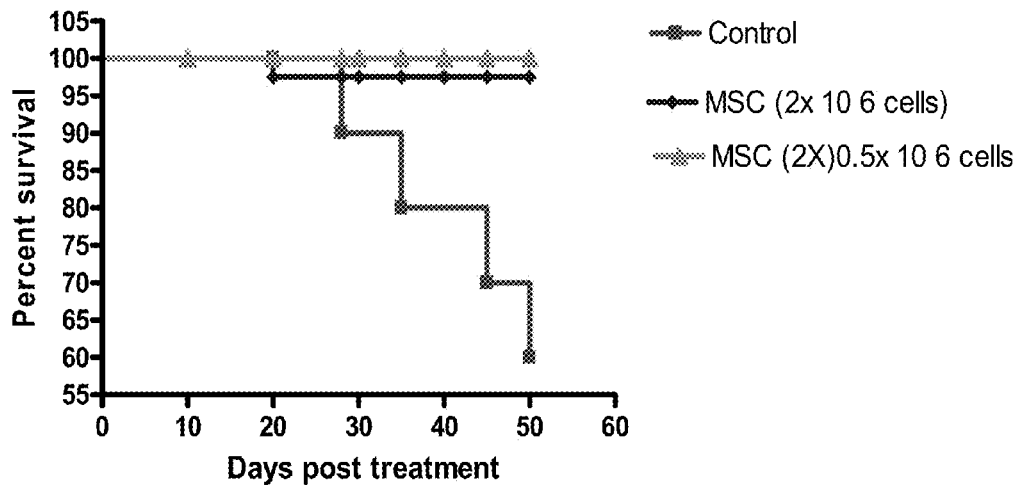
FIG. 37A shows the rate of survival of BWF1 mice after treatment with MSCs (one dose of $2\times10^6$ cells, or two doses of $0.5\times10^6$ cells per dose) versus the rate of survival of control animals. Uppermost (green) line, two doses of $0.5\times10^6$ MSC administered, 100% survival at 50 days post treatment; middle (blue) line, one does of $2\times10^6$ MSC administered, about 95% survival at 50 days post treatment; lower (red) line, controls, about 60% survival at 50 days post treatment.
Figure 37B:
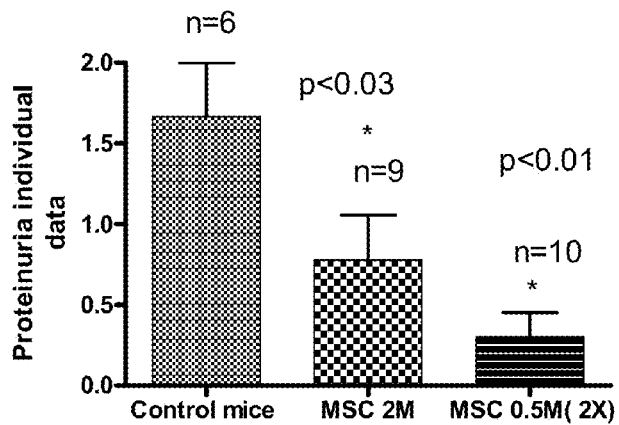
FIG. 37B shows the relative proteinuria (presence of an excess of serum proteins in the urine) for BWF1 mice after treatment with MSCs (one dose of $2\times10^6$ cells, or two doses of $0.5\times10^6$ cells per dose) versus control animals.

Administration of MSCs was Highly Effective in Prolonging Survival of BWF1 Mice (NZB×NZW)F1 (BWF1) lupus-prone mice were treated with hESC-derived MSCs either in one single dose of $2\times10^6$ cells, or in two doses of $0.5\times10^6$ cells per dose, with second dose being administered two weeks after the first (day 0). The rate of survival of hESC-MSC treated mice was compared to control animals. The hESC-treated and control animal cohorts included 20 animals each. As shown in FIG. 37A, forty percent (40%) of the control animals were deceased within 50 days, while the animals treated with the hESC-derived MSCs had a substantially improved rate of survival in comparison (95%-100% survival at 50 days). Relative to the control group, the animals treated with hESC-derived MSCs also showed a higher average weight after 7 weeks (post treatment), as well as increases in CD4+ Foxp3+ T cells and Regulatory T cells in peripheral blood samples. As shown in FIG. 37B, mice treated with the hESC-derived MSCs also had substantially lower levels of proteinuria (presence of an excess of serum proteins in the urine) relative to the control group.

REFERENCES CITED

1. Zappia, E., et al., *Mesenchymal stem cells ameliorate experimental autoimmune encephalomyelitis inducing T-cell anergy*. Blood, 2005. 106(5): p. 1755-61.
2. Gerdoni, E., et al., *Mesenchymal stem cells effectively modulate pathogenic immune response in experimental autoimmune encephalomyelitis*. Ann Neurol, 2007. 61(3): p. 219-27.
3. Lanza, C., et al., *Neuroprotective mesenchymal stem cells are endowed with a potent antioxidant effect in viva* J Neurochem, 2009. 110(5): p. 1674-84.
4. Rafei, M., et al., *Allogeneic mesenchymal stem cells for treatment of experimental autoimmune encephalomyelitis*. Mol Ther, 2009. 17(10): p. 1799-803.
5. Rafei, M., et al., *Mesenchymal stromal cells ameliorate experimental autoimmune encephalomyelitis by inhibiting CD4 Th 17 T cells in a CC chemokine ligand 2-dependent manner*. J Immunol, 2009. 182(10): p. 5994-6002.
6. Constantin, G., et al., *Adipose-derived mesenchymal stem cells ameliorate chronic experimental autoimmune encephalomyelitis*. Stem Cells, 2009. 27(10): p. 2624-35.
7. Uccelli, A. and D. J. Prockop, *Why should mesenchymal stem cells (MSCs) cure autoimmune diseases?* Curr Opin Immunol, 2010. 22(6): p. 768-74.
8. Ohtaki, H., et al., *Stem/progenitor cells from bone marrow decrease neuronal death in global ischemia by modulation of inflammatory/immune responses*. Proc Natl Acad Sci USA, 2008. 105(38): p. 14638-43.
9. Barberi, T., et al., *Derivation of multipotent mesenchymal precursors from human embryonic stem cells*. PLoS Med, 2005. 2(6): p. e161.
10. Hwang, N. S., et al., *In vivo commitment and functional tissue regeneration using human embryonic stem cell-derived mesenchymal cells*. Proc Natl Acad Sci USA, 2008. 105(52): p. 20641-6.
11. Olivier, E. N., A. C. Rybicki, and E. E. Bouhassira, *Differentiation of human embryonic stem cells into bipotent mesenchymal stem cells*. Stem Cells, 2006. 24(8): p. 1914-22.
12. Brown, S. E., W. Tong, and P. H. Krebsbach, *The derivation of mesenchymal stem cells from human embryonic stem cells*. Cells Tissues Organs, 2009. 189(1-4): p. 256-60.
13. Karlsson, C., Emanuelsson, K., Wessberg, F., Kajic, K., Axell, M. Z., Eriksson, P. S., Lindahl, A., Hyllner, J., and Strehl, R., *Human embryonic stem cell-derived mesenchymal progenitors-Potential in regenerative medicine*. Stem Cell Res., 2009. 3(1): 39-50.
14. Lu, S. J., Feng, Q., Caballero, S., Chen, Y., Moore, M. A., Grant, M. B., and Lanza, R., *Generation of functional hemangioblasts from human embryonic stem cells*, Nat. Methods 4 (2007) 501-509.
15. Lu, S. J., Luo, C., Holton, K., Feng, Q., Ivanova, Y., and Lanza, R., *Robust generation of hemangioblastic progenitors from human embryonic stem cells*, Regen. Med. 3 (2008) 693-704.

16. Klimanskaya, I., Chung, Y., Becker, S., Lu, S.-J., and Lanza, R., *Human embryonic stem-cell lines derived from single blastomeres*, Nature 444 (2006) 481-485.
17. Madsen, L. S., et al., *A humanized model for multiple sclerosis using HLA-DR2 and a human T-cell receptor*. Nat Genet, 1999. 23(3): p. 343-7.
18. Stromnes, I. M. and J. M. Goverman, *Passive induction of experimental allergic encephalomyelitis*. Nat Protoc, 2006. 1(4): p. 1952-60.
19. Liang, J., et al., *Allogeneic mesenchymal stem cells transplantation in treatment of multiple sclerosis*. Mult Scler, 2009. 15(5): p. 644-6.
20. Costa, M., et al., *The ESC line Envy expresses high levels of GFP in all differentiated progeny*. Nat Methods, 2005. 2(4): p. 259-60.
21. Pomper, M. G., et al., *Serial imaging of human embryonic stem-cell engraftment and teratoma formation in live mouse models*. Cell Res, 2009. 19(3): p. 370-9.
22. Phinney, D. G. and D. J. Prockop, *Concise review: mesenchymal stem/multipotent stromal cells: the state of transdifferentiation and modes of tissue repair—current views*. Stem Cells, 2007. 25(11): p. 2896-902.
23. Ryan, J. M., et al., *Interferon-gamma does not break, but promotes the immunosuppressive capacity of adult human mesenchymal stem cells*. Clin Exp Immunol, 2007. 149(2): p. 353-63.
24. DelaRosa, O. and E. Lombardo, *Modulation of adult mesenchymal stem cells activity by toll-like receptors: implications on therapeutic potential*. Mediators Inflamm, 2010.2010: p. 865601.
25. English, K., et al., *IFN-gamma and TNF-alpha differentially regulate immunomodulation by murine mesenchymal stem cells*. Immunol Left, 2007. 110(2): p. 91-100.
26. Barry, F., et al., *The SH-3 and SH-4 antibodies recognize distinct epitopes on CD73 from human mesenchymal stem cells*. Biochem Biophys Res Commun, 2001.289(2): p. 519-24.
27. Alhadlaq, A. and J. J. Mao, *Mesenchymal stem cells: isolation and therapeutics*. Stem Cells Dev, 2004. 13(4): p. 436-48.
28. Mikami, Y., et al., *CD271/p75NTR inhibits the differentiation of mesenchymal stem cells into osteogenic, adipogenic, chondrogenic, and myogenic lineages*. Stem Cells Dev, 2010.
29. Di Nicola, M., et al., *Human bone marrow stromal cells suppress T-lymphocyte proliferation induced by cellular or nonspecific mitogenic stimuli*. Blood, 2002. 99(10): p. 3838-43.
30. Johnson, T. A., F. R Jirik, and S. Fournier, *Exploring the roles of CD8(+) T lymphocytes in the pathogenesis of autoimmune demyelination*. Semin Immunopathol, 2010. 32(2): p. 197-209.
31. Huseby, E. S., C. Ohlen, and J. Goverman, *Cutting edge: myelin basic protein-specific cytotoxic T cell tolerance is maintained in vivo by a single dominant epitope in H-2k mice*. J Immunol, 1999. 163(3): p. 1115-8.
32. Tang, Q. and J. A. Bluestone, *Regulatory T-cell physiology and application to treat autoimmunity*. Immunol Rev, 2006.212: p. 217-37.
33. Boumaza, I., et al., *Autologous bone marrow-derived rat mesenchymal stem cells promote PDX-1 and insulin expression in the islets, alter T cell cytokine pattern and preserve regulatory T cells in the periphery and induce sustained normoglycemia*. J Autoimmun, 2009. 32(1): p. 33-4
34. Maccario, R., et al., *Interaction of human mesenchymal stem cells with cells involved in alloantigen-specific immune response favors the differentiation of CD4+ T-cell subsets expressing a regulatory/suppressive phenotype*. Haematologica, 2005. 90(4): p. 516-25.
35. Locatelli, F., R. Maccario, and F. Frassoni, *Mesenchymal stromal cells, from indifferent spectators to principal actors. Are we going to witness a revolution in the scenario of allograft and immune-mediated disorders?* Haematologica, 2007.92(7): p. 872-7.
36. Wan, Y. Y. and R. A. Flavell, *Identifying Foxp3-expressing suppressor T cells with a bicistronic reporter*. Proc Natl Acad Sci USA, 2005. 102(14): p. 5126-31.
37. Duijvestein et al. Stem Cells 29 (10): 1549-1558 (2011)
38. Liang et al. Cell Transplant 20 (9): 1395-1408 (2011)
39. Pizarro et al. Trends Mol Med 9 (5): 218-222 (2003)
40. Copland et al. IOVS 49 (12): 5458-5465 (2008)
41. Wakitani et al. Osteoarthritis and Cartilage 10: 199-206 (2002)
42. Mobasheri et al. Histol. Histopathol 24 (3): 347-366 (2009)
43. Noth et al. Nat Clin Pract Rheumato 4(7): 371-380 (2008)
44. Gotherstrom et al. Am J Obstet Gynecol 190(1): 239-45 (2004)
45. Rasmusson et al. Exp. Cell Research 312(12): 2169-79 (2006)
46. Newman et al. Inflamm Allergy Drug Targets 8(2): 110-123 (2009)
47. Le Blanc et al. Exp. Hematol. 31: 890-896 (2003)
48. Liu et al. J. of Immunol. 176: 2864-2871 (2006)

Each document cited herein (e.g., U.S. patents, U.S. published applications, non-patent literature, etc.) is hereby incorporated by reference in its entirety.

The invention claimed is:

1. A method for treating a disease or disorder, comprising administering to a subject in need thereof an effective amount of mesenchymal stromal cells or a preparation of mesenchymal stromal cells obtained by a method comprising culturing hemangioblasts under conditions that give rise to mesenchymal stromal cells.

2. The method of claim 1, that further comprises the transplantation of other cells or tissues; or that further comprises the transplantation of retinal, RPE, corneal, neural, immune, bone marrow, liver, or pancreatic cells.

3. The method of claim 1, wherein the disease or disorder is selected from multiple sclerosis, systemic sclerosis, hematological malignancies, myocardial infarction, organ transplantation rejection, chronic allograft nephropathy, cirrhosis, liver failure, heart failure, GvHD, tibial fracture, left ventricular dysfunction, leukemia, myelodysplastic syndrome, Crohn's disease, diabetes, chronic obstructive pulmonary disease, osteogenesis imperfecta, homozygous familial hypocholesterolemia, treatment following meniscectomy, adult periodontitis, vasculogenesis in patients with severe myocardial ischemia, spinal cord injury, osteodysplasia, critical limb ischemia, diabetic foot disease, primary Sjogren's syndrome, osteoarthritis, cartilage defects, multisystem atrophy, amyotropic lateral sclerosis, cardiac surgery, refractory systemic lupus erythematosis, living kidney allografts, non-malignant red blood cell disorders, thermal burn, Parkinson's disease, microfractures, epidermolysis bullosa, severe coronary ischemia, idiopathic dilated cardiomyopathy, osteonecrosis femoral head, lupus nephritis, bone void defects, ischemic cerebral stroke, after stroke, acute radiation syndrome, pulmonary disease, arthritis, bone regeneration, inflammatory respiratory conditions, respiratory conditions due to an acute injury, Adult Respiratory Distress Syndrome, post-traumatic Adult Respiratory Distress Syndrome, transplant lung disease, Chronic Obstructive Pulmonary Disease, emphysema, chronic obstructive bronchitis, bronchitis, an allergic reaction, damage due to bacterial pneumonia, damage due to viral pneumonia, asthma, exposure to irritants, tobacco use, atopic dermatitis, allergic rhinitis, hearing loss, autoimmune hearing loss, noise-induced hearing loss, psoriasis or any combination thereof.

4. The method of claim 1, wherein the disease or disorder is uveitis, an autoimmune disorder, an immune reaction against allogeneic cells, multiple sclerosis, bone loss, cartilage damage, or lupus.

5. The method of claim 1, wherein the mesenchymal stromal cells
   (a) are mitotically inactivated;
   (b) have replicative capacity to undergo at least 10 population doublings in cell culture with less than 25 percent of the cells undergoing cell death, senescing or differentiating into non-MSC cells by the tenth doubling;
   (c) have replicative capacity to undergo at least 5 passages in cell culture;
   (d) have replicative capacity to undergo at least 5 passages in cell culture with less than 25 percent of the cells undergoing cell death, senescing or differentiating into fibroblasts by the $5^{th}$ passage;
   (e) are HLA-genotypically identical; and/or
   (f) are genomically identical.

6. The method of claim 1, wherein the preparation of mesenchymal stromal cells comprises at least $10^6$ mesenchymal stromal cells and less than one percent of any other cell type, wherein the mesenchymal stromal cells have replicative capacity to undergo at least 10 population doublings in cell culture with less than 25 percent of the cells undergoing cell death, senescing or differentiating into non-MSC cells by the tenth doubling.

7. The method of claim 1, wherein
   (a) at least 30% of the mesenchymal stromal cells are positive for CD10; and/or
   (b) at least 60% of the mesenchymal stromal cells are positive for markers CD73, CD90, CD105, CD13, CD29, CD44, CD166 and HLA-ABC; and/or
   (c) less than 30% of the mesenchymal stromal cells are positive for markers CD31, CD34, CD45, CD133, FGFR2, CD271, Stro-1, CXCR4 and TLR3.

8. The method of claim 1, wherein
   (a) at least 50% of the mesenchymal stromal cells are positive for all of CD10, CD24, IL-11, AIRE-1, ANG-1, CXCL1, CD105, CD73, CD90, CD105, CD13, CD29, CD 44, CD166, CD274, and HLA-ABC; and
   (b) no more than 30% or no more than 10% or no more than 5% of the mesenchymal stromal cells are positive for CD31, CD34, CD45, CD133, FGFR2, CD271, Stro-1, CXCR4 or TLR3.

9. The method of claim 1, wherein the mesenchymal stromal cells
   (a) have replicative rates to undergo at least 10 population doublings in cell culture in less than 25 days; and/or
   (b) have a mean terminal restriction fragment length (TRF) that is longer than 8 kb; and/or
   (c) have a statistically decreased content and/or enzymatic activity, relative to mesenchymal stromal cells derived from bone marrow that have undergone five population doublings, of proteins involved in one or more of (i) cell cycle regulation and cellular aging, (ii) cellular energy and/or lipid metabolism, and (iii) apoptosis; and/or
   (d) have a statistically significant increased content and/or enzymatic activity of proteins involved in cytoskeleton structure and cellular dynamics relating thereto, relative to mesenchymal stromal cells derived from bone marrow; and/or
   (e) do not undergo more than a 75 percent increase in cells having a forward-scattered light value, measured by flow cytometry, greater than 5,000,000 over 10 population doublings in culture; and/or
   (f) in a resting state, express mRNA encoding interleukin-6 at a level which is less than ten percent of the IL-6 mRNA level expressed by mesenchymal stromal (IL-6) cells, in a resting state, derived from bone marrow or adipose tissue; and/or
   (g) induce a 40% or greater decrease in T-cell activation compared to mesenchymal stromal cells derived from bone marrow or adipose tissue; and/or
   (h) induce an increased regulatory T cell (Treg) induction and/or expansion compared to mesenchymal stromal cells derived from bone marrow or adipose tissue.

10. The method of claim 1, wherein the mesenchymal stromal cells have a potency in an immune regulatory assay greater than the potency of bone marrow derived mesenchymal stromal cells.

11. The method of claim 10, wherein the potency is assayed by an immune regulatory assay that determines an EC50 dose.

* * * * *